United States Patent
Li et al.

(10) Patent No.: US 11,220,503 B2
(45) Date of Patent: Jan. 11, 2022

(54) PHTHALAZINE DERIVATIVES, PREPARATION METHOD, PHARMACEUTICAL COMPOSITION AND USAGE THEREOF

(71) Applicant: Shanghai SIMR Biotech Co., Ltd., Shanghai (CN)

(72) Inventors: Shuai Li, Shanghai (CN); Yong Sun, Shanghai (CN)

(73) Assignee: Shanghai SIMR Biotech Co., Ltd., Shanghai (CN)

( * ) Notice: Subject to any disclaimer, the term of this patent is extended or adjusted under 35 U.S.C. 154(b) by 518 days.

(21) Appl. No.: 16/060,256

(22) PCT Filed: Dec. 8, 2016

(86) PCT No.: PCT/CN2016/108975
§ 371 (c)(1),
(2) Date: Sep. 25, 2018

(87) PCT Pub. No.: WO2017/097217
PCT Pub. Date: Jun. 15, 2017

(65) Prior Publication Data
US 2020/0165253 A1  May 28, 2020

(30) Foreign Application Priority Data
Dec. 8, 2015 (CN) .......................... 201510900083.4

(51) Int. Cl.
*C07D 487/04* (2006.01)
(52) U.S. Cl.
CPC .................. *C07D 487/04* (2013.01)
(58) Field of Classification Search
CPC ................................................. C07D 487/04
See application file for complete search history.

(56) References Cited

U.S. PATENT DOCUMENTS

| | | | |
|---|---|---|---|
| 6,200,975 | B1 | 3/2001 | Carling et al. |
| 6,313,125 | B1 | 11/2001 | Carling et al. |
| 2004/0043982 | A1 | 3/2004 | Chambers et al. |
| 2005/0043982 | A1 | 2/2005 | Nguyen |
| 2011/0224278 | A1 | 9/2011 | Carmichael et al. |

FOREIGN PATENT DOCUMENTS

| | | | |
|---|---|---|---|
| CN | 1871008 | A | 11/2006 |
| CN | 103239720 | A | 8/2013 |
| JP | 2001525802 | A | 12/2001 |
| JP | 2002525282 | A | 8/2002 |
| JP | 2003513975 | A | 4/2003 |
| JP | 2007509150 | A | 4/2007 |
| WO | 9222652 | A1 | 12/1992 |
| WO | 9413799 | A1 | 6/1994 |
| WO | 9850385 | A1 | 11/1998 |
| WO | 0242305 | A1 | 5/2002 |

OTHER PUBLICATIONS

Street et al. J. Med. Chem. 2004, 47, 3642-3657 .*
European Patent Office. Office Action for application 16872406.0. dated May 20, 2020.
Extended European search report issued in corresponding European No. 16872406.0, dated Jul. 4, 2019, 6 pages.
Notice of Reasons for Refusal issued in corresponding Japanese Application No. 2018-530763, dated Jun. 18, 2019, 9 pages.
The Second Office Action issued in corresponding Chinese Application No. 201510900083.4, dated Mar. 11, 2019, 10 pages.
Brickley, et al., Extrasynaptic GABA(A) Receptors: Their Function in the CNS and Implications for Disease, Neuron, 2012, 73(1):23-34.
Clement, et al., Gabra5-gene Haplotype Block Associated with Behavioral Properties of the Full Agonist Benzodiazepine Chlordiazepoxide, Behavioural Brain Research, 2012, 233:474-482.
Combourieu, et al., Thiomorpholine and Morpholine Oxidation by a Cytochrome P450 in *Mycobacterium aurum* MO1. Evidence of the Intermediates by In Situ 1H NMR, Biodegradation, 1998, 9:433-442.
Farrant, et al., Variations on an Inhibitory Theme: Phasic and Tonic Activation of GABA(A) Receptors, Nature Reviews Neuroscience, 2005, 6(3):215-229.
Goeders, et al., Benzodiazepine Receptor Binding In Vivo With [3H]-Ro 15-1788, Life Sciences, 1985, 37:345-355.
Harris, et al., Selective Influence on Contextual Memory: Physiochemical Properties Associated with Selectivity of Benzodiazepine Ligands at GABA(A) Receptors Containing the a5 Subunit, Journal of Medicinal Chemistry, 2008, 51:3788-3803.
Heldt, et al., Training-Induced Changes in the Expression of GABA(A)-Associated Genes in the Amygdala after the Acquisition and Extinction of Pavlovian Fear, European Journal of Neuroscience, 2007, 26(12):3631-3644.
Jones, et al., Pharmacokinetics and Metabolism Studies on (3-tert-butyl-7-(5-methylisoxazol-3-yl)-2-(1-methyl-1H-1,2,4-triazol-5-ylmethoxy) pyrazolo[1,5-d][1,2,4]triazine, a Functionally Selective GABA(A) a5 Inverse Agonist for Cognitive Dysfunction, Bioorganic & Medicinal Chemistry Letters, 2006, 16;872-875.

(Continued)

*Primary Examiner* — Emily A Bernhardt
(74) *Attorney, Agent, or Firm* — Quarles & Brady LLP

(57) ABSTRACT

The present invention provides a compound of formula I, a cis-trans isomer, an enantiomer, a diastereoisomer, a racemate, a solvate, a hydrate, or a pharmaceutical acceptable salt and ester thereof, a preparation method for preparing the same, a pharmaceutical composition comprising the same and a use of the compound as an α5-GABA$_A$ receptor regulator, wherein T, Z, A and Y are as defined in the description.

formula I

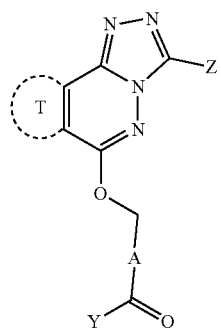

31 Claims, No Drawings

(56) References Cited

OTHER PUBLICATIONS

Lebsack, et al., Identification and Synthesis of [1,2,4]triazolo[3,4-a]phthalazine Derivatives as High-Affinity Ligands to the α2δ-1 Subunit of Voltage Gated Calcium Channel, Bioorganic & Medicinal Chemistry Letters, 2004, 14:2463-2467.

Lecker, et al., Potentiation of GABA(A) Receptor Activity by Volatile Anaesthetics is Reduced by α5GABAA Receptor-Preferring Inverse Agonists, British Journal of Anaesthesia, 2013, 110(S1):i73-i81.

Lee, et al., Upregulation of High-Affinity GABA(A) Receptors in Cultured Rat Dorsal Root Ganglion Neurons, Neuroscience, 2012, 208:133-142.

Savic, et al., PWZ-029, A Compound With Moderate Inverse Agonist Functional Selectivity at GABA(A) Receptors Containing α5 Subunits, Improves Passive, But Not Active, Avoidance Learning in Rats, Brain Research, 2008, 1208:150-159.

Sternfeld, et al., Selective, Orally Active γ-Aminobutyric AcidA α5 Receptor Inverse Agonists as Cognition Enhancers, Journal of Medicinal Chemistry, 2004, 47:2176-2179.

Street, et al., Synthesis and Biological Evaluation of 3-Heterocyclyl-7,8,9,10-tetrahydro-(7,10-ethano)-1,2,4-triazolo [3,4-a]phthalazines and Analogues as Subtype-Selective Inverse Agonists for the GABA(A)α5 Benzodiazepine Binding Site, Journal of Medicinal Chemistry, 2004, 47:3642-3657.

Tasan, et al., Altered GABA Transmission in a Mouse Model of Increased Trait Anxiety, Neuroscience, 2011, 183(7):71-80.

Wafford, et al., Differences in Affinity and Efficacy of Benzodiazepine Receptor Ligands at Recombinant gamma-aminobutyric AcidA Receptor Subtypes, Molecular Pharmacology, 1993, 43:240-244.

Xiao, et al., Identification of Gene Expression Profile of Dorsal Root Ganglion in the Rat Peripheral Axotomy Model of Neuropathic Pain, PNAS, 2002, 99(12):8360-8365.

Yeung, et al., Tonically Activated GABA(A) Receptors in Hippocampal Neurons Are High-Affinity, Low-Conductance Sensors for Extracellular GABA, Molecular Pharmacology, 2003, 63:2-8.

Zlokovic, Neurovascular Pathways to Neurodegeneration in Alzheimer's Disease and Other Disorders, Nature Reviews Neuroscience, 2011, 12(12):723-738.

PCT International Search Report, PCT/CN2016/108975, dated Mar. 15, 2017, 8 pages.

\* cited by examiner

PHTHALAZINE DERIVATIVES, PREPARATION METHOD, PHARMACEUTICAL COMPOSITION AND USAGE THEREOF

CROSS-REFERENCE TO RELATED APPLICATIONS

This application represents the U.S. national stage entry of International Application No. PCT/CN2016/108975 filed Dec. 8, 2016, which claims priority to Chinese Patent Application No. 201510900083.4 filed Dec. 8, 2015, the disclosure of which is incorporated herein by reference in its entirety and for all purposes.

TECHNICAL FIELD

The present disclosure relates to phthalazine derivatives, which can regulate α5-$GABA_A$ receptor, a method of preparing phthalazine derivatives, pharmaceutical compositions containing phthalazine derivatives, and uses of phthalazine derivatives as a medicament.

BACKGROUND

γ-aminobutyric acid (GABA) is an important inhibitory neurotransmitter in mammal central nervous system. There are two classes of GABA receptors in nature. One is $GABA_A$ receptor, which is a member of ligand-gated ion channel superfamily, and the other is $GABA_B$ receptor, which is a member of G protein-coupled receptor superfamily. It is found that there are several subunits in mammal $GABA_A$ receptor, including α1-6, β1-4, γ1-3, δ, ε, θ and ρ1-2, among which α subunit, β subunit and γ subunit are important for forming a complete and functional $GABA_A$ receptor, and α subunit is crucial for the interaction between benzodiazepine and $GABA_A$ receptor.

The percentage of $GABA_A$ receptor that contains α5 subunit (α5-$GABA_A$ receptor) in mammal brain $GABA_A$ receptors is less than 5%. The expression level of α5-$GABA_A$ receptor in cerebral cortex is very low, while the percentage of $GABA_A$ receptor in hippocampal tissue is more than 20%. There is almost no expression in other brain regions. Considering the specific distribution and functional research of α5-$GABA_A$ receptor in hippocampal tissue, a large number of pharmaceutical companies including Roche are working on α5-$GABA_A$ receptor. Many compounds have been synthesized gradually, particularly inverse agonists for α5-$GABA_A$ receptor in hippocampal tissue, and among them α5IA and MRK-016 showed good therapeutic effects on the treatment of cognition related diseases in animal models and clinical trials, especially for Alzheimer's disease. It is widely thought that α5-$GABA_A$ receptor inverse agonists can be used for the treatment of cognition related diseases, especially for Alzheimer's disease. The patent application US 2011 0224278 A1 discloses α5-$GABA_A$ receptor inverse agonists can be used for the treatment of multi-infarct dementia and stoke related diseases.

In the last decade, the studies have shown that the permeability of blood brain barrier (BBB) increases under some disease conditions, especially those neurodegenerative diseases like Alzheimer's and stroke (Zlokovic et al. Nat Rev Neurosci.; 12(12): 723-738). As a result, some normally impermeable compounds can get into the brain under these disease conditions and exert pharmacological effects. So the normally impermeable α5-$GABA_A$ receptor inverse agonists potentially can be used for the treatment of Alzheimer's and stroke due to the increased permeability.

In 2002, Dr. Xu Zhang's lab reported that the α5-$GABA_A$ receptor was mainly expressed in the small neurons and its expression level increased in the nerve transection model (Xiao H S et al., "Identification of gene expression profile of dorsal root ganglion in the rat peripheral axotomy model of neuropathic pain." Proc Natl Acad Sci USA. Jun. 11, 2002; 99(12)). The patent application CN103239720A discloses that the α5-$GABA_A$ receptor also expresses in the peripheral nerves system and its expression increases dramatically in the partial sciatic nerve injury model. The α5-$GABA_A$ receptor inverse agonists act to inhibit various pains by selectively binding to the α5-$GABA_A$ receptor of the peripheral nerves system. The animal model data show that the stronger the inverse agonism of the inverse agonist, the better the pain-inhibiting effect is.

There are many researches on the detection whether a compound is an inverse agonist or an antagonist of α5-$GABA_A$ receptors. For example, in the international patent application WO 92/22652 and WO 94/13799, α subunit combination α5, β3 and γ2 of $GABA_A$ receptor was used to detect the binding of the compounds and the subunit. For screening assay, the method developed by Goeders et al is widely used (Goeders N E and Kuhar M J (1985) Benzodiazepine binding in vivo with [.sup.3 H]Ro 15-1788. Life Sci 37:345-355). There are also many researches on the detection whether a ligand which can bind with α5-$GABA_A$ receptor is an agonist, an antagonist or an inverse antagonist of α5-$GABA_A$ receptors, for example the method of Wafford K A et al (Wafford K A, Whiting P J and Kemp J A (1993) Differences in affinity and efficacy of benzodiazepine receptor ligands on recombinant GABA.sub.A receptor subtypes. Mol. Pharmacol 43:240-244).

There are several methods to detect the compound permeability to the BBB. It has been reported that a radio labeled compound ($^3$H)R0-15-1788 (α5-$GABA_A$ receptor selective inverse agonist) can be used to detect the binding of a compound in brain (Jones et al., Pharmacokinetics and metabolism studies on (3-tert-butyl-7-(5-methylisoxazol-3-yl)-2-(1-methyl-1H-1,2,4-triazol-5-ylmethoxy) pyrazolo[1,5-d][1,2,4]triazine, a functionally selective GABAA α5 inverse agonist for cognitive dysfunction. Bioorg Med Chem Lett. 2006 Feb. 15; 16(4):872-5). The studies showed that MRK016 could efficiently block the binding of ($^3$H)R0-15-1788 in brain, while MRK016-M3 showed almost no blocking effect. Detecting the tissue distribution of a compound is the other method. For example, the distribution ratio of a compound in blood and brain can be used to decide its permeability to the BBB.

Previous studies have shown that inhibiting or decreasing the α5-$GABA_A$ receptor mediated extrasynaptic inhibition by drugs or gene method could improve cognitive and learning ability but also cause mild anxiety like behavior (Brickley, S. G. & Mody, I. Extrasynaptic $GABA_A$ receptors: their function in the CNS and implications for disease. Neuron 73, 23-34 (2012); Harris, D. et al. Selective influence on contextual memory: physiochemical properties associated with selectivity of benzodiazepine ligands at $GABA_A$ receptors containing the alpha 5 subunit. J. Med. Chem. 51, 3788-3803 (2008); Savic', M. M. et al. PWZ-029, a compound with moderate inverse agonist functional selectivity at $GABA_A$ receptors containing α5 subunits, improves passive, but not active, avoidance learning in rats. Brain Res. 1208, 150-159 (2008); Clément, Y. et al. Gabra5-gene haplotype block associated with behavioral properties of the full agonist benzodiazepine chlordiazepoxide. Behav. Brain Res. 233, 474-482 (2012). There are also studies showing that fear and anxiety behaviors are correlated with the decrease of Gabra5 mRNA (Heldt, S. A. & Ressler, K. J.

Training-induced changes in the expression of GABA A associated genes in the amygdala after the acquisition and extinction of Pavlovian fear. Eur. J. Neurosci. 26, 3631-3644 (2007); Tasan, R. O. et al. Altered GABA transmission in a mouse model of increased trait anxiety. Neuroscience 183, 71-80 (2011). Paolo Botta et al have reported that the α5-GABA$_A$ receptor plays a key role in the generation of fear and anxiety. Selective knocking out the expression of α5-GABA$_A$ receptor in some brain regions could induce fear and anxiety behaviors in animals. Taken together, due to their entry into brain and cause of fear and anxiety, it is impossible to use α5-GABA$_A$ receptor inverse agonists for drug development without modification.

SUMMARY

The purpose of this disclosure is to provide compounds of formula I, II, III or IV, a cis-trans isomer, an enantiomer, a diastereoisomer, a racemate, a solvate, a hydrate, or a pharmaceutical acceptable salt and ester thereof.

Another purpose of this disclosure is to provide the preparation method of the compounds of formula I, II, III or IV.

Another purpose of this disclosure is to provide the use of the compounds of formula I, II, III or IV as α5-GABA$_A$ receptor regulators, the use for the manufacture of a medicament for treating, preventing or improving α5-GABA$_A$ receptor related diseases selected from: cognition related diseases, Alzheimer's disease, dysmnesia, Down's syndrome, amyotrophic lateral sclerosis (ALS), drug addiction, restless leg syndrome, cognition deficiency, multi-infarct dementia, pain, stoke and attention deficit, or the use for the manufacture of a medicament for relieving pain.

Another purpose of this disclosure is to provide a pharmaceutical composition comprising a therapeutically effective amount of one or more compounds of formula I, II, III or IV or pharmaceutically acceptable salt thereof, and a pharmaceutically acceptable carrier and/or adjuvant thereof.

Another purpose of this disclosure is to provide a method of preventing, treating or improving α5-GABA$_A$ receptor related diseases, which comprises administering to patients compounds of formula I, II, III or IV or pharmaceutically acceptable salt or the composition thereof.

In the first aspect, the present disclosure provides a compound of formula I, or a cis-trans isomer, an enantiomer, a diastereoisomer, a racemate, a solvate, a hydrate, or a pharmaceutical acceptable salt and ester thereof,

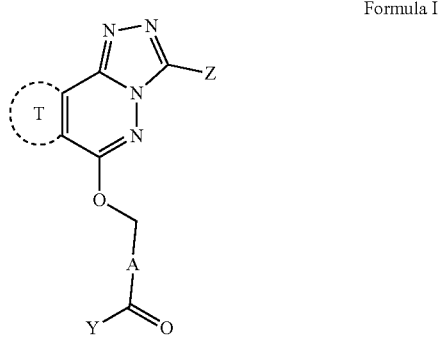

Formula I

Wherein:
T is C3-7 cycloalkyl, C4-7 cycloalkenyl, C6-8 bicycloalkyl, C6-10 aryl, or C3-7 heterocycloalkyl; preferably, T is phenyl;

Z is five membered heteroaryl that contains 1, 2 or 3 hetero-atoms independently selected from the group consisting of oxygen, nitrogen and sulfur; the five membered heteroaryl is optionally substituted by one or more substituents selected from the group consisting of hydroxyl, halogen, —R1, —OR1, —OC(O)R1, —NR2R3, CN, cyano (C1-6)alkyl or R2; preferably, Z is 5 membered heteroaryl that contains 1, 2 or 3 hetero-atoms independently selected from the group consisting of oxygen, nitrogen and sulfur and at most one of the heteroatoms is O or S, at least one of the heteroatoms is O or S when one of the heteroatoms is N, the five membered heteroaryl is optionally substituted by one or more substituents selected from the group consisting of C1-4 alkyl, hydroxyl, halogen, C1-4 alkyl substituted by hydroxyl or amino, C2-4 alkenyl, C2-4 alkynyl, C1-4 alkoxy; more preferably, Z is 5 membered heteroaryl that contains 1 or 2 hetero-atoms independently selected from the group consisting of oxygen, nitrogen and sulfur and at most one of the heteroatoms is O or S, one of the heteroatoms is O or S when one of the heteroatoms is N; preferably, Z represents 5 membered heteroaryl that contains 2 hetero-atoms independently selected from the group consisting of oxygen, nitrogen and sulfur and one of the heteroatoms is O or S, and the other heteroatom is N, the 5 membered heteroaryl is optionally substituted by one or more substituents selected from the group consisting of C1-6 alkyl or hydroxyl C1-6 alkyl; preferably, Z is oxadiazolyl, furyl, thienyl or isoxazolyl, wherein the oxadiazolyl, furyl, thienyl or isoxazolyl is optionally substituted by one or more substituents selected from the group consisting of C1-6 alkyl, hydroxyl C1-6 alkyl;

R1 is C1-6 alkyl, C2-6 alkenyl, C2-6 alkynyl, C3-6 cycloalkyl, C3-6 cycloalkyl (C1-6) alkyl, cyano(C1-6)alkyl, or C1-6 alkyl substituted by hydroxyl or amino, and R1 is optionally substituted by 1, 2 or 3 fluorine;

R2 or R3 are independently hydrogen, C1-6 alkyl, C2-6 alkenyl, C2-6 alkynyl, C3-6 cycloalkyl or CF3; alternatively, R2 and R3 together with the nitrogen atom to which they are attached, form a 4-7 membered hetero-alicyclic ring which contains the nitrogen atom and one other heteroatom selected from the group consisting of O, N and S, the hetero-alicyclic ring is optionally substituted by one or more R1;

A is —NR2-; alternatively, A is five-membered heteroarylene that contains 1, 2, 3 or 4 hetero-atoms independently selected from the group consisting of oxygen, nitrogen and sulfur and at most one of the heteroatoms is O or S, or six-membered heteroarylene that contains 1, 2 or 3 nitrogen atoms; the five- or six-membered heteroarylene is optionally condensed with phenyl or pyridinyl, and the heteroarylene is optionally substituted by Rx and/or Ry and/or Rz, Rx is halogen, —R1, —OR1, —OC(O)R1, —C(O)OR1, —NR2R3, —NR2C(O)R3, —OH or —CN, Ry is halogen, —R1, —OR1, —OC(O)R1, —NR2R3, —NR2C(O)R3, or CN, and Rz is —R1, —OR1 or —OC(O)R1, provided that when A is a pyridinyl derivative, the pyridinyl is optionally N-oxide form; or A is phenylene that is substituted by 1, 2 or 3 substituents independently selected from the group consisting of halogen, cyano, C1-6 alkyl, C2-6 alkenyl, C2-6 alkynyl and C3-6 cycloalkyl; preferably, A is five-membered heteroarylene that contains 1, 2, or 3 hetero-atoms independently selected from the group consisting of oxygen, nitrogen and sulfur and at most one of the heteroatoms is O or S; or six-membered heteroarylene or phenylene that contains 1, 2 or 3 nitrogen atoms; the five- or six-membered heteroarylene or phenylene is optionally substituted by a substituent selected from the group consisting of halogen, cyano, and C1-6 alkyl; preferably, A is phenylene, pyridinylene, or isoxazolylene, optionally substituted by 1, 2 or 3 substituents selected from the group consisting of halogen, cyano, and C1-6 alkyl.

Y is —NY1Y2 or —NH—NY3Y4;

Y1 is independently selected from the group consisting of H; C1-6 alkyl; C1-6 alkyl substituted by 1-5 substituents selected from the group consisting of amino, halogen, halogenated C1-6 alkoxy, hydroxyl, C1-6 alkoxy, (C1-6 alkyl, C1-6 alkyl)N-, (C1-6 alkyl, H)N—, nitro and C1-6 alkyl-S(O)2-;

Y2 is independently selected from the group consisting of H; C1-6 alkyl; C1-6 alkyl substituted by 1-5 substituents selected from the group consisting of amino, halogen, halogenated C1-6 alkoxy, hydroxyl, cycloalkyl, C1-6 alkoxy, (C1-6 alkyl, C1-6 alkyl)N-, (C1-6 alkyl, H)N—, nitro and C1-6 alkyl-S(O)2-; heteroaryl, or heteroaryl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-; cycloalkyl, or cycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-; heterocycloalkyl, or heterocycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-;

Preferably Y2 is independently selected from the group consisting of C1-6 alkyl; C1-6 alkyl substituted by 1-5 substituents selected from the group consisting of amino, halogen, halogenated C1-6 alkoxy, hydroxyl, C1-6 alkoxy, C3-6 cycloalkyl (C1-6 alkyl, C1-6 alkyl)N-, (C1-6 alkyl, H)N—, nitro and C1-6 alkyl-S(O)2-;

C3-7 heteroaryl that contains 1-3 hetero-atoms independently selected from nitrogen, oxygen or sulfur, C3-7 heteroaryl that contains 1-3 hetero-atoms independently selected from nitrogen, oxygen or sulfur and is substituted by 1-4 substituents independently selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-;

C3-7 cycloalkyl, or C3-7 cycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-;

C3-7 heterocycloalkyl that contains 1-3 hetero-atoms independently selected from nitrogen, oxygen or sulfur, C3-7 heterocycloalkyl that contains 1-3 hetero-atoms independently selected from nitrogen, oxygen or sulfur and is substituted by 1-4 substituents selected independently from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, nitro and C1-6 alkyl-S(O)2-;

Preferably Y2 is C1-6 alkyl; C1-6 alkyl substituted by hydroxyl, halogen or C1-6 alkoxy; morpholinyl; C3-6 cycloalkyl substituted by hydroxyl; tetrahydrofuranyl, tetrahydropyranyl, pyrazolyl optionally substituted by C1-6 alkyl;

alternatively, Y1 and Y2 together with the nitrogen atom to which they are attached, form a 4-6 membered heterocycloalkyl which contains the nitrogen atom and 0, 1 or more heteroatom selected from O and S, and the sulfur atom can be its oxide form;

Preferably Y1 and Y2 together with the nitrogen atom to which they are attached, form azetidinyl, morpholinyl, piperidinyl, pyrrolidinyl, dioxidothiomorpholinyl, oxidothiomorpholinyl; Y1 and Y2 together with the nitrogen atom to which they are attached, form azetidin-1-yl, morpholin-4-yl, piperidin-1-yl, pyrrolidin-1-yl, 1-oxidothiomorpholin-4-yl and 1,1-dioxido-thiomorpholin-4-yl;

Y3 and Y4 are independently selected from the group consisting of hydrogen, C1-6 alkyl, SO$_2$—C1-6 alkyl, cycloalkyl and heterocyclyl, optionally substituted by 1-4 substituents selected from the group consisting of halogen, cyano, hydroxyl, C1-6 alkyl and C1-6 alkoxy, alternatively, Y3 and Y4 together with the nitrogen atom to which they are attached, form a heterocyclyl, and the heterocyclyl is optionally substituted by 1-4 substituents selected from the group consisting of halogen, cyano, hydroxyl, oxo, C1-6 alkyl and C1-6 alkoxy;

Preferably Y3 and Y4 are independently selected from the group consisting of hydrogen, C1-6 alkyl, SO$_2$—C1-6 alkyl, C3-7 cycloalkyl and C3-7 heterocyclyl, optionally substituted by 1-4 substituents selected from the group consisting of halogen, cyano, hydroxyl, C1-6 alkyl and C1-6 alkoxy, alternatively, Y3 and Y4 together with the nitrogen atom to which they are attached, form C3-7 heterocyclyl, more preferably the C3-7 heterocyclyl is piperidinyl, morpholinyl, thiomorpholinyl, dioxidothiomorpholinyl, oxidothiomorpholinyl and pyrrolidinyl, which are substituted by 1-4 substituents selected from the group consisting of halogen, cyano, hydroxyl, oxo, C1-6 alkyl and C1-6 alkoxy, more preferably Y3 and Y4 are independently selected from the group consisting of hydrogen, C1-6 alkyl, and SO$_2$—C1-6 alkyl, Y3 and Y4 together with the nitrogen atom to which they are attached, form morpholin-4-yl, piperidin-1-yl, pyrrolidin-1-yl, and 1,1-dioxido-thiomorpholin-4-yl;

The present disclosure provides a compound of formula II:

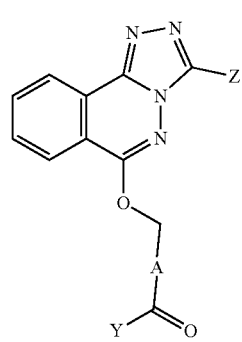

Wherein:

Z is 5 membered heteroaryl that contains 1, 2 or 3 hetero-atoms independently selected from the group consisting of oxygen, nitrogen and sulfur and at most one of the heteroatoms is O or S, at least one of the heteroatoms is O or S when one of the heteroatoms is N, the 5 membered heteroaryl is optionally substituted by one or more substituents selected from the group consisting of C1-4 alkyl, hydroxyl, halogen, C1-4 alkyl substituted by hydroxyl or amino, C2-4 alkenyl, C2-4 alkynyl, and C1-4 alkoxy;

A is five-membered heteroarylene that contains 1, 2 or 3 hetero-atoms independently selected from the group consisting of oxygen, nitrogen and sulfur and at most one of the heteroatoms is O or S, or six-membered heteroarylene or phenylene that contains 1, 2 or 3 nitrogen atoms, the five- or six-membered heteroarylene or phenylene is optionally substituted by a substituent selected from the group consisting of halogen, cyano, and C1-6 alkyl;

Y is —NY1Y2 or —NH—NY3Y4;

Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N— and C1-6 alkyl-S(O)2-;

Y2 is independently selected from the group consisting of C1-6 alkyl; C1-6 alkyl substituted by 1-5 substituents selected from the group consisting of amino, hydroxyl, C1-6 alkoxy, cycloalkyl, (C1-6 alkyl, C1-6 alkyl)N-, (C1-6 alkyl, H)N—, and C1-6 alkyl-S(O)2-;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;

C3-6 cycloalkyl, C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)2-;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, C1-6 alkoxyC1-6 alkyl, C1-6 alkyl and C1-6 alkyl-S(O)2-;

alternatively, Y1 and Y2 together with the nitrogen atom to which they are attached, form a 4-6 membered heterocycloalkyl which contains the nitrogen atom and 0, 1 or more heteroatom selected from O and S; the sulfur atom can be its oxide form;

Y3 and Y4 are independently selected from the group consisting of hydrogen, C1-6 alkyl, SO2-C1-6 alkyl; alternatively, Y3 and Y4 together with the nitrogen atom to which they are attached, form a heterocyclyl, the heterocyclyl is selected from the group consisting of piperidinyl, morpholinyl, dioxidothiomorpholinyl and oxidothiomorpholinyl.

In another preferred embodiment, Z of formula II or I is 5 membered heteroaryl that contains 2 hetero-atoms independently selected from the group consisting of oxygen, nitrogen and sulfur and one of the heteroatoms is O or S, the other heteroatom is N, the 5 membered heteroaryl is optionally substituted by one or more substituents selected from the group consisting of C1-6 alkyl and hydroxyl C1-6 alkyl.

In another preferred embodiment, Z of formula II or I is represents oxadiazolyl, furyl, thienyl or isoxazolyl, the isoxazolyl is optionally substituted by one or more substituents selected from the group consisting of H, C1-6 alkyl, and hydroxyl C1-6 alkyl.

In another preferred embodiment, A of formula II or I is phenylene, pyridinylene, or isoxazolylene; A is optionally substituted by 1, 2 or 3 substituents selected from the group consisting of halogen, cyano, and C1-6 alkyl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, hydroxyl C1-6 alkyl; A is phenylene, pyridinylene, or isoxazolylene; A is optionally substituted by 1, 2 or 3 substituents selected from the group consisting of halogen, cyano, and C1-6 alkyl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, hydroxyl C1-6 alky; A is phenylene, pyridinylene, or isoxazolylene; A is optionally substituted by 1, 2 or 3 substituents selected from the group consisting of halogen, cyano, and C1-6 alkyl; Y is —NY1Y2 or —NH—NY3Y4; Y1 is H or C1-6 alkyl;

Y2 is independently selected from the group consisting of C1-6 alkyl; C1-6 alkyl substituted by 1-5 substituents selected from the group consisting of amino, hydroxyl, and C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;

C4-6 cycloalkyl, C3-6 cycloalkyl substituted by 1-4 substituents selected from the group consisting of hydroxyl;

C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents;

alternatively, Y1 and Y2 together with the nitrogen atom to which they are attached, form morpholinyl, piperidinyl, oxidothiomorpholinyl and dioxidothiomorpholinyl;

Y3 and Y4 are independently selected from the group consisting of hydrogen, methyl and SO2-methyl, Y3 and Y4 together with the nitrogen atom to which they are attached, form a heterocyclyl selected from the group consisting of piperidinyl, morpholinyl and dioxidothiomorpholinyl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or C1-6 alkyl;

Y2 is independently selected from the group consisting of C1-6 alkyl; C1-6 alkyl substituted by 1-5 substituents selected from the group consisting of hydroxyl, and C1-6 alkoxy;

C5-6 heteroaryl that contains 1-3 hetero-atoms independently selected from nitrogen, oxygen or sulfur, or C5-6 heteroaryl that contains 1-3 hetero-atoms independently selected from nitrogen, oxygen or sulfur and is substituted by C1-6 alkyl;

C4-6 cycloalkyl, C3-6 cycloalkyl substituted by 1-4 substituents selected from the group consisting of hydroxyl;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents;

alternatively, Y1 and Y2 together with the nitrogen atom to which they are attached, form morpholinyl and piperidinyl;

Y3 and Y4 are independently selected from the group consisting of hydrogen, methyl and SO2-methyl, Y3 and Y4 together with the nitrogen atom to which they are attached, form a heterocyclyl selected from the group consisting of morpholin-4-yl, piperidin-1-yl and 1,1-dioxido-thiomorpholin-4-yl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, C1-6 alkyl;

Y is —NY1Y2 or —NH—NY3Y4;

Y1 is H or methyl;

Y2 is independently selected from the group consisting of C1-6 alkyl; C1-6 alkyl substituted by 1-5 substituents selected from the group consisting of hydroxyl, and C1-6 alkoxy;

Y3 and Y4 are independently selected from the group consisting of hydrogen and methyl, Y3 and Y4 together with the nitrogen atom to which they are attached, form a heterocyclyl selected from the group consisting of morpholin-4-yl, piperidin-1-yl and 1,1-dioxido-thiomorpholin-4-yl.

In another preferred embodiment, Z of formula II or I oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or methyl;

Y2 is selected from the group consisting of methyl, ethyl, methoxyethyl or hydroxypropyl;

Y3 and Y4 are independently selected from the group consisting of hydrogen and methyl, or Y3 and Y4 together with the nitrogen atom to which they are attached, form a heterocyclyl selected from the group consisting of morpholin-4-yl, piperidin-1-yl and 1,1-dioxido-thiomorpholin-4-yl.

The present disclosure provides a compound of formula III:

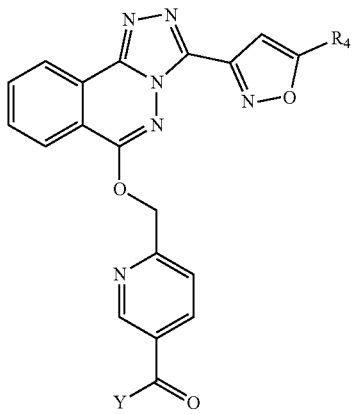

Wherein
R4 is C1-4 alkyl, hydroxyl substituted C1-4 alkyl;
Y is —NY1Y2 or —NH—NY3Y4;

Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N— and C1-6 alkyl-S(O)2-;

Y2 is independently selected from the group consisting of C1-6 alkyl; C1-6 alkyl substituted by 1-5 substituents selected from the group consisting of amino, hydroxyl, C1-6 alkoxy, cycloalkyl, (C1-6 alkyl, C1-6 alkyl)N-, (C1-6 alkyl, H)N— and C1-6 alkyl-S(O)2-;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl; C3-6 cycloalkyl, C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)2-;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, C1-6 alkoxyC1-6 alkyl, C1-6 alkyl and C1-6 alkyl-S(O)2-;

alternatively, Y1 and Y2 together with the nitrogen atom to which they are attached, form a 4-6 membered heterocycloalkyl which contains the nitrogen atom and 0, 1 or more heteroatom selected from O and S, and the sulfur atom can be its oxide form;

Y3 and Y4 are independently selected from the group consisting of hydrogen, C1-6 alkyl, SO2-C1-6 alkyl, alternatively, Y3 and Y4 together with the nitrogen atom to which they are attached, form a heterocyclyl selected from the group consisting of piperidinyl, morpholinyl, dioxido-thiomorpholinyl and oxidothiomorpholinyl.

The present disclosure provides a compound of formula IV:

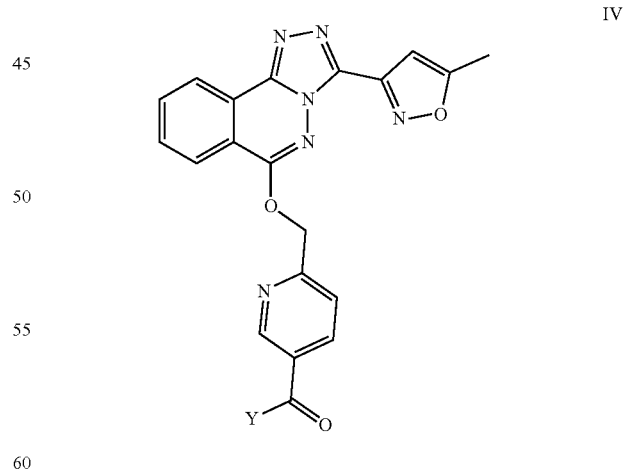

Wherein
Y is —NY1Y2 or —NH—NY3Y4;

Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N— and C1-6 alkyl-S(O)2-;

Y2 is independently selected from the group consisting of C1-6 alkyl; C1-6 alkyl substituted by 1-5 substituents selected from the group consisting of amino, hydroxyl, C1-6 alkoxy, cycloalkyl, (C1-6 alkyl, C1-6 alkyl)N-, (C1-6 alkyl, H)N— and C1-6 alkyl-S(O)2-;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;

C3-6 cycloalkyl, C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)2-;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, C1-6 alkoxyC1-6 alkyl, C1-6 alkyl and C1-6 alkyl-S(O)2-;

alternatively, Y1 and Y2 together with the nitrogen atom to which they are attached, form a 4-6 membered heterocycloalkyl which contains the nitrogen atom and 0, 1 or more heteroatom selected from O and S, and the sulfur atom can be its oxide form;

Y3 and Y4 are independently selected from the group consisting of hydrogen, C1-6 alkyl, SO2-C1-6 alkyl, alternatively, Y3 and Y4 together with the nitrogen atom to which they are attached, form a heterocyclyl, and the heterocyclyl is selected from the group consisting of piperidinyl, morpholinyl, dioxidothiomorpholinyl and oxidothiomorpholinyl.

In another preferred embodiment, a compound of formula IV wherein, Y is —NY1Y2 or —NH—NY3Y4;

Y1 is independently selected from the group consisting of H, C1-6 alkyl, or C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, and C1-6 alkyl-S(O)2-;

Y2 is independently selected from the group consisting of C1-6 alkyl; C1-6 alkyl substituted by 1-5 substituents selected from the group consisting of amino, hydroxyl, and C1-6 alkoxy;

C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with C1-6 alkyl;

C4-6 cycloalkyl; C3-6 cycloalkyl substituted by 1-4 substituents selected from the group consisting of hydroxyl;

C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents;

alternatively, Y1 and Y2 together with the nitrogen atom to which they are attached, form morpholinyl, piperidinyl, oxido-thiomorpholinyl and dioxido-thiomorpholinyl;

Y3 and Y4 are independently selected from the following groups: hydrogen, methyl and SO2-methyl, Y3 and Y4 together with the nitrogen atom to which they are attached, form a heterocyclyl selected from the group consisting of morpholinyl, piperidinyl and dioxido-thiomorpholinyl.

In another preferred embodiment, the compound has formula IV:

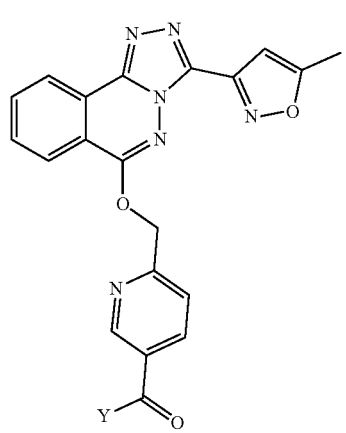

IV

Wherein

Y is —NY1Y2 or —NH—NY3Y4;

Y1 is independently selected from the group consisting of H or C1-6 alkyl;

Y2 is independently selected from the group consisting of C1-6 alkyl; C1-6 alkyl substituted by 1-5 substituents selected from the group consisting of hydroxyl, and C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;

C4-6 cycloalkyl, C3-6 cycloalkyl substituted by 1-4 substituents selected from the group consisting of hydroxyl;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents;

alternatively, Y1 and Y2 together with the nitrogen atom to which they are attached, form morpholinyl and piperidinyl;

Y3 and Y4 are independently selected from the following groups: hydrogen, methyl and SO2-methyl, Y3 and Y4 together with the nitrogen atom to which they are attached, form a heterocyclyl selected from the group consisting of morpholin-4-yl, piperidin-1-yl and 1,1-dioxido-thiomorpholin-4-yl.

In another preferred embodiment, the compound has formula IV:

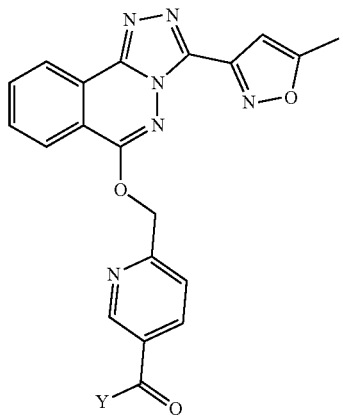

IV

Wherein
Y is —NY1Y2 or —NH—NY3Y4;
Y1 is H or methyl;
Y2 is independently selected from the group consisting of C1-6 alkyl; C1-6 alkyl substituted by 1-5 substituents selected from the group consisting of hydroxyl, and C1-6 alkoxy;
Y3 and Y4 are independently selected from the following groups: hydrogen and methyl, Y3 and Y4 together with the nitrogen atom to which they are attached, form a heterocyclyl selected from the group consisting of morpholin-4-yl, piperidin-1-yl and 1,1-dioxido-thiomorpholin-4-yl.

In another preferred embodiment, a compound of formula IV:

IV

Wherein
Y is —NY1Y2 or —NH—NY3Y4;
Y1 is H or methyl;
Y2 is independently selected from the group consisting of methyl, ethyl, 2-methoxy ethyl, or hydroxylpropyl;
Y3 and Y4 are independently selected from the following groups: hydrogen, and methyl, Y3 and Y4 together with the nitrogen atom to which they are attached, form a heterocyclyl selected from the group consisting of morpholin-4-yl, piperidin-1-yl and 1,1-dioxido-thiomorpholin-4-yl.

In another preferred embodiment, a compound of formula I is independently selected from the group consisting of

| number | formula | Chemical name |
|---|---|---|
| 01 |  | 6-(((3-(5-methylisoxazol-3-yl)-[1,2,4]triazolo[3,4-a]phthalazin-6-yl)oxy)methyl)-N-morpholinonicotinamide |
| 02 |  | (R)-N-(1-hydroxypropan-2-yl)-6-(((3-(5-methylisoxazol-3-yl)-[1,2,4]triazolo[3,4-a]phthalazin-6-yl)oxy)methyl)nicotinamide |

-continued

| number | formula | Chemical name |
|---|---|---|
| 03 | 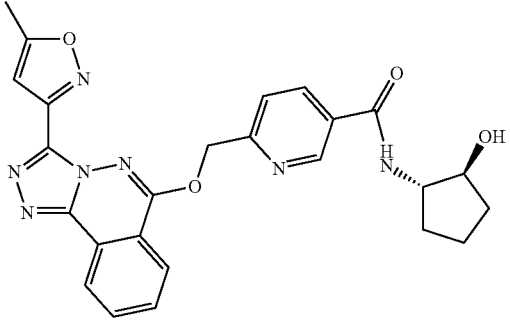 [SMILES: Cc1cc(-c2nnc3c4ccccc4c(OCc4ccc(C(=O)N[C@H]5CCC[C@@H]5O)cn4)nn23)no1] | N-((1S,2S)-2-hydroxycyclopentyl)-6-(((3-(5-methyl-isoxazol-3-yl)-[1,2,4]triazolo[3,4-a]phthalazin-6-yl)oxy)methyl)nicotinamide |
| 04 | 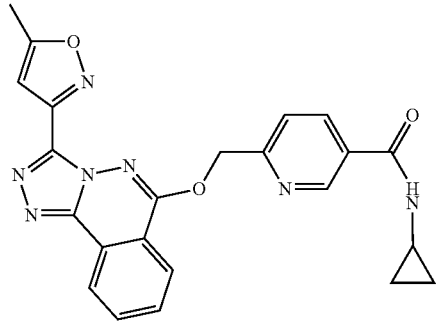 [SMILES: Cc1cc(-c2nnc3c4ccccc4c(OCc4ccc(C(=O)NC5CC5)cn4)nn23)no1] | N-cyclopropyl-6-(((3-(5-methylisoxazol-3-yl)-[1,2,4]triazolo[3,4-a]phthalazin-6-yl)oxy)methyl)nicotinamide |
| 05 | 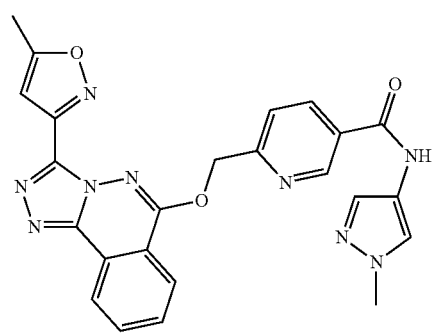 [SMILES: Cc1cc(-c2nnc3c4ccccc4c(OCc4ccc(C(=O)Nc5cnn(C)c5)cn4)nn23)no1] | N-(1-methyl-1H-pyrazol-4-yl)-6-(((3-(5-methylisoxazol-3-yl)-[1,2,4]triazolo[3,4-a]phthalazin-6-yl)oxy)methyl)nicotinamide |
| 06 | 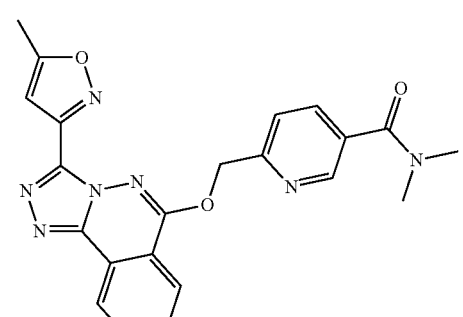 | N,N-dimethyl-6-(((3-(5-methylisoxazol-3-yl)-[1,2,4]triazolo[3,4-a]phthalazin-6-yl)oxy)methyl)nicotinamide |

-continued

| number | formula | Chemical name |
| --- | --- | --- |
| 07 | 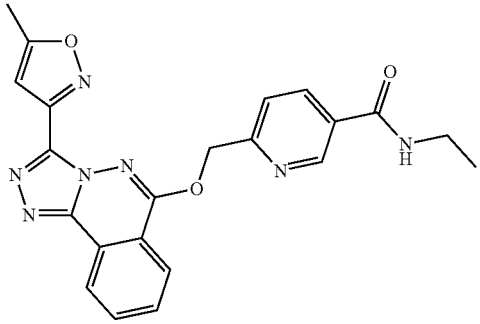 [SMILES: CCNC(=O)c1ccc(COc2nn3c(-c4cc(C)on4)nnc3c3ccccc23)nc1] | N-ethyl-6-(((3-(5-methylisoxazol-3-yl)-[1,2,4]triazolo[3,4-a]phthalazin-6-yl)oxy)methyl)nicotinamide |
| 08 | 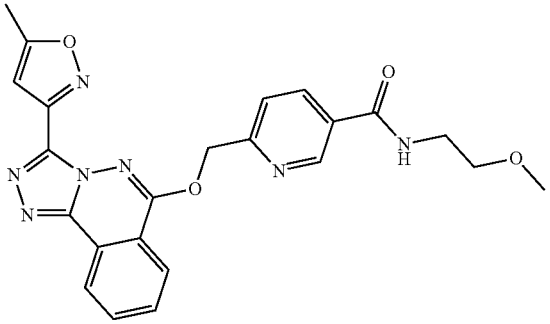 | N-(2-methoxyethyl)-6-(((3-(5-methylisoxazol-3-yl)-[1,2,4]triazolo[3,4-a]phthalazin-6-yl)oxy)methyl)nicotinamide |
| 09 | 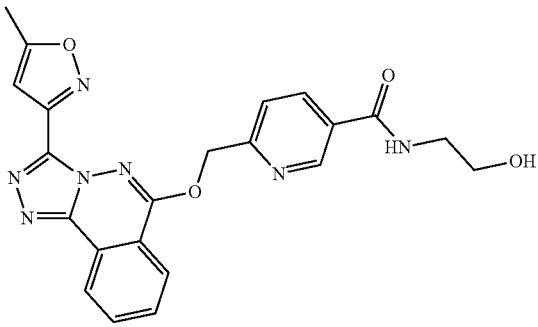 [SMILES: Cc1cc(-c2nnc3c4ccccc4c(OCc4ccc(C(=O)NCCO)cn4)nn23)no1] | N-(2-hydroxyethyl)-6-(((3-(5-methylisoxazol-3-yl)-[1,2,4]triazolo[3,4-a]phthalazin-6-yl)oxy)methyl)nicotinamide |
| 10 | 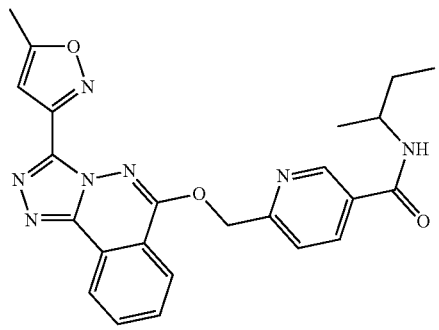 [SMILES: CCC(C)NC(=O)c1ccc(COc2nn3c(-c4cc(C)on4)nnc3c3ccccc23)nc1] | N-(2-butyl)-6-(((3-(5-methylisoxazol-3-yl)-[1,2,4]triazolo[3,4-a]phthalazin-6-yl)oxy)methyl)nicotinamide |

-continued

| number | formula | Chemical name |
|---|---|---|
| 11 | 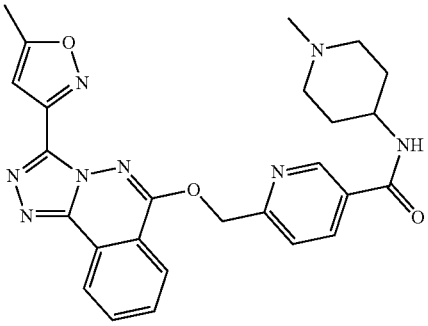 [SMILES: Cc1cc(-c2nnc3c4ccccc4c(OCc4ccc(C(=O)NC5CCN(C)CC5)cn4)nn23)no1] | 6-(((3-(5-methylisoxazol-3-yl)-[1,2,4]triazolo[3,4-a]phthalazin-6-yl)oxy)methyl)-N-(1-methylpiperidin-4-yl)nicotinamide |
| 12 | 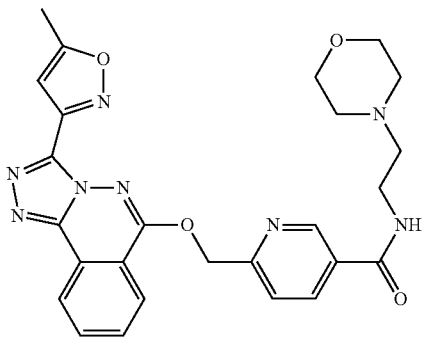 [SMILES: Cc1cc(-c2nnc3c4ccccc4c(OCc4ccc(C(=O)NCCN5CCOCC5)cn4)nn23)no1] | 6-(((3-(5-methylisoxazol-3-yl)-[1,2,4]triazolo[3,4-a]phthalazin-6-yl)oxy)methyl)-N-(2-morpholinoethyl)nicotinamide |
| 13 | 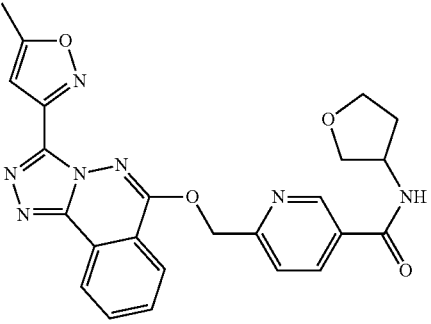 [SMILES: Cc1cc(-c2nnc3c4ccccc4c(OCc4ccc(C(=O)NC5CCOC5)cn4)nn23)no1] | 6-(((3-(5-methylisoxazol-3-yl)-[1,2,4]triazolo[3,4-a]phthalazin-6-yl)oxy)methyl)-N-(tetrahydrofuran-3-yl)nicotinamide |
| 14 | 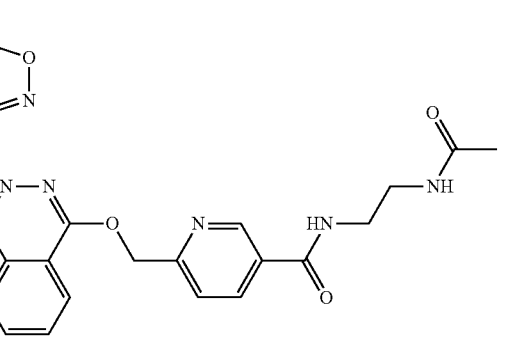 | N-(2-acetamidoethyl)-6-(((3-(5-methylisoxazol-3-yl)-[1,2,4]triazolo[3,4-a]phthalazin-6-yl)oxy)methyl)nicotinamide |

| number | formula | Chemical name |
| --- | --- | --- |
| 15 | | N-((1S)-2-methoxycyclopentyl)-6-(((3-(5-methyl-isoxazol-3-yl)-[1,2,4]triazolo[3,4-a]phthalazin-6-yl)oxy)methyl)nicotinamide |
| 16 | | N-methyl-6-(((3-(5-methylisoxazol-3-yl)-[1,2,4]triazolo[3,4-a]phthalazin-6-yl)oxy)methyl)-N-(2-morpholino-ethyl)nicotinamide |
| 17 | | (6-(((3-(5-methylisoxazol-3-yl)-[1,2,4]triazolo[3,4-a]phthalazin-6-yl)oxy)methyl)pyridin-3-yl)(4-methyl-piperazin-1-yl)methanone |
| 18 | | N-(1-acetylpyrrolidin-3-yl)-6-(((3-(5-methylisoxazol-3-yl)-[1,2,4]triazolo[3,4-a]phthalazin-6-yl)oxy)methyl)nicotinamide |

| number | formula | Chemical name |
|---|---|---|
| 19 | | 1-(6-(((3-(5-methylisoxazol-3-yl)-[1,2,4]triazolo[3,4-a]phthalazin-6-yl)oxy)methyl)nicotinoyl)piperidine-3-carboxamide |
| 20 | | 6-(((3-(5-methylisoxazol-3-yl)-[1,2,4]triazolo[3,4-a]phthalazin-6-yl)oxy)methyl)-N-((tetrahydrofuran-3-yl)methyl)nicotinamide |
| 21 | | N-(2,2-difluoroethyl)-6-(((3-(5-methylisoxazol-3-yl)-[1,2,4]triazolo[3,4-a]phthalazin-6-yl)oxy)methyl)nicotinamide |
| 22 | | (4-methoxypiperidin-1-yl)(6-(((3-(5-methylisoxazol-3-yl)-[1,2,4]triazolo[3,4-a]phthalazin-6-yl)oxy)methyl)pyridin-3-yl)methanone |

-continued

| number | formula | Chemical name |
|---|---|---|
| 23 | 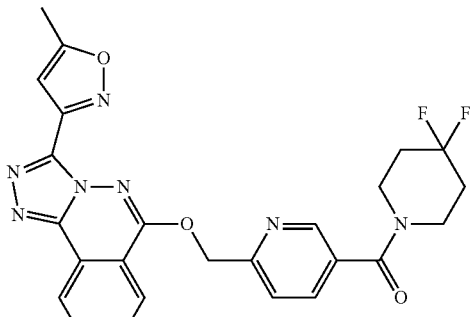 | (4,4-difluoropiperidin-1-yl)(6-(((3-(5-methylisoxazol-3-yl)-[1,2,4]triazolo[3,4-a]phthalazin-6-yl)oxy)methyl)pyridin-3-yl)methanone |
| 24 | 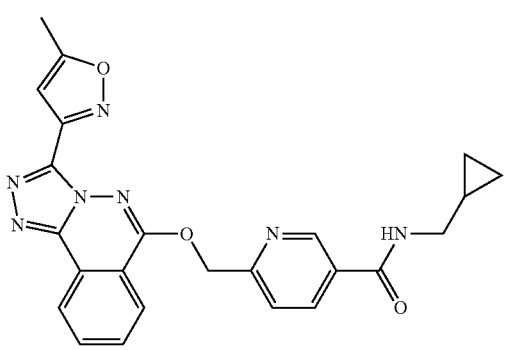 [SMILES: Cc1cc(-c2nnc3c4ccccc4c(OCc4ccc(C(=O)NCC5CC5)cn4)nn23)no1] | N-(cyclopropylmethyl)-6-(((3-(5-methylisoxazol-3-yl)-[1,2,4]triazolo[3,4-a]phthalazin-6-yl)oxy)methyl)nicotinamide |
| 25 | 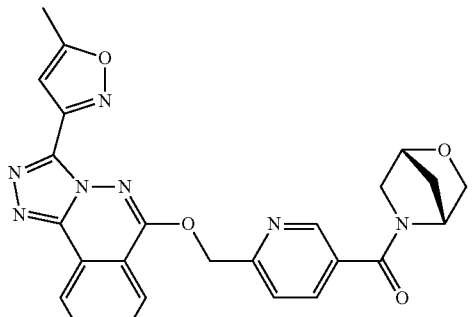 | (1R,4R)-2-oxa-5-azabicyclo[2.2.1]heptan-5-yl(6-(((3-(5-methylisoxazol-3-yl)-[1,2,4]triazolo[3,4-a]phthalazin-6-yl)oxy)methyl)pyridin-3-yl)methanone |
| 26 | 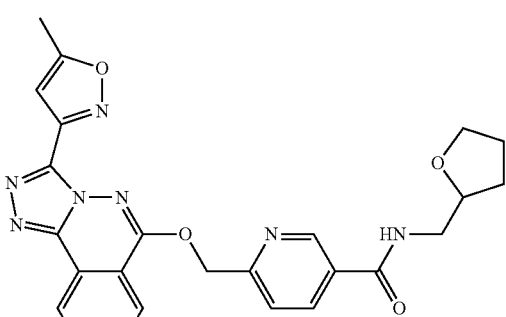 | 6-(((3-(5-methylisoxazol-3-yl)-[1,2,4]triazolo[3,4-a]phthalazin-6-yl)oxy)methyl)-N-((tetrahydrofuran-2-yl)methyl)nicotinamide |

-continued

| number | formula | Chemical name |
|---|---|---|
| 27 | | 6-(((3-(5-methylisoxazol-3-yl)-[1,2,4]triazolo[3,4-a]phthalazin-6-yl)oxy)methyl)-N-(2-(methylsulfonyl)ethyl)nicotinamide |
| 28 | | 6-(((3-(5-methylisoxazol-3-yl)-[1,2,4]triazolo[3,4-a]phthalazin-6-yl)oxy)methyl)nicotinamide |
| 29 | | 2-(6-(((3-(5-methylisoxazol-3-yl)-[1,2,4]triazolo[3,4-a]phthalazin-6-yl)oxy)methyl)nicotinamido)acetic acid |
| 30 | | 6-(((3-(5-methylisoxazol-3-yl)-[1,2,4]triazolo[3,4-a]phthalazin-6-yl)oxy)methyl)-N-(2,2,2-trifluoroethyl)nicotinamide |

-continued

| number | formula | Chemical name |
|---|---|---|
| 31 | 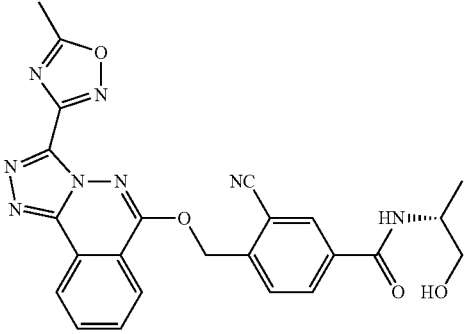 [SMILES: Cc1nc(-c2nnc3c4ccccc4c(OCc4ccc(C(=O)N[C@H](C)CO)cc4C#N)nn23)no1] | (R)-3-cyano-N-(1-hydroxypropan-2-yl)-4-(((3-(5-methyl-1,2,4-oxadiazol-3-yl)-[1,2,4]triazolo[3,4-a]phthalazin-6-yl)oxy)methyl)benzamide |
| 32 | 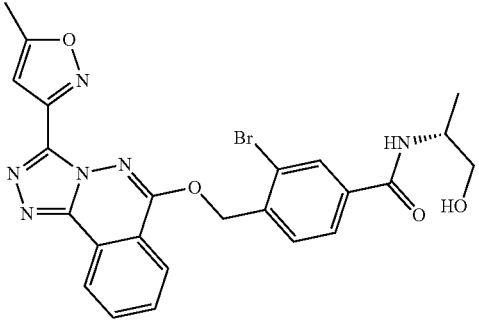 [SMILES: Cc1cc(-c2nnc3c4ccccc4c(OCc4ccc(C(=O)N[C@H](C)CO)cc4Br)nn23)no1] | (R)-3-bromo-N-(1-hydroxypropan-2-yl)-4-(((3-(5-methylisoxazol-3-yl)-[1,2,4]triazolo[3,4-a]phthalazin-6-yl)oxy)methyl)benzamide |
| 33 | 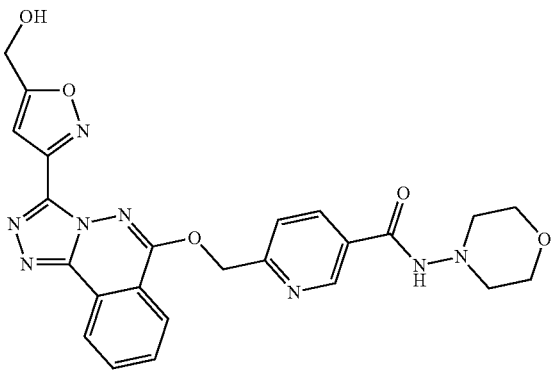 [SMILES: O=C(NN1CCOCC1)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N-morpholino-nicotinamide |
| 34 | 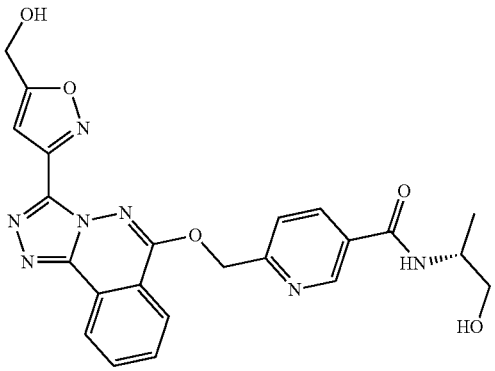 [SMILES: C[C@H](CO)NC(=O)c1ccc(COc2nn3c(-c4cc(CO)on4)nnc3c3ccccc23)nc1] | (R)-6-(((3-(5-(hydroxymethyl)isoxazol-3-yl)-[1,2,4]triazolo[3,4-a]phthalazin-6-yl)oxy)methyl)-N-(1-hydroxypropan-2-yl)nicotinamide |

| number | formula | Chemical name |
|---|---|---|
| 35 | 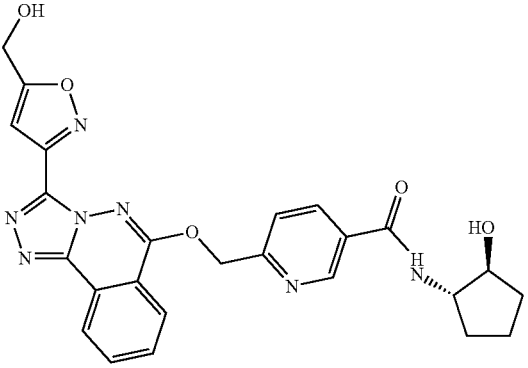 [SMILES: O=C(N[C@H]1CCC[C@@H]1O)c1ccc(COc2nn3c(-c4cc(CO)on4)nnc3c3ccccc23)nc1] | N-((1S,2S)-2-hydroxycyclopentyl)-6-(((3-(5-(hydroxymethyl)isoxazol-3-yl)-[1,2,4]triazolo[3,4-a]phthalazin-6-yl)oxy)methyl)nicotinamide |
| 36 | 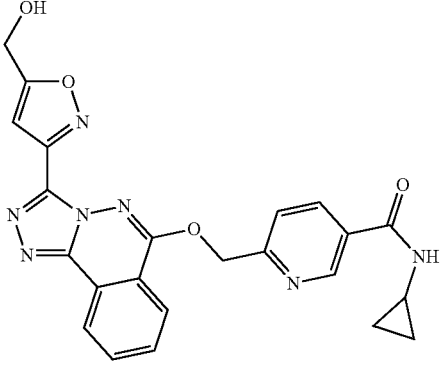 [SMILES: O=C(NC1CC1)c1ccc(COc2nn3c(-c4cc(CO)on4)nnc3c3ccccc23)nc1] | N-cyclopropyl-6-(((3-(5-(hydroxymethyl)isoxazol-3-yl)-[1,2,4]triazolo[3,4-a]phthalazin-6-yl)oxy)methyl)nicotinamide |
| 37 | 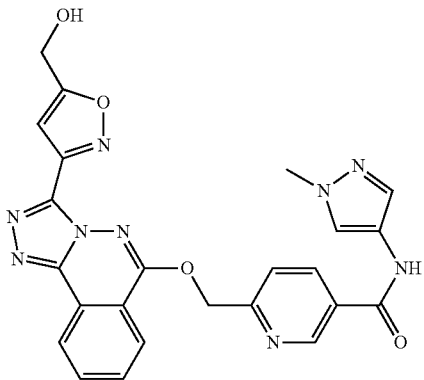 [SMILES: Cn1cc(NC(=O)c2ccc(COc3nn4c(-c5cc(CO)on5)nnc4c4ccccc34)nc2)cn1] | 6-(((3-(5-(hydroxymethyl)isoxazol-3-yl)-[1,2,4]triazolo[3,4-a]phthalazin-6-yl)oxy)methyl)-N-(1-methyl-1H-pyrazol-4-yl)nicotinamide |
| 38 | 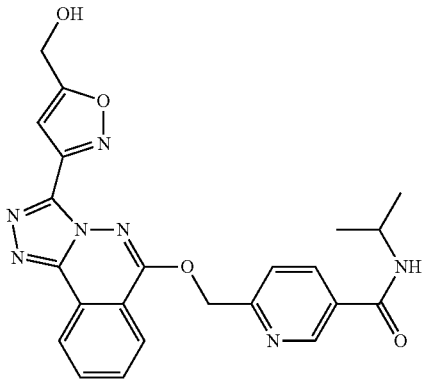 [SMILES: CC(C)NC(=O)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N-isopropyl nicotinamide |

-continued

| number | formula | Chemical name |
|---|---|---|
| 39 | | N-(2-hydroxyethyl)-6-(((3-(5-(hydroxymethyl)isoxazol-3-yl)-[1,2,4]triazolo[3,4-a]phthalazin-6-yl)oxy)methyl)nicotinamide |
| 40 | | (1,1-dioxidothiomorpholino)(6-(((3-(5-(hydroxymethyl)isoxazol-3-yl)-[1,2,4]triazolo[3,4-a]phthalazin-6-yl)oxy)methyl)pyridin-3-yl)methanone |
| 41 | | (6-(((3-(5-(hydroxymethyl)isoxazol-3-yl)-[1,2,4]triazolo[3,4-a]phthalazin-6-yl)oxy)methyl)pyridin-3-yl)(morpholino)methanone |
| 42 | | 6-(((3-(5-(hydroxymethyl)isoxazol-3-yl)-[1,2,4]triazolo[3,4-a]phthalazin-6-yl)oxy)methyl)-N-(2,2,2-trifluoroethyl)nicotinamide |

-continued

| number | formula | Chemical name |
|---|---|---|
| 43 | | 6-(((3-(5-(hydroxymethyl)isoxazol-3-yl)-[1,2,4]triazolo[3,4-a]phthalazin-6-yl)oxy)methyl)-N-(2-methoxy-ethyl)nicotinamide |
| 44 | | 6-(((3-(5-(hydroxymethyl)isoxazol-3-yl)-[1,2,4]triazolo[3,4-a]phthalazin-6-yl)oxy)methyl)-N-(tetrahydro-2H-pyran-4-yl)nicotinamide |
| 45 | | 6-(((3-(5-(hydroxymethyl)isoxazol-3-yl)-[1,2,4]triazolo[3,4-a]phthalazin-6-yl)oxy)methyl)-N,N-dimethyl-nicotinamide |
| 46 | | N-ethyl-6-(((3-(5-(hydroxymethyl)isoxazol-3-yl)-[1,2,4]triazolo[3,4-a]phthalazin-6-yl)oxy)methyl)nicotnamide |

-continued

| number | formula | Chemical name |
|---|---|---|
| 47 | | 6-(((3-(5-(hydroxymethyl)isoxazol-3-yl)-[1,2,4]triazolo[3,4-a]phthalazin-6-yl)oxy)methyl)-N-(tetrahydrofuran-3-yl)nicotinamide |
| 48 | | N-cyclobutyl-6-(((3-(5-(hydroxymethyl)isoxazol-3-yl)-[1,2,4]triazolo[3,4-a]phthalazin-6-yl)oxy)methyl)nicotinamide |
| 49 | | azetidin-1-yl(6-(((3-(5-(hydroxymethyl)isoxazol-3-yl)-[1,2,4]triazolo[3,4-a]phthalazin-6-yl)oxy)methyl)pyridin-3-yl)methanone |
| 50 | | (6-(((3-(5-(hydroxymethyl)isoxazol-3-yl)-[1,2,4]triazolo[3,4-a]phthalazin-6-yl)oxy)methyl)pyridin-3-yl)(1-oxidothiomorpholino)methanone |

-continued

| number | formula | Chemical name |
|---|---|---|
| 51 | 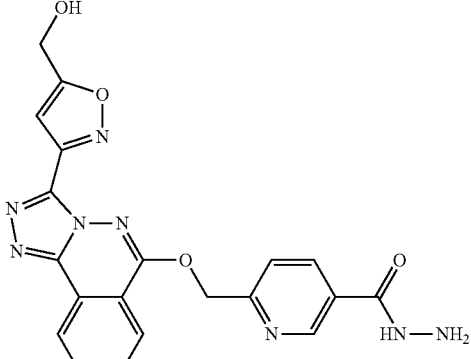 | 6-(((3-(5-(hydroxymethyl)isoxazol-3-yl)-[1,2,4]triazolo[3,4-a]phthalazin-6-yl)oxy)methyl)nicotinohydrazide |
| 52 | 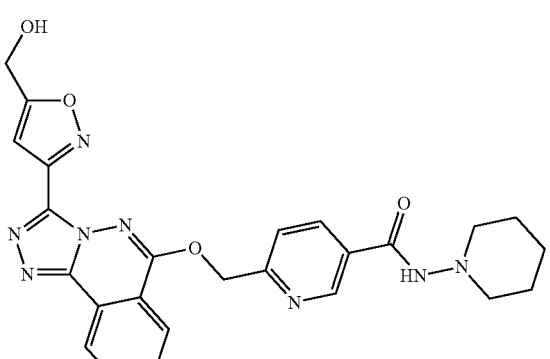 | 6-(((3-(5-(hydroxymethyl)isoxazol-3-yl)-[1,2,4]triazolo[3,4-a]phthalazin-6-yl)oxy)methyl)-N-(piperidin-1-yl)nicotinamide |
| 53 | 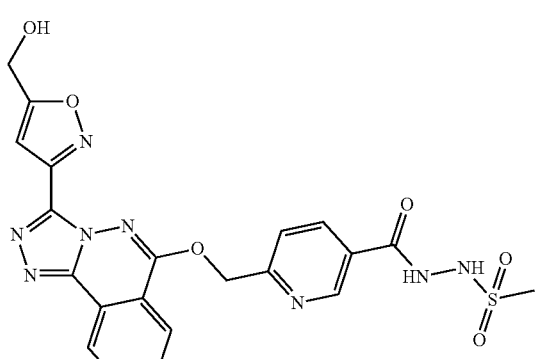 | N'-(6-(((3-(5-(hydroxymethyl)isoxazol-3-yl)-[1,2,4]triazolo[3,4-a]phthalazin-6-yl)oxy)methyl)nicotinoyl)methanesulfonohydrazide |
| 54 | 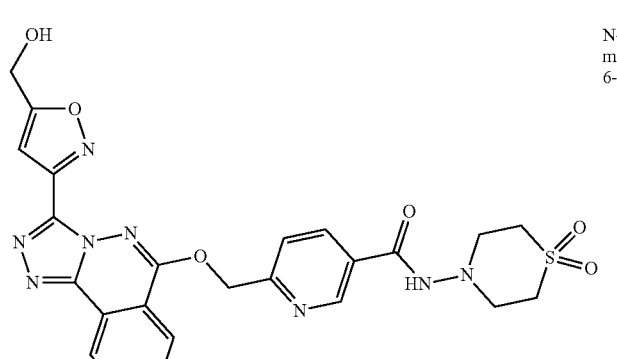 | N-(1,1-dioxidothiomorpholino)-6-(((3-(5-(hydroxymethyl)isoxazol-3-yl)-[1,2,4]triazolo[3,4-a]phthalazin-6-yl)oxy)methyl)nicotinamide |

-continued

| number | formula | Chemical name |
|---|---|---|
| 55 | | (R)-3-cyano-4-(((3-(5-(hydroxymethyl)isoxazol-3-yl)-[1,2,4]triazolo[3,4-a]phthalazin-6-yl)oxy)methyl)-N-(1-hydroxypropan-2-yl)benzamide |
| 56 | | 3-cyano-N-((1S,2S)-2-hydroxycyclopentyl)-4-(((3-(5-(hydroxymethyl)isoxazol-3-yl)-[1,2,4]triazolo[3,4-a]phthalazin-6-yl)oxy)methyl)benzamide |
| 57 | | (R)-N-(1-hydroxypropan-2-yl)-6-(((3-(5-methyl-1,2,4-oxadiazol-3-yl)-[1,2,4]triazolo[3,4-a]phthalazin-6-yl)oxy)methyl)nicotinamide |
| 58 | | (R)-N-(1-hydroxypropan-2-yl)-3-(((3-(5-methyl-isoxazol-3-yl)-[1,2,4]triazolo[3,4-a]phthalazin-6-yl)oxy)methyl)isoxazole-5-carboxamide |

-continued

| number | formula | Chemical name |
|---|---|---|
| 59 | | (R)-6-(((3-(furan-3-yl)-[1,2,4]triazolo[3,4-a]phthalazin-6-yl)oxy)methyl)-N-(1-hydroxypropan-2-yl)nicotinamide |
| 60 | | (R)-N-(1-hydroxypropan-2-yl)-6-(((3-(thiophen-3-yl)-[1,2,4]triazolo[3,4-a]phthalazin-6-yl)oxy)methyl)nicotinamide |
| 61 | | (R)-6-(((3-(5-(hydroxymethyl)isoxazol-3-yl)-[1,2,4]triazolo[3,4-a]phthalazin-6-yl)oxy)methyl)-N-(1-hydroxypropan-2-yl)-2-methylnicotinamide |
| 62 | | 3-cyano-N-ethyl-4-(((3-(5-methylisoxazol-3-yl)-[1,2,4]triazolo[3,4-a]phthalazin-6-yl)oxy)methyl)benzamide |

In another preferred embodiment, a compound of formula I which is independently selected from the group consisting of

| number | formula | Chemical name |
|---|---|---|
| 01 | 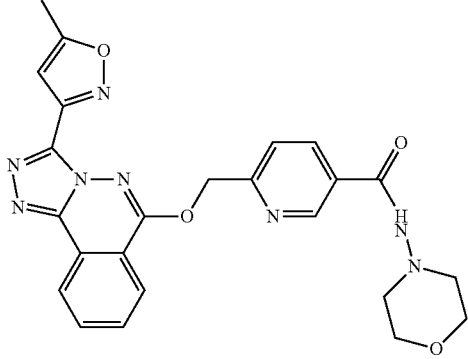 [SMILES: Cc1cc(-c2nnc3c4ccccc4c(OCc4ccc(C(=O)NN5CCOCC5)cn4)nn23)no1] | 6-(((3-(5-methylisoxazol-3-yl)-[1,2,4]triazolo[3,4-a]phthalazin-6-yl)oxy)methyl)-N-morpholinonicotinamide |
| 06 | 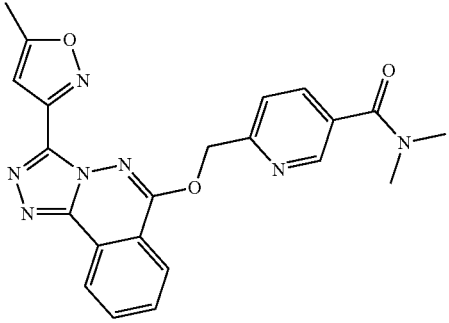 | N,N-dimethyl-6-(((3-(5-methylisoxazol-3-yl)-[1,2,4]triazolo[3,4-a]phthalazin-6-yl)oxy)methyl)nicotinamide |
| 07 | 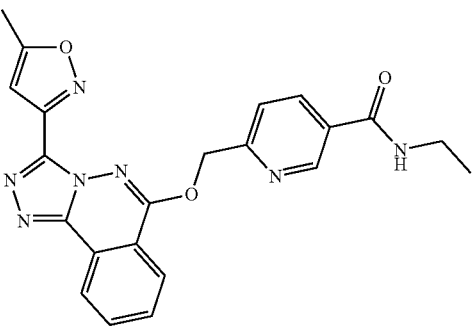 [SMILES: CCNC(=O)c1ccc(COc2nn3c(-c4cc(C)on4)nnc3c3ccccc23)nc1] | N-ethyl-6-(((3-(5-methylisoxazol-3-yl)-[1,2,4]triazolo[3,4-a]phthalazin-6-yl)oxy)methyl)nicotinamide |
| 08 | 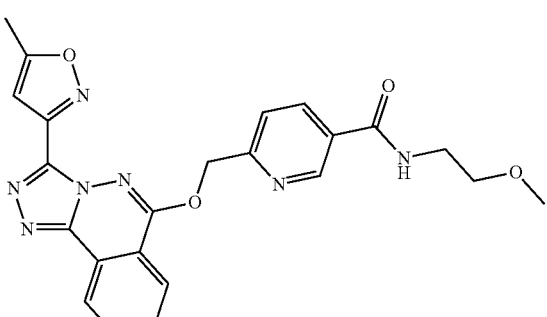 | N-(2-methoxyethyl)-6-(((3-(5-methylisoxazol-3-yl)-[1,2,4]triazolo[3,4-a]phthalazin-6-yl)oxy)methyl)nicotinamide |

| number | formula | Chemical name |
|---|---|---|
| 24 | 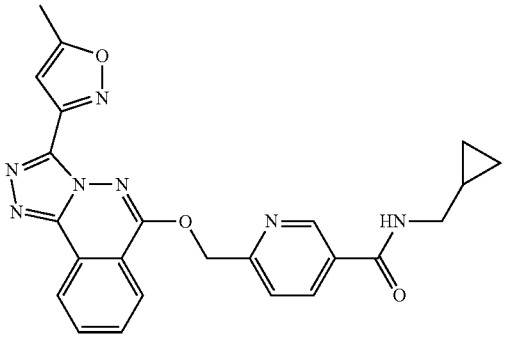 | N-(cyclopropylmethyl)-6-(((3-(5-methylisoxazol-3-yl)-[1,2,4]triazolo[3,4-a]phthalazin-6-yl)oxy)methyl)nicotinamide |

In the second aspect, the present disclosure provides a compound of formula I, a cis-trans isomer, an enantiomer, a diastereoisomer, a racemate, a solvate, a hydrate, or a pharmaceutical acceptable salt and ester thereof,

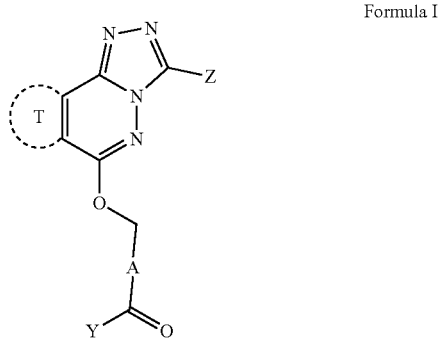

Formula I

Wherein:

T is C3-7 cycloalkyl, C4-7 cycloalkenyl, C6-8 bicycloalkyl, C6-10 aryl, or C3-7 heterocycloalkyl; preferably T is phenyl;

Z is five membered heteroaryl that contains 1, 2 or 3 hetero-atoms independently selected from the group consisting of oxygen, nitrogen and sulfur; the five membered heteroaryl is optionally substituted by one or more substituents selected from the group consisting of hydroxyl, halogen, —R1, —OR1, —OC(O)R1, —NR2R3, CN, cyano (C1-6)alkyl or R2; preferably, Z is 5 membered heteroaryl that contains 1, 2 or 3 hetero-atoms independently selected from the group consisting of oxygen, nitrogen and sulfur and at most one of the heteroatoms is O or S, at least one of the heteroatoms is O or S when one of the heteroatoms is N, the 5 membered heteroaryl is optionally substituted by one or more substituents selected from the group consisting of C1-4 alkyl, hydroxyl, halogen, C1-4 alkyl substituted by hydroxyl or amino, C2-4 alkenyl, C2-4 alkynyl, C1-4 alkoxy; more preferably Z is 5 membered heteroaryl that contains 2 hetero-atoms independently selected from the group consisting of oxygen, nitrogen and sulfur and one of the heteroatoms is O or S, the other heteroatom is N, the 5 membered heteroaryl is optionally substituted by one or more substituents selected from the group consisting of C1-6 alkyl or hydroxyl C1-6 alkyl;

R1 is C1-6 alkyl, C2-6 alkenyl, C2-6 alkynyl, C3-6 cycloalkyl, C3-6 cycloalkyl (C1-6) alkyl, cyano(C1-6)alkyl, or C1-6 alkyl substituted by hydroxyl or amino, and R1 is optionally substituted by 1, 2 or 3 fluorine;

R2 or R3 are independently hydrogen, C1-6 alkyl, C2-6 alkenyl, C2-6 alkynyl, C3-6 cycloalkyl or CF3; alternatively, R2 and R3 together with the nitrogen atom to which they are attached, form a 4-7 membered hetero-alicyclic ring which contains the nitrogen atom and one other heteroatom selected from the group consisting of O, N and S, the hetero-alicyclic ring is optionally substituted by one or more R1;

A is —NR2-; alternatively, A is five-membered heteroarylene that contains 1, 2, 3 or 4 hetero-atoms independently selected from the group consisting of oxygen, nitrogen and sulfur and at most one of the heteroatoms is O or S, or six-membered heteroarylene that contains 1, 2 or 3 nitrogen atoms; the five- or six-membered heteroarylene is optionally condensed with phenyl or pyridinyl, and the five- or six-membered heteroarylene is optionally substituted by Rx and/or Ry and/or Rz, Rx is halogen, —R1, —OR1, —OC(O)R1, —C(O)OR1, —NR2R3, —NR2C(O)R3, —OH or —CN, Ry is halogen, —R1, —OR1, —OC(O)R1, —NR2R3, —NR2C(O)R3, or CN, and Rz is —R1, —OR1 or —OC(O)R1, provided that when A is a pyridinyl derivative, the pyridinyl is optionally N-oxide form; or A is phenylene that is substituted by 1, 2 or 3 substituents independently selected from the group consisting of halogen, cyano, C1-6 alkyl, C2-6 alkenyl, C2-6 alkynyl, and C3-6 cycloalkyl; preferably, A is five-membered heteroarylene that contains 1, 2, or 3 hetero-atoms independently selected from the group consisting of oxygen, nitrogen and sulfur and at most one of the heteroatoms is O or S, or six-membered heteroarylene or phenylene that contains 1, 2 or 3 nitrogen atoms; the five- or six-membered heteroarylene or phenylene is optionally substituted by a substituent selected from the group consisting of halogen, cyano, and C1-6 alkyl Y is —NY1Y2 or —NH—NY3Y4;

Y1 is independently selected from the group consisting of H; C1-6 alkyl; C1-6 alkyl substituted by 1-5 substituents selected from the group consisting of amino, halogen, halogenated C1-6 alkoxy, hydroxyl, C1-6 alkoxy, (C1-6 alkyl, C1-6 alkyl)N-, (C1-6 alkyl, H)N—, nitro and C1-6 alkyl-S(O)2-;

Y2 is independently selected from the group consisting of H; C1-6 alkyl-S(O)2-; amino; NH—S(O)2-; C1-6 alkoxy; C1-6 alkyl; C1-6 alkyl substituted by 1-5 substituents selected from the group consisting of amino, substituted amino, halogen, halogenated C1-6 alkoxy, hydroxyl, C1-6 alkoxy, carboxyl, cycloalkyl, (C1-6 alkyl, C1-6 alkyl)N-, (C1-6 alkyl, H)N—, nitro, C1-6 alkyl-S(O)2-, heterocycloalkyl, or heterocycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-; heteroaryl, or heteroaryl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-; cycloalkyl, or cycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-; heterocycloalkyl, or heterocycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-;

Preferably, Y2 is independently selected from the group consisting of C1-6 alkyl; C1-6 alkyl substituted by 1-5 substituents selected from the group consisting of amino, substituted amino, hydroxyl, C1-6 alkoxy, carboxyl, halogen, cycloalkyl, (C1-6 alkyl, C1-6 alkyl)N-, (C1-6 alkyl, H)N— and C1-6 alkyl-S(O)2-, heterocycloalkyl, or heterocycloalkyl substituted by 1-4 substituents selected from the group consisting of acetamido, acetyl, C1-6 alkoxy, and C1-6 alkyl;

H; C1-6 alkyl-S(O)2-; amino; NH—S(O)2-; C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;

C3-6 cycloalkyl, C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)2-;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, acetyl, S(O)2-, C1-6 alkoxyC1-6 alkyl, C1-6 alkyl and C1-6 alkyl-S(O)2-;

alternatively, Y1 and Y2 together with the nitrogen atom to which they are attached, form a 4-6 membered heterocycloalkyl which contains the nitrogen atom and 0, 1 or more heteroatom selected from O and S; the sulfur atom can be its oxide form;

alternatively, Y1 and Y2 together with the nitrogen atom to which they are attached, form a 4-6 membered heterocycloalkyl which contains 1-3 heteroatoms selected from N, O and S, the sulfur atom can be its oxide form, the heterocycloalkyl is substituted by 1-4 substituents selected from the group consisting of C1-6 alkyl, C1-6 alkylS(O)2-, C1-6 alkoxy, halogenated C1-6 alkyl, NH2C(=O)—, and halogen;

alternatively, Y1 and Y2 together with the nitrogen atom to which they are attached, form C5-10 oxaazabicycloalkyl;

Preferably, Y1 and Y2 together with the nitrogen atom to which they are attached, form morpholinyl, piperidinyl, piperazinyl, azetidinyl, oxazabicycloheptanyl; the morpholinyl, piperidinyl, piperazinyl, azetidinyl, oxazabicycloheptanyl are optionally substituted by 1-4 substituents selected from the group consisting of C1-6 alkyl, C1-6 alkyl-S(O)2-, C1-6 alkoxy, halogen, NH2C(=O)—; the sulfur atom of the morpholinyl can be its oxide form;

Y3 and Y4 are independently selected from the group consisting of hydrogen, C1-6 alkyl, SO$_2$—C1-6 alkyl, cycloalkyl and heterocyclyl, optionally substituted by 1-4 substituents selected from the group consisting of halogen, cyano, hydroxyl, C1-6 alkyl and C1-6 alkoxy, alternatively, Y3 and Y4 together with the nitrogen atom to which they are attached, form a heterocyclyl, and the heterocyclyl is optionally substituted by 1-4 substituents selected from the group consisting of halogen, cyano, hydroxyl, oxo, C1-6 alkyl and C1-6 alkoxy;

Preferably Y3 and Y4 are independently selected from the group consisting of hydrogen, C1-6 alkyl, SO$_2$—C1-6 alkyl, C3-7 cycloalkyl and C3-7 heterocyclyl, optionally substituted by 1-4 substituents selected from the group consisting of halogen, cyano, hydroxyl, C1-6 alkyl and C1-6 alkoxy, alternatively, Y3 and Y4 together with the nitrogen atom to which they are attached, form C3-7 heterocyclyl, more preferably the C3-7 heterocyclyl is piperidinyl, morpholinyl, thiomorpholinyl, dioxidothiomorpholinyl, oxidothiomorpholinyl and pyrrolidinyl, which are substituted by 1-4 substituents selected from the group consisting of halogen, cyano, hydroxyl, oxo, C1-6 alkyl and C1-6 alkoxy, more preferably Y3 and Y4 are independently selected from the group consisting of hydrogen, C1-6 alkyl, SO$_2$—C1-6 alkyl, Y3 and Y4 together with the nitrogen atom to which they are attached, form morpholin-4-yl, piperidin-1-yl, pyrrolidin-1-yl, and 1,1-dioxido-thiomorpholin-4-yl;

all of hydrogen atoms of the above substituents can be replaced by deuterium.

In another preferred embodiment, a compound of formula II:

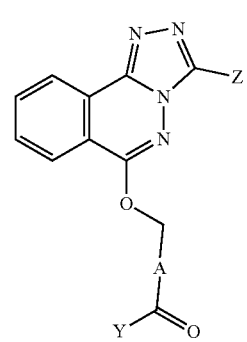

Wherein:

Z is 5 membered heteroaryl that contains 1, 2 or 3 hetero-atoms independently selected from the group consisting of oxygen, nitrogen and sulfur and at most one of the heteroatoms is O or S, at least one of the heteroatoms is O or S when one of the heteroatoms is N, the heteroaryl is optionally substituted by one or more substituents selected from the group consisting of C1-4 alkyl, hydroxyl, halogen, C1-4 alkyl substituted by hydroxyl or amino, C2-4 alkenyl, C2-4 alkynyl, and C1-4 alkoxy;

A is five-membered heteroarylene that contains 1, 2 or 3 hetero-atoms independently selected from the group consisting of oxygen, nitrogen and sulfur and at most one of the heteroatoms is O or S, or six-membered heteroarylene or phenylene that contains 1, 2 or 3 nitrogen atoms, the five- or six-membered heteroarylene or phenylene is optionally substituted by a substituent selected from the group consisting of halogen, cyano, and C1-6 alkyl;

Y is —NY1Y2 or —NH—NY3Y4;

Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, nitro and C1-6 alkyl-S(O)2-;

Y2 is independently selected from the group consisting of C1-6 alkyl; C1-6 alkyl substituted by 1-5 substituents selected from the group consisting of amino, substituted amino, hydroxyl, C1-6 alkoxy, carboxyl, halogen, cycloalkyl, (C1-6 alkyl, C1-6 alkyl)N-, (C1-6 alkyl, H)N— and C1-6 alkyl-S(O)2-, heterocycloalkyl, or heterocycloalkyl substituted by 1-4 substituents selected from the group consisting of acetamido, acetyl, C1-6 alkoxy, and C1-6 alkyl;

H; C1-6 alkyl-S(O)2-; amino; NH—S(O)2-; C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;

C3-6 cycloalkyl, C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)2-;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, acetyl, S(O)2-, C1-6 alkoxyC1-6 alkyl, C1-6 alkyl and C1-6 alkyl-S(O)2-;

alternatively, Y1 and Y2 together with the nitrogen atom to which they are attached, form a 4-6 membered heterocycloalkyl which contains the nitrogen atom and 0, 1 or more heteroatom selected from O and S; the sulfur atom can be its oxide form;

alternatively, Y1 and Y2 together with the nitrogen atom to which they are attached, form a 4-6 membered heterocycloalkyl which contains 1-3 heteroatoms selected from N, O and S, the sulfur atom can be its oxide form, the heterocycloalkyl is substituted by 1-4 substituents selected from the group consisting of C1-6 alkyl, C1-6 alkylS(O)2-, C1-6 alkoxy, halogenated C1-6 alkyl, NH2C(=O)—, and halogen;

alternatively, Y1 and Y2 together with the nitrogen atom to which they are attached, form C5-10 oxaazabicycloalkyl;

Y3 and Y4 are independently selected from the group consisting of hydrogen, C1-6 alkyl, and SO2-C1-6 alkyl;

alternatively, Y3 and Y4 together with the nitrogen atom to which they are attached, form a heterocyclyl, the heterocyclyl is selected from the group consisting of piperazinyl, morpholinyl, dioxidothiomorpholinyl and oxidothiomorpholinyl.

In another preferred embodiment, Z of formula II or I is 5 membered heteroaryl that contains 2 hetero-atoms independently selected from the group consisting of oxygen, nitrogen and sulfur and one of the heteroatoms is O or S, the other heteroatom is N, the heteroaryl is optionally substituted by one or more substituents selected from the group consisting of C1-6 alkyl and hydroxyl C1-6 alkyl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, and hydroxyl C1-6 alkyl.

In another preferred embodiment, A of formula II or I is phenylene, pyridinylene, or isoxazolylene; A is optionally substituted by 1, 2 or 3 substituents selected from the group consisting of halogen, cyano, and C1-6 alkyl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, and hydroxyl C1-6 alky;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or C1-6 alkyl;

Y2 is independently selected from the group consisting of C1-6 alkyl; C1-6 alkyl substituted by 1-5 substituents selected from the group consisting of amino, substituted amino, hydroxyl, C1-6 alkoxy, carboxyl, halogen, C1-6 alkyl-S(O)2-; cycloalkyl, heterocycloalkyl, or heterocycloalkyl substituted by 1-4 substituents selected from the group consisting of acetamido, acetyl, C1-6 alkoxy, and C1-6 alkyl;

H; C1-6 alkyl-S(O)2-; amino; NH—S(O)2-; C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with alkyl;

C4-6 cycloalkyl, cyclopropyl, C3-6 cycloalkyl optionally substituted by 1-4 substituents selected from the group consisting of hydroxyl, C1-6 alkyl, and C1-6 alkoxy;

C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents selected from the group consisting of C1-6 alkyl, acetyl, and S(O)2-;

alternatively, Y1 and Y2 together with the nitrogen atom to which they are attached, form a 4-6 membered heterocycloalkyl which contains the nitrogen atom and 0, 1 or more heteroatom selected from O and S, and the sulfur atom can be its oxide form;

alternatively, Y1 and Y2 together with the nitrogen atom to which they are attached, form a 4-6 membered heterocycloalkyl which contains 1-3 heteroatoms selected from N, O and S, the sulfur atom can be its oxide form, and the heterocycloalkyl is optionally substituted by 1-4 substituents selected from the group consisting of C1-6 alkyl, C1-6 alkylS(O)2-, C1-6 alkoxy, halogenated C1-6 alkyl, NH2C(=O)—, and halogen;

alternatively, Y1 and Y2 together with the nitrogen atom to which they are attached, form C5-10 oxaazabicycloalkyl;

Y3 and Y4 are independently selected from the group consisting of hydrogen, methyl, and —SO2-methyl;

Y3 and Y4 together with the nitrogen atom to which they are attached, form a heterocyclyl, and the heterocyclyl is selected from the group consisting of piperidinyl, morpholinyl, and dioxidothiomorpholinyl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or C1-6 alkyl;

Y2 is independently selected from the group consisting of C1-6 alkyl; C1-6 alkyl substituted by 1-5 substituents selected from the group consisting of hydroxyl, C1-6 alkoxy, amido, halogen, carboxyl, C3-6 cycloalkyl, C4-6 heterocycloalkyl that contains 1-3 hetero-atoms independently selected from nitrogen, oxygen or sulfur, C1-6 alkyl-S(O)2-;

H; C1-6 alkyl-S(O)2-; amino; NH—S(O)2-; C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted by alkyl;

C4-6 cycloalkyl, cyclopropyl, C3-6 cycloalkyl optionally substituted by 1-4 substituents selected from the group consisting of hydroxyl, C1-6 alkyl, and C1-6 alkoxy;

C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents selected from the group consisting of C1-6 alkyl, acetyl, and S(O)2-;

alternatively, Y1 and Y2 together with the nitrogen atom to which they are attached, form morpholinyl, piperidinyl, piperazinyl, azetidinyl, oxazabicycloheptanyl; the morpholinyl, piperidinyl, piperazinyl, azetidinyl, oxazabicycloheptanyl are optionally substituted by 1-4 substituents selected from the group consisting of C1-6 alkyl, C1-6 alkyl-S(O)2-, C1-6 alkoxy, halogen, and NH2C(=O)—; the sulfur atom of the morpholinyl can be its oxide form;

Y3 and Y4 are independently selected from the group consisting of hydrogen, methyl, and SO2-methyl;

Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or methyl;

Y2 is independently selected from the group consisting of C1-6 alkyl; C1-6 alkyl substituted by 1-5 substituents selected from the group consisting of hydroxyl, C1-6 alkoxy, acetamido, fluorine, carboxyl, morpholinyl, cyclopropyl, and tetrahydro furyl;

H; C1-6 alkyl-S(O)2-; amino; NH—S(O)2-; C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted by alkyl;

C3-6 cycloalkyl; C3-6 cycloalkyl optionally substituted by 1-4 substituents selected from the group consisting of hydroxyl, methoxy, and methyl;

C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents selected from the group consisting of methyl, and acetyl;

alternatively, Y1 and Y2 together with the nitrogen atom to which they are attached, form morpholinyl, piperidinyl, piperazinyl, azetidinyl, oxazabicycloheptanyl; the morpholinyl, piperidinyl, piperazinyl, azetidinyl, oxazabicycloheptanyl are optionally substituted by 1-4 substituents selected from the group consisting of methyl, methoxy, fluorine, NH2C(=O)—; the sulfur atom of the morpholinyl can be its oxide form;

Y3 and Y4 are independently selected from the group consisting of hydrogen, and methyl;

Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

In another preferred embodiment, Z of formula II or I is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or methyl;

Y2 is selected from the group consisting of methyl, ethyl, methoxyethyl, hydroxypropyl, acetamidoethyl, H, —CH2COOH, hydroxycyclopentyl, cyclopropyl, methylpyrazolyl, morpholinyl, hydroxyethyl, butyl, methylpiperidinyl, morpholinylethyl, tetrahydrofuranyl, methoxycyclopentyl, acetylpyrrolidinyl, tetrahydrofuranylmethyl, difluoroethyl, cyclopropylmethyl, methylsulfonylethyl, trifluoroethyl, isopropyl, tetrahydropyranyl, cyclobutyl, amino, piperidinyl, methyl sulfonyl, dioxidothiomorpholinyl, and hydroxymethylethyl;

alternatively, Y1 and Y2 together with the nitrogen atom to which they are attached, form methylpiperazinyl, carboxamidepiperidinyl, methoxypiperidinyl, difluoropiperidinyl, oxaazabicycloheptanyl, dioxidothiomorpholinyl, morpholinyl, azetidinyl, and oxidothiomorpholinyl;

Y3 and Y4 are independently selected from the group consisting of H and methyl, or Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

In another preferred embodiment, a compound of formula III:

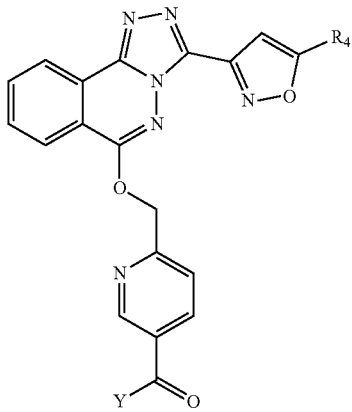

Wherein
R4 is C1-4 alkyl, hydroxyl substituted C1-4 alkyl;
Y is —NY1Y2 or —NH—NY3Y4;
Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, nitro and C1-6 alkyl-S(O)2-;
Y2 is independently selected from the group consisting of C1-6 alkyl; C1-6 alkyl substituted by 1-5 substituents selected from the group consisting of amino, substituted amino, hydroxyl, C1-6 alkoxy, carboxyl, halogen, cycloalkyl, (C1-6 alkyl, C1-6 alkyl)N-, (C1-6 alkyl, H)N— and C1-6 alkyl-S(O)2-, heterocycloalkyl, or heterocycloalkyl substituted by 1-4 substituents selected from the group consisting of acetamido, acetyl, C1-6 alkoxy, and C1-6 alkyl;
H; C1-6 alkyl-S(O)2-; amino; NH—S(O)2-; C1-6 alkoxy;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with C1-6 alkyl;
C3-6 cycloalkyl; C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)2-;
C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, acetyl, S(O)2-, C1-6 alkoxyC1-6 alkyl, C1-6 alkyl and C1-6 alkyl-S(O)2-;
alternatively, Y1 and Y2 together with the nitrogen atom to which they are attached, form a 4-6 membered heterocycloalkyl which contains the nitrogen atom and 0, 1 or more heteroatom selected from O and S, and the sulfur atom can be its oxide form;
alternatively, Y1 and Y2 together with the nitrogen atom to which they are attached, form a 4-6 membered heterocycloalkyl which contains 1-3 heteroatoms selected from N, O and S, the sulfur atom can be its oxide form, and the heterocycloalkyl is substituted by 1-4 substituents selected from the group consisting of C1-6 alkyl, C1-6 alkylS(O)2-, C1-6 alkoxy, halogenated C1-6 alkyl, NH2C(=O)—, and halogen;
alternatively, Y1 and Y2 together with the nitrogen atom to which they are attached, form C5-10 oxaazabicycloalkyl;
Y3 and Y4 are independently selected from the group consisting of hydrogen, C1-6 alkyl, and SO2—C1-6 alkyl;
alternatively, Y3 and Y4 together with the nitrogen atom to which they are attached, form a heterocyclyl, and the heterocyclyl is selected from the group consisting of piperidinyl, morpholinyl, dioxidothiomorpholinyl and oxidothiomorpholinyl.

In another preferred embodiment, a compound of formula IV:

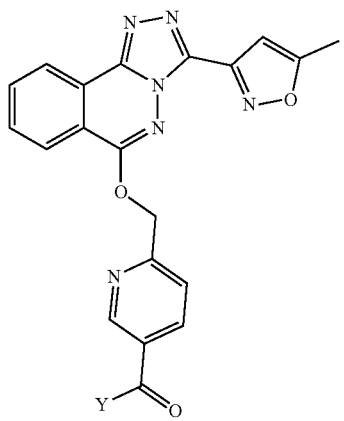

Wherein
Y is —NY1Y2 or —NH—NY3Y4;
Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, nitro and C1-6 alkyl-S(O)2-;
Y2 is independently selected from the group consisting of C1-6 alkyl; C1-6 alkyl substituted by 1-5 substituents selected from the group consisting of amino, substituted amino, hydroxyl, C1-6 alkoxy, carboxyl, halogen, cycloalkyl, (C1-6 alkyl, C1-6 alkyl)N-, (C1-6 alkyl, H)N— and C1-6 alkyl-S(O)2-, heterocycloalkyl, or heterocycloalkyl substituted by 1-4 substituents selected from the group consisting of acetamido, acetyl, C1-6 alkoxy, and C1-6 alkyl;
H; C1-6 alkyl-S(O)2-; amino; NH—S(O)2-; C1-6 alkoxy;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with C1-6 alkyl;
C3-6 cycloalkyl; C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)2-;
C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, acetyl, S(O)2-, C1-6 alkoxyC1-6 alkyl, C1-6 alkyl and C1-6 alkyl-S(O)2-;

alternatively, Y1 and Y2 together with the nitrogen atom to which they are attached, form a 4-6 membered heterocycloalkyl which contains the nitrogen atom and 0, 1 or more heteroatom selected from O and S, and the sulfur atom can be its oxide form;

alternatively, Y1 and Y2 together with the nitrogen atom to which they are attached, form a 4-6 membered heterocycloalkyl which contains 1-3 heteroatoms selected from N, O and S, the sulfur atom can be its oxide form, and the heterocycloalkyl is substituted by 1-4 substituents selected from the group consisting of C1-6 alkyl, C1-6 alkylS(O)2-, C1-6 alkoxy, halogenated C1-6 alkyl, NH2C(=O)—, and halogen;

alternatively, Y1 and Y2 together with the nitrogen atom to which they are attached, form C5-10 oxaazabicycloalkyl;

Y3 and Y4 are independently selected from the group consisting of hydrogen, C1-6 alkyl, and SO$_2$—C1-6 alkyl;

alternatively, Y3 and Y4 together with the nitrogen atom to which they are attached, form a heterocyclyl, and the heterocyclyl is selected from the group consisting of piperidinyl, morpholinyl, dioxidothiomorpholinyl and oxidothiomorpholinyl.

In another preferred embodiment, a compound of formula IV:

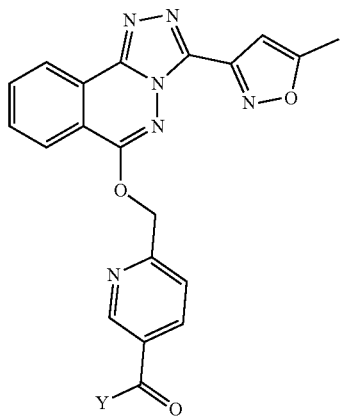

IV

Wherein
Y is —NY1Y2 or —NH—NY3Y4;
Y1 is independently selected from the group consisting of H, C1-6 alkyl, or C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, and C1-6 alkyl-S(O)2-;
Y2 is independently selected from the group consisting of C1-6 alkyl; C1-6 alkyl substituted by 1-5 substituents selected from the group consisting of amino, substituted amino, hydroxyl, C1-6 alkoxy, halogen, carboxyl, C3-6 cycloalkyl, and C4-6 heterocycloalkyl that contains 1-3 hetero-atoms independently selected from nitrogen, oxygen or sulfur;
H; C1-6 alkyl-S(O)2-; amino; NH—S(O)2-; C1-6 alkoxy;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with C1-6 alkyl;

C4-6 cycloalkyl; cyclopropyl; C3-6 cycloalkyl substituted by 1-4 substituents selected from the group consisting of hydroxyl, C1-6 alkyl, and C1-6 alkoxy;
C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents selected from the group consisting of C1-6 alkyl, acetyl, and S(O)2-;

alternatively, Y1 and Y2 together with the nitrogen atom to which they are attached, form morpholinyl, piperidinyl, piperazinyl, azetidinyl, oxazabicycloheptanyl; the morpholinyl, piperidinyl, piperazinyl, azetidinyl, oxazabicycloheptanyl are optionally substituted by 1-4 substituents selected from the group consisting of C1-6 alkyl, C1-6 alkyl-SO2, C1-6 alkoxyl, halogen, and NH2C(=O)—; the sulfur atom of the morpholinyl can be its oxide form;

Y3 and Y4 are independently selected from the following groups: hydrogen, methyl and SO2-methyl;

Y3 and Y4 together with the nitrogen atom to which they are attached, form a heterocyclyl, and the heterocyclyl is selected from the group consisting of morpholinyl, piperidinyl and dioxido-thiomorpholinyl.

In another preferred embodiment, a compound of formula IV:

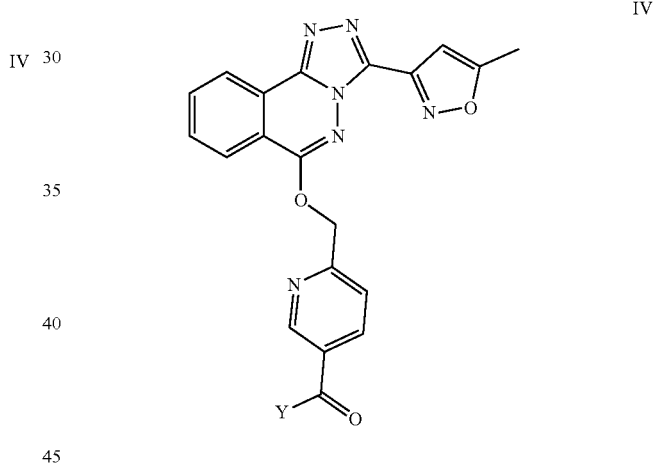

IV

Wherein
Y is —NY1Y2 or —NH—NY3Y4;
Y1 is independently selected from the group consisting of H or C1-6 alkyl;
Y2 is independently selected from the group consisting of C1-6 alkyl; C1-6 alkyl substituted by 1-5 substituents selected from the group consisting of hydroxyl, C1-6 alkoxy, acetamido, fluorine, carboxyl, C3-6 cycloalkyl, C4-6 heterocycloalkyl that contains 1-3 hetero-atoms independently selected from nitrogen, oxygen or sulfur;
H; C1-6 alkyl-S(O)2-; amino; NH—S(O)2-; C1-6 alkoxy;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfurs and is substituted with methyl;
C4-6 cycloalkyl; cyclopropyl; C3-6 cycloalkyl substituted by 1-4 substituents selected from the group consisting of hydroxyl, C1-6 alkyl, and C1-6 alkoxy;
C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents selected from the group consisting of C1-6 alkyl, acetyl, and S(O)2-;

Y1 and Y2 together with the nitrogen atom to which they are attached, form morpholinyl, piperidinyl, piperazinyl, azetidinyl, oxazabicycloheptanyl; the morpholinyl, piperidinyl, piperazinyl, azetidinyl, oxazabicycloheptanyl are optionally substituted by 1-4 substituents selected from the group consisting of C1-6 alkyl, C1-6 alkyl-SO2, C1-6 alkoxyl, halogen, NH2C(=O)—; the sulfur atom of the morpholinyl can be its oxide form;

Y3 and Y4 are independently selected from the following groups: hydrogen, methyl and SO2-methyl;

Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

In another preferred embodiment, a compound of formula IV:

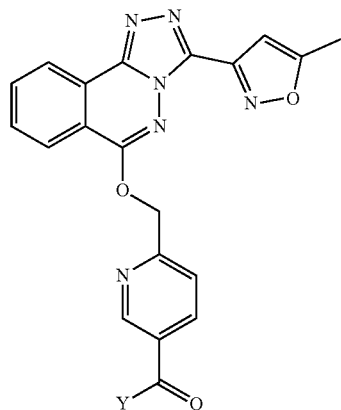

IV

Wherein
Y is —NY1Y2 or —NH—NY3Y4;
Y1 is H or methyl;
Y2 is independently selected from the group consisting of C1-6 alkyl; C1-6 alkyl substituted by 1-5 substituents selected from the group consisting of hydroxyl, C1-6 alkoxy, acetamido, fluorine, carboxyl, morpholinyl, cyclopropyl, and tetrahydro-furanyl;
H; C1-6 alkyl-S(O)2-; amino; NH—S(O)2-; C1-6 alkoxy;
C3-6 cycloalkyl; C3-6 cycloalkyl substituted by 1-4 substituents selected from the group consisting of hydroxyl, methoxy and methyl;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfurs and is substituted with methyl;
C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents selected from the group consisting of methyl, acetyl and S(O)2-;

Y1 and Y2 together with the nitrogen atom to which they are attached, form morpholinyl, piperidinyl, piperazinyl, azetidinyl, oxazabicycloheptanyl; the morpholinyl, piperidinyl, piperazinyl, azetidinyl, oxazabicycloheptanyl are optionally substituted by 1-4 substituents selected from the group consisting of C1-6 alkyl, C1-6 alkyl-SO2, C1-6 alkoxy, halogen, NH2C(=O)—; the sulfur atom of the morpholinyl can be its oxide form;

Y3 and Y4 are independently selected from the following groups: hydrogen and methyl;

Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

In another preferred embodiment, a compound of formula IV:

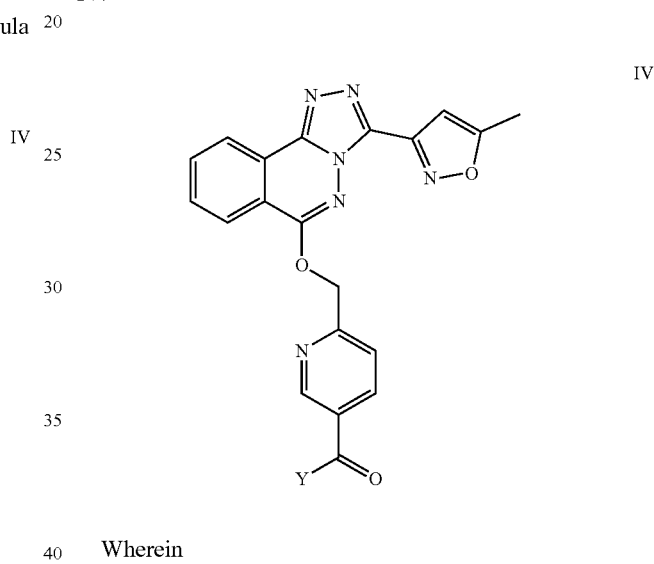

IV

Wherein
Y is —NY1Y2 or —NH—NY3Y4;
Y1 is H or methyl;
Y2 is selected from the group consisting of methyl, ethyl, 2-methoxyethyl, hydroxypropyl, acetamidoethyl, H, —CH2COOH, hydroxycyclopentyl, cyclopropyl, methylpyrazolyl, morpholinyl, hydroxyethyl, butyl, methylpiperidinyl, morpholinylethyl, tetrahydrofuranyl, methoxycyclopentyl, acetylpyrrolidinyl, tetrahydrofuranylmethyl, difluoroethyl, cyclopropylmethyl, methyl sulfonyl ethyl, trifluoroethyl, isopropyl, tetrahydropyranyl, cyclobutyl, amino, piperidinyl, methyl sulfonyl, dioxidothiomorpholinyl, and hydroxymethylethyl;

alternatively, Y1 and Y2 together with the nitrogen atom to which they are attached, form methylpiperazinyl, carboxamidepiperidinyl, methoxypiperidinyl, difluoropiperidinyl, oxaazabicycloheptanyl, dioxidothiomorpholinyl, morpholinyl, azetidinyl, and oxidothiomorpholinyl;

Y3 and Y4 are independently selected from the group consisting of hydrogen and methyl;

Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

In another preferred embodiment, a compound of formula IV:

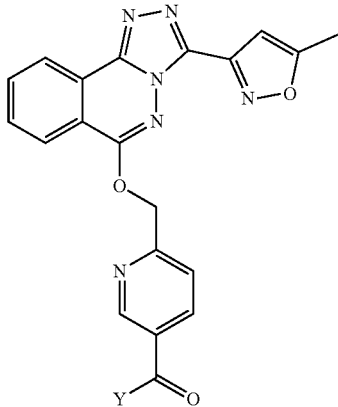

IV

Wherein
Y is —NY1Y2;
Y1 is H;
Y2 is selected from the group consisting of methyl, ethyl, methoxyethyl, hydroxypropyl, acetamidoethyl, H, —CH2COOH, hydroxycyclopentyl, cyclopropyl, methylpyrazolyl, morpholinyl, hydroxyethyl, butyl, methylpiperidinyl, morpholinylethyl, tetrahydrofuranyl, methoxycyclopentyl, acetylpyrrolidinyl, tetrahydrofuranylmethyl, difluoroethyl, cyclopropylmethyl, methyl sulfonyl ethyl and trifluoroethyl;

alternatively, Y1 and Y2 together with the nitrogen atom to which they are attached, form methylpiperazinyl, carboxamidepiperidinyl, methoxypiperidinyl, difluoropiperidinyl, and oxaazabicycloheptanyl.

In another preferred embodiment, a compound of formula II,

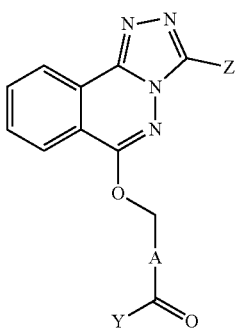

II

Wherein
Z is methylisoxazolyl;
A is cyanophenylene or pyridylidene;
Y is —NY1Y2;
Y1 is H;
Y2 is selected from the group consisting of C1-6 alkyl; C1-6 alkyl substituted by 1-3 substituents selected from C3-6 cycloalkyl or C1-6 alkoxy; C1-6 alkoxy.

In the third aspect, the present disclosure provides a composition comprising the compound as defined above or a pharmaceutically acceptable salt thereof.

In the fourth aspect, the present disclosure provides a use of the compound as defined above or a composition as defined above for the manufacture of a medicament.

In the fifth aspect, the present disclosure provides a method of treating or preventing diseases which comprises administering to patients a therapeutically effective amount of the compound as defined above or the composition as defined above.

In the sixth aspect, the present disclosure provides a use of the compound as defined above or the composition as defined above for the manufacture of a medicament for treating or preventing α5-GABA$_A$ receptor related diseases.

In the seventh aspect, the present disclosure provides a method of treating or preventing α5-GABAA receptor related diseases which comprises administering to patients a therapeutically effective amount of a compound as defined above or a composition as defined above.

In the eighth aspect, the present disclosure provides a use of a compound as defined above or a composition as defined above for the manufacture of a medicament for treating or preventing the following diseases: pain, Alzheimer's disease, multi-infarct dementia and stoke.

In a preferred embodiment, the pain diseases are selected from the group consisting of neuropathic pain, inflammatory pain and cancer pain.

In another preferred embodiment, the pain diseases are selected from the group consisting of headache, facial pain, neck pain, shoulder pain, back pain, thoracic pain, abdominal pain, dorsopathy, waist pain, lower limb pain, muscle and bone pain, vascular pain, gout, arthritis pain, visceral pain, the pain caused by infectious diseases (for example AIDS pain and postherpetic neuralgia), boniness pain, sickle cell anemia associated pain, autoimmune disease associated pain, multiple sclerosis or inflammation associated pain, injury or surgery caused chronic pain, nociceptive pain, painful diabetes, trigeminal neuralgia, waist or cervix radiculopathy, glossopharyngeal neuralgia, autonomic nerve reflex pain, reflex sympathetic dystrophy pain, nerve root avulsion pain, cancer pain, chemical injury pain, toxin pain, nutrition deficiency pain, virus or bacteria infection pain, and degenerative osteoarthropathy pain.

The present disclosure provides a method of treating or preventing pain, Alzheimer's disease, multi-infarct dementia and stoke, which comprises administering to patients a therapeutically effective amount of a compound as defined above or a composition as defined above.

In another preferred embodiment, the pain diseases are selected from the group consisting of neuropathic pain, inflammatory pain and cancer pain.

In another preferred embodiment, the pain diseases are selected from the group consisting of headache, facial pain, neck pain, shoulder pain, back pain, thoracic pain, abdominal pain, dorsopathy, waist pain, lower limb pain, muscle and bone pain, vascular pain, gout, arthritis pain, visceral pain, the pain caused by infectious diseases (for example AIDS pain and postherpetic neuralgia), boniness pain, sickle cell anemia associated pain, autoimmune disease associated pain, multiple sclerosis or inflammation associated pain, injury or surgery caused chronic pain, nociceptive pain, painful diabetes, trigeminal neuralgia, waist or cervix radiculopathy, glossopharyngeal neuralgia, autonomic nerve reflex pain, reflex sympathetic dystrophy pain, nerve root avulsion pain, cancer pain, chemical injury pain, toxin pain, nutrition deficiency pain, virus or bacteria infection pain, and degenerative osteoarthropathy pain.

The present disclosure provides a process for producing a compound of formula II as defined above:

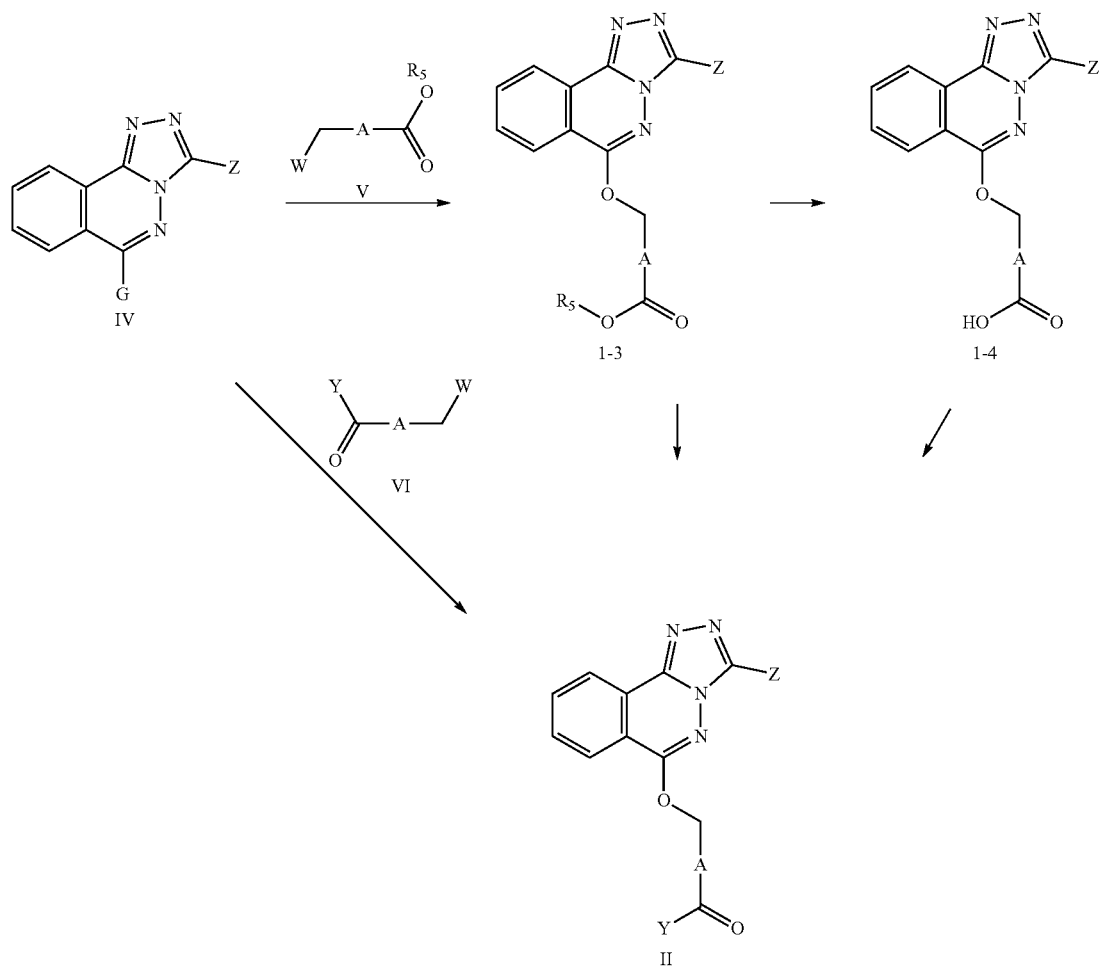

a) reacting a compound of formula IV

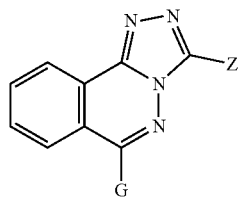

with

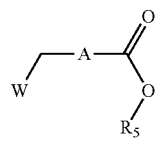

to obtain a compound of formula 1-3, wherein Z, Y and A are as defined above; G and W are selected from the group consisting of Cl, Br, I, OH, OTs, OTf and OMs; R5 represents alkyl, methyl, ethyl, tert-butyl and benzyl; then reaction a compound 1-3

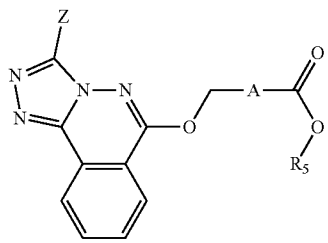

with Y, wherein Z, Y, and A are as defined above, or
b) reacting a compound of formula 1-4:

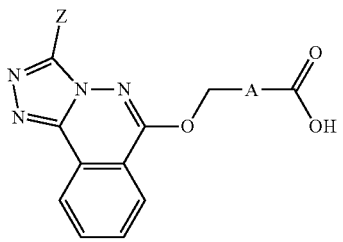

with Y, wherein Z, Y, and A are as defined above;

c) saponificating a compound of formula 1-3 to a compound of formula 1-4, which is then reacted with Y; wherein Z, Y, and A are as defined above; or d) reacting a compound of formula

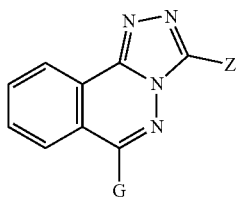

with

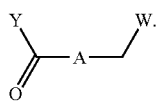

In the compound of formula I of the present disclosure, T is C3-7 cycloalkyl, C4-7 cycloalkenyl, C6-8 bicycloalkyl, C6-10 aryl, or C3-7 heterocycloalkyl; preferably, T is phenyl;

In the compound of formula I, II of the present disclosure, Z is five membered heteroaryl that contains 1, 2 or 3 hetero-atoms independently selected from the group consisting of oxygen, nitrogen and sulfur; the five membered heteroaryl is optionally substituted by one or more substituents selected from the group consisting of hydroxyl, halogen, —R1, —OR1, —OC(O)R1, —NR2R3, CN, cyano (C1-6)alkyl or R2; wherein R1 is C1-6 alkyl, C2-6 alkenyl, C2-6 alkynyl, C3-6 cycloalkyl, C3-6 cycloalkyl (C1-6) alkyl, cyano(C1-6)alkyl, or C1-6 alkyl substituted by hydroxyl or amino, and R1 is optionally substituted by 1, 2 or 3 fluorine; R2 or R3 are independently hydrogen, C1-6 alkyl, C2-6 alkenyl, C2-6 alkynyl, C3-6 cycloalkyl or CF3; alternatively, R2 and R3 together with the nitrogen atom to which they are attached, form a 4-7 membered heteroalicyclic ring which contains the nitrogen atom and one other heteroatom selected from the group consisting of O, N and S, the hetero-alicyclic ring is optionally substituted by one or more R1; preferably Z is 5 membered heteroaryl that contains 1, 2 or 3 hetero-atoms independently selected from the group consisting of oxygen, nitrogen and sulfur and at most one of the heteroatoms is O or S, at least one of the heteroatoms is O or S when one of the heteroatoms is N, the heteroaryl is optionally substituted by one or more substituents selected from the group consisting of C1-4 alkyl, hydroxyl, halogen, C1-4 alkyl substituted by hydroxyl or amino, C2-4 alkenyl, C2-4 alkynyl, C1-4 alkoxy; more preferably, Z is 5 membered heteroaryl that contains 1 or 2 hetero-atoms independently selected from the group consisting of oxygen, nitrogen and sulfur and at most one of the heteroatoms is O or S, one of the heteroatoms is O or S when one of the heteroatoms is N; preferably, Z represents 5 membered heteroaryl that contains 2 hetero-atoms independently selected from the group consisting of oxygen, nitrogen and sulfur and one of the heteroatoms is O or S, the other heteroatom is N, the heteroaryl is optionally substituted by one or more substituents selected from the group consisting of C1-6 alkyl or hydroxyl C1-6 alkyl; preferably, Z is oxadiazolyl, furyl, thienyl or isoxazolyl, the oxadiazolyl, furyl, thienyl or isoxazolyl is optionally substituted by one or more substituents selected from the group consisting of C1-6 alkyl, and hydroxyl C1-6 alkyl; preferably, Z is oxadiazolyl, furyl, thienyl or isoxazolyl, the oxadiazolyll is optionally substituted by one or more substituents selected from the group consisting of methyl, and hydroxyl methyl;

In the compound of formula I, II of the present disclosure, A is —NR2-; alternatively, A is five-membered heteroaryl that contains 1, 2, 3 or 4 hetero-atoms independently selected from the group consisting of oxygen, nitrogen and sulfur and at most one of the heteroatoms is O or S, or six-membered heteroarylene that contains 1, 2 or 3 nitrogen atoms; the five- or six-membered heteroarylene is optionally condensed with phenyl or pyridinyl, and the five- or six-membered heteroarylene is optionally substituted by Rx and/or Ry and/or Rz, Rx is halogen, —R1, —OR1, —OC(O)R1, —C(O)OR1, —NR2R3, —NR2C(O)R3, —OH or —CN, Ry is halogen, —R1, —OR1, —OC(O)R1, —NR2R3, —NR2C(O)R3, or CN, and Rz is —R1, —OR1 or —OC(O)R1, provided that when A is a pyridinyl derivative, the pyridinyl is optionally N-oxide form; or A is phenylene that is substituted by 1, 2 or 3 substituents independently selected from the group consisting of halogen, cyano, C1-6 alkyl, C2-6 alkenyl, C2-6 alkynyl and C3-6 cycloalkyl; preferably, A is five-membered heteroarylene that contains 1, 2 or 3 hetero-atoms independently selected from the group consisting of oxygen, nitrogen and sulfur and at most one of the heteroatoms is O or S, or six-membered heteroarylene or phenylene that contains 1, 2 or 3 nitrogen atoms, the five- or six-membered heteroarylene or phenylene is optionally substituted by a substituent selected from the group consisting of halogen, cyano, and C1-6 alkyl; preferably, A is phenylene, pyridinylene, or isoxazolylene; A is optionally substituted by 1, 2 or 3 substituents selected from the group consisting of halogen, cyano, C1-6 and alkyl.

In the compound of formula I, II, III and IV of the present disclosure, Y is —NY1Y2 or —NH—NY3Y4;

Y1 is independently selected from the group consisting of H; C1-6 alkyl; C1-6 alkyl substituted by 1-5 substituents selected from the group consisting of amino, halogen, halogenated C1-6 alkoxy, hydroxyl, C1-6 alkoxy, (C1-6 alkyl, C1-6 alkyl)N-, (C1-6 alkyl, H)N—, nitro and C1-6 alkyl-S(O)2-; preferably Y1 is H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, nitro and C1-6 alkyl-S(O)2-; more preferably Y1 is H or C1-6 alkyl; more preferably Y1 is H or methyl;

Y2 is independently selected from the group consisting of H; C1-6 alkyl; C1-6 alkyl substituted by 1-5 substituents selected from the group consisting of amino, halogen, halogenated C1-6 alkoxy, hydroxyl, C1-6 alkoxy, cycloalkyl, (C1-6 alkyl, C1-6 alkyl)N-, (C1-6 alkyl, H)N—, nitro and C1-6 alkyl-S(O)2-; heteroaryl, or heteroaryl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-; cycloalkyl, or cycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-; heterocycloalkyl, or heterocycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-;

Preferably Y2 is independently selected from the group consisting of C1-6 alkyl; C1-6 alkyl substituted by 1-5 substituents selected from the group consisting of amino, halogen, halogenated C1-6 alkoxy, hydroxyl, C1-6 alkoxy, C3-6 cycloalkyl, (C1-6 alkyl, C1-6 alkyl)N-, (C1-6 alkyl, H)N—, nitro and C1-6 alkyl-S(O)2-;

C3-7 heteroaryl that contains 1-3 hetero-atoms independently selected from nitrogen, oxygen or sulfur, C3-7 heteroaryl that contains 1-3 hetero-atoms independently selected from nitrogen, oxygen or sulfur and is substituted by 1-4 substituents selected independently from the followings: acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-;

C3-7 cycloalkyl, or C3-7 cycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)2-;

C3-7 heterocycloalkyl that contains 1-3 hetero-atoms independently selected from nitrogen, oxygen or sulfur, C3-7 heterocycloalkyl that contains 1-3 hetero-atoms independently selected from nitrogen, oxygen or sulfur and is substituted by 1-4 substituents selected independently from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, nitro and C1-6 alkyl-S(O)2-;

More preferably, Y2 is independently selected from the group consisting of C1-6 alkyl; C1-6 alkyl substituted by 1-5 substituents selected from the group consisting of amino, hydroxyl, C1-6 alkoxy, cycloalkyl, (C1-6 alkyl, C1-6 alkyl)N-, (C1-6 alkyl, H)N—, and C1-6 alkyl-S(O)2-;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;

C3-6 cycloalkyl, C3-6 cycloalkyl optionally substituted by 1-4 substituents selected from the group consisting of amino, hydroxyl, hydroxylC1-6 alkyl, C1-6 alkoxy, C1-6 alkoxyl-C1-6 alkyl, C1-6 alkyl, (C1-6 alkyl, C1-6 alkyl)N-, (C1-6 alkyl, H)N—, and C1-6 alkyl-S(O)2-;

C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, C1-6 alkoxyl-C1-6 alkyl, C1-6 alkyl, and C1-6 alkyl-S(O)2-;

More preferably, Y2 is independently selected from the group consisting of C1-6 alkyl; C1-6 alkyl substituted by 1-5 substituents selected from the group consisting of amino, hydroxyl, and C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with alkyl;

C4-6 cycloalkyl, C3-6 cycloalkyl optionally substituted by 1-4 substituents selected from the group consisting of hydroxyl;

C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents;

Preferably Y2 is C1-6 alkyl; C1-6 alkyl substituted by hydroxyl, halogen or C1-6 alkoxy; morpholinyl; C3-6 cycloalkyl; hydroxy substituted C3-6 cycloalkyl; pyrazolyl substituted by C1-6 alkyl; tetrahydrofuranyl, tetrahydropyranyl;

Preferably Y2 is independently selected from the group consisting of C1-6 alkyl; C1-6 alkyl substituted by 1-5 substituents selected from the group consisting of hydroxyl, and C1-6 alkoxy;

Most preferably Y2 is independently selected from the group consisting of methyl, ethyl, methoxyethyl, or hydroxylpropyl;

alternatively, Y1 and Y2 together with the nitrogen atom to which they are attached, form a 4-6 membered heterocycloalkyl which contains the nitrogen atom and 0, 1 or more heteroatom selected from O and S; the sulfur atom can be its oxide form;

Preferably Y1 and Y2 together with the nitrogen atom to which they are attached, form azetidinyl, morpholinyl, piperidinyl, pyrrolidinyl, dioxidothiomorpholinyl, oxidothiomorpholinyl; Y1 and Y2 together with the nitrogen atom to which they are attached, form azetidin-1-yl, morpholin-4-yl, piperidin-1-yl, pyrrolidin-1-yl, 1-oxidothiomorpholin-4-yl and 1,1-dioxido-thiomorpholin-4-yl;

Y3 and Y4 are independently selected from the group consisting of hydrogen, C1-6 alkyl, $SO_2$—C1-6 alkyl, cycloalkyl and heterocyclyl, optionally substituted by 1-4 substituents selected from the group consisting of halogen, cyano, hydroxyl, C1-6 alkyl and C1-6 alkoxy, alternatively, Y3 and Y4 together with the nitrogen atom to which they are attached, form a heterocyclyl, and the heterocyclyl is optionally substituted by 1-4 substituents selected from the group consisting of halogen, cyano, hydroxyl, oxo, C1-6 alkyl and C1-6 alkoxy;

Preferably Y3 and Y4 are independently selected from the group consisting of hydrogen, C1-6 alkyl, $SO_2$—C1-6 alkyl, C3-7 cycloalkyl and C3-7 heterocyclyl, optionally substituted by 1-4 substituents selected from the group consisting of halogen, cyano, hydroxyl, C1-6 alkyl and C1-6 alkoxy, preferably Y3 and Y4 are independently selected from the group consisting of hydrogen, C1-6 alkyl, and $SO_2$—C1-6 alkyl.

alternatively, Y3 and Y4 together with the nitrogen atom to which they are attached, form C3-7 heterocyclyl, more preferably the C3-7 heterocyclyl is piperidinyl, morpholinyl, thiomorpholinyl, dioxidothiomorpholinyl, oxidothiomorpholinyl and pyrrolidinyl, which are substituted by 1-4 substituents selected from the group consisting of halogen, cyano, hydroxyl, oxo, C1-6 alkyl and C1-6 alkoxy, more preferably Y3 and Y4 are independently selected from the group consisting of hydrogen, C1-6 alkyl, and SO$_2$—C1-6 alkyl, Y3 and Y4 together with the nitrogen atom to which they are attached, form morpholin-4-yl, piperidin-1-yl, pyrrolidin-1-yl, and 1,1-dioxido-thiomorpholin-4-yl;

more preferably Y3 and Y4 are independently selected from the group consisting of hydrogen, methyl and SO$_2$-methyl, Y3 and Y4 together with the nitrogen atom to which they are attached, form morpholinyl, piperidinyl and dioxothiomorpholinyl;

more preferably Y3 and Y4 are independently selected from the group consisting of hydrogen and methyl and SO$_2$-methyl, Y3 and Y4 together with the nitrogen atom to which they are attached, form morpholin-4-yl, piperidin-1-yl and 1,1-dioxido-thiomorpholin-4-yl.

more preferably Y3 and Y4 are independently selected from the group consisting of hydrogen and methyl, Y3 and Y4 together with the nitrogen atom to which they are attached, form morpholin-4-yl, piperidin-1-yl and 1,1-dioxido-thiomorpholin-4-yl.

Chemical Description and Terminology

Unless otherwise indicated, the following definitions are set forth to illustrate and define the meaning and scope of the various terms used to describe the disclosure herein.

The following definitions of the general terms apply irrespective of whether the terms in question appear alone or in combination.

The nomenclature used in this application is based on AutoNom™ 2000, a Beilstein Institute computerized system for the generation of IUPAC systematic nomenclature. Chemical structures shown herein were obtained using ChemDraw version 12. Any open valency appearing on a carbon, oxygen, sulfur or nitrogen atom in the structures herein indicates the presence of a hydrogen atom.

The term "substituted", unless specifically defined otherwise, means that the specified group or moiety can bear 1, 2, 3, 4, 5 or 6 substituents. Where any group carries multiple substituents and a variety of possible substituents is provided, the substituents are independently selected and need not be the same.

The term "unsubstituted" means that the specified group bears no substituents.

The term "optionally substituted" means that the specified group is unsubstituted or substituted by one or more substituents, independently selected from the group consisting of the group of possible substituents.

When indicating the number of substituents, the term "one or more" means from one substituent to the highest possible number of substitution, i.e. replacement of one hydrogen up to replacement of all hydrogens by substituents. 1, 2, 3, 4 or 5 substituents are preferred, unless specifically defined otherwise.

The term "halogen" refers to fluorine, chlorine, bromine and iodine, in particular fluorine.

The term "lower-alkyl" denotes a saturated straight- or branched-chain group containing from 1 to 6 carbon atoms, which is interchangeable with C1-6 alkyl described in the present specification. The examples of C1-6 alkyl include methyl, ethyl, propyl, isopropyl, n-butyl, isobutyl, sec-butyl or tert-butyl, as well as those groups specifically illustrated by the examples herein below. In particular lower-alkyl groups are methyl and n-butyl.

The term "lower-alkoxy" denotes a group —O—R wherein R is lower-alkyl as defined above.

The term "cycloalkyl" refers to a monovalent saturated cyclic hydrocarbon radical of 3 to 7 ring carbon atoms, in particular 3 to 6 carbon atoms, such as cyclopropyl, cyclobutyl, cyclopentyl or cyclohexyl, as well as those groups specifically illustrated by the examples herein below.

The term "heterocyclyl" refers to a saturated or partly unsaturated monocyclic or polycyclic ring containing a heteroatom, preferably 3 to 7 membered saturated or partly unsaturated monocyclic ring containing one, two or three ring heteroatoms selected from N, O and S. One or two ring heteroatoms are preferred. In particular, heterocyclyl are 4 to 6 membered heterocyclyl comprising one or two ring heteroatoms selected from N, O and S. S is optionally substituted by two oxo groups. Examples for heterocyclyl moieties are pyrrolidinyl, tetrahydro-furanyl, tetrahydropyranyl, tetrahydro-thienyl, tetrahydro-pyridinyl, tetrahydro-pyrryl, azetidinyl, thiazolidinyl, oxazolidinyl, piperidinyl, morpholinyl, thiomorpholinyl, 1,1-dioxido-thiomorpholin-4-yl, piperazinyl, azepanyl, diazepanyl, oxazabicycloheptanyl or dihydro-oxazolyl, as well as those groups specifically illustrated by the examples herein below. Specific heterocyclyls include morpholin-4-yl, piperidin-1-yl, pyrrolidin-1-yl, thiomorpholin-4-yl, and 1,1-dioxido-thiomorpholin-4-yl, preferably, the heterocyclyl is morpholin-4-yl, pyrrolidin-1-yl, and 1,1-dioxido-thiomorpholin-4-yl.

The term "aryl" refers to a monovalent aromatic carbocyclic ring system, comprising 6 to 14, in particular 6 to 10, carbon atoms and having at least one aromatic ring or multiple condensed rings in which at least one ring is aromatic. Examples for aryl are phenyl, naphthyl, biphenyl or indanyl, as well as those groups specifically illustrated by the examples herein below. Preferred aryl is phenyl. Aryl can also be substituted e.g. as defined below and in the claims.

The term "heteroaryl" refers to an aromatic group containing heteroatoms, preferably an aromatic 5 to 6 membered monocyclic ring or 9 to 10 membered bicyclic ring containing 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl or isoquinolinyl, as well as those groups specifically illustrated by the examples herein below. Heteroaryl can also be substituted e.g. as defined below and in the claims. More particularly heteroaryl groups are 5-fluoro-pyridine-2-yl.

The term "lower-alkyl substituted by halogen" refers to lower-alkyl groups which are mono- or multiply substituted with halogen. Examples of lower-alkyl substituted by halogen groups are e.g. CFH$_2$, CF$_2$H, CF$_3$, CF$_3$CH$_2$, CF$_3$(CH$_2$)$_2$, (CF$_3$)$_2$CH or CF$_2$H—CF$_2$, as well as those groups specifically illustrated by the examples herein below.

The term "lower-alkyl substituted by hydroxy" denotes a lower-alkyl group as defined above wherein at least one of the hydrogen atoms of the alkyl group is replaced by a hydroxy group. Examples of lower-alkyl substituted by hydroxy include but are not limited to methyl, ethyl, propyl, isopropyl, isobutyl, sec-butyl, tert-butyl, pentyl or n-hexyl substituted by one or more hydroxy group(s), in particular with one, two or three hydroxy groups, preferably with one or two hydroxy group.

Compounds of formula I, II, III and IV can form pharmaceutically acceptable acid addition salts. Examples of such pharmaceutically acceptable salts are salts of compounds of formula I, II, III and IV with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula I, II, III and IV which comprise an acidic group, such as e.g. a COOH group, can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts.

The term "pharmaceutically acceptable esters" embraces derivatives of the compounds of formula I, II, III and IV, in which a carboxy group has been converted to an ester. Lower-alkyl, lower-alkyl substituted by hydroxy, lower-alkyl substituted by lower-alkoxy, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aryl-lower-alkyl esters are examples of suitable esters. The methyl, ethyl, propyl, butyl and benzyl esters are preferred esters. The term "pharmaceutically acceptable esters" furthermore embraces compounds of formula I, II, III and IV in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Preparation Method

The disclosure further relates to a process for the manufacture of compounds of formula II as defined above, which process comprises:

a) reacting a compound of formula IV

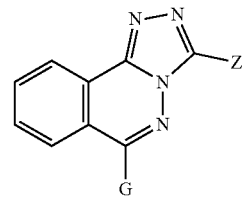

IV with

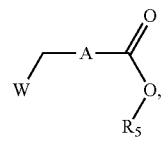

V wherein G and W are Cl, Br, I, OH, OTs, OTf and OMs and the like; $R_5$ represent alkyl, methyl, ethyl, tert-butyl and benzyl, then reacting a compound of formula (1-3)

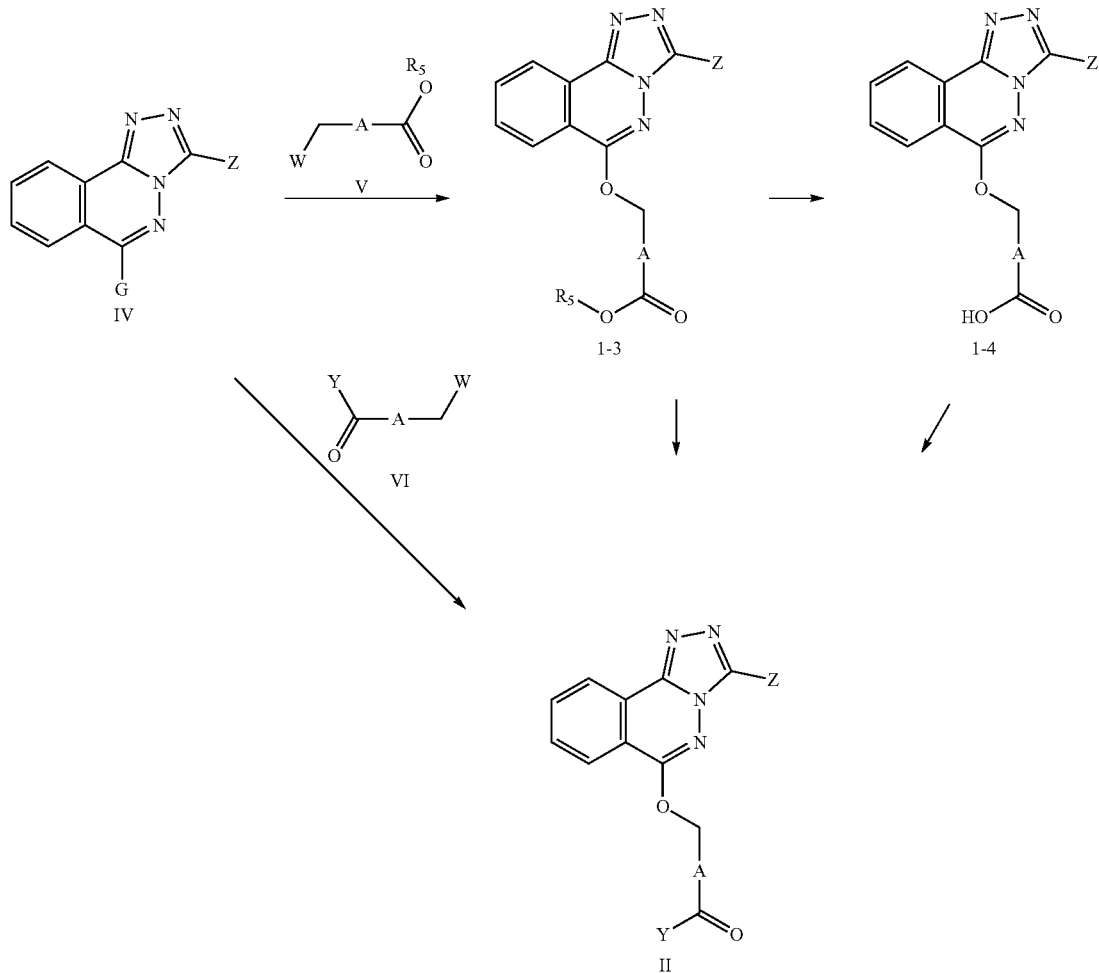

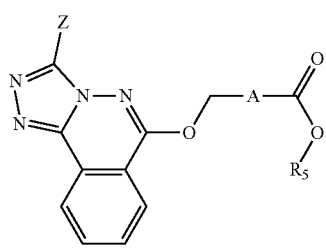

with Y or, b) reacting a compound of formula (1-4):

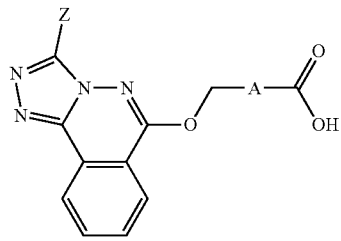

with Y; or c) saponificating a compound of formula (1-3) to a compound of formula 1-4, which is then reacted with Y; or d) reacting a compound of formula

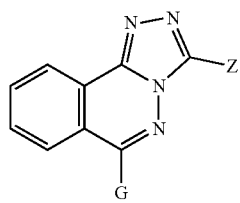   IV with

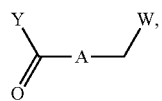   VI wherein Z, Y, A are as defined above.

The reaction of the compound of formula

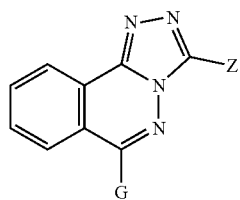   IV with

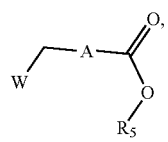   V wherein G and W represent Cl, Br, I, OH, OTs, OTf and OMs can be carried out under conditions as described in the examples or under conditions well known to the person skilled in the art. For example, the reaction can be performed in the presence of LDA, NaH, Potassium tert-butoxide or Sodium tert-butoxide and the like, and in a suitable solvent like dioxane at room temperature e.g. at 20° C. Alternatively, the reaction can be carried out under a condition for preparing an ether, for example, under Mitsunobu condition such as PPh$_3$ and DEAD, a phase transfer catalyst such as TBAB and crown ether.

The reaction of the compound of formula

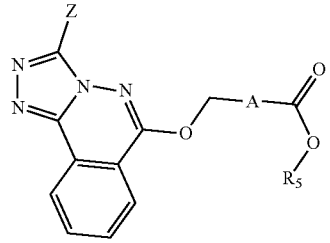   1-3 with Y to give the compound of formula I can be carried out under conditions as described in the examples or under conditions well known to the person skilled in the art. For example, the reaction can be performed in the presence of Al(Me)$_3$, and in a suitable solvent like dioxane at elevated temperatures e.g. at 85-95° C.

The reaction of the compound of formula

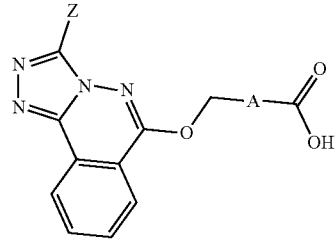   (1-4)

with Y to give a compound of formula II can be carried out under conditions as described in the examples or under conditions well known to the person skilled in the art. For example, the reaction can be performed in the presence of Hünigs Base (N,N-diisopropylethylamine) and O-(benzotriazol-1-yl)-N,N,N',N'-tetramethyluronium tetrafluoroborate in a suitable solvent like dimethylformamide at room temperature. Alternatively, the reaction can be performed in the presence of 1,1'-carbonyldiimidazole in a suitable solvent like dimethylformamide at elevated temperatures e.g. at 80° C. Furthermore, the reaction can be performed in the presence of 1-ethyl-3-(3-dimethylaminopropyl) carbodiimide hydrochloride, N1-hydroxybenzotriazole and Hunigs Base (N, N-diisopropylethylamine) in a suitable solvent like dichloromethane at room temperature.

The saponification reaction of a compound of formula

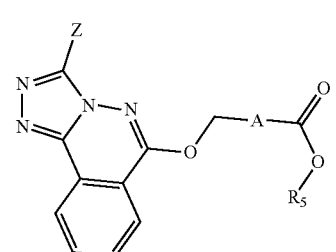   (1-3)

to give a compound of formula (1-4) can be carried out under conditions as described in the examples or under conditions well known to the person skilled in the art. For example, the reaction can be performed in the presence of NaOH, and in a suitable solvent like water at room temperature. Alternatively, the reaction can be performed in the presence of NaOH or LiOH, and in a suitable solvent like THF or water at room temperature. Or the reaction can be carried out under other conditions well known to the person skilled in the art, such as the deprotection of Bn by hydrogenation and hydrolysis of t-Bu under acidic conditions.

The reaction of a compound of formula

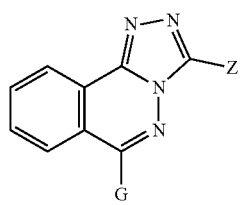

IV with

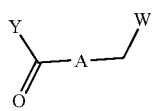

VI to give a compound of formula II can be carried out under conditions as described in the examples or under conditions well known to the person skilled in the art. For example, the reaction can be performed in the presence of LDA, NaH, potassium tert-butoxide or sodium tert-butoxide, and in a suitable solvent (1,4-dioxane, THF or DMF) at room temperature such as 20° C. Or the reaction can be performed under Mitsunobu condition such as PPh3 and DEAD, a phase transfer catalyst such as TBAB and crown ether to give the ether compound. The reaction is performed in a suitable solvent such as 1,4-dioxane, THF or DMF at elevated temperatures e.g. at 80° C., in the presence of a corresponding base or catalysts.

The present disclosure relates to the formula (II) compound defined above, which is prepared by the preparation method described defined above.

Compounds of formula II and pharmaceutically acceptable salts in the present disclosure can be prepared by the following method.

If the preparation method is not described in the examples, then the formula (II) compound and its intermediate products can be prepared according to a similar method or by the method described above. The known raw materials in this field may be commercially available, or may be prepared in a similar way based on known methods or known methods in the field.

It is understandable that the formula (II) compound of the present disclosure can be transformed by the functional group to become the derivatives which can be converted into the parent compound in the body.

If the preparation method is not described in the examples, then the formula (II) compound and its intermediate products can be prepared according to a similar method or by the method described above. The known raw materials in this field may be commercially available, or may be prepared in a similar way based on known methods or known methods in the field.

It is understandable that the formula (II) compound of the present disclosure can be transformed by the functional group to become the derivatives which can be converted into the parent compound in the body.

As mentioned above, the new compound of the present disclosure and pharmaceutical acceptable salt and ester thereof are of important pharmacological properties and can act as an inverse agonist for the α5-GABA$_A$ receptor. Therefore, the present disclosure can be used alone or in combination with other drugs for treatment or prevention of diseases mediated by GABAA receptor ligand containing α5 subunits. The diseases include but are not limited to pain, alzheimer's disease, multi-infarct dementia and stroke.

Therefore, the present disclosure also relates to a pharmaceutical composition, which comprises a compound as defined above and an acceptable carrier and/or adjuvant.

Also, the present disclosure also includes compounds as described above, used in the preparation of a medicament to treat or prevent α5-GABA$_A$ receptor related diseases, especially in the treatment or prevention of the following diseases: pain, alzheimer's disease, multiple infarction dementia and stroke.

Preferably, the compound can be used in the preparation of a medicament for the treatment or prevention of pain.

More preferably, the compound can be used in the preparation of a medicament for the treatment or prevention neuropathic pain, inflammatory pain and cancer pain.

As used herein, "cancer pain" represents the pain occurs during the development process of malignant tumor. Currently, it is thought that there are three mechanisms of cancer pain, i.e. the pain caused directly by cancer development, the pain caused after cancer treatment and the concurrent painful diseases of cancer patients.

As used herein, "neuropathic pain" represents the pain caused by the primary damage and dysfunction of the nervous system.

As used herein, "inflammatory pain" represents the pain caused by local acute inflammation or chronic inflammation.

As used herein, "treatment" also includes preventive administration, preventing or eliminating the diseases after the establishment of the diseases.

As used herein, "patient" is defined as any warm-blooded animal, including but not limited to mice, cavies, dogs, horses or humans. Preferably, the patient is human.

As used herein, "acute pain" is defined as the pain caused by the injury of skin, body structure or internal organs and/or noxious stimulation of the diseases, or the pain caused by the abnormal function of muscle or internal organs that does not produce a real tissue injury.

As used herein, "chronic pain" is defined as the pain that lasts a period of time that exceeds the common course or healing time of acute diseases, or that is associated with the chronic pathological processes that cause continuous pain, or that relapses for several months or years with certain interval. If pain still exists after treatment that should cure the disease or exceeding the common course, such pain can be regarded as chronic pain. The time duration that the pain lasts depends on the nature of pain and the treatment process associated with pain. If the pain exceeds common treatment process, then this pain is chronic. Chronic pain includes but not limits to headache, facial pain, neck pain, shoulder pain, thoracic pain, abdominal pain, back pain, waist pain, lower limb pain, muscle and bone pain, somatoform disorder associated pain, visceral pain, painful diabetic neuropathy, vascular pain, gout, arthritis pain, cancer pain, autonomic nerve reflex pain, the pain caused by infectious diseases such as AIDS and herpes zoster, the pain caused by autoimmune disease such as rheumatism, the pain caused by acute or chronic inflammation, postoperative pain and post-burning pain.

The drugs disclosed by this disclosure can efficiently treat the chronic pain defined as above, and the drugs disclosed by this disclosure can be used to treat hyperalgia accompanied with other diseases, including hyperalgesia, allodynia, algesia enhancement and pain memory enhancement. This disclosure will improve the treatment of pain.

As used herein, "headache" can be divided into primary headache and secondary headache. Primary headache includes tension headache, migraine headache and cluster headache, and secondary headache is caused by other diseases. Headache is caused when pain sensitive tissue on head and face undergoes lesion or get stimulated. These pain sensitive tissues are distributed on scalp, face, oral cavity and throat. Since they are mainly muscles and vessels in head with abundant nerve fibers and sensitive to pain, headache is caused when these tissues are injured.

As used herein, "facial pain" includes but is not limited to trigeminal neuralgia, atypical facial pain, facial palsy and facial spasm.

As used herein, "trigeminal neuralgia" is a unique chronic painful disease, also referred as tic douloureux, representing transient, paroxysmal and repeated electric shock-like severe pain in trigeminal nerve area, or accompanied with ipsilateral facial spasm. Trigeminal neuralgia can be divided into two classes: primary and secondary. Primary trigeminal neuralgia means no neurological sign is found clinically and no organic disease is detected. Secondary trigeminal neuralgia means neurological signs are found clinically and organic diseases such as tumor and inflammation are detected.

As used herein, "atypical facial pain" represents pain caused by various diseases, appearing as persistent burning pain, non-intermittent and independent of particular action or stimulation. The pain is often bilateral and exceeds the area of trigeminal nerve to even cervical skin. The etiology can be the stimulation of nasosinusitis, malignant tumor, jaw and skull base infection or injured trigeminal nerve.

As used herein, "neck pain, back pain, shoulder pain" represent the pain caused by acute or chronic muscle strain and bone joint degeneration and injury. The common diseases that cause neck, shoulder and upper limb pain include cervicoshoulder myofascitis, neck desmitis, cervical spondylopathy, scapulohumeral periarthritis, thoracic outlet syndrome, external humeral epicondylitis, etc. Alternatively, these terms represent the pain cause by autoimmune diseases rheumatoid arthritis, ankylosing spondylitis and rheumatic arthritis. Other diseases that can cause neck pain, back pain and shoulder pain are tumors on neck and shoulder, neuritis, arteriovenous disease and various infections as well as referred pain induced by lesions of thoracic and abdominal organs.

As used herein, "thoracic, abdominal, and back pain" represent the pain caused by diseases in thoracic and abdominal organs and thoracic and abdominal wall tissues, including but not limited to intercostal neuralgia, intercostal chondritis, angina pectoris, abdominal pain (acute abdominal organ pain) and waist and back myofascial pain syndrome.

As used herein, "waist pain, lower limb pain" represent low back, lumbosacral, sacroiliac, hip, buttocks and lower limb pain. Generally, waist pain and lower limb pain are not independent diseases, but a common feature of various diseases, with diverse clinical manifestation and complex etiology. Such pain is mainly induced by degeneration and injury, including but not limited to the pain involving lumbar disc herniation, acute lumbar sprain, ischialgia, osteoporosis, third lumbar trans-verse process syndrome, piriformis syndrome, knee osteoarthritis, coccygodynia and calcanodynia.

As used herein, "muscle and bone pain" includes but is not limited to myofascial pain, trauma-caused pain and chronic regional pain syndrome.

As used herein, "painful diabetes" represents the pain caused by nerve injury concurrent with diabetes. The nerve injury in diabetes is caused at least partly by blood flow reduction and hyperglycemia. Some diabetes patients do not suffer neuropathy, while others suffer this disease at early stage. Diabetic neuropathy can be divided into mononeuropathy that involves one or several lesion sites and systemic polyneuropathy. The polyneuropathy can be dispersive and symmetrical, generally and mainly involving mode of sensation (Merrit's Textbook of Neurology, the 9th version, edited by LPRownland LP). The manifestation of diabetic neuropathy includes plant nerve dysfunction, and cause dysregulation involving heart, smooth muscle and gland, resulting in hypotension, diarrhea, constipation and impotence. Diabetic neuropathy often develops in stages. The early stage takes place in nerve ending area. Plant neuropathy or sensory neuropathy occurs in feet and brain neuropathy occurs in face and periocular area with intermittent pain and the sense of tingling. In the following stages, the pain become more severe and occurs more frequently. Finally, when analgesia happens in one area, the disease develops into painless neuropathy. Due to lack of pain as the sign of injury, the risk of severe tissue damage is greatly increased.

As used herein, "visceral pain" includes but is not limited to the pain of inflammatory bowel syndrome (IBS), with or without chronic fatigue syndrome (CFS), inflammatory bowel disease (IBD) and interstitial cystitis.

As used herein, "vascular pain" represents the pain generated by the following one or more factors. Firstly, improper perfusion of tissue, resulting in temporary or continuous ischemia, e.g. the ischemia in limb muscles during physical exercise. Secondly, delayed change, e.g. ulcer or gangrene in skin or abdominal organs. Thirdly, the sudden and accelerated change of diameter of great vessels, e.g. the change of arterial aneurysm. Fourthly, aortic rupture, resulting in blood spillover and the stimulation of nociceptive fibers in peritoneum or pleura parietal layers. Fifthly, strong cramp caused by the severe stimulation of artery endothelium by intra-arterial injection. Sixthly, the damage of venous return, leading to a large number of edema of rapidly expanded fascia compartment (Bonica et al. The Management of Pain, Volume 1 (the 2nd version), Philadelphia; Leas & Feboger, 1990). The examples include but are not limited to arteriosclerosis obliterans, thromboangiitis angiitis, acute arterial closure, embolism, congenital arteriovenous aneurysm, vasospasm diseases, Rayaud's disease, acrocyanosis, acute venous closure, thrombophlebitis, varicosity and lymphedema.

As used herein, "autonomic nerve reflex pain" represents the pain caused by "reflex sympathetic dystrophy". For reflex sympathetic dystrophy, after the body suffers an acute or chronic injury, severe ambulatory pain occurs and the body is sensitive to the sense of touch and pain, probably accompanied with edema and blood disorder, following symptoms like skin and musculoskeletal nutrition dystrophia and atrophy.

As used herein, "postoperative pain" represents a complex physiological response of body to the disease itself and the tissue injury caused by operation, showing an unpleasant psychological and behavior experience.

As used herein, "arthritis pain" includes but is not limited to the pain caused by osteoarthritis, rheumatoid arthritis, joint ankylosing spondylitis, psoriatic arthropathy, gout, pseudo gout, infectious arthritis, tendinitis, bursitis, bone damage and joint soft tissue inflammation.

As used herein, "postherpetic neuralgia" represents the subcutaneously long-standing severe pain in rash site after the healing of the rash of herpes zoster.

As used herein, "nociceptive pain" represents the pain caused by the tissue injury delivered by nociceptors, or the pain caused by the extended excitement of nociceptors. The pain caused by the extended excitement of nociceptors can be induced by both the persisting noxious stimulation of nociceptors, or the sensitization thereof, or both, or they can be induced by these factors and extended by their persistence, various reflex mechanisms and other factors.

Pharmaceutical Compositions

The present disclosure provides the use of pharmaceutical compositions comprising a therapeutically effective amount of the inverse agonists for the alpha 5 GABA A receptor. While the inverse agonists for the alpha 5 GABA A receptor for use in therapy according to the disclosure may be administered in the form of raw chemical compounds, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the present disclosure provides a pharmaceutical composition comprising the inverse agonists for the alpha 5 GABA A receptor, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions for use according to the disclosure may be those suitable for oral, rectal, bronchial, nasal, pulmonal, topical (including buccal and sublingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the present disclosure, in which matrices may be in the form of shaped articles, e.g. films or microcapsules.

The compound for use according to the present disclosure, together with a conventional additives, or diluent, may thus be prepared into the form of pharmaceutical compositions and unit dosages thereof. Such forms include solids, and in particular tablets, filled capsules, powder and pellet forms, and liquids, in particular aqueous or nonaqueous solutions, suspensions, emulsions, elixirs, and capsules filled with the same, all forms for oral administration, suppositories for rectal administration, and sterile injectable solutions for parenteral use. Such pharmaceutical compositions and unit dosage forms thereof may comprise conventional ingredients in conventional proportions, with or without additional active compounds or ingredients, and such unit dosage forms may contain any suitable effective amount of the active ingredient commensurate with the intended daily dosage range to be employed.

The compound for use according to the present invention can be administered in a wide variety of oral and parenteral dosage forms. It will be obvious to those skilled in the art that the following dosage forms may comprise, as the active component, either a compound of the present disclosure or a pharmaceutically acceptable salt of a compound of the present disclosure.

For preparing pharmaceutical compositions from a compound for use according to the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in water-polyethylene glycol.

The compound for use according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis, the compound of the present disclosure may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co., Easton, Pa.).

The amount of active components in unit dosage form varies based on particular application and the efficacy of active components, which can be adjusted from 0.01 mg to about 0.1 g. For example, in medical application, 0.01 to about 100 mg of such medicine can be administrated in capsule three times a day. If necessary, the composition can also contain other compatible therapeutic agents.

Therapeutic Method

For therapeutic application, the original dose of the compound used in this invention is 0.001 mg to 10 mg/kg body weight per day. Nevertheless, the dose can vary based on patient's requirement, the severity of the disease to be treated and the compound to be used. Generally speaking, the dose that is below the optimal dose of the compound is used at the beginning, then gradually increasing the dose to achieve the optimal effect. For convenience, total daily dose can be further divided when desired.

The pharmaceutical composition of this invention can also be used in combination with other therapeutic agents for the treatment of pain, Alzheimer's disease, multi-infarct dementia and stoke simultaneously, including but not limited to morphine and Gabapentin etc.

Therefore, this invention provides a drug for treating pain, Alzheimer's disease, multi-infarct dementia and stoke. The drug is not only effective, but also has not obvious side effects. Another purpose of this invention is to provide a drug with high safety to special patients such as elderly people and patients suffering liver or kidney failure or cardiovascular diseases.

EXAMPLES

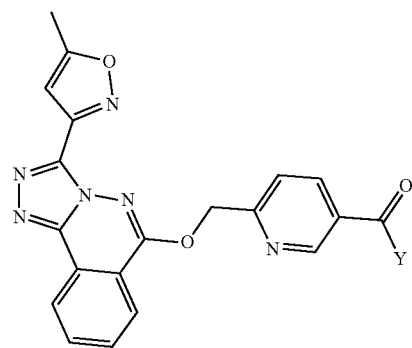

1-30

Scheme 1

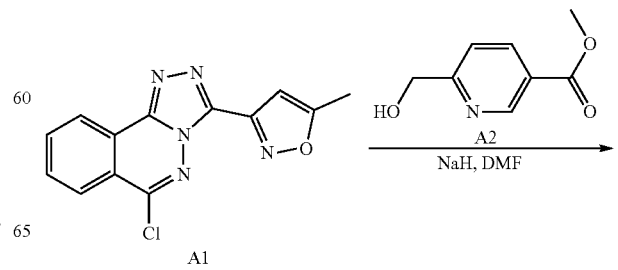

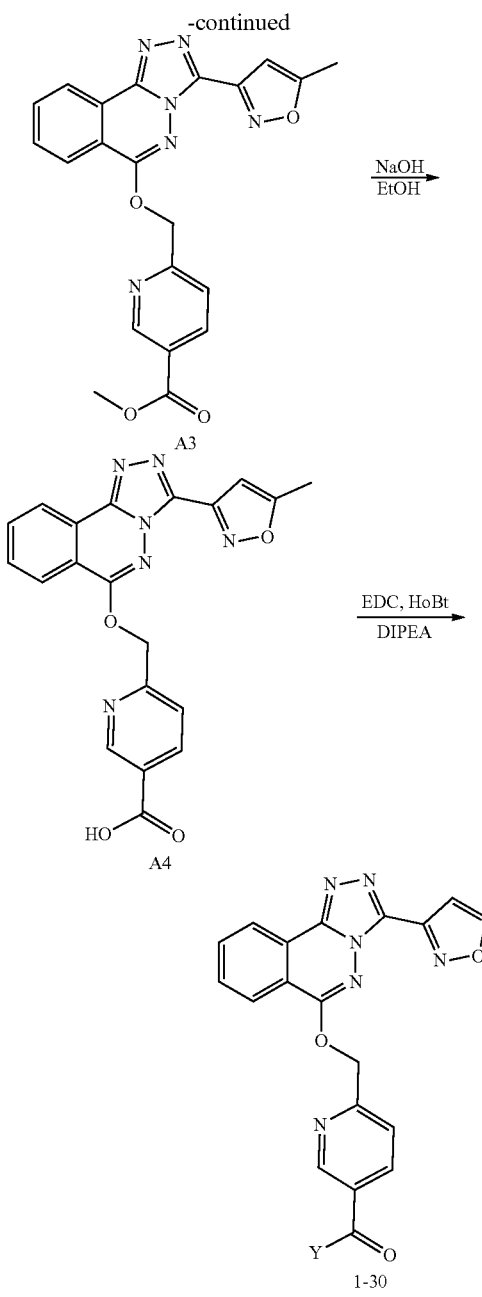

The Experimental Procedures

Step 1

6-[3-(5-Methyl-isoxazol-3-yl)-[1,2,4]triazolo[3,4-a] phthalazin-6-yloxymethyl]-nicotinic acid methyl ester (A3)

To a solution of A2 (1.75 g, 10.5 mmol) (Refer: Leslie J. Street, Francine Sternfeld, et al. *J. Med. Chem.* 2004, 47, 3642-3657) in DMF (150 mL) was added NaH (400 mg, 1.9 eq) at 0° C. under Ar and stirred for 15 minutes at this temperature. Then A1 (Refer.: Sternfeld, Francine; Carling, Robert W, et al. *J. Med. Chem.*, 2004, 47, 2176-2179)(1.5 g, 5.2 mmol) was added and the mixture was stirred at RT for 1.5 h. TLC (DCM:MeOH=20:1, Rf=0.3) showed the starting material was consumed completely. 30 mL of ice water was added to the reaction mixture and the mixture was adjusted to pH 5~6 with aqueous citric acid (2N), concentrated to remove most DMF. The residue was partitioned between ethyl acetate (300 mL) and water (300 mL). The separated organic layer was washed with water (200 mL*3) and brine (50 mL), dried over anhydrous $Na_2SO_4$ and concentrated. The residue was purified by silica gel chromatography eluted with DCM to give a crude product (1.19 g, 54.2% yield).

$^1$H NMR (400 MHz, CDCl3) δ: 9.24 (d, 1H), 8.71~8.69 (d, 1H), 8.36~8.32 (m, 2H), 7.98 (t, 1H), 7.87~7.85 (t, 2H), 6.79 (s, 1H), 5.82 (s, 2H), 3.96 (s, 3H), 2.58 (s, 3H).

Step 2

6-((3-(5-methylisoxazol-3-yl)-[1,2,4]triazolo[3,4-a] phthalazin-6-yloxy)methyl)nicotinic acid (A4)

To a solution of A3 (1.8 g, 4.3 mmol) in EtOH (20 mL) was added aqueous NaOH solution (2.5N, 2.5 mL) at RT and stirred for 1 hour. TLC (DCM:MeOH=10:1, Rf=0.2) showed the starting material was consumed completely. The reaction mixture was adjusted to pH 5~6 with aqueous citric acid (2N), filtered and the filtrate was washed with EtOH (5 mL) and DCM (8 mL). Then the filter cake was added to DCM (10 mL) and stirred for 1 h. The mixture was filtered by suction filtration and the filter cake was washed with DCM (2 mL) once, dried to give a crude product (550 mg, 31.6%).

Step 3

Example 01

6-((3-(5-methylisoxazol-3-yl)-[1,2,4]triazolo[3,4-a] phthalazin-6-yloxy)methyl)-N-morpholinonicotinamide (01)

A DMF solution (5 mL) containing HOBt (68 mg, 0.496 mmol), EDCI (95 mg, 0.496 mmol), and A4 (100 mg, 0.248 mmol) was stirred at room temperature for 10 mins under Ar. 4-aminomorpholine (CAS: 4319-49-7) (30.6 mg, 0.3 mmol) and DIPEA (130 mg, 0.992 mmol) were added to the reaction mixture successively. The mixture was stirred at RT for 12 h. TLC (DCM:MeOH=10:1, Rf=0.4) showed the starting material was consumed completely. DCM (25 mL) was added to the reaction mixture and then the resulting mixture was poured into 30 mL water, and adjusted to pH 5~6 with aqueous citric acid (2N). The organic layer was separated and washed with water (20 mL*2), dried over anhydrous $Na_2SO_4$, and concentrated. The residue was purified by preparative TLC to give product (36 mg, 29.7%) as a white solid. $^1$H NMR (400 MHz, DMSO-d6) δ: 9.76 (s, 1H), 8.99 (s, 1H), 8.61~8.60 (d, 1H), 8.59 (d, 1H), 8.38~8.36 (m, 2H), 8.23~7.85 (m, 2H), 6.93 (s, 1H), 5.78 (s, 2H), 3.68 (s, 4H), 2.90 (s, 4H), 2.58 (s, 3H); LC-MS: m/z (ES+) for $C_{24}H_{22}N_8O_4$ 487.15 [M+1]$^+$.

Example 02

(R)—N-(1-hydroxypropan-2-yl)-6-((3-(5-methyl-isoxazol-3-yl)-[1,2,4]triazolo[3,4-a]phthalazin-6-yloxy)methyl)nicotinamide (02)

The procedure was the same as example 1: The title product (02) was obtained from the starting materials A4 and D-amino-propanol (CAS: 35320-23-1): (35 mg, 20.5%) as a white solid. $^1$H NMR (400 MHz, DMSO-d6) δ: 9.06~9.05 (d, 1H), 8.60~8.58 (d, 1H), 8.37~8.35 (d, 2H), 8.27 (d, 1H), 8.13 (t, 1H), 8.00 (t, 1H), 7.87~7.85 (d, 1H), 6.93 (s, 1H), 5.77 (s, 2H), 4.77~4.74 (t, 1H), 4.05~4.02 (m, 1H), 3.45 (m, 1H), 3.37 (m, 1H), 3.33 (s, 1H), 2.58 (s, 3H), 2.01~1.99 (m, 1H), 1.15~1.13 (d, 3H); LC-MS: m/z (ES+) for $C_{23}H_{21}N_7O_4$ 460.14 [M+1]$^+$.

Example 03

N-((1S,2S)-2-hydroxycyclopentyl)-6-(((3-(5-methyl-isoxazol-3-yl)-[1,2,4]triazolo[3,4-a]phthalazin-6-yl)oxy)methyl)nicotinamide (03)

The procedure was the same as example 1: The title product was obtained from the starting materials A4 and trans-(1S,2S)-2-Aminocyclopentanol Hydrochloride (CAS: 68327-04-8): (75 mg, 65.8%) as a white solid. $^1$H NMR (400 MHz, DMSO-d6) δ: 9.04 (d, 1H), 8.60~8.58 (d, 1H), 8.48~8.46 (d, 1H), 8.38~8.36 (d, 1H), 8.28~8.25 (d, 1H), 8.15~8.12 (t, 1H), 8.02~8.00 (t, 1H), 7.87~7.85 (d, 1H), 6.93 (s, 1H), 5.78 (s, 2H), 4.81~4.80 (d, 1H), 4.02~3.99 (m, 2H), 2.58 (s, 3H), 2.02~1.99 (m, 2H), 1.87~1.46 (m, 4H); LC-MS: m/z (ES+) for $C_{25}H_{23}N_7O_4$ 486.19 [M+1]$^+$.

Example 04

N-cyclopropyl-6-(((3-(5-methylisoxazol-3-yl)-[1,2,4]triazolo[3,4-a]phthalazin-6-yl)oxy)methyl) nicotinamide (04)

The procedure was the same as example 1: The title product was obtained from the starting materials A4 and cyclopropylamine (CAS: 765-30-0): 54 mg (50%) as a white solid. $^1$H NMR (400 MHz, DMSO-d6) δ: 9.02~9.01 (d, 1H), 8.69~8.68 (d, 1H), 8.59~8.57 (d, 1H), 8.37~8.35 (d, 1H), 8.25~8.23 (d, 1H), 8.13~8.11 (t, 1H), 8.01~7.99 (t, 1H), 7.86~7.84 (d, 1H), 6.93 (d, 1H), 5.76 (d, 2H), 2.87~2.86 (m, 1H), 2.57 (s, 3H), 0.73~0.71 (m, 2H), 0.59~0.58 (m, 2H); LC-MS: m/z (ES+) for $C_{23}H_{19}N_7O_3$ 442.15 [M+1]$^+$.

Example 05

N-(1-methyl-1H-pyrazol-4-yl)-6-(((3-(5-methyl-isoxazol-3-yl)-[1,2,4]triazolo[3,4-a]phthalazin-6-yl)oxy)methyl)nicotinamide (05)

The procedure was the same as example 1: The title product was obtained from the starting materials A4 and 4-amino-1-methylpyrazole (CAS: 69843-13-6): 53 mg (44.3%) as a white solid. $^1$H NMR (400 MHz, DMSO-d6) δ: 10.67 (s, 1H), 9.15 (s, 1H), 8.61~8.59 (d, 1H), 8.40~8.36 (t, 2H), 8.16~8.12 (t, 1H), 8.04~8.01 (m, 2H), 7.93~7.91 (d, 1H), 7.58 (d, 1H), 6.95 (s, 1H), 5.80 (s, 2H), 3.83 (s, 3H), 2.59 (s, 3H); LC-MS: m/z (ES+) for $C_{24}H_{19}N_9O_3$ 482.13 [M+1]$^+$.

Example 06

N,N-dimethyl-6-(((3-(5-methylisoxazol-3-yl)-[1,2,4]triazolo[3,4-a]phthalazin-6-yl)oxy)methyl)nicotinamide (06)

The procedure was the same as example 1: The title product was obtained from the starting materials A4 and dimethylamine hydrochloride (CAS: 506-59-2): 60 mg (70%) as a white solid. $^1$H NMR (400 MHz, DMSO-d6) δ: 8.67 (s, 1H), 8.57 (d, 1H J=8.0), 8.35 (d, 1H J=8.0), 8.11 (t, 1H J=7.6), 7.99~7.93 (m, 2H), 7.81 (d, 1H J=8.0), 6.91 (s, 1H), 5.74 (s, 2H), 3.00 (s, 3H), 2.92 (s, 3H), 2.57 (s, 3H). LC-MS: m/z (ES+) for $C_{22}H_{19}N_7O_3$ 430.12 [M+1]$^+$.

Example 07

N-ethyl-6-(((3-(5-methylisoxazol-3-yl)-[1,2,4]tri-azolo[3,4-a]phthalazin-6-yl)oxy)methyl)nicotina-mide (07)

The procedure was the same as example 1: The title product was obtained from the starting materials A4 and ethylamine hydrochloride (CAS: 557-66-4): 105 mg, 75% as a white solid. $^1$H NMR (400 MHz, DMSO-d6) δ: 9.03 (d, 1H J=1.6), 8.72 (t, 1H J=5.2), 8.58 (d, 1H J=8.0), 8.37 (d, 1H J=8.0), 8.26~8.24 (m, 1H), 8.12 (t, 1H J=7.2), 7.99 (t, 1H J=7.2), 7.86 (d, 1H J=8.0), 6.91 (s, 1H), 5.75 (s, 2H), 3.38~3.25 (m, 2H), 2.56 (s, 3H), 1.13 (t, 3H J=7.2); LC-MS: m/z (ES+) for $C_{22}H_{19}N_7O_3$ 430.0 [M+1]$^+$.

Example 08

N-(2-methoxyethyl)-6-(((3-(5-methylisoxazol-3-yl)-[1,2,4]triazolo[3,4-a]phthalazin-6-yl)oxy)methyl)nicotinamide (08)

The procedure was the same as example 1: The title product was obtained from the starting materials A4 and 2-methoxyethylamine (CAS: 109-85-3): 42 mg, 63% as a white solid. $^1$H NMR (400 MHz, DMSO-d6) δ: 9.03 (s, 1H), 8.80 (t, 1H J=4.4), 8.55 (d, 1H J=8.0), 8.34 (d, 1H J=8.0), 8.28~8.25 (m, 1H), 8.10 (t, 1H J=7.2), 7.97 (t, 1H J=7.6), 7.84 (d, 1H J=8.4), 6.87 (s, 1H), 5.73 (s, 2H), 3.50~3.30 (m, 4H), 3.26 (s, 3H), 2.55 (s, 3H); LC-MS: m/z (ES+) for $C_{23}H_{21}N_7O_4$ 460.11 [M+1]$^+$.

Example 09

N-(2-hydroxyethyl)-6-(((3-(5-methylisoxazol-3-yl)-[1,2,4]triazolo[3,4-a]phthalazin-6-yl)oxy)methyl)nicotinamide (09)

The procedure was the same as example 1: The title product was obtained from the starting materials A4 and ethanolamine (CAS: 141-43-5): 45 mg, 63% as a white solid. $^1$H NMR (400 MHz, DMSO-d6) δ: 9.04 (s, 1H), 8.72 (t, 1H J=5.2), 8.57 (d, 1H J=7.6), 8.36 (d, 1H J=7.6), 8.28~8.24 (m, 1H), 8.11 (t, 1H J=7.6), 7.96 (t, 1H J=7.6), 7.85 (d, 1H J=8.4), 6.90 (s, 1H), 5.75 (s, 2H), 4.80 (t, 1H J=5.2), 3.55~3.48 (m, 2H), 3.31~3.38 (m, 2H), 2.56 (s, 3H); LC-MS: m/z (ES+) for $C_{22}H_{19}N_7O_4$ 446.02 [M+1]$^+$.

Example 10

N-(2-butyl)-6-(((3-(5-methylisoxazol-3-yl)-[1,2,4]triazolo[3,4-a]phthalazin-6-yl)oxy)methyl)nicotina-mide (10)

The procedure was the same as example 1: The title product was obtained from the starting materials A4 and iso-butyl amine (CAS: 78-81-9): 10 mg, 16% as off-white solid. $^1$H NMR (400 MHz, DMSO-d6) δ 9.01 (d, J=1.6 Hz, 1H), 8.55 (d, J=7.8 Hz, 1H), 8.34 (dd, J=13.9, 8.1 Hz, 2H), 8.23 (dd, J=8.2, 2.2 Hz, 1H), 8.13-8.06 (m, 1H), 7.99-7.93 (m, 1H), 7.81 (d, J=8.0 Hz, 1H), 6.88 (d, J=0.9 Hz, 1H), 5.73 (s, 2H), 3.90 (dt, J=14.0, 7.1 Hz, 1H), 2.54 (d, J=0.6 Hz, 3H), 1.48 (td, J=13.5, 6.7 Hz, 2H), 1.11 (d, J=6.6 Hz, 3H), 0.84 (t, J=7.4 Hz, 3H); LC-MS: m/z (ES+) for $C_{24}H_{23}N_7O_3$ 458 [M+1]$^+$.

Example 11

6-(((3-(5-methylisoxazol-3-yl)-[1,2,4]triazolo[3,4-a]phthalazin-6-yl)oxy)methyl)-N-(1-methylpiperidin-4-yl)nicotinamide (11)

The procedure was the same as example 1: The title product was obtained from the starting materials A4 and 4-amino-1-methylpiperidine (CAS: 41838-46-4): 75 mg, 65.8% as off-white solid.

$^1$H NMR (400 MHz, DMSO-d6) δ 9.01 (d, J=1.9 Hz, 1H), 8.60-8.47 (m, 2H), 8.30 (d, J=8.1 Hz, 1H), 8.24 (dd, J=8.2, 2.0 Hz, 1H), 8.08 (s, 1H), 7.95 (s, 1H), 7.81 (d, J=8.2 Hz, 1H), 6.87 (s, 1H), 5.72 (s, 2H), 3.86-3.80 (m, 1H), 3.01-2.96 (m, 2H), 2.53 (s, 3H), 2.38-2.31 (m, 5H), 1.85-1.80 (m, 2H), 1.64-1.68 (m, 2H). LC-MS: m/z (ES+) for $C_{26}H_{26}N_8O_3$ 499 [M+1]$^+$.

Example 12

6-(((3-(5-methylisoxazol-3-yl)-[1,2,4]triazolo[3,4-a]phthalazin-6-yl)oxy)methyl)-N-(2-morpholinoethyl)nicotinamide (12)

The procedure was the same as example 1: The title product was obtained from the starting materials A4 and N-(2-aminoethyl) morpholine (CAS: 2038-03-1)): 54 mg, 50% as a white solid. $^1$H NMR (400 MHz, DMSO-d6) δ 9.01 (s, 1H), 8.69 (s, 1H), 8.53 (s, 1H), 8.27 (d, J=35.0 Hz, 2H), 8.08 (s, 1H), 7.95 (s, 1H), 7.82 (s, 1H), 6.87 (s, 1H), 5.72 (s, 2H), 4.02-3.95 (m, 1H), 3.58-3.51 (m, 3H), 3.24-3.01 (m, 4H), 2.53 (s, 3H), 2.43-2.28 (m, 3H), 1.98-1.92 (m, 1H). LC-MS: m/z (ES+) for $C_{26}H_{26}N_8O_4$ 515 [M+1]$^+$.

Example 13

6-(((3-(5-methylisoxazol-3-yl)-[1,2,4]triazolo[3,4-a]phthalazin-6-yl)oxy)methyl)-N-(tetrahydrofuran-3-yl)nicotinamide (13)

The procedure was the same as example 1: The title product was obtained from the starting materials A4 and tetrahydrofuran-3-amine (CAS: 88675-24-5)): 53 mg, 60% as off-white solid. $^1$H NMR (400 MHz, DMSO-d6) δ 9.02 (s, 1H), 8.75 (d, J=6.2 Hz, 1H), 8.52 (d, J=7.9 Hz, 1H), 8.34-8.20 (m, 2H), 8.08 (t, J=7.4 Hz, 1H), 7.94 (t, J=7.7 Hz, 1H), 7.82 (d, J=8.1 Hz, 1H), 6.88 (s, 1H), 5.72 (s, 2H), 4.44 (s, 1H), 3.88-3.76 (m, 2H), 3.68 (dd, J=14.1, 8.1 Hz, 1H), 3.57 (dd, J=8.9, 4.1 Hz, 1H), 2.53 (s, 3H), 2.13 (dt, J=14.9, 8.0 Hz, 1H), 1.96-1.83 (m, 1H).
LC-MS: m/z (ES+) for $C_{24}H_{21}N_7O_4$ 472 [M+1]$^+$.

Example 14

N-(2-acetamidoethyl)-6-(((3-(5-methylisoxazol-3-yl)-[1,2,4]triazolo[3,4-a]phthalazin-6-yl)oxy)methyl)-nicotinamide (14)

The procedure was the same as example 1: The title product was obtained from the starting materials A4 and N-(2-aminoethyl)acetamide (CAS: 1001-53-2)): 58 mg, 80% as a white solid. $^1$H NMR (400 MHz, DMSO-d6) δ9.00 (d, J=1.6 Hz, 1H), 8.73 (t, J=5.6 Hz, 1H), 8.54 (d, J=7.6 Hz, 1H), 8.33 (d, J=8.1 Hz, 1H), 8.22 (dd, J=8.1, 2.3 Hz, 1H), 8.09 (t, J=7.7 Hz, 1H), 7.96 (t, J=7.2 Hz, 2H), 7.83 (d, J=8.3 Hz, 1H), 6.89 (s, 1H), 5.73 (s, 2H), 3.29-3.24 (m, 2H), 3.18 (t, J=5.8 Hz, 2H), 2.54 (s, 3H), 1.76 (s, 3H). LC-MS: m/z (ES+) for $C_{24}H_{22}N_8O_4$ 487 [M+1]$^+$.

Example 15

N-((1S)-2-methoxycyclopentyl)-6-(((3-(5-methylisoxazol-3-yl)-[1,2,4]triazolo[3,4-a]phthalazin-6-yl)oxy)methyl)nicotinamide (15)

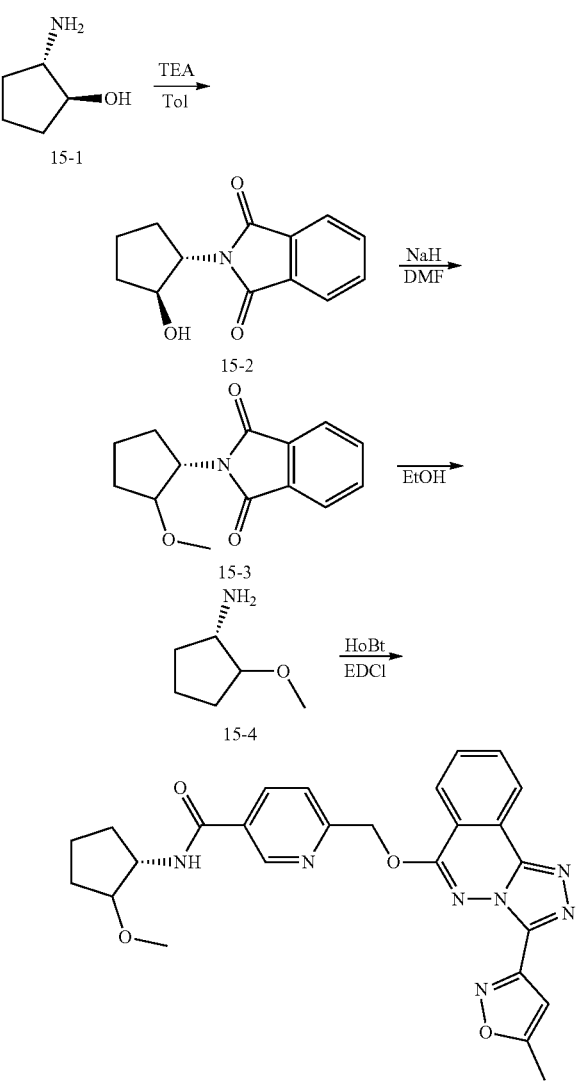

The Synthesis of Compound 15-4

2-((1S,2S)-2-hydroxycyclopentyl)isoindoline-1,3-dione (15-2)

Trans-(1S,2S)-2-Aminocyclopentanol hydrochloride 15-1 (CAS: 68327-04-8) (1.37 g, 10 mmol) and Et$_3$N (3 g, 30 mmol) were added to 40 mL of toluene and stirred at RT for 5 mins. Then phthalic anhydride (1.48 g, 10 mmol) was added under stirring and the reaction mixture was refluxed under stirring for 4 h. TLC showed the reaction was completed. After cooled to r. t., the reaction mixture was quenched with 40 mL of water. The organic layer was dried with anhydrous $Na_2SO_4$ and concentrated under reduced pressure. The residue was purified with chromatography column to give 1.7 g white solid, 73.5%.

2-((1S)-2-methoxycyclopentyl)isoindoline-1,3-dione (15-3)

NaH (177 mg, 4.4 mmol) was added to a solution of 15-2 (850 mg, 3.68 mmol) in DMF (3 mL) at 0° C., in portions and stirred until no bubbles were generated and then MeI (624 mg, 4.4 mmol) was added over 20 minutes. The reaction mixture was warmed to r. t. for 2 h. TLC (PETROLEUM ETHER:EA=2:1, Rf=0.8) showed that the reaction was completed. And then it was quenched with water, extracted with EtOAc and the organic phase was dried. The residue was purified by column to give 600 mg white solid, 66%.

(1S)-2-methoxycyclopentanamine (15-4)

The solution of 15-3 (700 mg, 2.85 mmol) and hydrazine hydrate (500 mg, 8.49 mmol) were added to 15 ml of EtOH and then heated to reflux for 3 h under stirring. TLC (PETROLEUM ETHER:EA=1:1) showed the reaction was completed. And then it was quenched with 1 N NaOH, extracted with DCM (6*20 mL). The organic phases were combined and dried by rotary evaporator to give 200 mg of oil. 61%.

N-((1S)-2-methoxycyclopentyl)-6-(((3-(5-methylisoxazol-3-yl)-[1,2,4]triazolo[3,4-a]phthalazin-6-yl)oxy)methyl)nicotinamide (15)

The procedure was the same as example 1: The title product was obtained from the starting materials A4 and an intermediate 15-4: 190 mg, 63% as a white solid.
$^1$H NMR (400 MHz, DMSO-d6) δ: 9.03 (d, J=1.6 Hz, 1H), 8.56 (t, J=8.0 Hz, 2H), 8.34-8.24 (m, 2H), 8.10 (t, J=7.6 Hz, 1H), 7.97 (t, J=7.6 Hz, 1H), 7.86 (d, J=8.0 Hz, 1H), 6.89 (s, 1H), 5.75 (s, 2H), 4.22-4.15 (m, 1H), 3.72-3.67 (m, 1H), 3.25 (s, 3H), 2.56 (s, 3H), 2.04-1.83 (m, 2H), 1.75-1.48 (m, 4H). LC-MS: m/z (ES+) for $C_{26}H_{25}N_7O_4$ 500.0 [M+1]$^+$.

Example 16

N-methyl-6-(((3-(5-methylisoxazol-3-yl)-[1,2,4]triazolo[3,4-a]phthalazin-6-yl)oxy)methyl)-N-(2-morpholinoethyl)nicotinamide (16)

The procedure was the same as example 1: The title product was obtained from the starting materials A4 and N-methyl-2-morpholin-4-ylethanamine (CAS: 41239-40-1): 45 mg, 71% as a white solid.
$^1$H NMR (400 MHz, DMSO-d6) δ: δ 8.62 (d, J=1.1 Hz, 1H), 8.53 (d, J=8.1 Hz, 1H), 8.31 (d, J=8.1 Hz, 1H), 8.08 (t, J=7.7 Hz, 1H), 7.94 (t, J=7.7 Hz, 1H), 7.88 (dd, J=7.9, 1.7 Hz, 1H), 7.77 (d, J=7.4 Hz, 1H), 6.88 (s, 1H), 5.71 (s, 2H), 3.54 (s, 3H), 3.29-3.18 (m, 3H), 2.92 (d, J=23.7 Hz, 3H), 2.54 (s, 4H), 2.37 (d, J=43.8 Hz, 3H), 2.01 (s, 2H). LC-MS: m/z (ES+) for $C_{27}H_{28}N_8O_4$ 529 [M+1]$^+$.

Example 17

(6-(((3-(5-methylisoxazol-3-yl)-[1,2,4]triazolo[3,4-a]phthalazin-6-yl)oxy)methyl)pyridin-3-yl)(4-methylpiperazin-1-yl)methanone (17)

The procedure was the same as example 1: The title product was obtained from the starting materials A4 and N-methylpiperazine (CAS: 109-01-3): 100 mg, 88% as a white solid.
$^1$H NMR (400 MHz, DMSO-d6) δ 8.62 (d, J=1.5 Hz, 1H), 8.55 (d, J=8.0 Hz, 1H), 8.33 (d, J=7.9 Hz, 1H), 8.09 (t, J=7.1 Hz, 1H), 7.96 (t, J=7.2 Hz, 1H), 7.88 (dd, J=8.0, 2.1 Hz, 1H), 7.78 (d, J=8.0 Hz, 1H), 6.90 (d, J=0.8 Hz, 1H), 5.72 (s, 2H), 3.62-3.58 (m, 2H), 3.35-3.30 (s, 2H), 2.54 (s, 3H), 2.37-2.33 (m, 2H), 2.26-2.22 (m, 2H), 2.17 (s, 3H). LC-MS: m/z (ES+) for $C_{25}H_{24}N_8O_3$ 485 [M+1]$^+$.

Example 18

N-(1-acetylpyrrolidin-3-yl)-6-(((3-(5-methylisoxazol-3-yl)-[1,2,4]triazolo[3,4-a]phthalazin-6-yl)oxy)methyl)nicotinamide (18)

The procedure was the same as example 1: The title product was obtained from the starting materials A4 and 1-(3-aminopyrrolidin-1-yl)ethanone (CAS: 833483-45-7): 100 mg, 87% as a white solid.
$^1$H NMR (400 MHz, DMSO-d6) δ 9.04-8.98 (m, 1H), 8.75 (dd, J=17.7, 6.6 Hz, 1H), 8.53 (d, J=7.9 Hz, 1H), 8.30 (d, J=7.9 Hz, 1H), 8.24 (dd, J=8.2, 2.2 Hz, 1H), 8.07 (dd, J=11.2, 4.0 Hz, 1H), 7.95 (t, J=7.5 Hz, 1H), 7.83 (dd, J=8.2, 3.1 Hz, 1H), 6.88 (d, J=0.7 Hz, 1H), 5.72 (s, 2H), 4.44 (ddd, J=30.1, 11.5, 5.9 Hz, 1H), 3.76-3.53 (m, 1H), 3.53-3.31 (m, 3H), 2.53 (s, 3H), 2.14-2.08 (m, 1H), 2.00-1.83 (m, 4H). LC-MS: m/z (ES+) for $C_{26}H_{24}N_8O_4$ 513 [M+1]$^+$.

Example 19

1-(6-(((3-(5-methylisoxazol-3-yl)-[1,2,4]triazolo[3,4-a]phthalazin-6-yl)oxy)methyl)nicotinoyl)piperidine-3-carboxamide (19)

The procedure was the same as example 1: The title product was obtained from the starting materials A4 and piperidine-3-carboxamide (CAS: 4138-26-5): 75 mg, 60% as a white solid.
$^1$H NMR (400 MHz, DMSO-d6) δ 8.62 (s, 1H), 8.55 (d, J=8.2 Hz, 1H), 8.33 (d, J=8.0 Hz, 1H), 8.09 (t, J=7.6 Hz, 1H), 7.96 (t, J=7.8 Hz, 1H), 7.88 (s, 1H), 7.79 (d, J=8.2 Hz, 1H), 7.39-7.25 (m, 1H), 6.90-6.81 (m, 2H), 5.72 (s, 2H), 4.41-4.22 (m, 1H), 3.49-3.45 (m, 1H), 3.25-3.11 (m, 1H), 3.04-2.99 (s, 1H), 2.87-2.82 (m, 1H), 2.54 (s, 3H), 2.31-2.27 (m, 1H), 1.92-1.87 (m, 1H), 1.58-1.52 (m, 2H), 1.43-1.38 (m, 1H). LC-MS: m/z (ES+) for $C_{26}H_{24}N_8O_4$ 513 [M+1]$^+$.

Example 20

6-(((3-(5-methylisoxazol-3-yl)-[1,2,4]triazolo[3,4-a]phthalazin-6-yl)oxy)methyl)-N-((tetrahydrofuran-3-yl)methyl)nicotinamide (20)

The procedure was the same as example 1: The title product was obtained from the starting materials A4 and 3-aminomethyltetrahydrofuran (CAS: 165253-31-6): 50 mg, 63% as a white solid.

¹H NMR (400 MHz, DMSO-d6) δ 9.01 (d, J=2.1 Hz, 1H), 8.77 (s, 1H), 8.55 (d, J=7.7 Hz, 1H), 8.33 (d, J=8.0 Hz, 1H), 8.23 (dd, J=8.0, 2.1 Hz, 1H), 8.10 (t, J=7.1 Hz, 1H), 7.96 (t, J=7.6 Hz, 1H), 7.83 (d, J=8.2 Hz, 1H), 6.88 (s, 1H), 5.74 (s, 2H), 3.75-3.54 (m, 3H), 3.46-3.42 (m, 1H), 3.25-3.21 (m, 2H), 2.54 (s, 3H), 1.93-1.89 (m, 2H), 1.59-1.55 (m, 1H). LC-MS: m/z (ES+) for $C_{25}H_{23}N_7O_4$ 486 [M+1]⁺.

Example 21

N-(2,2-difluoroethyl)-6-(((3-(5-methylisoxazol-3-yl)-[1,2,4]triazolo[3,4-a]phthalazin-6-yl)oxy)methyl)nicotinamide (21)

The procedure was the same as example 1: The title product was obtained from the starting materials A4 and 2,2-difluoroethylamine (CAS: 430-67-1): 100 mg, 80% as a white solid.
¹H NMR (400 MHz, DMSO-d6) δ 9.08-9.04 (m, 2H), 8.55 (d, J=7.5 Hz, 1H), 8.34 (d, J=8.3 Hz, 1H), 8.27 (dd, J=8.2, 2.3 Hz, 1H), 8.12-8.07 (m, 1H), 7.97 (t, J=7.2 Hz, 1H), 7.85 (d, J=8.1 Hz, 1H), 6.88 (d, J=0.9 Hz, 1H), 6.11 (tt, J=55.4, 4.1 Hz, 1H), 5.73 (s, 2H), 3.75-3.61 (m, 2H), 2.54 (d, J=0.8 Hz, 3H). LC-MS: m/z (ES+) for $C_{22}H_{17}F_2N_7O_3$ 466 [M+1]⁺.

Example 22

(4-methoxypiperidin-1-yl)(6-(((3-(5-methylisoxazol-3-yl)-[1,2,4]triazolo[3,4-a]phthalazin-6-yl)oxy)methyl)pyridin-3-yl)methanone (22)

The procedure was the same as example 1: The title product was obtained from the starting materials A4 and 4-methoxypiperidine (CAS: 4045-24-3): 50 mg, 56% as a white solid.
¹H NMR (400 MHz, DMSO-d6) δ 8.66 (d, J=1.5 Hz, 1H), 8.59 (d, J=8.0 Hz, 1H), 8.37 (d, J=8.0 Hz, 1H), 8.12 (dd, J=11.2, 4.2 Hz, 1H), 8.02-7.97 (m, 1H), 7.92 (dd, J=8.0, 2.2 Hz, 1H), 7.81 (d, J=8.1 Hz, 1H), 6.94 (d, J=0.8 Hz, 1H), 5.76 (s, 2H), 3.96-3.87 (m, 1H), 3.49-3.39 (m, 2H), 3.26 (s, 3H), 3.22-3.09 (m, 2H), 2.58 (d, J=0.6 Hz, 3H), 1.92-1.75 (m, 2H), 1.53-1.39 (m, 2H). LC-MS: m/z (ES+) for $C_{26}H_{25}N_7O_4$ 500 [M+1]⁺.

Example 23

(4,4-difluoropiperidin-1-yl)(6-(((3-(5-methylisoxazol-3-yl)-[1,2,4]triazolo[3,4-a]phthalazin-6-yl) oxy)methyl)pyridin-3-yl)methanone (23)

The procedure was the same as example 1: The title product was obtained from the starting materials A4 and 4,4-difluoropiperidine hydrochloride (CAS: 144230-52-4): 60 mg, 58% as a white solid.
¹H NMR (400 MHz, DMSO-d6) δ 8.69 (d, J=1.5 Hz, 1H), 8.55 (d, J=7.8 Hz, 1H), 8.33 (d, J=8.0 Hz, 1H), 8.09 (t, J=7.6 Hz, 1H), 7.95 (dd, J=12.9, 4.8 Hz, 2H), 7.81 (d, J=8.0 Hz, 1H), 6.91 (s, 1H), 5.73 (s, 2H), 3.80-3.59 (m, 2H), 3.47-3.33 (m, 2H), 2.55 (s, 3H), 2.12-1.93 (m, 4H). LC-MS: m/z (ES+) for $C_{25}H_{21}F_2N_7O_3$ 506 [M+1]⁺.

Example 24

N-(cyclopropylmethyl)-6-(((3-(5-methylisoxazol-3-yl)-[1,2,4]triazolo[3,4-a]phthalazin-6-yl)oxy) methyl)nicotinamide (24)

The procedure was the same as example 1: The title product was obtained from the starting materials A4 and cyclopropylmethanamine (CAS: 2516-47-4): 65 mg, 41% as a white solid.
¹H NMR (400 MHz, DMSO-d6) δ 9.07 (d, J=1.8 Hz, 1H), 8.83 (t, J=5.6 Hz, 1H), 8.60 (d, J=8.0 Hz, 1H), 8.38 (d, J=8.0 Hz, 1H), 8.29 (dd, J=8.2, 2.2 Hz, 1H), 8.14 (t, J=7.6 Hz, 1H), 8.01 (t, J=7.7 Hz, 1H), 7.87 (d, J=8.1 Hz, 1H), 6.93 (s, 1H), 5.78 (s, 2H), 3.18 (t, J=6.2 Hz, 2H), 2.59 (s, 3H), 1.09-0.96 (m, 1H), 0.53-0.35 (m, 2H), 0.24 (q, J=4.9 Hz, 2H). LC-MS: m/z (ES+) for $C_{24}H_{21}N_7O_3$ 456 [M+1]⁺.

Example 25

(1R,4R)-2-oxa-5-azabicyclo[2.2.1]heptan-5-yl(6-(((3-(5-methylisoxazol-3-yl)-[1,2,4]triazolo[3,4-a]phthalazin-6-yl)oxy)methyl)pyridin-3-yl)methanone (25)

The procedure was the same as example 1: The title product was obtained from the starting materials A4 and 2-Oxa-5-azabicyclo[2.2.1]heptane hydrochloride (CAS: 909186-56-7): 87 mg, 67% as a white solid.
¹H NMR (400 MHz, DMSO-d6) δ 8.62 (d, J=1.5 Hz, 1H), 8.55 (d, J=8.0 Hz, 1H), 8.33 (d, J=7.9 Hz, 1H), 8.09 (t, J=7.1 Hz, 1H), 7.96 (t, J=7.2 Hz NMR (400 MHz, dmso) δ 8.74 (dd, J=21.3, 1.5 Hz, 1H), 8.55 (d, J=7.7 Hz, 1H), 8.33 (d, J=8.1 Hz, 1H), 8.09 (t, J=7.2 Hz, 1H), 8.05-7.93 (m, 2H), 7.79 (dd, J=11.2, 8.2 Hz, 1H), 6.89 (d, J=14.0 Hz, 1H), 5.73 (d, J=4.6 Hz, 2H), 4.83-4.31 (m, 2H), 3.85 (dd, J=40.0, 7.4 Hz, 1H), 3.68 (dd, J=40.0, 6.3 Hz, 1H), 3.50 (t, J=10.0 Hz, 1H), 3.24 (d, J=9.6 Hz, 1H), 2.54 (s, 3H), 1.91-1.69 (m, 2H). LC-MS: m/z (ES+) for $C_{25}H_{21}N_7O_4$ 484 [M+1]⁺.

Example 26

6-(((3-(5-methylisoxazol-3-yl)-[1,2,4]triazolo[3,4-a]phthalazin-6-yl)oxy)methyl)-N-((tetrahydrofuran-2-yl)methyl)nicotinamide (26)

The procedure was the same as example 1: The title product was obtained from the starting materials A4 and furfurylamine (CAS: 4795-29-3): 60 mg, 63% as a white solid.
¹H NMR (400 MHz, DMSO) δ9.02 (d, J=1.7 Hz, 1H), 8.77 (t, J=5.8 Hz, 1H), 8.55 (d, J=7.9 Hz, 1H), 8.33 (d, J=8.3 Hz, 1H), 8.24 (dd, J=8.2, 2.2 Hz, 1H), 8.09 (t, J=7.6 Hz, 1H), 7.96 (t, J=7.6 Hz, 1H), 7.82 (d, J=8.1 Hz, 1H), 6.88 (s, 1H), 5.73 (s, 2H), 4.02-3.89 (m, 1H), 3.67 (ddd, J=58.7, 14.5, 7.4 Hz, 2H), 3.36-3.31 (m, 2H), 2.54 (s, 3H), 1.94-1.73 (m, 3H), 1.59-1.48 (m, 1H), LC-MS: m/z (ES+) for $C_{25}H_{23}N_7O_4$ 486 [M+1]⁺.

Example 27

6-(((3-(5-methylisoxazol-3-yl)-[1,2,4]triazolo[3,4-a]phthalazin-6-yl)oxy)methyl)-N-(2-(methylsulfonyl)ethyl)nicotinamide (27)

The procedure was the same as example 1: The title product was obtained from the starting materials A4 and 2-aminoethylmethyl sulfone (CAS: 49773-20-8): 100 mg, 80% as a white solid.
¹H NMR (400 MHz, DMSO) δ 9.05 (d, J=1.8 Hz, 1H), 9.01 (t, J=5.6 Hz, 1H), 8.59 (d, J=7.8 Hz, 1H), 8.38 (d, J=8.1 Hz, 1H), 8.27 (dd, J=8.2, 2.2 Hz, 1H), 8.14 (t, J=7.2 Hz, 1H), 8.01 (t, J=7.2 Hz, 1H), 7.89 (d, J=8.2 Hz, 1H), 6.93 (d, J=0.7 Hz, 1H), 5.78 (s, 2H), 3.71 (dd, J=12.6, 6.5 Hz, 2H), 3.41 (t, J=6.8 Hz, 2H), 3.06 (s, 3H), 2.58 (s, 3H). LC-MS: m/z (ES+) for $C_{23}H_{21}N_7O_5S$ 508 [M+1]⁺.

Example 28

6-(((3-(5-methylisoxazol-3-yl)-[1,2,4]triazolo[3,4-a]phthalazin-6-yl)oxy)methyl)nicotinamide (28)

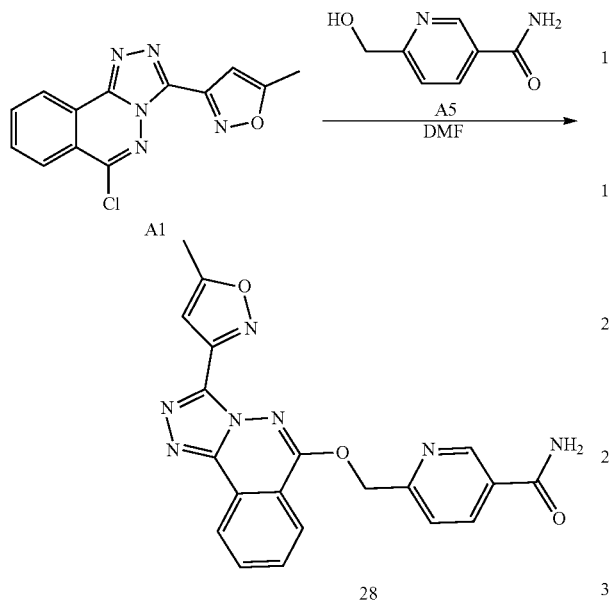

A yellow suspension of A1 (100 mg, 0.35 mmol, 6-hydroxymethyl-3-pyridine-carboxamide A5 (CAS: 119646-49-0) (40 mg, 0.35 mmol) and Cs$_2$CO$_3$ (227 mg, 0.70 mmol) in 20 mL of DMF was stirred at r. t. overnight at Ar. TLC (DCM:MeOH=20:1, Rf=0.3) showed the reaction was completed. The reaction mixture was concentrated under reduced pressure. The residue was purified by column chromatography to give the title product 77 mg (55%) as a white solid.

$^1$H NMR (400 MHz, DMSO) δ 9.04 (d, J=2.0 Hz, 1H), 8.54 (d, J=8.0 Hz, 1H), 8.33 (d, J=8.1 Hz, 1H), 8.26 (dd, J=8.2, 2.2 Hz, 1H), 8.17 (s, 1H), 8.08 (d, J=7.9 Hz, 1H), 7.95 (t, J=7.7 Hz, 1H), 7.81 (d, J=8.2 Hz, 1H), 7.60 (s, 1H), 6.87 (s, 1H), 5.73 (s, 2H), 2.54 (s, 3H). LC-MS: m/z (ES+) for C$_{20}$H$_{15}$N$_7$O$_3$ 402 [M+1]$^+$.

Example 29

2-(6-(((3-(5-methylisoxazol-3-yl)-[1,2,4]triazolo[3,4-a]phthalazin-6-yl)oxy)methyl)nicotinamido)acetic acid (29)

The procedure was the same as example 1: The ester product was obtained from the starting materials A4 and tert-butyl 2-aminoacetate (CAS: 6456-74-2), and then the ester product was stirred with trifluoroacetaic acid at r.t. to give the title product: 100 mg, 60% as a white solid.

$^1$H NMR (400 MHz, DMSO) δ 12.66 (s, 1H), 9.07 (dd, J=12.8, 6.8 Hz, 2H), 8.54 (d, J=7.7 Hz, 1H), 8.34 (d, J=7.9 Hz, 1H), 8.27 (dd, J=8.3, 2.0 Hz, 1H), 8.09 (t, J=7.7 Hz, 1H), 7.96 (t, J=7.7 Hz, 1H), 7.85 (d, J=8.1 Hz, 1H), 6.86 (s, 1H), 5.74 (s, 2H), 3.93 (d, J=5.8 Hz, 2H), 2.53 (s, 3H). LC-MS: m/z (ES+) for C$_{22}$H$_{17}$N$_7$O$_5$ 460 [M+1]$^+$.

Example 30

6-(((3-(5-methylisoxazol-3-yl)-[1,2,4]triazolo[3,4-a]phthalazin-6-yl)oxy)methyl)-N-(2,2,2-trifluoroethyl)nicotinamide (30)

The procedure was the same as example 1: The title product was obtained from the starting materials A4 and 2,2,2-trifluoroethylamine (CAS: 753-90-2): 56 mg, 48% as a white solid.

$^1$H NMR (400 MHz, dmso) δ 9.32 (t, J=6.2 Hz, 1H), 9.06 (d, J=2.0 Hz, 1H), 8.55 (d, J=7.9 Hz, 1H), 8.35 (d, J=8.0 Hz, 1H), 8.29 (dd, J=8.2, 2.3 Hz, 1H), 8.09 (dd, J=11.2, 4.2 Hz, 1H), 7.97 (t, J=7.8 Hz, 1H), 7.86 (d, J=8.3 Hz, 1H), 6.87 (d, J=0.8 Hz, 1H), 5.75 (s, 2H), 4.18-4.02 (m, 2H), 2.53 (s, 3H). LC-MS: m/z (ES+) for C$_{22}$H$_{16}$F$_3$N$_7$O$_3$ 484 [M+1]$^+$.

31

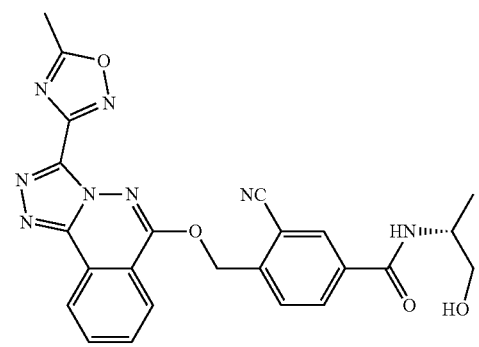

Scheme 2

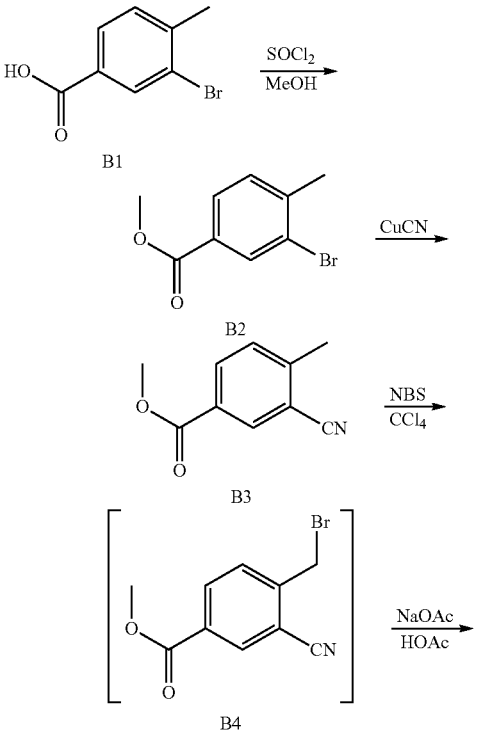

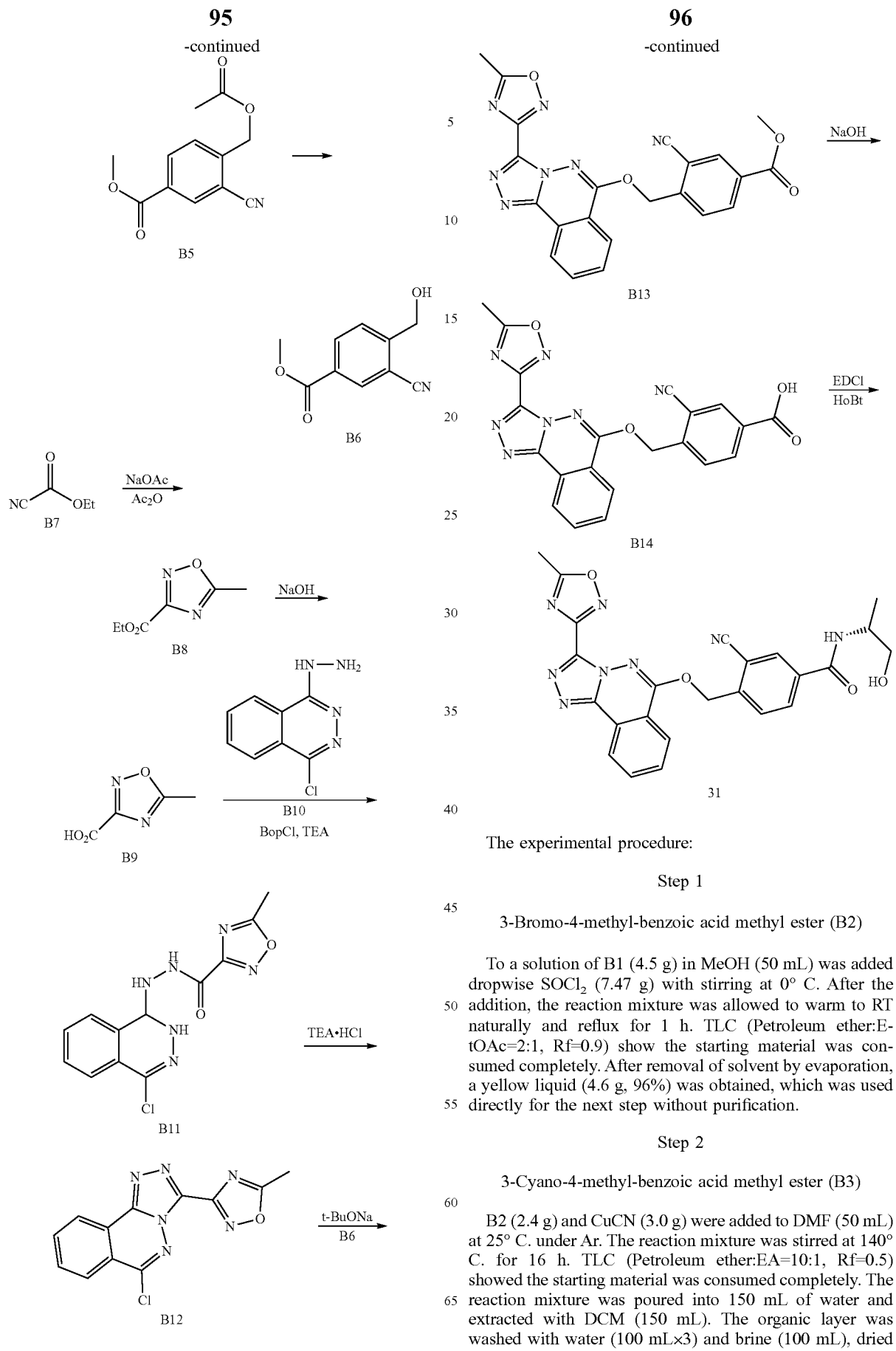

The experimental procedure:

Step 1

3-Bromo-4-methyl-benzoic acid methyl ester (B2)

To a solution of B1 (4.5 g) in MeOH (50 mL) was added dropwise $SOCl_2$ (7.47 g) with stirring at 0° C. After the addition, the reaction mixture was allowed to warm to RT naturally and reflux for 1 h. TLC (Petroleum ether:EtOAc=2:1, Rf=0.9) show the starting material was consumed completely. After removal of solvent by evaporation, a yellow liquid (4.6 g, 96%) was obtained, which was used directly for the next step without purification.

Step 2

3-Cyano-4-methyl-benzoic acid methyl ester (B3)

B2 (2.4 g) and CuCN (3.0 g) were added to DMF (50 mL) at 25° C. under Ar. The reaction mixture was stirred at 140° C. for 16 h. TLC (Petroleum ether:EA=10:1, Rf=0.5) showed the starting material was consumed completely. The reaction mixture was poured into 150 mL of water and extracted with DCM (150 mL). The organic layer was washed with water (100 mL×3) and brine (100 mL), dried over $Na_2SO_4$ and concentrated. The residue was purified by column chromatography TLC to give the product B3 (1.4 g, 76.3%).

Step 3

4-Bromomethyl-3-cyano-benzoic acid methyl ester (B4)

To a solution of B3 (1.4 g) in $CCl_4$ (35 mL) was added NBS (1.56 g) and BPO (40 mg) at RT. The reaction mixture was allowed to reflux for 72 hrs. TLC (Petroleum ether:EtOAc=5:1, Rf=0.7) showed the starting material was consumed completely. After the reaction mixture was cooled to RT, the reaction mixture was quenched by addition of 40 mL $H_2O$, followed by 40 mL 10% aqueous $NaHCO_3$ and separated. The organic layer was dried over anhydrous $Na_2SO_4$ and evaporated under reduced pressure to dryness to afford a crude product (1.5 g, 95%) as a yellow liquid.

Step 4&5

3-Cyano-4-hydroxymethyl-benzoic acid methyl ester (B6)

To a solution of B4 (2.03 g) in AcOH was added AcONa (3.3 g) at RT, and the reaction mixture was allowed to reflux for 16 hrs. TLC-1 (Petroleum ether:EtOAc=3:1, Rf=0.4) showed the starting material was consumed completely. After the reaction mixture was cooled to RT, the reaction mixture was quenched by addition of 100 mL $H_2O$ and 80 mL EtOAc and separated, the organic layer was washed with 10% aq $NaHCO_3$, dried over anhydrous $Na_2SO_4$ and evaporated uner reduced pressure to dryness to afford crude B5 as a yellow liquid. The crude product was dissolved in 60 mL MeOH and 4.24 g $Na_2CO_3$ was added and stirred at RT for 1 h. TLC (Petroleum ether:EtOAc=3:1, Rf=0.01) showed the starting material was consumed completely. The reaction mixture was filtered and the filter cake was washed with a small amount of MeOH. The combined filtrates were concentrated under reduced pressure to dryness to give a crude product. The crude product was purified by silica gel chromatography eluted with Petroleum ether:EtOAc=2:1 to give the product B6 (0.6 g, 39%) as a white solid.

Step 6

5-Methyl-[1,2,4]oxadiazole-3-carboxylic acid ethyl ester (B8)

Acetyl chloride (18 g, 175 mmol) was added into acetic acid (10.5 g, 175 mmol) with stirring at 25° C. to give acetic anhydride for further use. To a 100-mL RBF was added hydroxylamine-HCl (8.6 g), followed by acetic acid (48 mL) and ethyl cyanoformate B7 (10 g) and the mixture was stirred at RT. Then sodium acetate (10.1 g) was added portionwise over 15 min. The reaction mixture was stirred for 2 h at 18-28° C. The reaction mixture was cooled to 15° C. and acetic anhydride was added to the mixture slowly over 20 mins. The temperature increased to 26° C. after the addition. The reaction mixture was stirred for an additional 15 min. The reaction mixture was heated at 99° C. for 12 h. The slurry was cooled to room temperature, and acetic acid was removed under vacuum. Ethyl acetate 100 mL and water 20 mL were added to the reaction mixture. The solution was neutralized with 30% $K_2CO_3$ (37 mL) to pH 7 and separated. The aqueous layer was extracted with ethyl acetate (30 mL*2). The combined organic layer was washed with water (20 mL), dried over anhydrous $Na_2SO_4$ and evaporated to dryness to give B8 (15 g, 95%) as a white solid.

Step 7

5-Methyl-[1,2,4]oxadiazole-3-carboxylic acid (B9)

To a solution of B8 (20 g, 128 mmol) in EtOH (100 mL) was added aqueous NaOH (2N, 62 mL) at RT and stirred for 1 hour. TLC (Petroleum ether:EA=2:1, Rf=0.5) showed the starting material was consumed completely. The reaction mixture was quenched with satd aq NH4Cl, was concentrated under reduced pressure. To the residue was added MeOH. The mixture was filtered and concentrated uder reduced pressure to afford B9 (8 g, 49%) as a white solid.

Step 8

5-Methyl-[1,2,4]oxadiazole-3-carboxylic acid N'-(4-chloro-1,2-dihydro-phthalazin-1-yl)-hydrazide (B11)

To a solution of B9 (789 mg) and TEA (1.56 g) in DCM (100 mL) was added bis(2-oxo-3-oxazolidinyl) phosphonic chloride (BOP—Cl, 1.57 g) in one portion with stirring at 0° C. under Ar. The mixture was stirred at 0° C. for 20 mins. B10 (prepared according to J. Med. Chem., 2004, 47, 2176-2179) (1g) was added. The resulting mixture was stirred at 0° C. for 1 h and then stirred at room temperature overnight. TLC (DCM:MeOH=10:1, Rf=0.5) showed the starting material was consumed completely. The reaction mixture was filtered and the filtrate was washed with water (15 mL), dried over anhydrous $Na_2SO_4$ and concentrated. The residue was purified by column chromatography to give product (300 mg, 19%).

Step 9

6-Chloro-3-(5-methyl-[1,2,4]oxadiazol-3-yl)-[1,2,4]triazolo[3,4-a]phthalazine (B12)

B11 (800 mg) and triethylamine chlorhydrate (69 mg) in xylene (100 mL) was stirred at refluxing for 0.5 h. TLC (DCM:MeOH=20:1, Rf=0.7) showed most of the starting material was consumed. After cooled to RT, the reaction mixture was washed with 10 mL water. The aqueous layer was extracted with EtOAc (20 mL×2). The combined organic layers were dried over anhydrous $Na_2SO_4$. After concentration, the crude product was purified by silica gel chromatography eluted with Petroleum ether:EtOAc=2:1 to give a pure product (580 mg) as a yellow solid.

$^1$H NMR (400 MHz, DMSO-d6) δ: 8.82 (d, 1H J=8.0), 8.35 (d, 1H J=8.4), 8.13~8.06 (m, 1H), 8.02~7.94 (m, 1H), 2.79 (s, 3H).

Example 31

(R)-3-cyano-N-(1-hydroxypropan-2-yl)-4-(((3-(5-methyl-1,2,4-oxadiazol-3-yl)-[1,2,4]triazolo[3,4-a]phthalazin-6-yl)oxy)methyl)benzamide (31)

The procedure was the same as example 1: the title product was obtained from the saponification reaction of the starting material B13 (for the method for preparing B13 from B12, please refer to A3) and then condensation with D-Amino-propanol (CAS: 35320-23-1: 40 mg, 33% as a white solid. $^1$H NMR (400 MHz, DMSO-d6) δ: 8.57 (d, 1H J=8.0), 8.42~8.33 (m, 2H), 8.28 (d, 2H J=8.0), 8.19~7.98 (m, 4H), 5.83 (s, 2H), 4.80~4.70 (m, 1H), 4.06~3.96 (m, 1H), 3.48~3.41 (m, 1H), 3.37~3.31 (m, 1H), 2.80 (s, 3H), 1.11 (d, 3H J=6.4); LC-MS: m/z (ES+) for $C_{24}H_{20}N_8O_4$ 485.27 $[M+1]^+$.
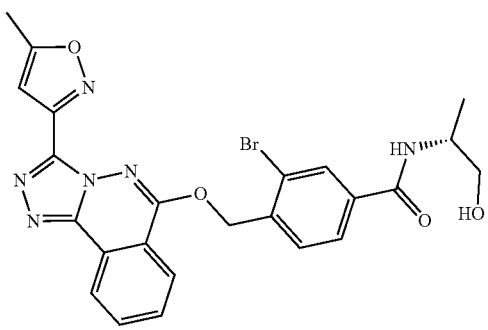
32
Scheme 3
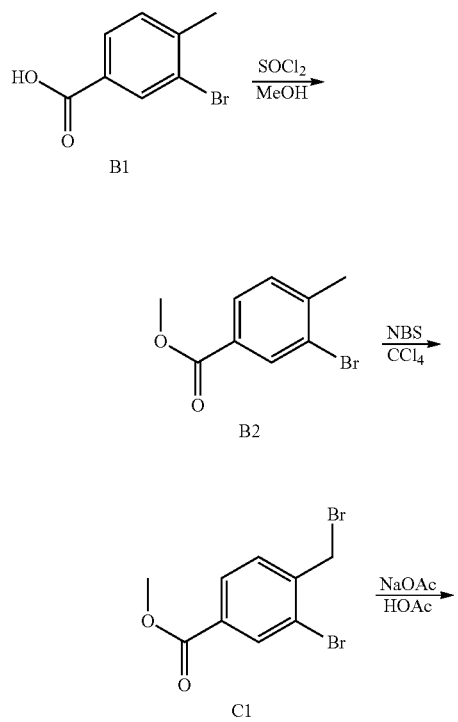
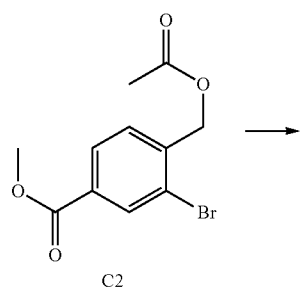
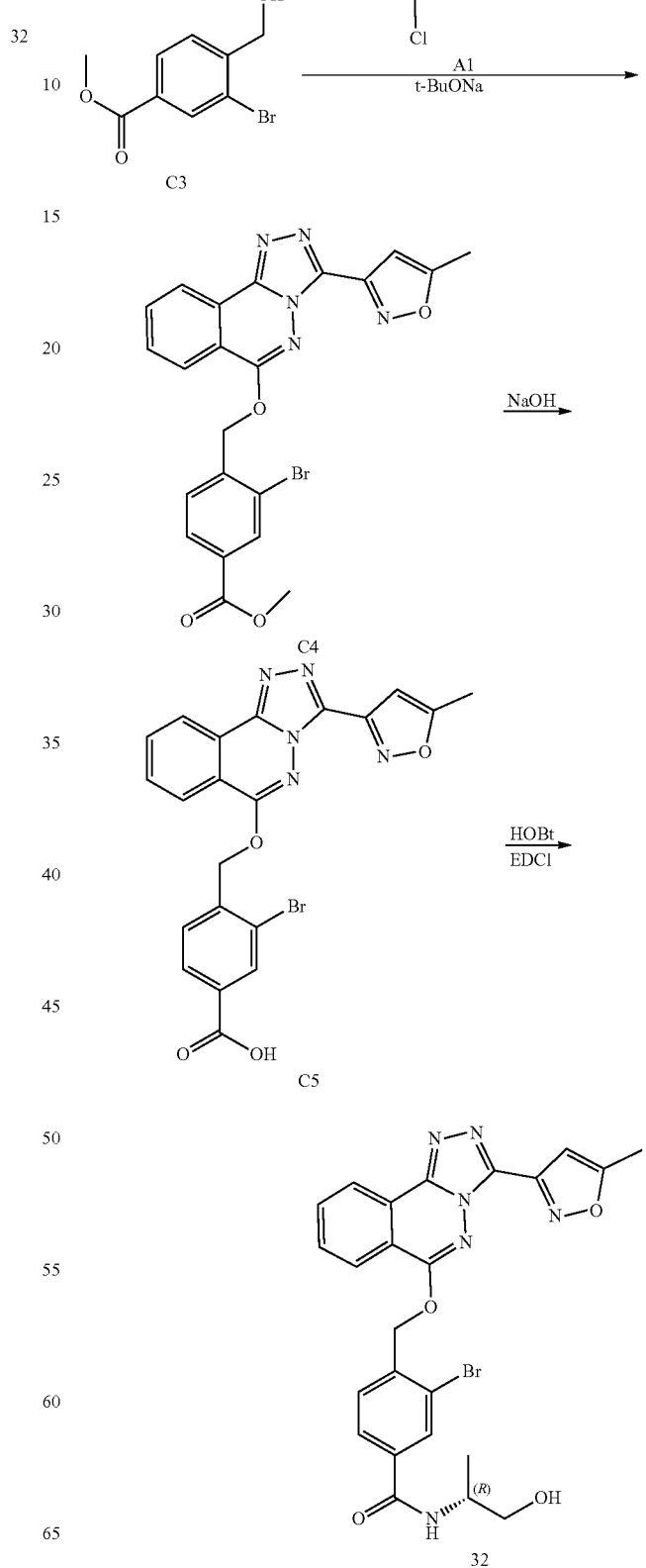

The Experimental Procedures

3-Bromo-4-bromomethyl-benzoic acid methyl ester (C1)

To a solution of B2 (3.6 g, 15.7 mmol) (prepared according to scheme 2) in $CCl_4$ (40 mL) was added NBS (3.2 g, 18 mmol) and a catalytic amount of AIBN at RT, the reaction mixture was allowed to reflux for 14 hrs. TLC (Petroleum ether:EtOAc=10:1, Rf=0.5) showed about ⅔ of the starting materials were consumed. 0.2 eq NBS was added and refluxed 3 hrs, and the reaction didn't work any more. After the reaction mixture was cooled to RT, the reaction mixture was quenched by addition of 40 mL $H_2O$, followed by 40 mL 10% aqueous $NaHCO_3$. The organic layer was dried over anhydrous $Na_2SO_4$ and evaporated to dryness to afford a crude product (5.3 g, 125%) as a yellow liquid.

4-Acetoxymethyl-3-bromo-benzoic acid methyl ester (C2)

To a solution of C1 (4.5 g, 14.6 mmol) in AcOH (20 mL) was added anhydrous AcONa (6 g, 73 mmol) at RT, and the reaction mixture was allowed to reflux for 14 hrs. TLC (Petroleum ether:EtOAc=10:1, Rf=0.3) showed the starting material was consumed completely. After the reaction mixture was cooled to RT, the reaction mixture was quenched by the addition of 200 mL $H_2O$ and 150 mL EtOAc, the organic layer was washed with 10% aq $NaHCO_3$, dried over anhydrous $Na_2SO_4$ and evaporated to dryness to afford crude C2 (5.3 g, 125%) as a yellow liquid. The crude product was used directly for the next step without purification.

3-Bromo-4-hydroxymethyl-benzoic acid methyl ester (C3)

The crude product C2 (5.3 g, 14.6 mmol) was added to 20 mL MeOH and $Na_2CO_3$ (7.7 g, 73 mmol) was added and stirred at RT for 1 h. TLC (Petroleum ether:EtOAc=10:1, Rf=0.1) showed the starting material was consumed completely. The reaction mixture was filtered and the filter cake was washed with MeOH. The combined filtrates were concentrated to dryness to give a crude product. The crude product was purified by silica gel chromatography to give product (1.5 g, 41.9%) as a white solid.

3-Bromo-4-[3-(5-methyl-isoxazol-3-yl)-[1,2,4]triazolo[3,4-a]phthalazin-6-yloxymethyl]-benzoic acid methyl ester (C4)

To a solution of A1 (155 mg, 0.55 mmol) and C3 (200 mg, 0.82 mmol) in THF (60 mL) was added t-BuOK (92 mg, 0.82 mmol) in portions during a period of 10 mins at 0° C. under N2. After addition, the reaction mixture was stirred at 0° C. for 0.5 h and then kept at RT for 1 h. TLC (DCM:MeOH=20:1, Rf=0.4) showed the starting material was consumed completely. The reaction mixture was concentrated to dryness. The crud product was used directly in the next step without further purification

3-Bromo-4-[3-(5-methyl-isoxazol-3-yl)-[1,2,4]triazolo[3,4-a]phthalazin-6-yloxymethyl]-benzoic acid (C5)

To the solution of C4 (the residue of the previous step, 268 mg, 0.55 mmol) in EtOH (20 mL) was added 10% NaOH (5 mL) with stirring at RT. The mixture was stirred for 0.5 h at RT. TLC (DCM:MeOH=20:1, Rf=0.2) showed the starting material was consumed completely. The reaction mixture was concentrated under reduced pressure to remove EtOH. 20 mL of water was added to the residue and the resulting mixture was extracted with EtOAc (30 mL×2). The aqueous layer was adjusted to pH=4 with citric acid and concentrated. The residue was purified through column chromatography to give the product (120 mg, 46.1%) as a yellow solid.

Example 32

(R)-3-bromo-N-(1-hydroxypropan-2-yl)-4-(((3-(5-methylisoxazol-3-yl)-[1,2,4]triazolo[3,4-a]phthalazin-6-yl)oxy)methyl)benzamide (32)

A DMF solution (3 mL) containing HOBt (18 mg, 0.13 mmol), EDCI (26 mg, 0.13 mmol), and C5 (50 mg, 0.1 mmol) was stirred at room temperature for 10 mins under $N_2$. (R)-2-amino-n-propanol (10 mg, 0.13 mmol) and DIPEA (40 mg, 0.3 mmol) were added to the reaction mixture by turn. The mixture was stirred at RT for 12 h. TLC (DCM:MeOH=10:1, Rf=0.4) showed the starting material was consumed completely. Most DMF was evaporated from the reaction mixture. To the residue were added DCM (10 mL) and water (10 mL), and the resulting mixture was adjusted to pH 5~6 with aqueous HCl. The organic layer was washed with water (5 mL×2), dried over anhydrous $Na_2SO_4$, and concentrated under reduced pressure. The residue was purified by preparative TLC to give the product (10 mg, 17.8%) as a yellow solid. $^1$H NMR (400 MHz, DMSO-d6) δ: 8.59~8.57 (d, 1H), 8.31~8.26 (m, 2H), 8.21 (s, 1H), 8.14~8.10 (t, 1H), 7.99~7.95 (t, 1H), 7.90~7.87 (t, 2H), 6.99 (s, 1H), 5.74 (s, 2H), 4.75~4.72 (t, 1H), 4.04~3.97 (m, 1H), 3.46~3.42 (m, 1H), 3.37~3.30 (m, 1H), 2.58 (s, 3H), 1.13~1.11 (d, 3H); LC-MS: m/z (ES+) for $C_{24}H_{21}BrN_6O_4$ 537.12 [M+1]$^+$.

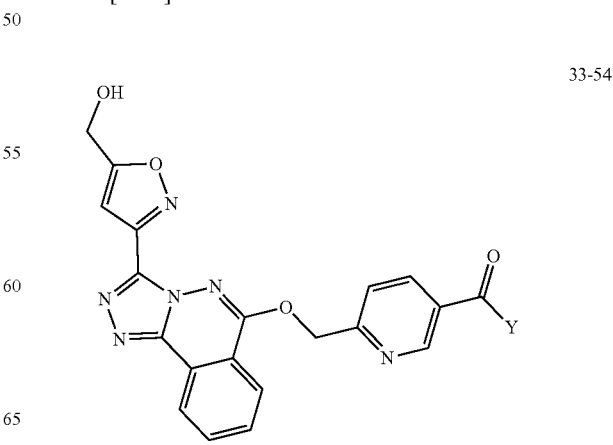

33-54

Scheme 4

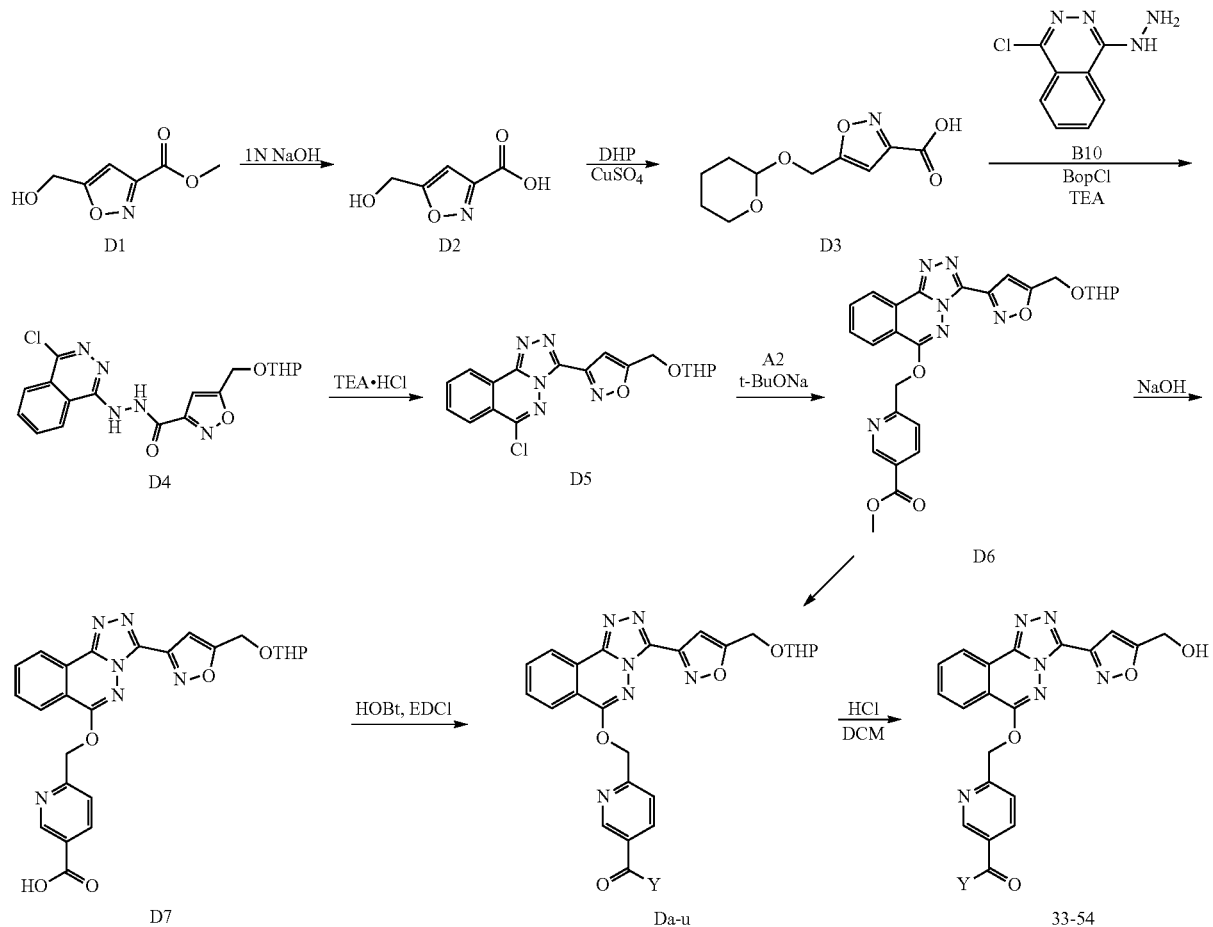

The Experimental Procedures 5-(hydroxymethyl)isoxazole-3-carboxylic acid (D2)

D1 (1 g, 6.4 mmol) was added to 1N aqueous NaOH solution (10 mL) and then was stirred at room temperature for 1.5 h. TLC (Petroleum ether:EtOAc=2:1, Rf=0.01) showed the starting material was consumed completely. Brine (20 mL) was added and the pH of the solution was adjusted to 2 by addition of diluted HCl. The acidic solution was extracted with 8×60 mL of ethyl acetate. The combined organic layers were dried over anhydrous $Na_2SO_4$. The solvent was evaporated to give D2 (0.8 g, 90%) as a white solid.

5-(((tetrahydro-2H-pyran-2-yl)oxy)methyl)isoxazole-3-carboxylic acid (D3)

Into the mixture of 3,4-dihydro-2H-pyran (DHP, 9 g, 107 mmol) and D2 (14 g, 98 mmol) in acetonitrile (200 mL) was added cupric sulfate pentahydrate (1.2 g, 4.9 mmol). The resulting mixture was stirred for 1 h at room temperature. TLC (DCM:MeOH=10:1, Rf=0.4) showed the starting material was consumed completely. The mixture was filtered. The filtrate was dried over anhydrous $Na_2SO_4$ and concentrated to dryness to give a crude product. The crude product was used directly for the next step without purification.

N'-(4-chlorophthalazin-1-yl)-5-(((tetrahydro-2H-pyran-2-yl)oxy)methyl)isoxazole-3-carbohydrazide (D4)

To a solution of D3 (the crude product from the previous step, 9.1 g, 40 mmol) and TEA (12.4 g, 123 mmol) in DCM (900 mL) was added bis(2-oxo-3-oxazolidinyl)phosphonic chloride (BOP—Cl, 10.2 g, 40 mmol) in one portion with stirring at 0° C. under $N_2$. The mixture was stirred at 0° C. for 20 mins. B10 (6 g, 30.8 mmol) was added. The resulting mixture was stirred at 0° C. for 1 h and then stirred at room temperature overnight. TLC (DCM:MeOH=20:1, Rf=0.5) showed the starting material was consumed completely. The reaction mixture was poured into 500 mL water and separated after being stirred. The organic layer was washed with water (500 mL×2) and dried over anhydrous $Na_2SO_4$. After concentration, the crude product was used directly for the next step without purification.

3-(6-chloro-[1,2,4]triazolo[3,4-a]phthalazin-3-yl)-5-(((tetrahydro-2H-pyran-2-yl)oxy)methyl)isoxazole (D5)

D4 (the crude product from the previous step, 20 g, 49 mmol) and triethylamine chlorhydrate (2 g, 15 mmol) in xylene (750 mL) was stirred at refluxing for 0.5 h. TLC (DCM:MeOH=20:1, Rf=0.7) showed the starting material was consumed completely. After cooled to RT, the reaction mixture was washed with 500 mL water. The aqueous layer was extracted with EtOAc (200 mL×2). The combined organic layers were dried over anhydrous $Na_2SO_4$. After concentration, the crude product was purified by silica gel chromatography to give pure product (8 g) as a yellow solid and a crude product (4 g) as a red solid.

methyl

6-(((3-(5-(((tetrahydro-2H-pyran-2-yl)oxy)methyl) isoxazol-3-yl)-[1,2,4]triazolo[3,4-a]phthalazin-6-yl) oxy)methyl)nicotinate (D6)

To a solution of D5 (2 g, 5.2 mmol) and methyl 6-(hydroxymethyl)nicotinate (1.73 g, 10.4 mmol) in THF (400 mL) was added KOtBu in portions during a period of 10 mins at 0° C. under N2. The reaction mixture was stirred at 0° C. for 0.5 h and then kept at RT for 1 h. TLC (DCM:MeOH=20:1, Rf=0.3) showed the starting material was consumed completely. The reaction mixture was concentrated to dryness. The crude product was used directly in the next step without purification.

6-(((3-(5-(((tetrahydro-2H-pyran-2-yl)oxy)methyl) isoxazol-3-yl)-[1,2,4]triazolo[3,4-a]phthalazin-6-yl) oxy)methyl)nicotinic acid (D7)

To the solution of D6 (the residue of the previous step) in EtOH (30 mL) was added 10% NaOH (8 mL) with stirring at RT. The mixture was stirred for 0.5 h at RT. TLC (DCM:MeOH=20:1, Rf=0.1) showed the starting material was consumed completely. The reaction mixture was concentrated under reduced pressure to remove EtOH. 20 mL of water was added to the residue and the resulting mixture was extracted with EtOAc (30 mL×2). The aqueous layer was adjusted to pH=4 with diluted HCl and a lot of solid precipitated. The mixture was suck filtered and the filter cake was washed with 5 mL water, dried in vacuum to give D7 (1.5 g, 46.1%) as a yellow solid.

Example 33

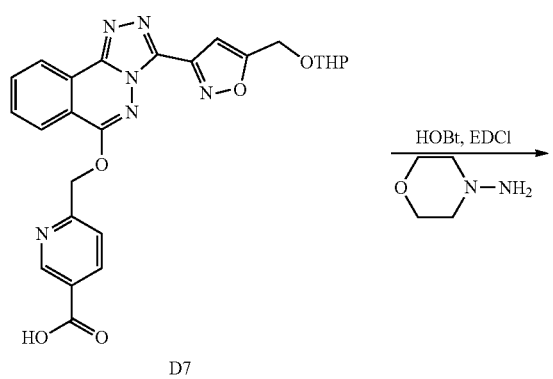

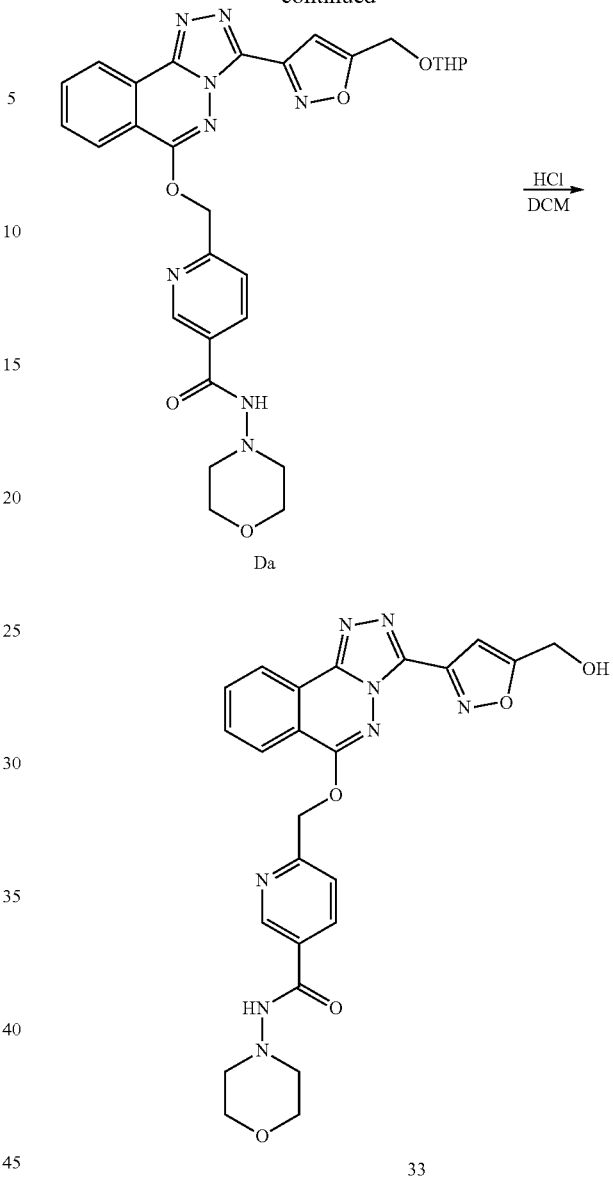

6-(((3-(5-(hydroxymethyl)isoxazol-3-yl)-[1,2,4]triazolo[3,4-a]phthalazin-6-yl)oxy)methyl)-N-morpholinonicotinamide (33)

A DMF solution (5 mL) containing HOBt (54 mg), EDCI (76.7 mg), and D7 (105 mg) was stirred at room temperature for 10 mins under N2. Morpholin-4-ylamine (49 mg) (CAS: 4319-49-7) and DIPEA (130 mg) were added to the reaction mixture by turn. The mixture was stirred at RT for 60 h. TLC (DCM:MeOH=20:1, Rf=0.3) showed the starting material was consumed completely. To the reaction mixture were added DCM (25 mL) and 30 mL water. The organic layer was washed with water (20 mL*2), dried over anhydrous $Na_2SO_4$, and concentrated under reduced pressure. The residue was purified by silica gel column to give product Da (76.4 mg, 65%) as white solid.

107

N-morpholin-4-yl-6-{3-[5-(tetrahydropyran-2-yloxylmethyl)isoxazol-3-yl]-[1,2,4]triazolo[3,4-a]phthalazin-6-yl)oxy)methyl)-nicotinamide (Da)

To a solution of Da (76.4 mg) in DCM (5 mL) were added a drop of con. HCl and the resulting mixture was stirred for 16 h at room temperature. TLC (DCM:MeOH=10:1, Rf=0.3) showed the starting material was consumed completely. The mixture was filtered and the filter cake was washed with DCM (5 mL×2). The combined filtrate was concentrated under reduced pressure and the residue was purified through a short silica gel column to give product 33 (48 mg, 73.3%) as a white solid.

$^1$H NMR (400 MHz, DMSO-d6) δ: 9.73 (s, 1H), 8.96 (d, 1H J=1.6), 8.58 (d, 1H J=8.0), 8.35 (d, 1H J=8.0), 8.22~8.19 (m, 1H), 8.16~8.11 (m, 1H), 8.03~7.98 (m, 1H), 7.86 (d, 1H J=8.0), 7.11 (s, 1H), 5.85 (t, 1H J=6.0), 5.76 (s, 2H), 4.72 (d, 2H J=6.0), 3.8~3.65 (m, 4H), 2.94~2.87 (m, 4H); LC-MS: m/z (ES+) for $C_{24}H_{22}N_8O_5$ 503.25 [M+1]$^+$.

Example 34

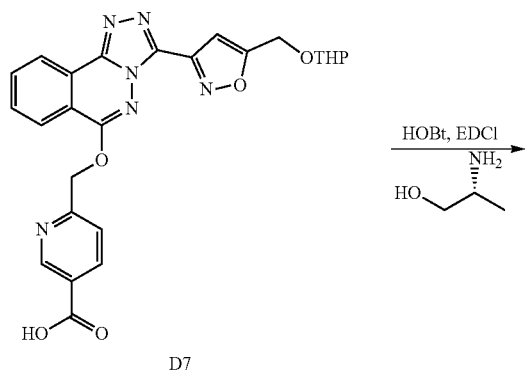

D7

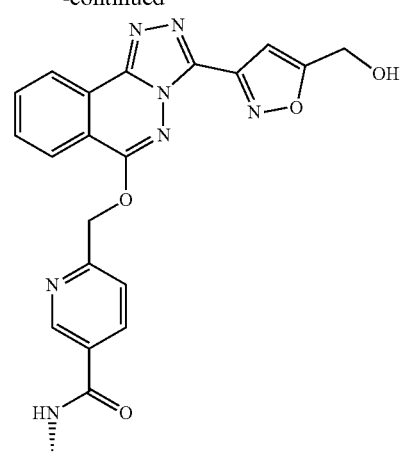

34

(R)-6-(((3-(5-(hydroxymethyl)isoxazol-3-yl)-[1,2,4]triazolo[3,4-a]phthalazin-6-yl)oxy)methyl)-N-(1-hydroxypropan-2-yl)nicotinamide (34)

The experimental procedure is the same as example 33:

The intermediate product Db was obtained from the condensation reaction of D7 and (R)-2-Amino-n-propanol. And then, it THP was deprotected to give the title compound 78 mg (100%) as an off-white solid.

$^1$H NMR (400 MHz, DMSO-d6) δ: 9.07 (d, 1H J=1.6), 8.61~8.53 (m, 2H), 8.40~8.30 (m, 2H), 8.16~8.10 (m, 1H), 8.05~7.95 (m, 1H), 7.84 (d, 1H J=8.4), 7.13 (s, 1H), 5.76 (s, 2H), 4.73 (s, 2H), 4.05~3.97 (m, 1H), 3.50~3.42 (m, 2H), 1.12 (d, 3H J=6.4); LC-MS: m/z (ES+) for $C_{23}H_{21}N_7O_5$ 476.17 [M+1]$^+$.

Example 35

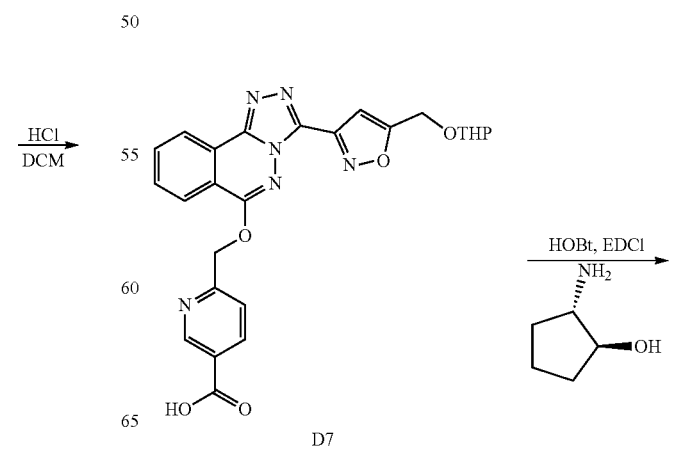

Db

D7

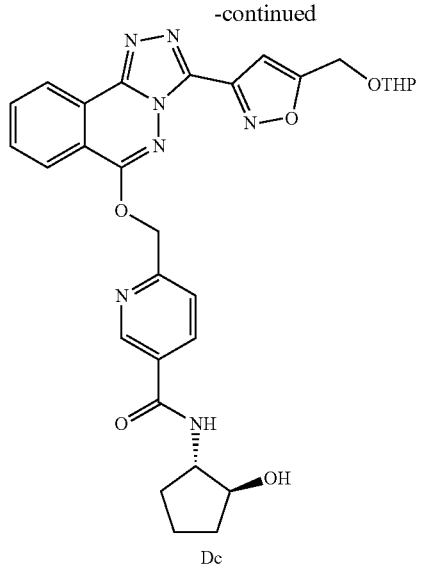

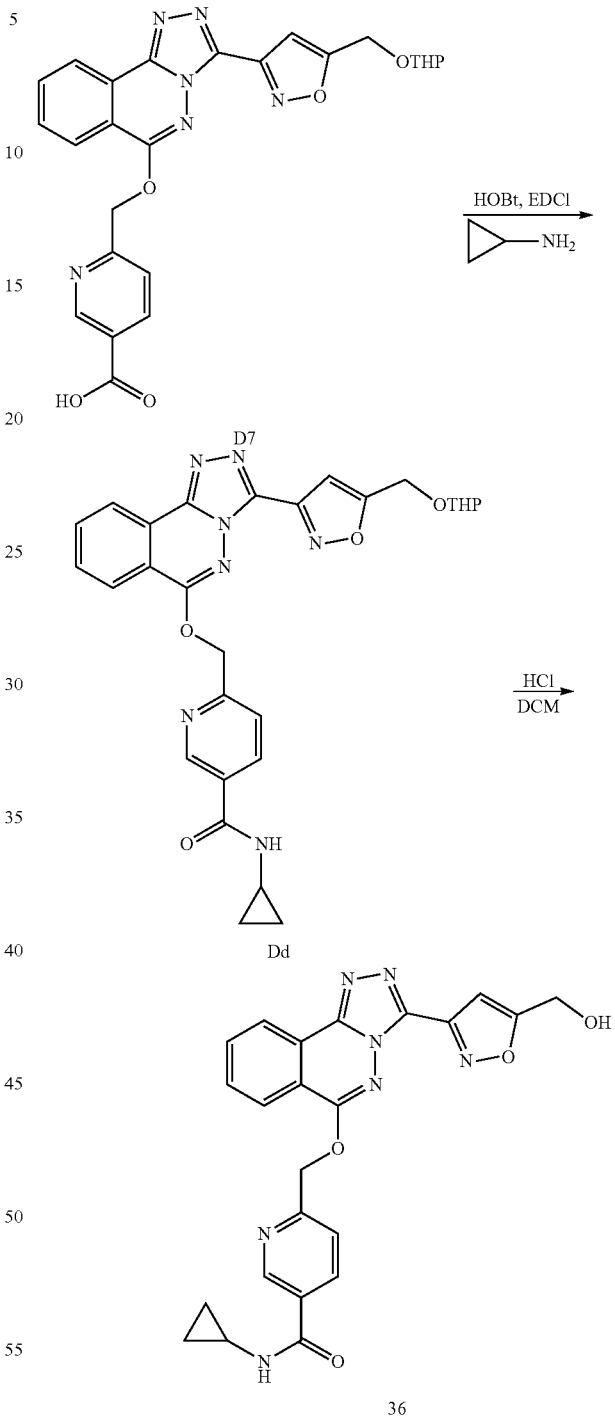

Example 36

N-((1S,2S)-2-hydroxycyclopentyl)-6-(((3-(5-(hydroxymethyl)isoxazol-3-yl)-[1,2,4]triazolo[3,4-a]phthalazin-6-yl)oxy)methyl)nicotinamide (35)

The experimental procedure is the same as example 33:

The intermediate product Dc was obtained from the condensation reaction of D7 and trans-(1S,2S)-2-aminocyclopentanol Hydrochloride (CAS: 68327-04-8). And then, it THP was deprotected to give the title compound 20 mg (46.9%) as a yellow solid.

$^1$H NMR (400 MHz, DMSO-d6) δ: 9.02 (d, 1H), 8.60~8.58 (d, 1H), 8.47~8.45 (d, 1H), 8.37~8.35 (d, 1H), 8.27~8.24 (m, 1H), 8.15~8.11 (t, 1H), 8.02~7.98 (t, 1H), 7.87~7.85 (d, 1H), 7.13 (s, 1H) 5.76 (s, 2H), 4.73 (s, 2H), 4.01~3.97 (m, 2H), 2.01~1.82 (m, 3H), 1.68~1.62 (m, 2H), 1.49~1.45 (m, 2H); LC-MS: m/z (ES+) for $C_{25}H_{23}N_7O_5$ 502.19 [M+1]$^+$.

N-cyclopropyl-6-(((3-(5-(hydroxymethyl)isoxazol-3-yl)-[1,2,4]triazolo[3,4-a]phthalazin-6-yl)oxy)methyl) nicotinamide (36)

The experimental procedure is the same as example 33:
The intermediate product Dd was obtained from the condensation reaction of D7 and cyclopropylamine (CAS:

765-30-0). And then, it THP was deprotected to give the title compound 38 mg (50.8%) as a white solid.

¹H NMR (400 MHz, DMSO-d6) δ: 9.00 (d, 1H J=1.2), 8.65 (d, 1H J=4.0), 8.57 (d, 1H J=8.0), 8.35 (d, 1H J=8.0), 8.25~8.22 (m, 1H), 8.15~8.10 (m, 1H), 8.02~7.97 (m, 1H), 7.85 (d, 1H J=8.0), 7.11 (s, 1H), 5.85 (t, 1H J=6.0), 5.76 (s, 2H), 4.72 (d, 2H J=6.0), 2.90~2.80 (m, 1H), 0.75~0.69 (m, 2H), 0.61~0.56 (m, 2H); LC-MS: m/z (ES+) for C₂₃H₁₉N₇O₄ 458.21 [M+1]⁺.

Example 37

6-(((3-(5-(hydroxymethyl)isoxazol-3-yl)-[1,2,4]tri-azolo[3,4-a]phthalazin-6-yl)oxy)methyl)-N-(1-methyl-1H-pyrazol-4-yl)nicotinamide (37)

The experimental procedure is the same as example 33:

The intermediate product De was obtained from the condensation reaction of D7 and 4-amino-1-methyl-1H-pyrazole (CAS: 69843-13-6). And then, it THP was deprotected to give the title compound 41 mg (88%) as an off-white solid.

¹H NMR (400 MHz, DMSO-d6) δ: 10.70 (s, 1H), 9.14 (s, 1H), 8.58 (d, 1H J=7.6), 8.37 (d, 2H J=6.8), 8.13 (t, 1H J=6.4), 8.06~7.91 (m, 3H), 7.58 (s, 1H), 7.13 (s, 1H), 5.88 (t, 1H J=6.0), 5.79 (s, 2H), 4.73 (d, 2H J=6.0), 3.82 (s, 3H); LC-MS: m/z (ES+) for C₂₄H₁₉N₉O₄ 498.27 [M+1]⁺.

Example 38

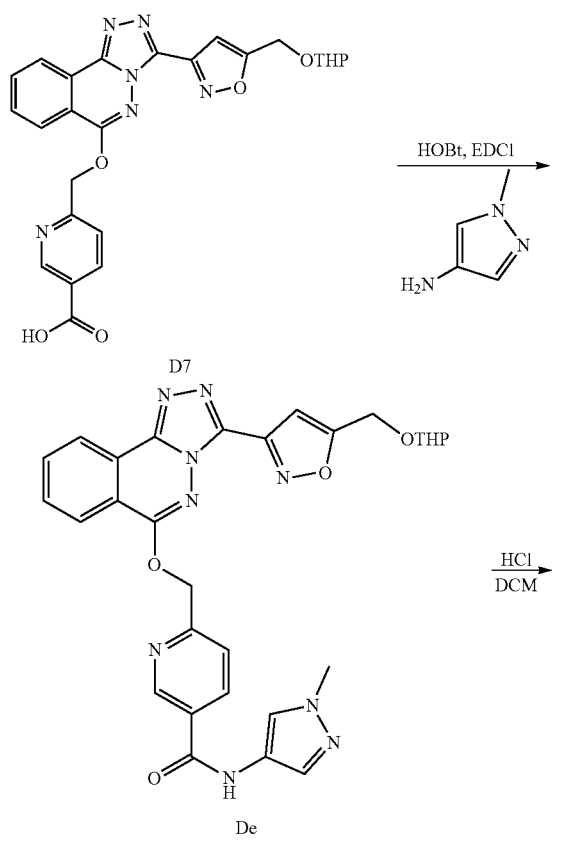

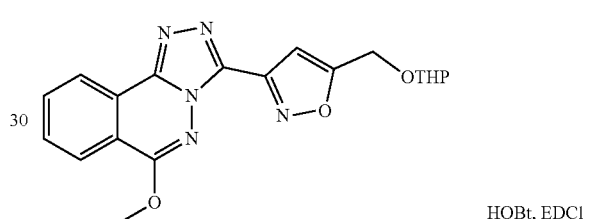

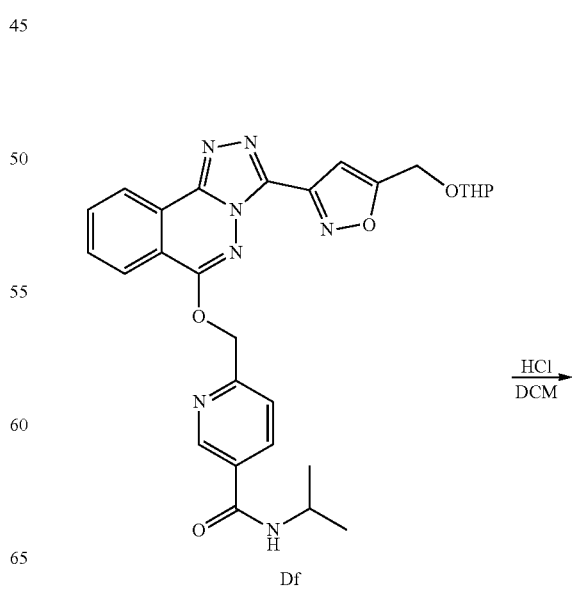

-continued

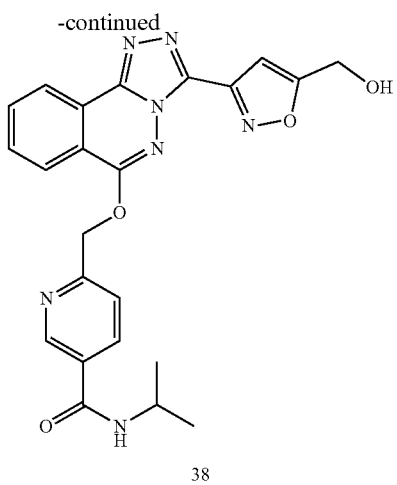

38

6-(((3-(5-(hydroxymethyl)isoxazol-3-yl)-[1,2,4]triazolo[3,4-a]phthalazin-6-yl)oxy)methyl)-N-iso propylnicotinamide (38)

The experimental procedure is the same as example 33:
The intermediate product Df was obtained from the condensation reaction of D7 and isopropylamine (CAS: 75-31-0). And then, its THP was deprotected to give the title compound 66 mg (90%) as a white solid.
$^1$H NMR (400 MHz, DMSO-d6) δ: 9.03 (d, 1H J=1.6), 8.60 (d, 1H J=7.6), 8.45 (d, 1H J=7.6), 8.35 (d, 1H J=8.0), 8.28~8.24 (m, 1H), 8.16~8.10 (m, 1H), 8.03~7.98 (m, 1H), 7.85 (d, 1H J=8.0), 7.13 (s, 1H), 5.88 (s, 1H), 5.76 (s, 2H), 4.73 (s, 2H), 4.16~4.05 (m, 1H), 1.16 (d, 6H J=6.4); LC-MS: m/z (ES+) for $C_{23}H_{21}N_7O_4$ 460.27 [M+1]$^+$.

Example 39

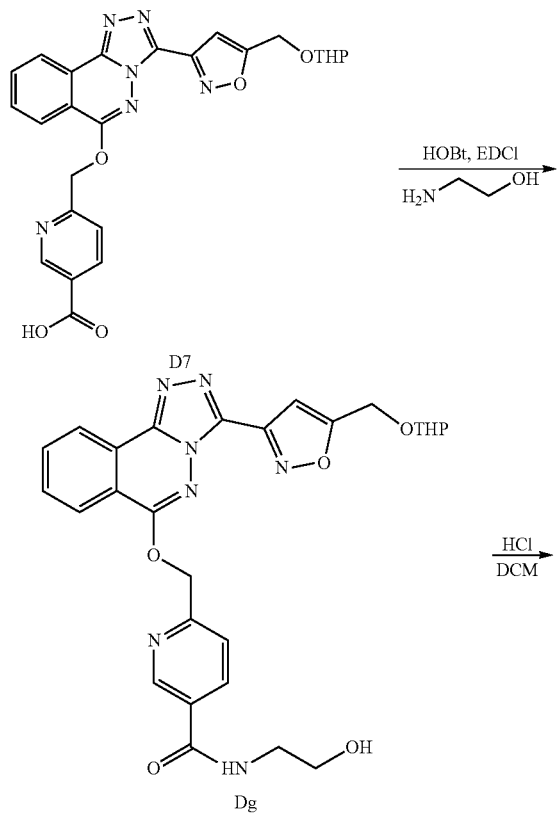

-continued

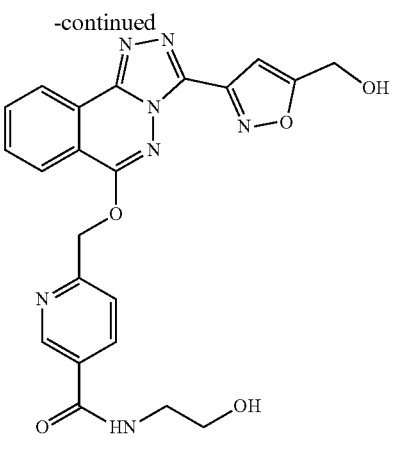

39

N-(2-hydroxyethyl)-6-(((3-(5-(hydroxymethyl)isoxazol-3-yl)-[1,2,4]triazolo[3,4-a]phthalazin-6-yl)oxy)methyl)nicotinamide (39)

The experimental procedure is the same as example 33:
The intermediate product Dg was obtained from the condensation reaction of D7 and ethanolamine (CAS: 141-43-5). And then, its THP was deprotected to give the title compound 66 mg (90%) as a white solid.
$^1$H NMR (400 MHz, DMSO-d6) δ: 9.04 (d, 1H J=1.6), 8.70 (t, 1H J=5.6), 8.58 (d, 1H J=8.0), 8.37 (d, 1H J=7.6), 8.30~8.26 (m, 1H), 8.16~8.10 (m, 1H), 8.03~7.98 (m, 1H), 7.86 (d, 1H J=8.4), 7.13 (s, 1H), 5.86 (t, 1H J=6.4), 5.76 (s, 2H), 4.78~4.72 (m, 3H), 3.55~3.45 (m, 2H), 3.38~3.32 (m, 2H); LC-MS: m/z (ES+) for $C_{22}H_{19}N_7O_5$ 462.25 [M+1]$^+$.

Example 40

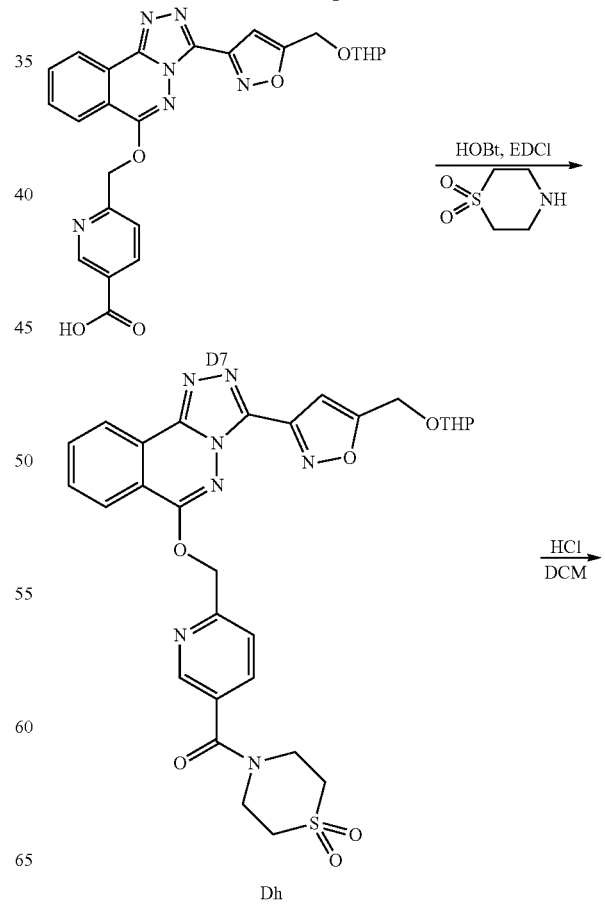

115

-continued

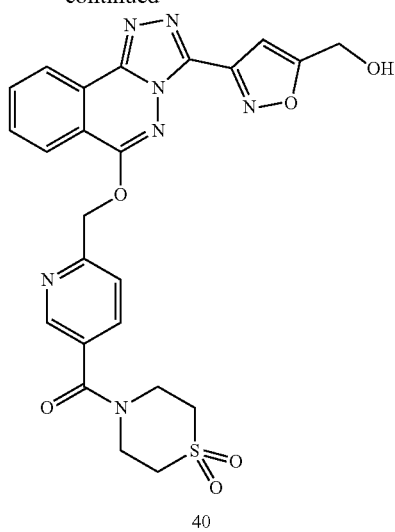

40

(1,1-dioxidothiomorpholino)(6-(((3-(5-(hydroxymethyl)isoxazol-3-yl)-[1,2,4]triazolo[3,4-a]phthalazin-6-yl)oxy)methyl)pyridin-3-yl)methanone (40)

The experimental procedure is the same as example 33:

The intermediate product Dh was obtained from the condensation reaction of D7 and thiomorpholine 1,1-Dioxide Hydrochloride (CAS: 59801-62-6). And then, its THP was deprotected to give the title compound 58 mg (83.9%) as a white solid.

$^1$H NMR (400 MHz, DMSO-d6) δ: 8.75 (d, 1H J=1.2), 8.58 (d, 1H J=8.0), 8.36 (d, 1H J=8.4), 8.13 (t, 1H J=7.6), 8.05~7.97 (m, 2H), 7.85 (d, 1H J=8.0), 7.12 (s, 1H), 5.85 (t, 1H J=6.0), 5.75 (s, 2H), 4.73 (d, 2H J=6.0), 4.12~3.95 (m, 2H), 3.82~3.65 (m, 2H), 3.22~3.35 (m, 4H); LC-MS: m/z (ES+) for $C_{24}H_{21}N_7O_6S$ 536.24 [M+1]$^+$.

Example 41

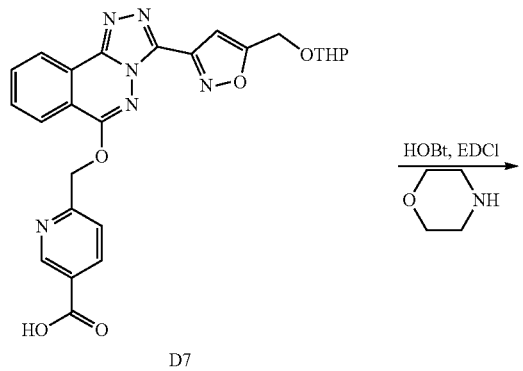

116

-continued

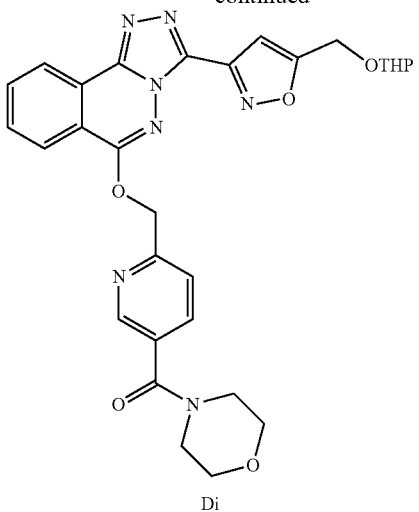

Di

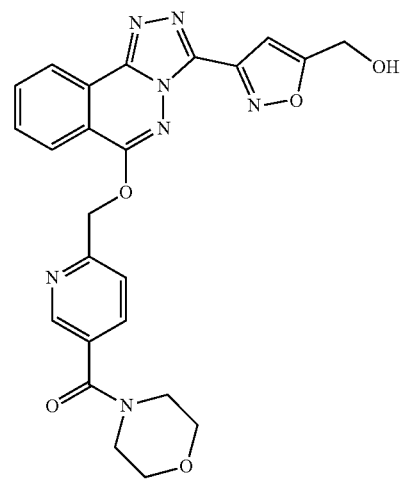

41

(6-(((3-(5-(hydroxymethyl)isoxazol-3-yl)-[1,2,4]triazolo[3,4-a]phthalazin-6-yl)oxy)methyl)pyridin-3-yl)(morpholino)methanone (41)

The experimental procedure is the same as example 33:

The intermediate product Di was obtained from the condensation reaction of D7 and morpholine (CAS: 110-91-8). And then, its THP was deprotected to give the title compound 70 mg (90.5%) as a white solid.

$^1$H NMR (400 MHz, DMSO-d6) δ: 8.67 (d, 1H J=1.6), 8.60 (d, 1H J=3.6), 8.36 (d, 1H J=8.0), 8.13 (t, 1H J=7.2), 8.02~7.92 (m, 2H), 7.82 (d, 1H J=8.0), 7.11 (s, 1H), 5.85 (t, 1H J=6.0), 5.75 (s, 2H), 4.72 (d, 2H J=6.0), 3.70~3.5 (m, 6H), 3.35~3.25 (m, 2H); LC-MS: m/z (ES+) for $C_{24}H_{21}N_7O_5$ 488.26 [M+1]$^+$.

Example 42

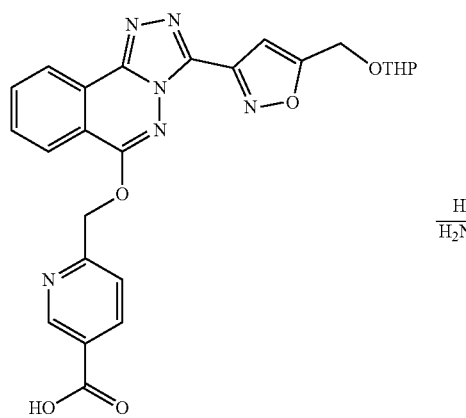

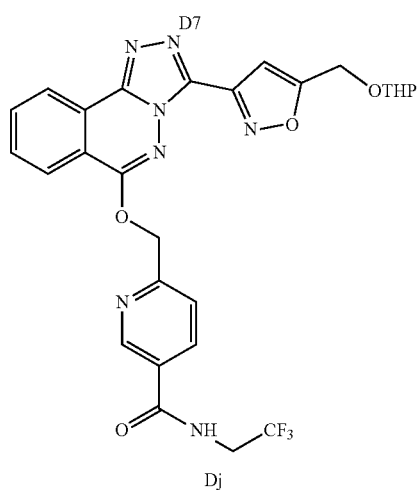

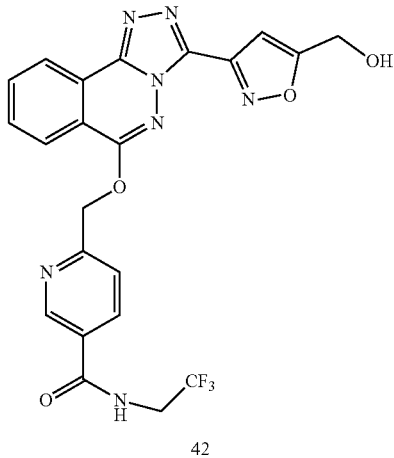

6-(((3-(5-(hydroxymethyl)isoxazol-3-yl)-[1,2,4]tri-azolo[3,4-a]phthalazin-6-yl)oxy)methyl)-N-(2,2,2-trifluoroethyl)nicotinamide (42)

The experimental procedure is the same as example 33:
The intermediate product Dj was obtained from the condensation reaction of D7 and Trifluoroethylamine hydrochloride (CAS: 373-88-6). And then, its THP was deprotected to give the title compound 57 mg (88%) as a white solid.

$^1$H NMR (400 MHz, DMSO-d6) δ: 9.34 (t, 1H J=6.0), 9.08 (d, 1H J=1.6), 8.56 (d, 1H J=8.0), 8.38~8.30 (m, 2H), 8.12 (t, 1H, J=7.6), 7.99 (t, 1H J=8.0), 7.92 (d, 2H, J=8), 7.11 (s, 1H), 5.86 (t, 1H J=6.0), 5.77 (s, 2H), 4.72 (d, 2H J=6.0), 4.20~4.08 (m, 2H); LC-MS: m/z (ES+) for $C_{22}H_{16}F_3N_7O_4$ 500.20 [M+1]$^+$.

Example 43

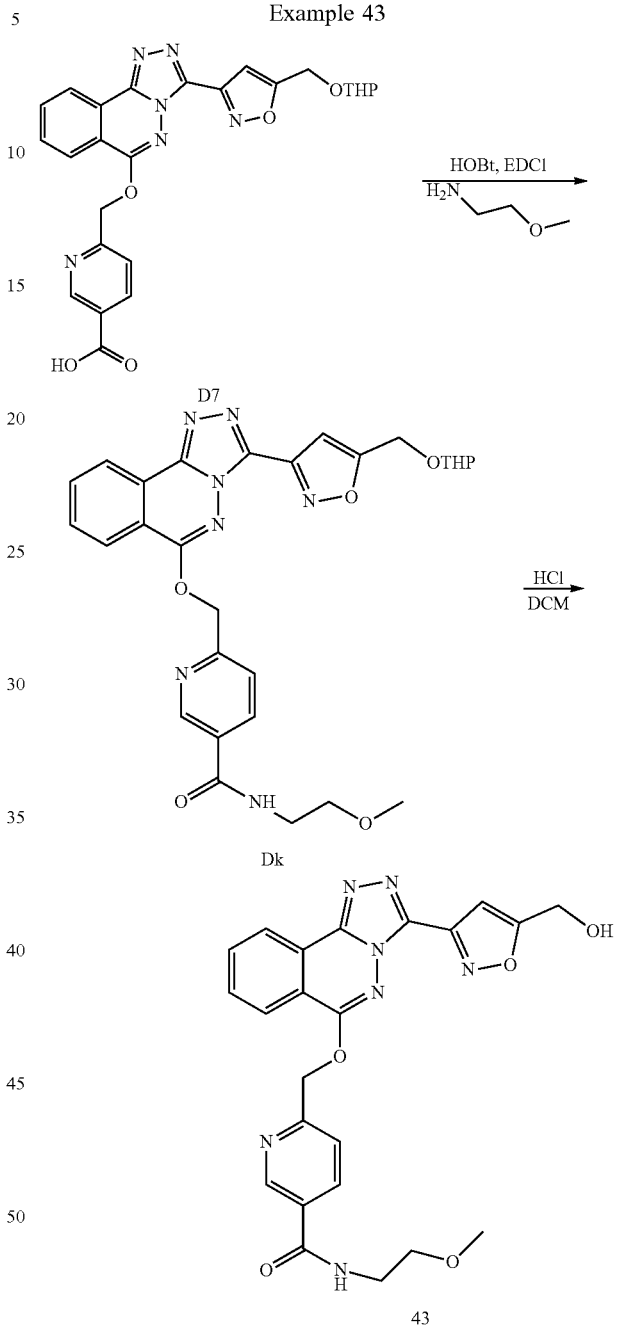

6-(((3-(5-(hydroxymethyl)isoxazol-3-yl)-[1,2,4]tri-azolo[3,4-a]phthalazin-6-yl)oxy)methyl)-N-(2-methoxyethyl)nicotinamide (43)

The experimental procedure is the same as example 33:
The intermediate product Dk was obtained from the condensation reaction of D7 and 2-methoxyethylamine (CAS: 109-85-3). And then, its THP was deprotected to give the title compound 57 mg (85%) as a white solid.

$^1$H NMR (400 MHz, DMSO-d6) δ: 9.04 (d, 1H J=1.6), 8.78 (t, 1H J=4.8), 8.58 (d, 1H J=8.0), 8.36 (d, 1H J=8.0), 8.30~8.26 (m, 1H), 8.16~8.10 (m, 1H), 8.03~7.98 (m, 1H), 7.86 (d, 1H J=8.0), 7.12 (s, 1H), 5.86 (t, 1H J=6.4), 5.76 (s, 2H), 4.72 (d, 2H J=6.0), 3.50~3.40 (m, 4H), 3.26 (s, 3H); LC-MS: m/z (ES+) for $C_{23}H_{21}N_7O_5$ 476.26 [M+1]$^+$.

Example 44

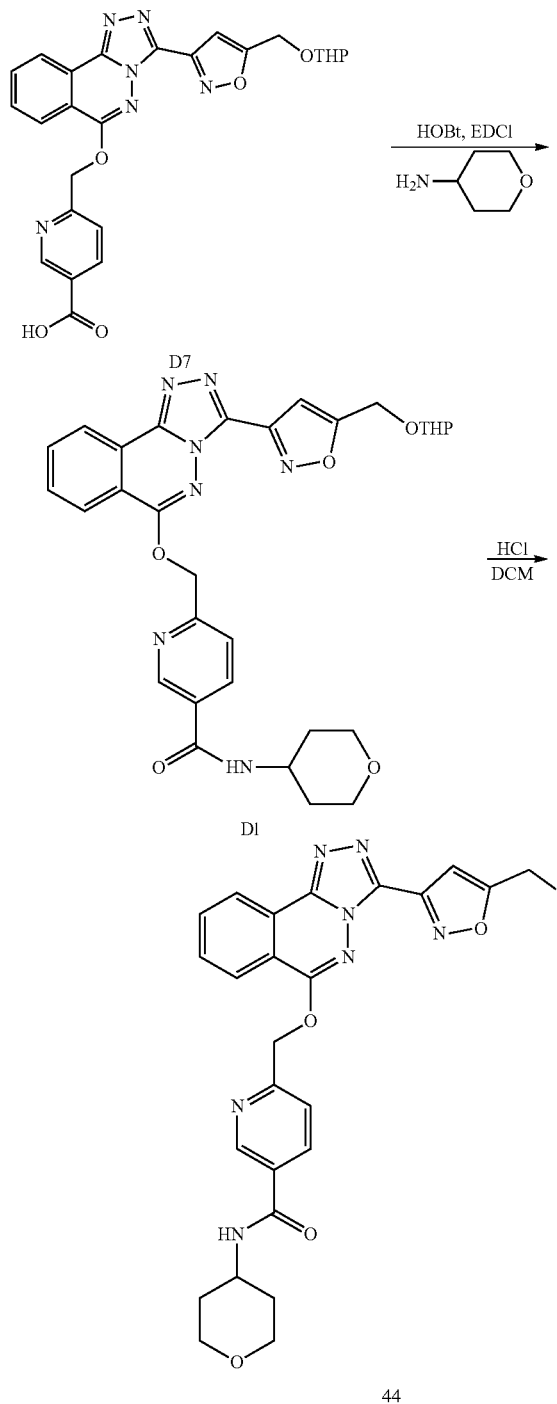

44

6-(((3-(5-(hydroxymethyl)isoxazol-3-yl)-[1,2,4]tri-azolo[3,4-a]phthalazin-6-yl)oxy)methyl)-N-(tetra-hydro-2H-pyran-4-yl)nicotinamide (44)

The experimental procedure is the same as example 33:

The intermediate product D1 was obtained from the condensation reaction of D7 and 4-aminotetrahydropyran hydrochloride (CAS: 33024-60-1). And then, its THP was deprotected to give the title compound 51.7 mg (63.8%) as a white solid.

$^1$H NMR (400 MHz, DMSO-d6) δ: 9.03 (s, 1H), 8.58 (d, 1H J=7.6), 8.53 (d, 1H J=7.6), 8.35 (d, 1H J=8.0), 8.28~8.25 (m, 1H), 8.16~8.10 (m, 1H), 8.03~7.98 (m, 1H), 7.85 (d, 1H J=8.0), 7.12 (s, 1H), 5.86 (t, 1H J=5.6), 5.76 (s, 2H), 4.72 (d, 2H J=6.0), 4.07~3.83 (m, 4H), 1.82~1.75 (m, 2H), 1.62~1.52 (m, 2H); LC-MS: m/z (ES+) for $C_{25}H_{23}N_7O_5$ 502.26 [M+1]$^+$.

Example 45

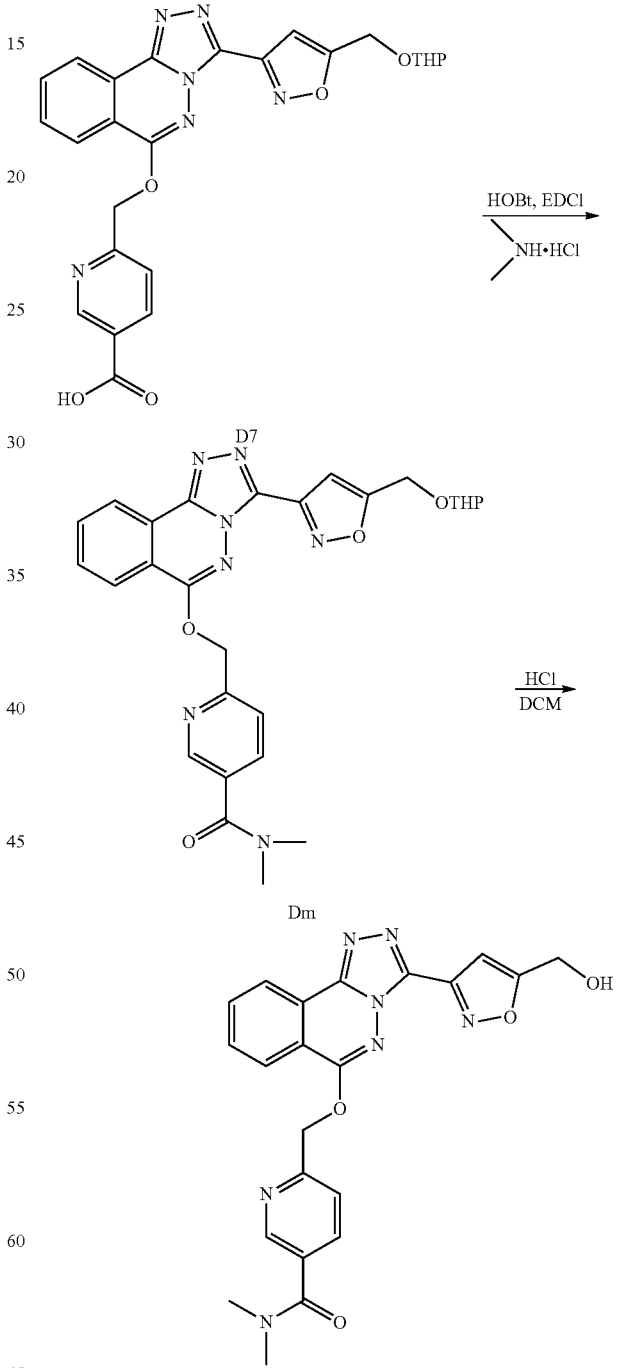

45

6-(((3-(5-(hydroxymethyl)isoxazol-3-yl)-[1,2,4]tri-azolo[3,4-a]phthalazin-6-yl)oxy)methyl)-N,N-dimethylnicotinamide (45)

The experimental procedure is the same as example 33:

The intermediate product Dm was obtained from the condensation reaction of D7 and dimethylamine hydrochloride (CAS: 506-59-2). And then, its THP was deprotected to give the title compound 74 mg (96%) as a white solid.

$^1$H NMR (400 MHz, DMSO-d6) δ: 8.67 (d, 1H J=1.6), 8.58 (d, 1H J=8.0), 8.36 (d, 1H J=8.0), 8.16~8.11 (m, 1H), 8.02~7.92 (m, 2H), 7.81 (d, 1H J=8.0), 7.12 (s, 1H), 5.85 (t, 1H J=6.0), 5.75 (s, 2H), 4.72 (d, 2H J=6.0), 3.00 (s, 3H), 2.92 (s, 3H); LC-MS: m/z (ES+) for $C_{22}H_{19}N_7O_4$ 446.28 [M+1]$^+$.

Example 46

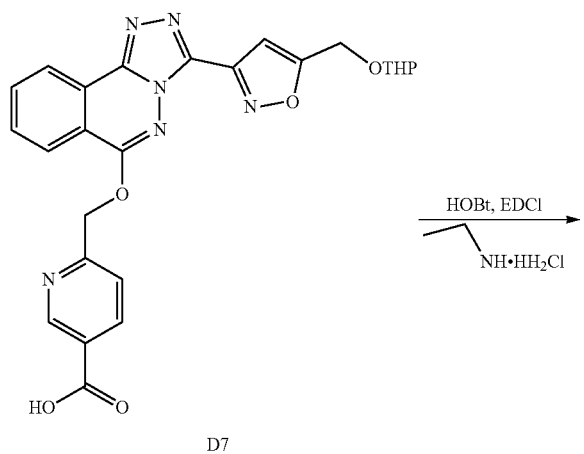

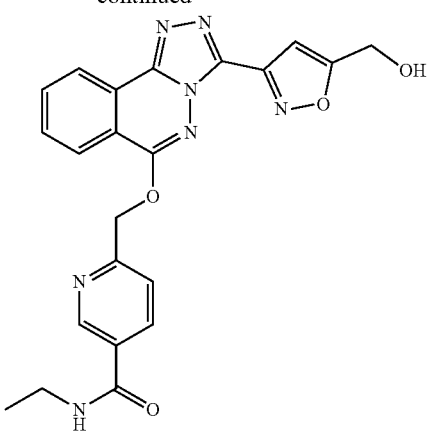

N-ethyl-6-(((3-(5-(hydroxymethyl)isoxazol-3-yl)-[1,2,4]triazolo[3,4-a]phthalazin-6-yl)oxy)methyl)nicotinamide (46)

The experimental procedure is the same as example 33:

The intermediate product Dn was obtained from the condensation reaction of D7 and ethylamine Hydrochloride (CAS: 557-66-4). And then, its THP was deprotected to give the title compound 80 mg (92%) as a white solid.

$^1$H NMR (400 MHz, DMSO-d6) δ: 9.03 (d, 1H J=1.6), 8.70 (t, 1H J=5.2), 8.59 (d, 1H J=8.0), 8.38 (d, 1H J=8.4), 8.27~8.24 (m, 1H), 8.13 (t, 1H J=7.6), 7.99 (t, 1H J=7.6), 7.87 (d, 1H J=8.4), 7.12 (s, 1H), 5.86 (t, 1H J=6.0), 5.76 (s, 2H), 4.74 (d, 2H J=6.0), 3.38~3.25 (m, 2H), 1.13 (t, 3H J=7.2); LC-MS: m/z (ES+) for $C_{22}H_{19}N_7O_4$ 446.00 [M+1]$^+$.

Example 47

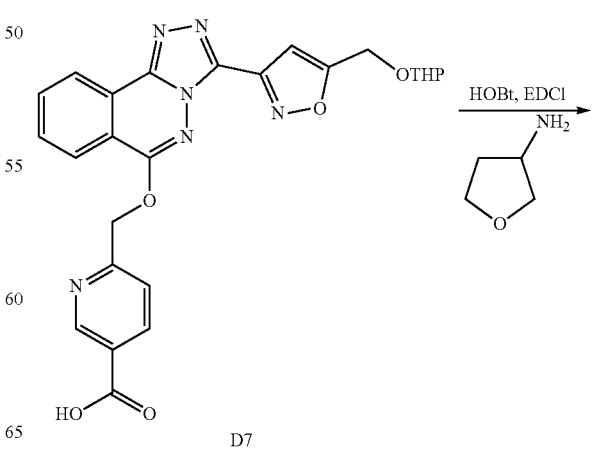

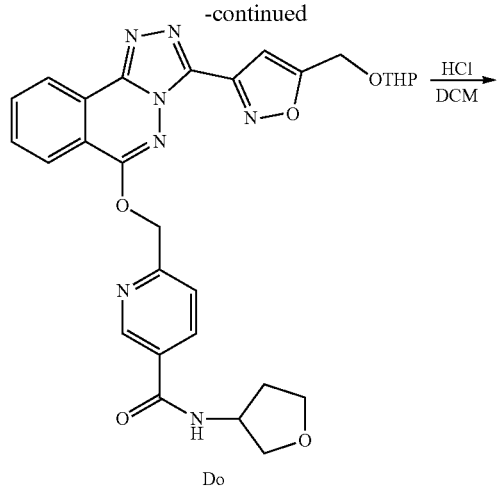

6-(((3-(5-(hydroxymethyl)isoxazol-3-yl)-[1,2,4]tri-
azol[3,4-a]phthalazin-6-yl)oxy)methyl)-N-(tetrahy-
drofuran-3-yl)nicotinamide (47)

The experimental procedure is the same as example 33:

The intermediate product Do was obtained from the condensation reaction of D7 and tetrahydrofuran-3-amine hydrochloride (CAS: 204512-94-7). And then, its THP was deprotected to give the title compound 79 mg (92%) as off-white solid.

$^1$H NMR (400 MHz, DMSO-d6) δ: 9.04 (d, 1H J=1.6), 8.76 (d, 1H J=6.4), 8.57 (d, 1H J=8.0), 8.35 (d, 1H J=8.0), 8.30~8.26 (m, 1H), 8.16~8.10 (m, 1H), 8.02~7.97 (m, 1H), 7.86 (d, 1H J=8.4), 7.12 (s, 1H), 5.86 (t, 1H J=6.4), 5.76 (s, 2H), 4.72 (d, 2H J=6.0), 4.50~4.30 (m, 1H), 3.90~3.80 (m, 2H), 3.76~3.68 (m, 1H), 3.62~3.57 (m, 1H), 2.22~2.12 (m, 1H), 1.95~1.90 (m, 1H); LC-MS: m/z (ES+) for $C_{24}H_{21}N_7O_5$ 488.32 [M+1]$^+$.

Example 48

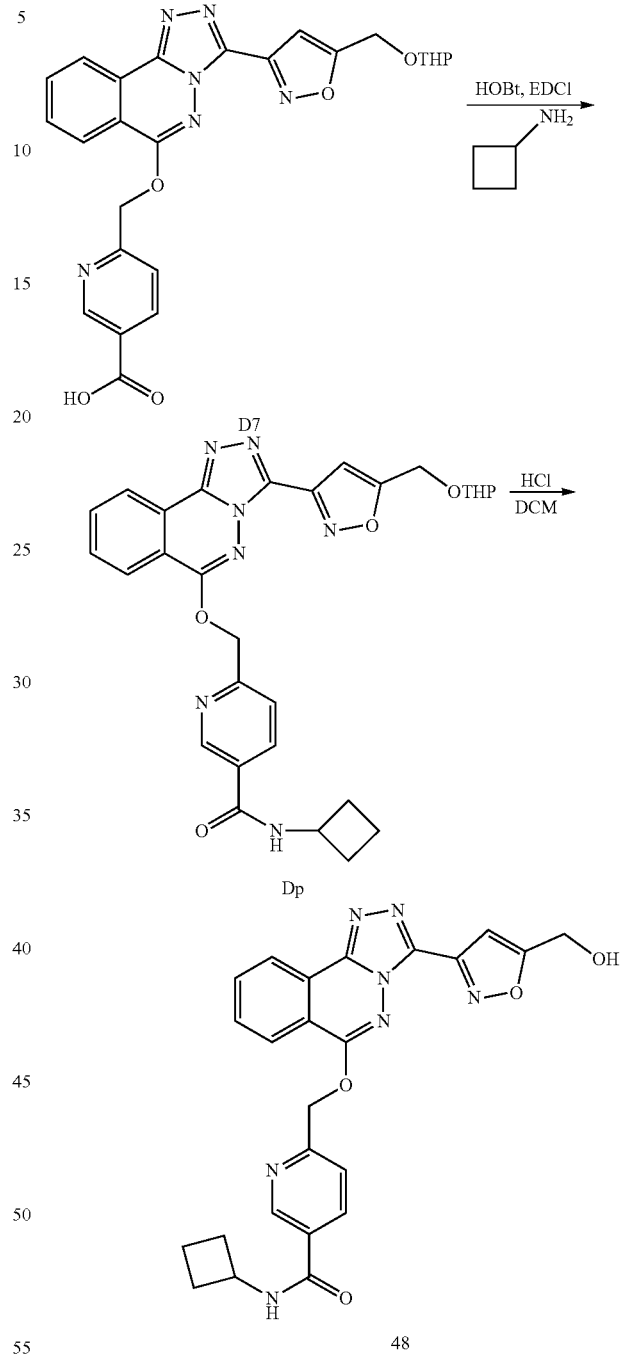

N-cyclobutyl-6-(((3-(5-(hydroxymethyl)isoxazol-3-
yl)-[1,2,4]triazolo[3,4-a]phthalazin-6-yl)oxy) meth-
yl)nicotinamide (48)

The experimental procedure is the same as example 33:

The intermediate product Dp was obtained from the condensation reaction of D7 and cyclobutanamine (CAS: 2516-34-9). And then, its THP was deprotected to give the title compound 61 mg (90%) as an off-white solid.

¹H NMR (400 MHz, DMSO-d6) δ: 9.02 (d, 1H J=1.6), 8.82 (d, 1H J=6.4), 8.58 (d, 1H J=7.6), 8.36 (d, 1H J=8.0), 8.28~8.24 (m, 1H), 8.16~8.10 (m, 1H), 8.02~7.98 (m, 1H), 7.86 (d, 1H J=8.4), 7.12 (s, 1H), 5.86 (t, 1H J=6.4), 5.76 (s, 2H), 4.72 (d, 2H J=6.0), 4.46~4.38 (m, 1H), 2.27~2.18 (m, 2H), 2.10~2.03 (m, 2H), 1.73~1.65 (m, 2H); LC-MS: m/z (ES+) for C$_{24}$H$_{21}$N$_7$O$_4$ 472.33 [M+1]$^+$.

Example 49

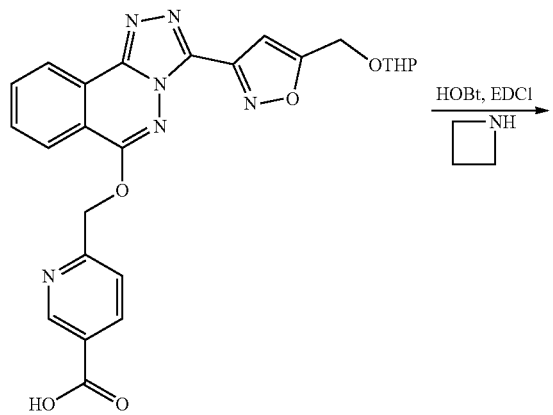

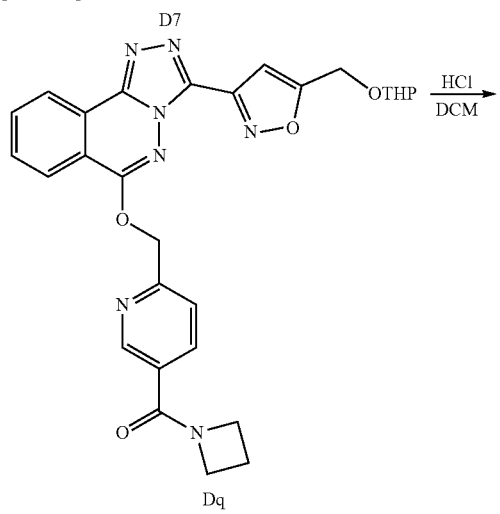

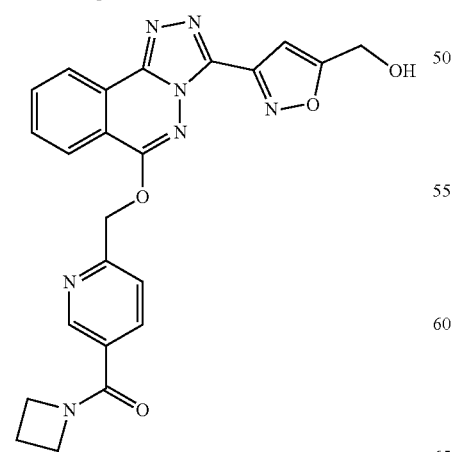

49 azetidin-1-yl-(6-(((3-(5-(hydroxymethyl)isoxazol-3-yl)-[1,2,4]triazolo[3,4-a]phthalazin-6-yl)oxy)methyl) pyridin-3-yl)methanone (49)

The experimental procedure is the same as example 33:

The intermediate product Dq was obtained from the condensation reaction of D7 and azetidine (CAS: 503-29-7). And then, its THP was deprotected to give the title compound 54 mg (88%) as a white solid.

¹H NMR (400 MHz, DMSO-d6) δ: 8.84 (d, 1H J=1.6), 8.58 (d, 1H J=7.6), 8.36 (d, 1H J=8.0), 8.16~8.05 (m, 2H), 8.02~7.98 (m, 1H), 7.83 (d, 1H J=8.0), 7.11 (s, 1H), 5.86 (t, 1H J=6.4), 5.76 (s, 2H), 4.72 (d, 2H J=6.0), 4.33 (t, 2H J=7.6), 4.07 (t, 2H J=7.6), 2.32~2.23 (m, 2H); LC-MS: m/z (ES+) for C$_{23}$H$_{19}$N$_7$O$_4$ 458.29 [M+1]$^+$.

Example 50

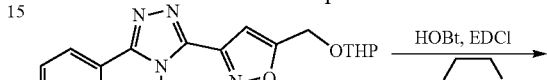

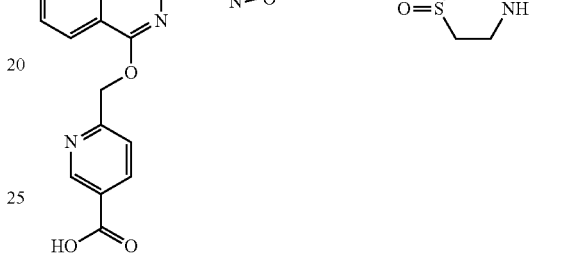

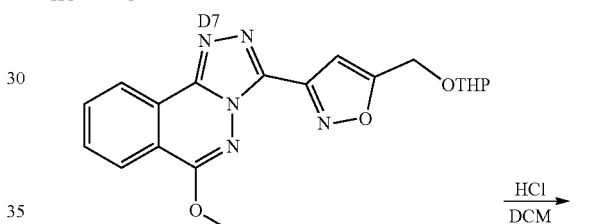

50

127

(6-(((3-(5-(hydroxymethyl)isoxazol-3-yl)-[1,2,4]triazolo[3,4-a]phthalazin-6-yl)oxy)methyl)pyridin-3-yl)(1-oxidothiomorpholino)methanone (50)

The experimental procedure is the same as example 33:

The intermediate product Dr was obtained from the condensation of D7 and thiomorpholine 1-oxide (refer: Biodegradation, 1998, 9, (6)433-442). And then, its THP was deprotected to give the title compound 75 mg (90%) as a white solid.

$^1$H NMR (400 MHz, DMSO-d6) δ: 8.71 (d, 1H J=1.6), 8.55 (d, 1H J=8.0), 8.33 (d, 1H J=8.0), 8.13~8.08 (m, 1H), 8.00~7.95 (m, 2H), 7.85 (d, 1H J=8.0), 7.11 (s, 1H), 5.89 (t, 1H J=6.0), 5.74 (s, 2H), 4.74 (d, 2H, J=5.6) 4.45~4.33 (m, 1H), 3.95~3.45 (m, 3H), 3.08~2.93 (m, 2H), 2.92~2.62 (m, 2H); LC-MS: m/z (ES+) for $C_{24}H_{21}N_7O_5S$ 520.21 [M+1]$^+$.

Example 51

6-(((3-(5-(hydroxymethyl)isoxazol-3-yl)-[1,2,4]triazolo[3,4-a]phthalazin-6-yl)oxy)methyl)nicotinohydrazide (51)

128

N'-(6-{3-[5-(tetrahydro-2H-pyran-2-yloxymethyl)isoxazol-3-yl]-[1,2,4]triazolo[3,4-a]phthalazin-6-yloxy-methyl}-pyridine-3-carbonyl)-nicotinamide (Ds)

To a solution of 3 mL of hydrazine hydrate in ethanol (15 mL) was added D6 (375 mg). The reaction mixture was stirred at r. t. for 5 h. The reaction mixture was filtrated and the filter cake was washed with ethanol and small amount of water. The cake was dried to give a white solid product. The crude product was used directly in the next step without purification.

6-(((3-(5-(hydroxymethyl)isoxazol-3-yl)-[1,2,4]triazolo[3,4-a]phthalazin-6-yl)oxy)methyl)nicotinohydrazide (51)

Ds (280 mg) was added to 25 mL of DCM and then 100 mg con. HCl was added. The reaction mixture was stirred at r. t. for 16 h. TLC (DCM:MeOH=10:1, Rf=0.4) showed that the reaction was completed. The reaction mixture was filtered and the filter cake was purified with chromatography column to give the title compound 180 mg (91.7%) as a white solid.

$^1$H NMR (400 MHz, DMSO-d6) δ: 11.86 (m, 1H), 9.11 (s, 1H), 8.59 (d, 1H J=7.6), 8.42~8.35 (m, 2H), 8.14 (t, 1H J=7.6), 8.01 (t, 1H J=7.6), 7.94 (d, 1H J=8.4), 7.10 (s, 1H), 5.80 (s, 2H), 4.73 (s, 2H); LC-MS: m/z (ES+) for $C_{20}H_{16}N_8O_4$ 433.24 [M+1]$^+$.

Example 52

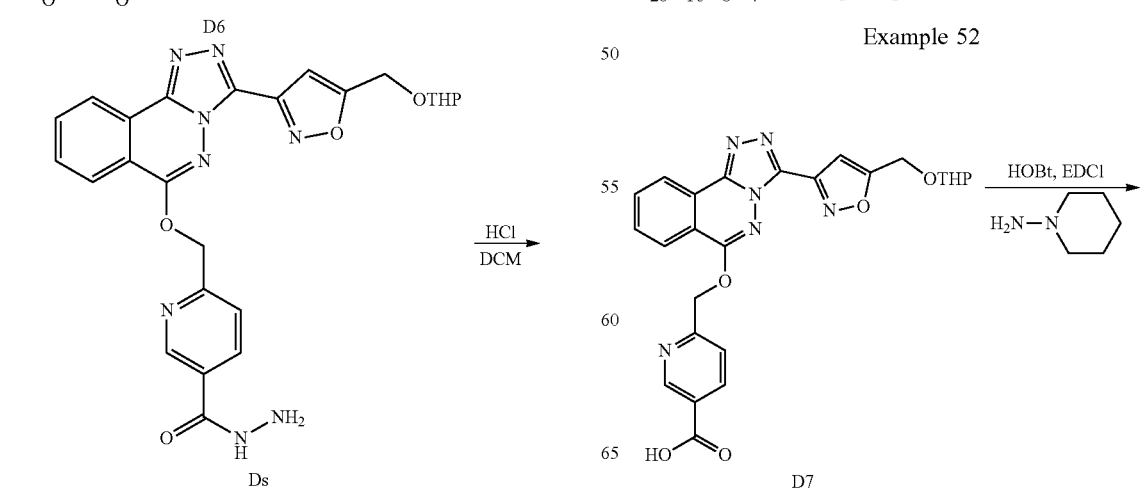

-continued

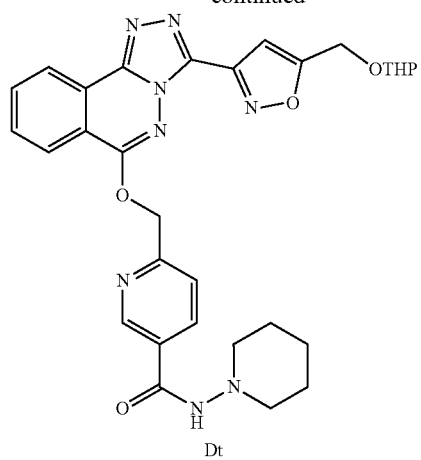

Dt

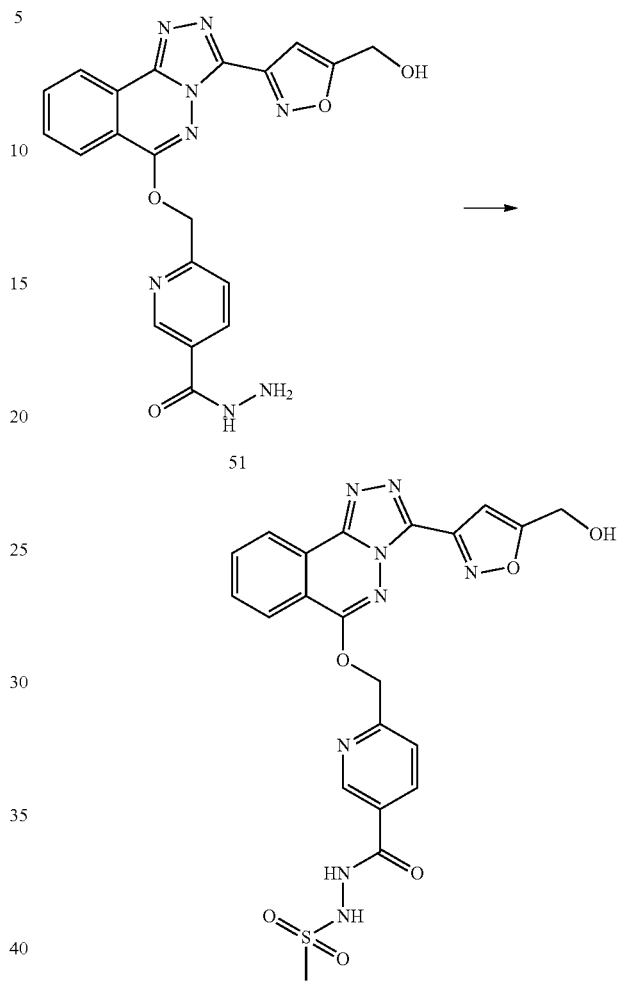

52

6-(((3-(5-(hydroxymethyl)isoxazol-3-yl)-[1,2,4]tri-azolo[3,4-a]phthalazin-6-yl)oxy)methyl)-N-(piperi-din-1-yl)nicotinamide (52)

The experimental procedure is the same as example 33:

The intermediate product Dt was obtained from the condensation of D7 and N-aminopiperidine hydrochloride (CAS: 63234-70-8). And then, its THP was deprotected to give the title compound 42 mg (70%) as a white solid.

$^1$H NMR (400 MHz, DMSO-d6) δ: 9.59 (s, 1H) 8.95 (d, 1H J=1.6), 8.58 (d, 1H J=7.6), 8.35 (d, 1H J=8.0), 8.21~8.10 (m, 2H), 8.03~7.97 (m, 1H), 7.84 (d, 1H J=8.0), 7.11 (s, 1H), 5.76 (s, 2H), 4.73 (s, 2H), 2.83 (t, 4H J=5.2), 1.63~1.56 (m, 4H), 1.40-1.33 (m, 2H); LC-MS: m/z (ES+) for $C_{25}H_{24}N_8O_4$ 501.36 [M+1]$^+$.

Example 53

N'-(6-(((3-(5-(hydroxymethyl)isoxazol-3-yl)-[1,2,4]triazolo[3,4-a]phthalazin-6-yl)oxy)methyl)nicoti-noyl)methanesulfonohydrazide (53)

To a suspension of 51 (60 mg) in pyridine (2 mL) was added MsCl (21.3 mg) dropwise. The mixture was stirred at room temperature for 16 h. The reaction was complete as detected by TLC (MeOH:DCM=1:10, Rf=0.4). The reaction mixture was concentrated, and the crude product was purified by silica gel chromatography to give 53 (4 mg, 5.6%) as a white solid.

$^1$H NMR (400 MHz, DMSO-d6) δ: 10.98 (s, 1H) 9.72 (s, 1H) 9.07 (d, 1H J=1.6), 8.57 (d, 1H J=8.0), 8.37 (d, 1H J=8.0), 8.33~8.30 (m, 1H), 8.16~8.11 (m, 1H), 8.03~7.98 (m, 1H), 7.90 (d, 1H J=8.4), 7.12 (s, 1H), 5.87 (t, 1H J=6.0), 5.78 (s, 2H), 4.72 (d, 2H J=5.6), 3.03 (s, 3H); LC-MS: m/z (ES+) for $C_{21}H_{18}N_8O_6S$ 511.26 [M+1]$^+$.

Example 54

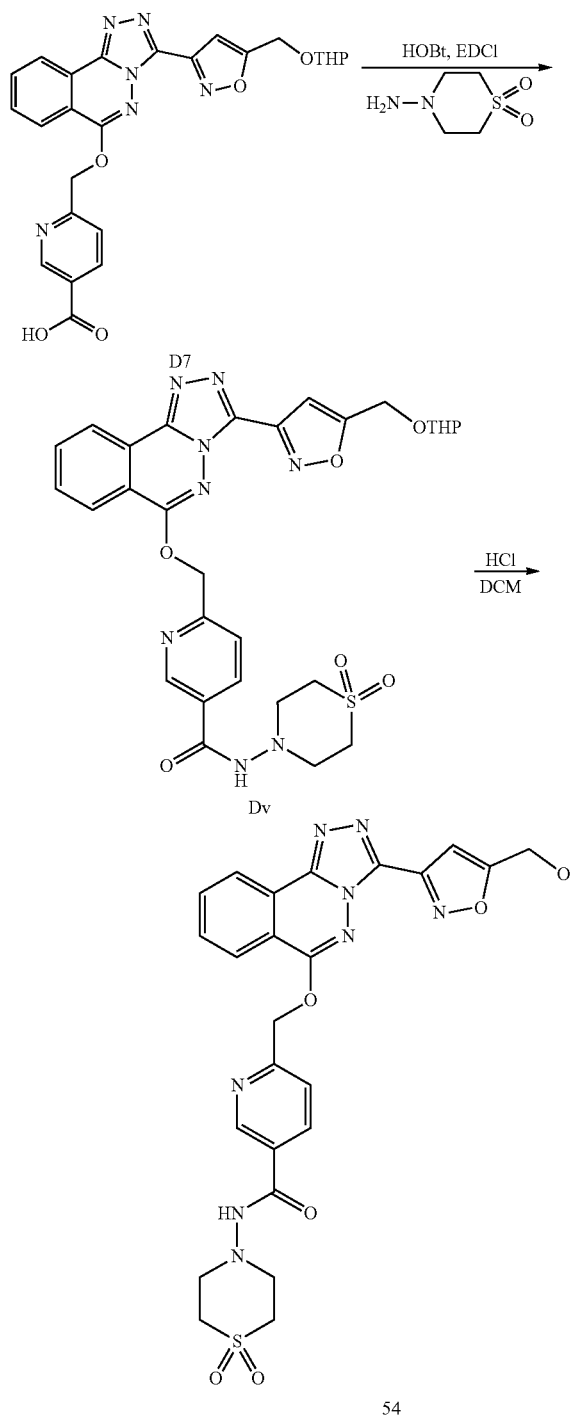

54

N-(1,1-dioxidothiomorpholino)-6-(((3-(5-(hydroxymethyl)isoxazol-3-yl)-[1,2,4]triazolo[3,4-a]phthalazin-6-yl)oxy)methyl)nicotinamide (54)

The experimental procedure is the same as example 33: The intermediate product Dv was obtained from the condensation of D7 and 1,1-dioxo-1,4-thiazinan-4-amine (CAS: 26494-76-8). And then, its THP was deprotected to give the title compound 30 mg (69%) as a white solid.

$^1$H NMR (400 MHz, DMSO-d6) δ: 10.08 (s, 1H) 8.99 (s, 1H) 8.58 (d, 1H J=8.0), 8.37~8.35 (d, 1H J=8.0), 8.22 (d, 1H J=8.0), 8.16~8.10 (m, 1H), 8.03~7.98 (m, 1H), 7.86 (d, 1H J=8.4), 7.11 (s, 1H), 5.88 (t, 1H J=6.0), 5.76 (s, 2H), 4.72 (d, 2H J=5.6), 3.44~3.39 (m, 4H), 3.30~3.25 (m, 4H); LC-MS: m/z (ES+) for $C_{24}H_{22}N_8O_6S$ 551.33 $[M+1]^+$.

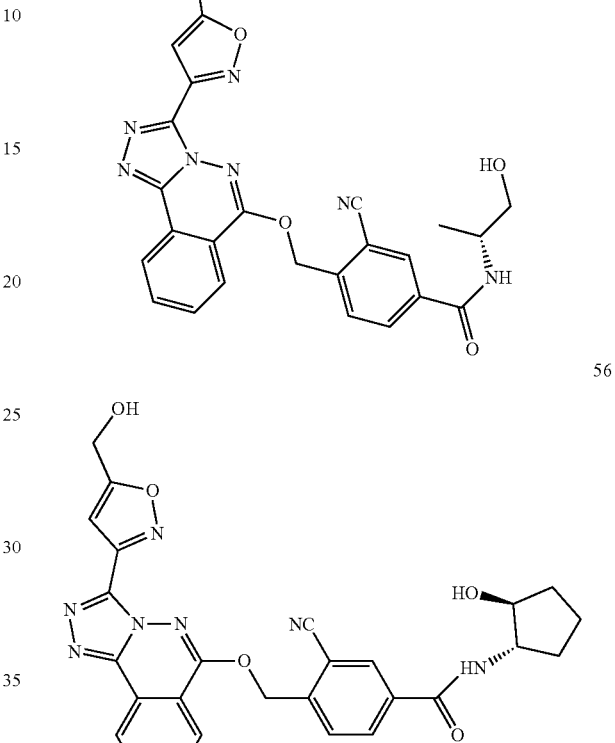

55

56

Scheme 5

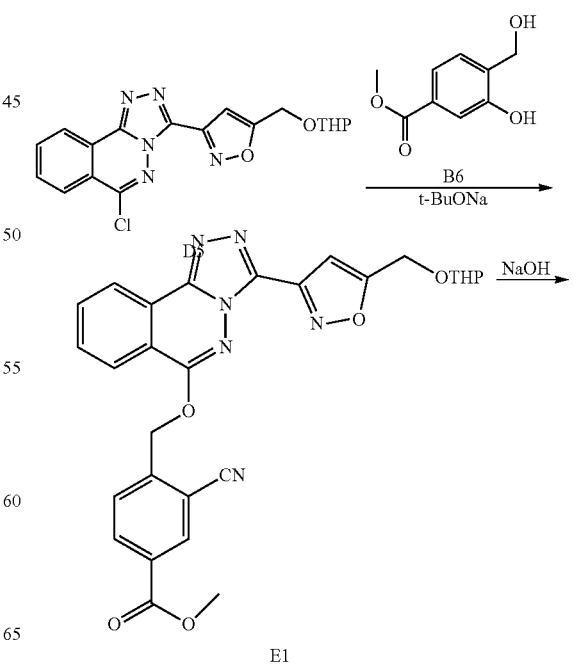

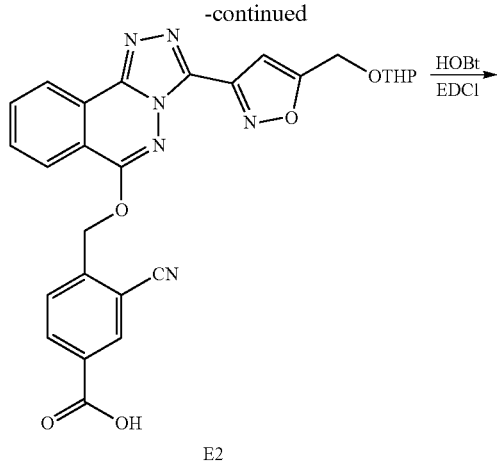

E2

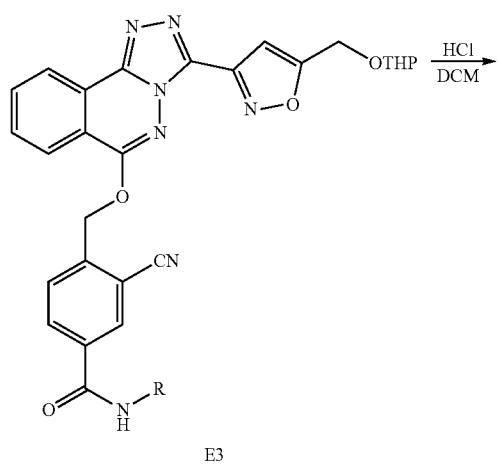

E3

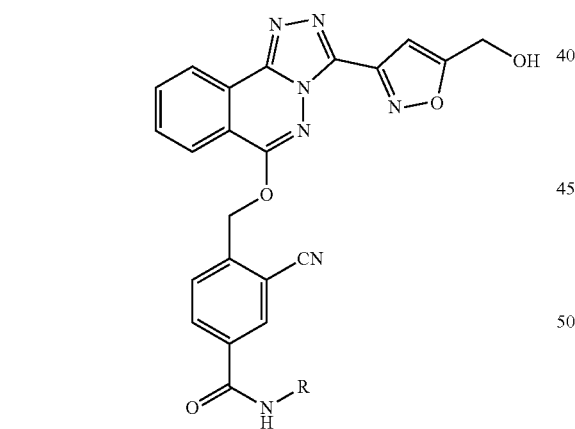

55, 56

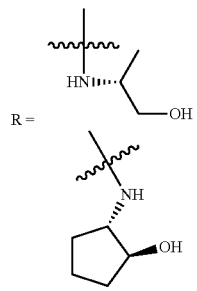

R =

The Experimental Procedures

3-Cyano-4-{3-[5-(tetrahydro-pyran-2-yloxymethyl)-isoxazol-3-yl]-[1,2,4]triazolo[3,4-a]phthalazin-6-yloxymethyl}-benzoic acid methyl ester (E1)

To a solution of D5 (400 mg) and B6 (400 mg) in dry THF was added t-NaOBu (200 mg) in portions during a period of 10 mins at 0° C. under Ar. The reaction mixture was stirred at 0° C. for 0.5 h and then kept at RT for 1 h. TLC (DCM:MeOH=20:1, Rf=0.5) showed the starting material was consumed completely. The reaction mixture was concentrated to dryness. The residue was used directly in the next step without purification.

3-Cyano-4-{3-[5-(tetrahydro-pyran-2-yloxymethyl)-isoxazol-3-yl]-[1,2,4]triazolo[3,4-a]phthalazin-6-yloxymethyl}-benzoic acid (E2)

To a solution of E1 (the residue of the previous step) in EtOH (10 mL) was added 10% NaOH (4 mL) with stirring at RT. The mixture was stirred for 0.5 h at RT. TLC (DCM:MeOH=20:1, Rf=0.1) showed the starting material was consumed completely. The reaction mixture was concentrated to remove EtOH. 20 mL of water was added to the residue and the resulting mixture was extracted with EtOAc (30 mL×2). The aqueous layer was quenched with satd aq NH4Cl. A solid precipitated. The mixture was filtered and the filter cake was washed with water, dried to give E2 (140 mg, 25.7%) as a white solid.

Example 55

(R)-3-cyano-4-(((3-(5-(hydroxymethyl)isoxazol-3-yl)-[1,2,4]triazolo[3,4-a]phthalazin-6-yl)oxy)methyl)-N-(1-hydroxypropan-2-yl)benzamide (55)

The procedure was the same as example 33: The title product was obtained from the starting materials E3 and (R)-(−)-2-Amino-1-propanol (CAS: 35320-23-1): 42 mg, 81.8% as a white solid.
$^1$H NMR (400 MHz, DMSO-d6) δ: 8.58 (d, 1H J=7.6), 8.42~8.36 (m, 2H), 8.27 (d, 1H J=8.0), 8.18 (m, 1H), 8.01~7.96 (m, 1H), 7.19 (s, 1H), 5.90~5.80 (m, 3H), 4.80~4.70 (m, 3H), 4.05~3.97 (t, 1H), 3.49~3.42 (m, 1H), 3.39~3.32 (m, 1H), 1.12 (d, 3H J=6.8); LC-MS: m/z (ES+) for $C_{25}H_{21}N_7O_5$ 500.31 [M+1]$^+$.

Example 56

3-cyano-N-((1S,2S)-2-hydroxycyclopentyl)-4-(((3-(5-(hydroxymethyl)isoxazol-3-yl)-[1,2,4]triazolo[3,4-a]phthalazin-6-yl)oxy)methyl)benzamide (56)

The procedure was the same as example 33: The title product was obtained from the starting materials E3 and trans-(1S,2S)-2-aminocyclopentanol hydrochloride (CAS: 68327-04-8): 44 mg, 78.5% as a white solid.
$^1$H NMR (400 MHz, DMSO-d6) δ: 8.58 (d, 1H J=8.0), 8.45 (d, 1H J=6.4), 8.39 (d, 1H J=1.6), 8.27 (d, 1H J=8.0), 8.17 (m, 1H), 8.04 (d, 1H J=8.0), 8.01~7.96 (m, 1H) 7.19 (s, 1H), 5.90~5.80 (m, 3H), 4.81~4.73 (m, 3H), 4.03~3.96 (t, 2H), 2.04~1.96 (m, 1H), 1.89~1.81 (m, 1H), 1.70~1.62 (m, 2H), 1.52~1.44 (m, 2H); LC-MS: m/z (ES+) for $C_{27}H_{23}N_7O_5$ 526.31 [M+1]$^+$.
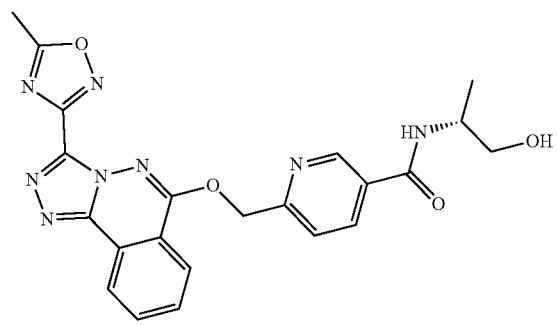
57
Scheme 6
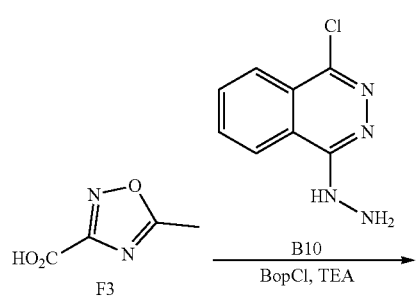
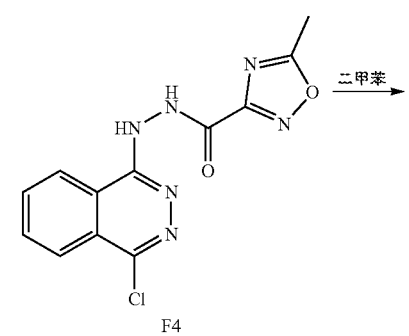
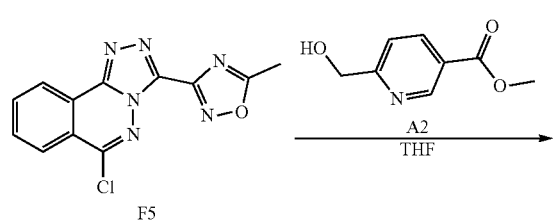
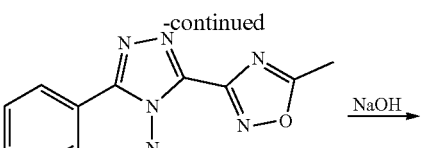
F6
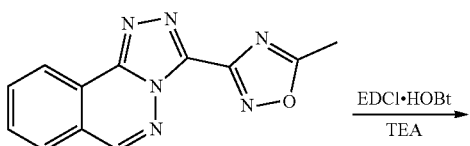
F7
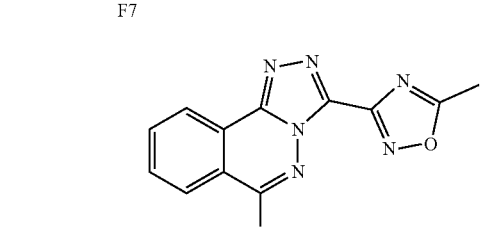
57
The Experimental Procedure
Step 1
5-Methyl-[1,2,4]oxadiazole-3-carboxylic acid ethyl ester (F2)
Acetyl chloride (18 g) was added into acetic acid (10.5 g) with stirring at 25° C. to give acetic anhydride. A 100-mL RBF was charged with hydroxylamine-HCl (8.6 g), followed by acetic acid (48 mL). Ethyl cyanoformate (10 g) was added, then sodium acetate (10.1 g) was added in portions over 15 min. The reaction was stirred for 2 h at 18-28° C. The reaction mixture was cooled to 15° C.; acetic anhydride was added to the mixture slowly over 20 min. The temperature increased to 26° C. during the addition. The reaction mixture was stirred for an additional 15 min. The reaction mixture was heated at 99° C. for 12 h. The reaction mixture was cooled to room temperature, and acetic acid was removed under vacuum. Ethyl acetate 100 mL and water 20 mL were added to the reaction mixture. The solution was neutralized with 30% $K_2CO_3$ (37 mL) to pH 7 and then separated. The aqueous phase was extracted twice with ethyl acetate (30 mL*2). The organic layer was washed with water (20 mL), dried over anhydrous $Na_2SO_4$ and evaporated to dryness to give F2 (15 g, 95%) as a white solid.

Step 2

5-Methyl-[1,2,4]oxadiazole-3-carboxylic acid (F3)

To a solution of F2 (20 g) in EtOH (100 mL) was added aqueous NaOH (2N, 62 mL) at RT and stirred for 1 hour. TLC (PETROLEUM ETHER:ETOAC=2:1, Rf=0.5) showed the starting material was consumed completely. The reaction mixture was quenched with satd aq NH4Cl, was concentrated under reduced pressure to provide a white solid. MeOH was added to dissolve the residue with stirring. The mixture was filtered and concentrated under reduced pressure to afford F3 (8 g, 49%) as a white solid.

Step 3

5-Methyl-[1,2,4]oxadiazole-3-carboxylic acid N'-(4-chloro-1,2-dihydro-phthalazin-1-yl)-hydrazide (F4)

To a solution of F3 (789 mg) and TEA (1.56 g) in DCM (100 mL) was added bis(2-oxo-3-oxazolidinyl) phosphonic chloride (BOP—Cl, 1.57 g) in one portion with stirring at 0° C. under Ar. The mixture was stirred at 0° C. for 20 mins. (4-chloro-1,2-dihydro-phthalazin-1-yl)-hydrazide B10 (1 g) was added. The resulting mixture was stirred at 0° C. for 1 h and then stirred at room temperature overnight. TLC (DCM:MeOH=10:1, Rf=0.5) showed the starting material was consumed completely. The reaction mixture was filtered and the filtrate was washed with water (15 mL), dried over anhydrous $Na_2SO_4$ and concentrated. The residue was purified by column chromatography to give the product (300 mg, 19%).

Step 4

6-Chloro-3-(5-methyl-[1,2,4]oxadiazol-3-yl)-[1,2,4]triazolo[3,4-a]phthalazine (F5)

F4 (800 mg) and triethylamine chlorhydrate (69 mg) in xylene (100 mL) was stirred at refluxing for 0.5 h. TLC (DCM:MeOH=20:1, Rf=0.7) showed the starting material was consumed completely. After cooled to RT, the reaction mixture was washed with 10 mL water. The aqueous layer was extracted with EtOAc (20 mL×2). The combined organic layers were dried over anhydrous $Na_2SO_4$. After concentration, the crude product was purified by silica gel chromatography eluted with PE:EtOAc=2:1 to give a pure product F5 (580 mg) as yellow solid.

$^1$H NMR (400 MHz, DMSO-d6) δ: 8.82 (d, 1H J=8.0), 8.35 (d, 1H J=8.4), 8.13~8.06 (m, 1H), 8.02~7.94 (m, 1H), 2.79 (s, 3H).

Step 5

Methyl 6-(((3-(5-methyl-1,2,4-oxadiazol-3-yl)-[1,2,4]triazolo[3,4-a]phthalazin-6-yl) oxy)methyl)nicotinate (F6)

To a solution of F5 (286 mg) and A2 (334 mg) in dry THF was added t-NaOBu (192 mg) in portions during a period of 10 mins at 0° C. under Ar. The reaction mixture was stirred at 0° C. for 0.5 h and then kept at RT for 1 h. TLC (DCM:MeOH=20:1, Rf=0.5) showed the starting material was consumed completely. The reaction mixture was concentrated to dryness. The residue was used directly in the next step without purification.

Step 6

6-(((3-(5-methyl-1,2,4-oxadiazol-3-yl)-[1,2,4]triazolo[3,4-a]phthalazin-6-yl) oxy)methyl)nicotinic acid (F7)

To the solution of F6 (the residue of the previous step) in EtOH (10 mL) was added 10% NaOH (1.6 mL) with stirring at RT. The mixture was stirred for 0.5 h at RT. TLC (DCM:MeOH=20:1, Rf=0.1) showed the starting material was consumed completely. The reaction mixture was concentrated to remove EtOH, and then sat aq $NH_4Cl$ was added. A solid precipitated. The mixture was filtered and the filter cake was washed with water, dried to give F7 (240 mg, 60%) as an off-white solid.

Step 7

Example 57

(R)—N-(1-hydroxypropan-2-yl)-6-(((3-(5-methyl-1,2,4-oxadiazol-3-yl)-[1,2,4]triazolo[3,4-a]phthalazin-6-yl)oxy)methyl)nicotinamide (57)

A DMF solution (5 mL) containing HOBt (81 mg), EDCI (115 mg), and F7 (120 mg) was stirred at room temperature for 10 mins under Ar. (R) 2-Amino-propan-1-ol (45 mg) and DIPEA (155 mg) was added to the reaction mixture by turn. The mixture was stirred at RT overnight. TLC (DCM:MeOH=20:1, Rf=0.3) showed the starting material was consumed completely. DCM (25 mL) and 30 mL water were added to the reaction mixture which was then separated. The organic layer was washed with water twice, dried over anhydrous $Na_2SO_4$, and concentrated. The residue was purified by silica gel column to give product (54 mg, 44.9%) as a white solid.

$^1$H NMR (400 MHz, DMSO-d6) δ: 9.01 (d, 1H J=1.2), 8.63~8.56 (m, 1H), 8.38~8.33 (m, 2H), 8.24~8.28 (m, 1H), 8.17~8.11 (m, 1H), 8.05~7.95 (m, 1H), 7.89 (d, 1H J=8.0), 5.72 (s, 2H), 4.74 (t, 2H J=6.0), 4.08~3.98 (m, 1H), 3.49~3.42 (m, 1H), 3.38~3.32 (m, 1H), 2.78 (s, 3H), 1.12 (d, 3H J=6.8); LC-MS: m/z (ES+) for $C_{22}H_{20}N_8O_4$ 461.30 [M+1]$^+$.

58

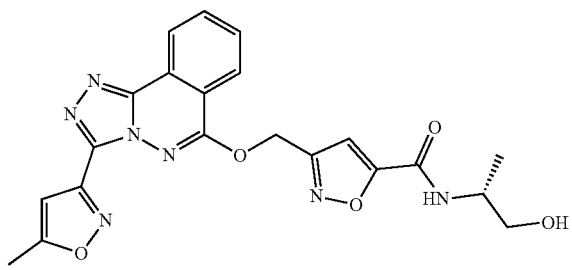

Scheme 7

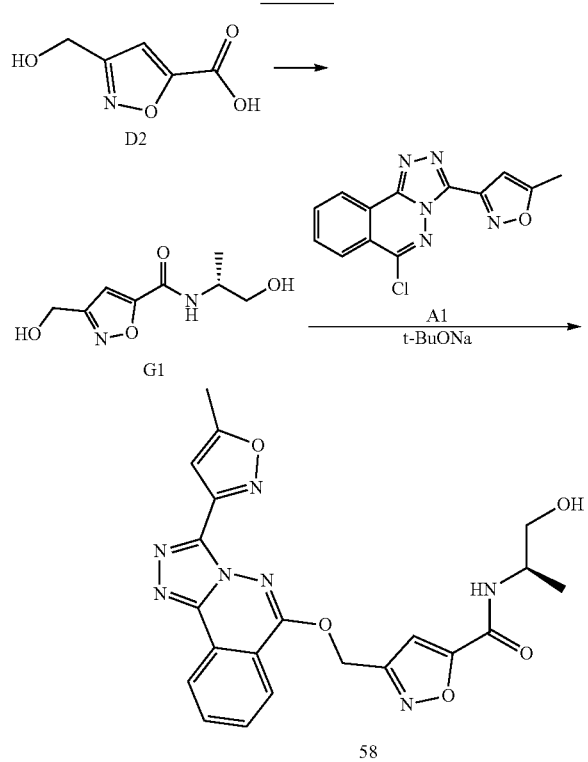

The Experimental Procedures

Step 1

(R)-3-(hydroxymethyl)-N-(1-hydroxypropan-2-yl)isoxazole-5-carboxamide (G1)

A DMF solution (30 mL) containing HOBt (878 mg, 6.5 mmol), EDCI (500 mg, 6.5 mmol), and D2 (715 mg, 5 mmol) in 50 mL one-neck bottle was stirred at room temperature under Ar. R-2-Amino-propan-1-ol and DIPEA was added to the reaction mixture by turn. The mixture was stirred at RT for overnight. TLC showed that the reaction was complete. To the reaction mixture was added THF. The organic layer was washed with brine twice, dried over anhydrous Na$_2$SO$_4$, and concentrated under reduced pressure to give product (600 mg, 60%) as yellow oil.

Step 2

Example 58

(R)—N-(1-hydroxypropan-2-yl)-3-(((3-(5-methylisoxazol-3-yl)-[1,2,4]triazolo[3,4-a]phthalazin-6-yl)oxy)methyl)isoxazole-5-carboxamide (58)

To a mixture of G1 (105 mg, 0.53 mmol) and A1 (100 mg, 0.35 mmol) in THF (50 mL) at 100 mL three neck reaction bottle was added t-BuONa (51 mg, 1.5 eq) at 0° C. under Ar, and then stirred at rt for 1.5 h. TLC (DCM:MeOH=20:1, Rf=0.4) showed the starting material was consumed completely. The reaction mixture was poured into 30 mL of water and extracted with DCM (50 mL×2). The organic layer was combined, washed with water and brine, dried over anhydrous Na$_2$SO$_4$ and concentrated. The residue was purified by silica gel chromatography to give the product 32 mg (yield: 22%) as a white solid.

$^1$H NMR (400 MHz, DMSO-d6) δ: 8.58 (d, J=7.6 Hz, 1H), 8.46 (d, J=8.0 Hz, 1H), 8.27 (d, J=8.0 Hz, 1H), 8.12 (t, J=7.2 Hz, 1H), 7.98 (t, 1H), 7.20 (s, 1H), 7.12 (s, 1H), 5.87 (s, 2H), 4.78 (t, J=5.6 Hz, 1H), 4.02-3.98 (m, 1H), 3.44-3.41 (m, 1H), 2.61 (s, 3H), 1.12 (d, J=6.8 Hz, 3H); LC-MS: m/z (ES+) for C$_{21}$H$_{19}$N$_7$O$_5$ 450.24 [M+1]$^+$.

59

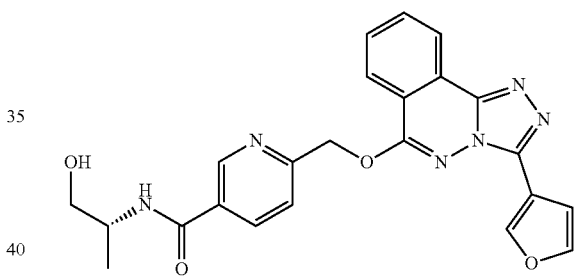

Scheme 8

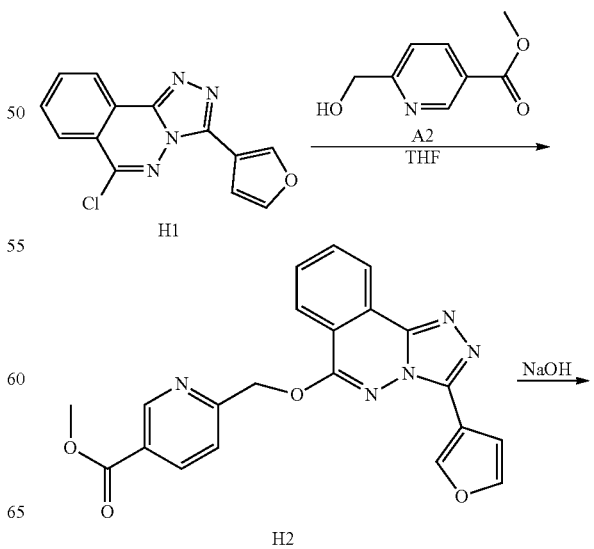

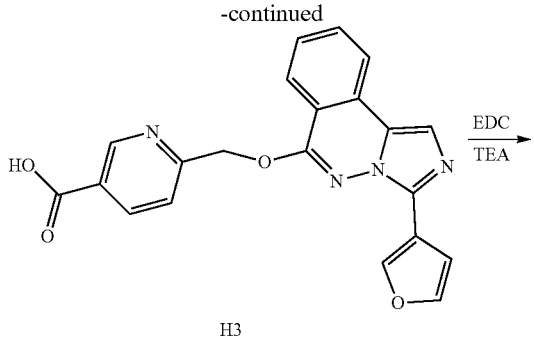

H3

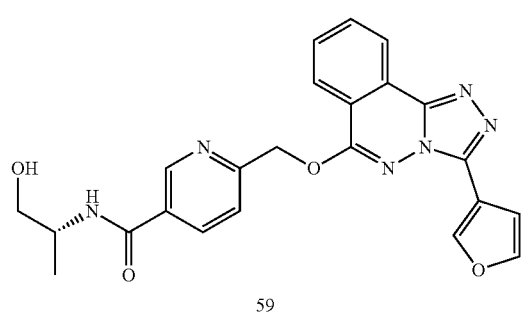

59

The Experimental Procedures 6-(3-furan-3-yl-[1,2,4]triazolo[3,4-a]phthalazin-6-yloxymethyl)-nicotinic acid methyl ester (H2)

To a solution of H1 (812 mg) (refer: U.S. Pat. No. 6,313,125) and 6-hydroxymethyl-nicotinic acid methyl ester (812 mg) in dry THF was added t-NaOBu (576 mg) in portions during a period of 10 mins at 0° C. under Ar. The reaction mixture was stirred at 0° C. for 0.5 h and then kept at RT for 1 h. TLC (DCM:MeOH=20:1, Rf=0.5) showed the starting material was consumed completely. The reaction mixture was concentrated to dryness. The residue was used directly in the next step. 6-(3-furan-3-yl-[1,2,4]triazolo[3,4-a]phthalazin-6-yloxymethyl)-nicotinic acid (H3)

To the solution of H2 (the residue of the previous step) in EtOH (10 mL) was added 10% NaOH (4.8 mL) with stirring at RT. The mixture was stirred for 0.5 h at RT. TLC (DCM:MeOH=20:1, Rf=0.1) showed the starting material was consumed completely. The reaction mixture was concentrated under reduced pressure to remove EtOH. To the residue was added 20 mL of water and the resulting mixture was extracted with EtOAc (30 mL×2). The aqueous layer was quenched with satd aq NH4Cl and a solid precipitated. The mixture was filtered and the filter cake was washed with 5 mL water, dried in vacuum to give H3 (500 mg, 43%) as an off-white solid.

Example 59

(R)-6-(((3-(furan-3-yl)-[1,2,4]triazolo[3,4-a]phthalazin-6-yl)oxy)methyl)-N-(1-hydroxypropan-2-yl)nicotinamide (59)

A DMF solution (5 mL) containing HOBt (81 mg, 0.6 mmol), EDCI (115 mg, 0.6 mmol), and H3 (116 mg, 0.3 mmol) was stirred at room temperature for 10 mins under Ar. (R) 2-amino-propan-1-ol (45 mg) and DIPEA (155 mg) was added to the reaction mixture by turn. The mixture was stirred at RT for 16 h. TLC (DCM:MeOH=20:1, Rf=0.3) showed the starting material was consumed completely. To the reaction mixture was added DCM (25 mL) and 30 mL water. The organic layer was washed with water (20 mL*2), dried over anhydrous $Na_2SO_4$, and concentrated. The residue was purified by silica gel column to give the product (23.8 mg, 17.8%) as a white solid. $^1$H NMR (400 MHz, DMSO-d6) δ: 9.04 (d, 1H J=1.6), 8.61 (s, 1H), 8.52 (d, 1H J=8.0), 8.34 (d, 2H J=8.0), 8.28~8.24 (m, 1H), 8.09 (t, 1H J=7.6), 7.99~7.92 (m, 2H), 7.79 (d, 1H J=8.0), 7.19 (d, 1H J=1.2), 5.83 (s, 2H), 4.74 (t, 1H J=5.6), 4.06~3.98 (m, 1H), 3.49~3.42 (m, 1H), 3.38~3.35 (m, 1H) 1.12 (d, 3H J=6.8); LC-MS: m/z (ES+) for $C_{23}H_{20}N_6O_4$ 445.30 $[M+1]^+$.

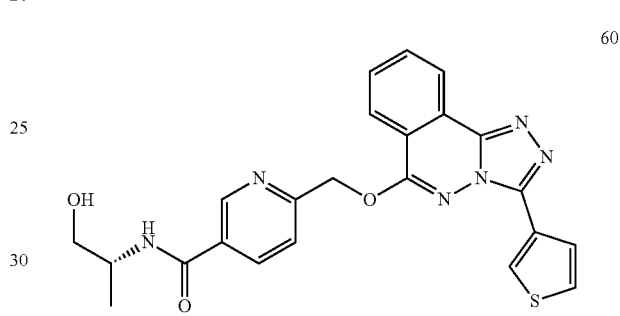

60

Scheme 9

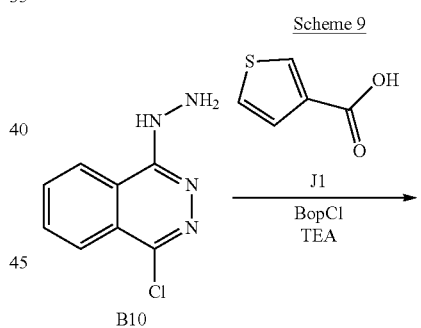

B10

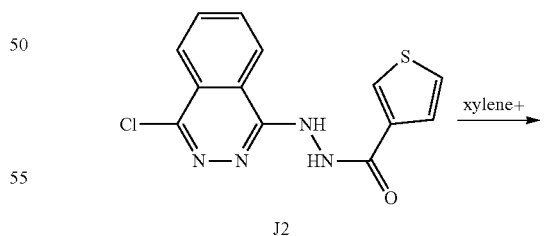

J2

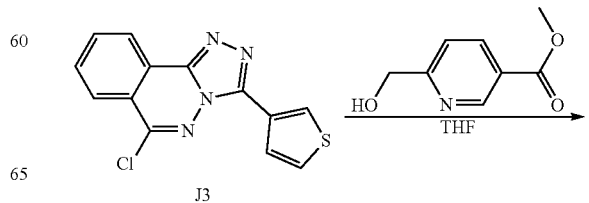

J3

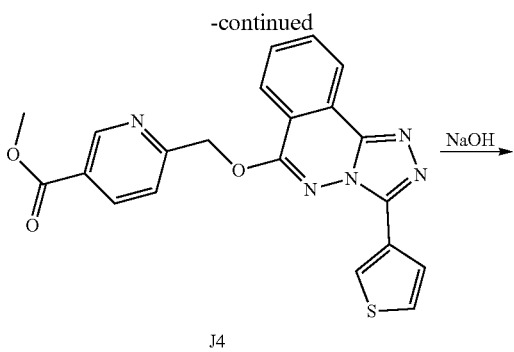

J4

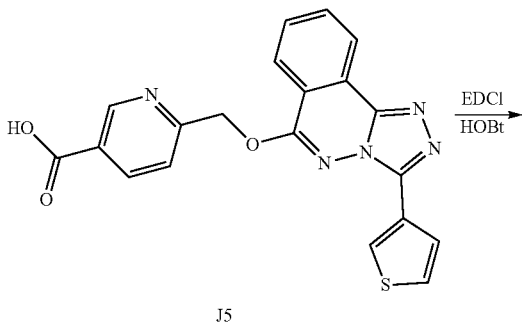

J5

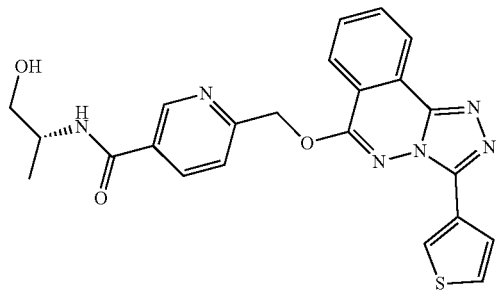

60

The Experimental Procedure

Thiophene-3-carboxylic acid N'-(4-chloro-phthalazin-1-yl)-hydrazide (J2)

To a solution of B10 (640 mg, 5 mmol) and TEA (1.58 g, 15 mmol) in DCM (40 mL) was added bis(2-oxo-3-oxazolidinyl)phosphonic chloride (BOP—Cl, 1.53 g, 6 mmol) in one portion with stirring at 0° C. under Ar. The mixture was stirred at 0° C. for 20 mins. J1 (970 mg, 4.98 mmol) was added. The resulting mixture was stirred at 0° C. for 1 h and then stirred at room temperature overnight. TLC (DCM:MeOH=10:1, Rf=0.5) showed the starting material was consumed completely. The reaction mixture was filtered and washed with water (15 mL), dried to give the product (0.9 g, 59%).

6-chloro-3-thiophen-3-yl-[1,2,4]triazolo[3,4-a]phthalazine (J3)

J2 (900 mg, 2.95 mmol) and triethylamine chlorhydrate (69 mg, 0.5 mmol) in xylene (100 mL) was stirred at refluxing for 0.5 h. TLC (DCM:MeOH=20:1, Rf=0.7) showed most of the starting material was consumed. After cooled to RT, the reaction mixture was diluted with 10 mL water.

The aqueous layer was extracted with EtOAc (20 mL×2). The combined organic layers were dried over anhydrous $Na_2SO_4$. After concentration, the crude product was purified by silica gel chromatography to give pure product (800 mg) as yellow solid.

6-(3-thiophen-3-yl-[1,2,4]triazolo[3,4-a]phthalazin-6-yloxymethyl)-nicotinic acid methyl ester (J4)

To a solution of J3 (717 mg) and 6-hydroxymethyl-nicotinic acid methyl ester in dry THF (100 mL) was added t-NaOBu (576 mg) in portions during a period of 10 mins at 0° C. under Ar. The reaction mixture was stirred at 0° C. for 0.5 h and then kept at RT for 1 h. TLC (DCM:MeOH=20:1, Rf=0.5) showed the starting material was consumed completely. The concentrated residue was used directly for the next step.

6-(3-thiophen-3-yl-[1,2,4]triazolo[3,4-a]phthalazin-6-yloxymethyl)-nicotinic acid (J5)

To the solution of J4 (the residue of the previous step) in EtOH (10 mL) was added 10% NaOH (4 mL) with stirring at RT. The mixture was stirred for 0.5 h at RT. TLC (DCM:MeOH=20:1, Rf=0.1) showed the starting material was consumed completely. The reaction mixture was concentrated to remove EtOH. To the residue was added 20 mL of water and the resulting mixture was extracted with EtOAc (30 mL×2). The aqueous layer was quenched with satd aq $NH_4Cl$ and a solid precipitated. The mixture was filtered and the filter cake was washed with 5 mL water, dried in vacuum to give J5 (500 mg, 51.7%) as off-white solid.

Example 60

(R)—N-(1-hydroxypropan-2-yl)-6-(((3-(thiophen-3-yl)-[1,2,4]triazolo[3,4-a]phthalazin-6-yl)oxy)methyl)nicotinamide (60)

A DMF solution (5 mL) containing HOBt (81 mg, 0.6 mmol), EDCI (115 mg, 0.6 mmol), and J5 (121 mg, 0.3 mmol) was stirred at room temperature for 10 mins under Ar. R-2-Amino-propan-1-ol (45 mg) and DIPEA (155 mg) were added to the reaction mixture by turn. The mixture was stirred at RT for 16 h. TLC (DCM:MeOH=20:1, Rf=0.3) showed the starting material was consumed completely. To the reaction mixture was added DCM (25 mL) and 30 mL water. The organic layer was washed with water (20 mL*2), dried over anhydrous $Na_2SO_4$, and concentrated under reduced pressure. The residue was purified by silica gel column to give the product (36 mg, 26%) as a white solid.

$^1$H NMR (400 MHz, DMSO-d6) δ: 9.04 (d, 1H J=1.6), 8.55~8.52 (m, 2H), 8.37~8.33 (m, 2H), 8.29~8.25 (m, 1H), 8.12~8.06 (m, 1H), 7.98~7.93 (m, 1H), 7.93~7.87 (m, 1H), 7.84~7.77 (m, 2H), 5.82 (s, 2H), 4.75 (t, 1H J=5.6), 4.06~3.99 (m, 1H), 3.49~3.42 (m, 1H), 3.38~3.35 (m, 1H) 1.12 (d, 3H J=6.8); LC-MS: m/z (ES+) for $C_{23}H_{20}N_6O_3S$ 461.30 [M+1]$^+$.

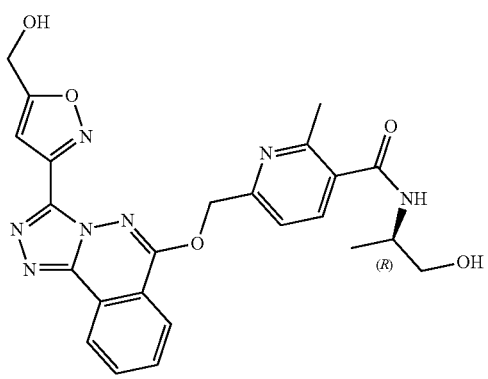

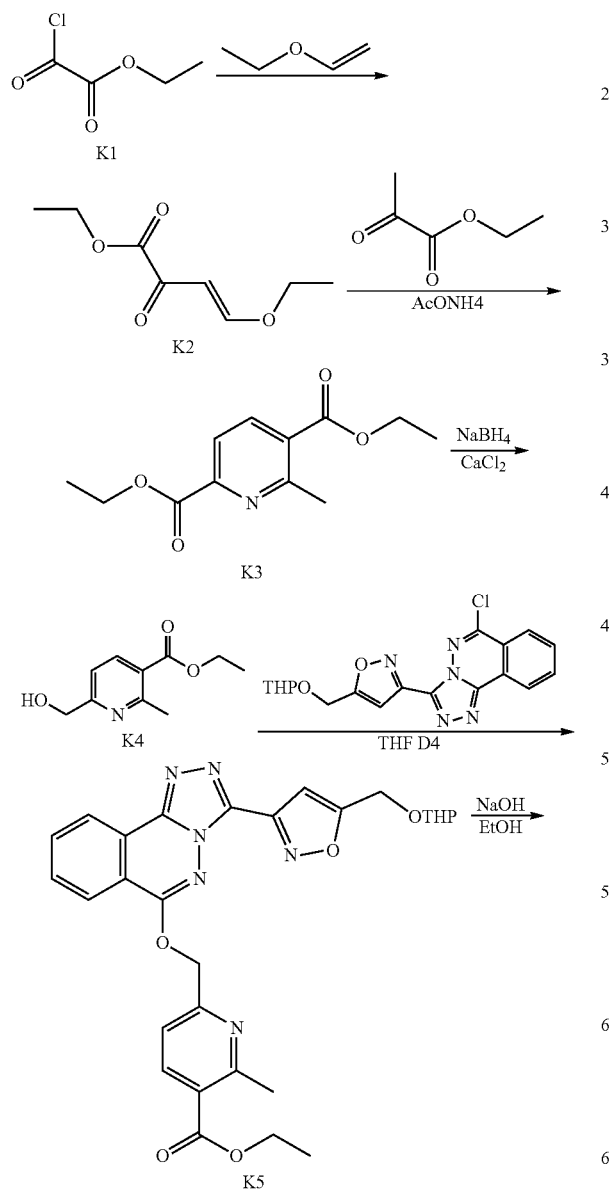

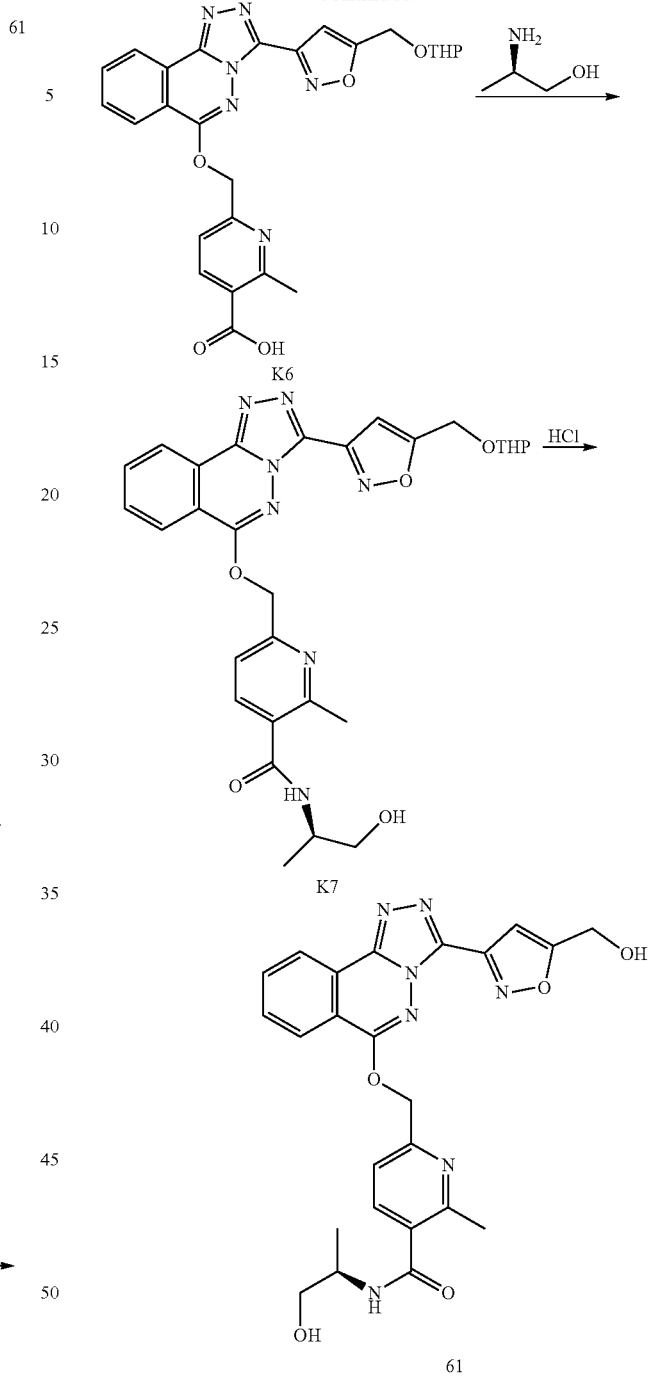

The Experimental Procedure 4-ethoxy-2-oxo-but-3-enoic acid ethyl ester (K2)

To a mixture of ethoxyethene (14.4 g, 200 mmol), TEA (12 g, 120 mmol) and Pd(AcO)$_2$ (3 mL) was added K1 (5.5 g, 40 mmol) dropwise at rt, and then the mixture was stirred at rt overnight. TLC showed the reaction was completed. The reaction mixture was filtrated, and the filter cake was washed with MTBE (50 mL), the filtrate was concentrated under reduce pressure to give the title product 7.3 g (yield: 100%) as a yellow oil.

Step 2

6-methyl-pyridine-2,5-dicarboxylic acid diethyl ester (K3)

A mixture of K2 (1.7 g, 10 mmol), ethyl 2-oxopropanoate (1.2 g, 10 mmol), AcONH$_4$ (1.2 g, 15 mmol) and AcOH (50 mL) was added to a bottle and then stirred at refluxing for overnignt. TLC showed the reaction was completed, the reaction mixture was concentrated under reduce pressure, and the residue was purified by silica gel chromatography (PETROLEUM ETHER:ETOAC=100:1-2:1) to give the title product (1.0 g, yield: 42%) as a dark oil.

Step 3

6-hydroxymethyl-2-methyl-nicotinic acid ethyl ester (K4)

To a mixture of K3 (1 g, 4 mmol), CaCl$_2$ (0.88 g, 6 mmol), EtOH (50 mL) and THF (50 mL) was added NaBH4 (0.228 g, 8 mmol) in three portions at 0° C. After the addition, the reaction mixture was stirred at rt overnight. TLC showed the reaction was completed, the reaction mixture was poured into ice water, extracted with EtOAc (100 mLX3), the organic layers were combined, and washed with brine, dried over anhydrous Na$_2$SO$_4$, concentrated under reduce pressure. The residue was purified by silica gel chromatography to give the title product 300 mg (yield: 38%) as an off-yellow solid.

2-methyl-6-{3-[5-(tetrahydro-pyran-2-yloxymethyl)-isoxazol-3-yl]-[1,2,4]triazolo[3,4-a]phthalazin-6-yloxymethyl}-nicotinic acid ethyl ester (K5)

To a solution of D4 (193 mg, 0.5 mmol) and K4 (98 mg, 0.5 mmol) in THF (20 mL) was added t-BuONa (70 mg, 0.75 mmol) at RT under N2 and stirred for 1.5 h. TLC (DCM:MeOH=20:1, Rf=0.4) showed the reaction was completed. The reaction mixture was used in next step.

2-Methyl-6-{3-[5-(tetrahydro-pyran-2-yloxymethyl)-isoxazol-3-yl]-[1,2,4]triazolo[3,4-a]phthalazin-6-yloxymethyl}-nicotinic acid (K6)

To the solution of K5 was added 10% NaOH (0.5 mL) with stirring at RT. The mixture was stirred for 0.5 h at RT. TLC (PE:EtOAc=2:1, Rf=0.01) showed the reaction was completed. The reaction mixture was concentrated under reduced pressure to remove THF. To the residue was added 2 mL of water and the resulting mixture was extracted with EtOAc. The aqueous layer was adjusted to pH=4 with citric acid. The precipitation was collected by filtrated, washed and dried to give the product 50 mg (yield: 19%) as a yellow solid.

N—((R)-1-hydroxypropan-2-yl)-2-methyl-6-(((3-(5-(((tetrahydro-2H-pyran-2-yl)oxy)methyl)isoxazol-3-yl)-[1,2,4]triazolo[3,4-a]phthalazin-6-yl)oxy)methyl) nicotinamide (K7)

A DMF solution (3 mL) containing HOBt (18 mg, 0.13 mmol), EDCI (26 mg, 0.13 mmol), and K6 (50 mg, 0.1 mmol) was stirred in the 25 mL one-necked bottle at room temperature under Ar. R-2-Amino-propan-1-ol and DIPEA were added to the reaction mixture by turn. The mixture was stirred at RT overnight. TLC showed the reaction was completed. To the reaction mixture was added DCM (25 mL). The organic layer was washed with water 3 times, dried over anhydrous Na$_2$SO$_4$, and concentrated under reduced pressure. The residue was purified by preparative TLC to give product (25 mg, yield: 42%) as a white solid.

Example 61

(R)-6-(((3-(5-(hydroxymethyl)isoxazol-3-yl)-[1,2,4]triazolo[3,4-a]phthalazin-6-yl)oxy)methyl)-N-(1-hydroxypropan-2-yl)-2-methylnicotinamide (61)

To the solution of K7 (25 mg, 0.04 mmol) in DCM (5 mL) was added con. HCl (0.1 mL). The reaction mixture was stirred at rt for 3 h, TLC showed the reaction was finished, the reaction mixture was adjusted to a pH of 8-9, concentrated under reduce pressure. The residue was purified by p-TLC to give a white solid 8 mg (yield: 42%).

$^1$H NMR (400 MHz, DMSO-d6) δ: 8.60 (d, J=8.0 Hz, 1H), 8.34 (d, J=8.0 Hz, 1H), 8.21 (d, J=8.0 Hz, 2H), 8.15 (d, J=8.0 Hz, 1H), 8.01 (d, J=8.0 Hz, 1H), 7.78 (d, J=8.0 Hz, 1H), 7.16 (s, 1H), 5.87 (t, J=6.4 Hz, 1H), 5.69 (s, 2H), 4.76-4.73 (m, 3H), 4.02-3.95 (m, 1H), 3.46-3.36 (m, 1H), 2.56 (s, 3H), 2.01-2.00 (m, 1H), 1.11 (d, J=6.4 Hz, 3H); LC-MS: m/z (ES+) for C$_{24}$H$_{23}$N$_7$O$_5$ 490.29 [M+1].

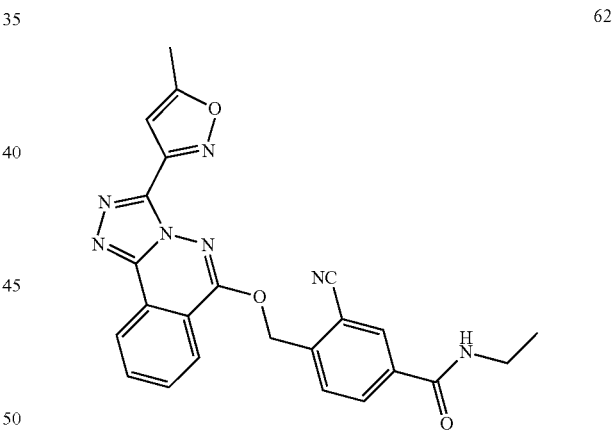

62

Scheme 11

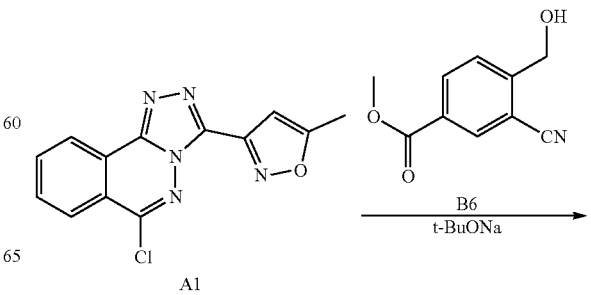

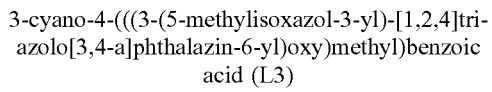

149

-continued

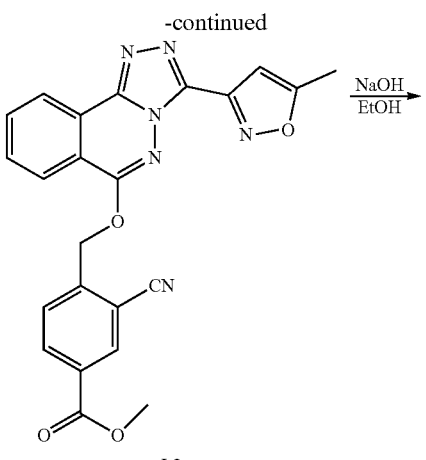

L2

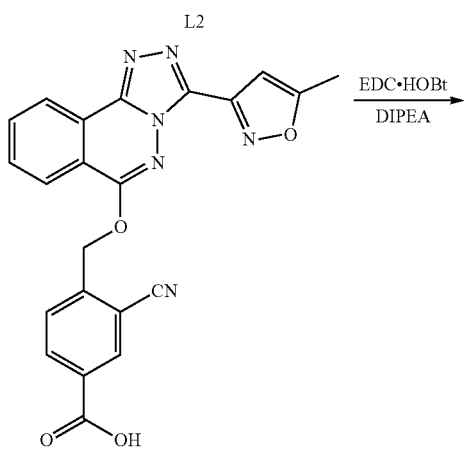

L3

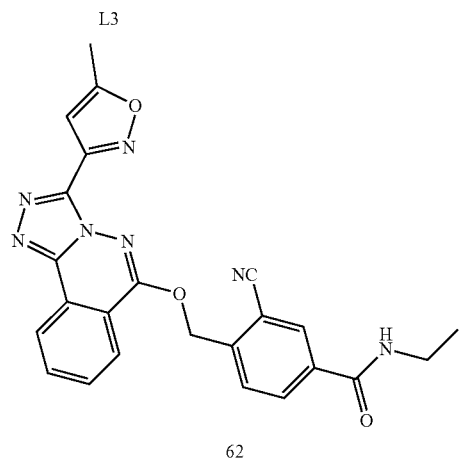

62

Methyl 3-cyano-4-(((3-(5-methylisoxazol-3-yl)-[1,2,4]triazolo[3,4-a]phthalazin-6-yl)oxy)methyl)benzoate (L2)

Under Ar, to a solution of A1 (300 mg) and B6 (300 mg) in anhydrous THF was added 180 mg t-BuOK in portions at 0° C. over 10 min. The reaction mixture was stirred for 30 min at 0° C., and warmed to r. t and stirred for 1 h. TLC (DCM:MeOH=20:1, Rf=0.4) showed the reaction was finished, The reaction mixture was concentrated and used directly in next step.

150

3-cyano-4-(((3-(5-methylisoxazol-3-yl)-[1,2,4]triazolo[3,4-a]phthalazin-6-yl)oxy)methyl)benzoic acid (L3)

To a solution of the crude product obtained in the previous step in 8 mL EtOH was added 3 mL 10% NaOH. The reaction mixture was stirred at r. t. for 30 min. TLC (DCM:MeOH=20:1, Rf=0.4) showed the reaction was finished, The reaction mixture was concentrated and diluted with 20 mL water, and extracted with EtOAc (30 mL×2). To the aqueous was added aq. NH4Cl to give a suspension mixture. The solid precipitates were filtered from the solution and the filter cake was dried to give the title product as a white solid 100 mg, 27%.

Example 62

3-cyano-N-ethyl-4-(((3-(5-methylisoxazol-3-yl)-[1,2,4]triazolo[3,4-a]phthalazin-6-yl)oxy)methyl)benzamide (62)

The procedure was the same as example 1: the title product was obtained from the starting materials L3 and ethylamine hydrochloride (CAS: 557-66-4): 32 mg, 86% as a white solid.

$^1$H NMR (400 MHz, DMSO-d6) δ: 1H NMR (400 MHz, dmso) δ 8.68 (s, 1H), 8.55 (d, J=7.9 Hz, 1H), 8.34 (d, J=1.4 Hz, 1H), 8.26 (d, J=8.1 Hz, 1H), 8.18-8.12 (m, 1H), 8.09 (t, J=7.6 Hz, 1H), 8.01 (d, J=8.1 Hz, 1H), 7.95 (t, J=7.2 Hz, 1H), 7.01 (s, 1H), 5.85 (s, 2H), 3.26 (d, J=7.5 Hz, 2H), 2.56 (s, 3H), 1.10 (t, J=7.2 Hz, 3H); LC-MS: m/z (ES+) for $C_{24}H_{19}N_7O_3$ 454 [M+1]$^+$.

Biological Experiment Methods:

Previous studies have revealed that the GABA$_A$ receptors mediate at least two modes of inhibition, the phasic inhibition and the tonic inhibition. When the GABA increases to the millimole level, the GABA$_A$ receptors will be desensitized rapidly, show low affinity for GABA and mediate phasic inhibition. When the GABA activates GABA$_A$ receptors at tens of micromole or hundreds of nano mole level, the high affinity extrasynaptic GABA$_A$ receptors will mediate tonic inhibition and regulate neuronal excitability and signal transmission (Farrant M et al. (2005) Variations on an inhibitory theme: phasic and tonic activation of GABA(A) receptors. Nat Rev Neurosci 6:215-229Y). Yeung J Y et al reported that the α5-GABA$_A$ receptor can be activated preferably by low level of GABA (Yeung J Y et al (2003). Tonically activated GABAA receptors in hippocampal neurons are high-affinity, low-conductance sensors for extracellular GABA. Mol Pharmacol; 63: 2-8). K. Y LEE et al reported that the sustainable high-affinity GABA$_A$ current induced by low level GABA is detected in dissociated cultured DRG neurons cultured for 24 hours and 20 μM of GABA can induce a ~100 pA/pF high-affinity GABA$_A$ current (Lee K Y et al. Upregulation of high-affinity GABA (A) receptors in cultured rat dorsal root ganglion neurons. Neuroscience 208 (2012) 133-142). In 2013, I. Lecker et al reported that L-655,708, an α5-GABA$_A$ specific inverse agonist, inhibits the current included by low level GABA (5, 50 and 500 nM) in the concentration dependent manner. When the GABA concentration is increased to 1 μM, the inhibition efficacy of the highest dose of L-655,708 is only ~15%. When the GABA concentration are higher, there is even no inhibition of L-655,708 on the current induced by GABA (I. Lecker et al (2013). Potentiation of GABAA receptor activity by volatile anaesthetics is reduced by α5-GABAA receptor-preferring inverse agonists. British Journal of Anaesthesia 110 (S1): i73-i81).

α5IA (U.S. Pat. No. 6,200,975B1) is a representative α5-GABA$_A$ inverse agonist.

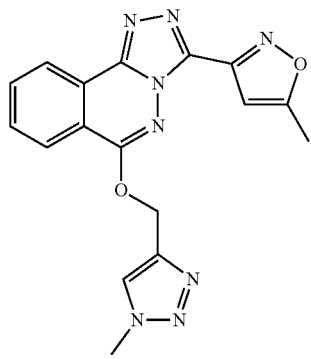

α5IA

1. Cell Level Screening

The inventors used electrophysiological methods to assay the inverse agonist efficacy of the substance to be tested. The detailed procedures are as follows: (1) Different subunits of GABA$_A$ receptors were expressed in human embryonic kidney cells 293 (HEK293). The cells were cultured in a culture medium and used as a cell model for screening potential analgesics. The α, β and γ subunits are necessary to form complete functional GABA$_A$ receptors. In this example, the inventor has established the following cell model: (a) α5 subunit (protein sequence is GenBank accession number: NP_001158509), β3 subunit (protein sequence is GenBank accession number: NP_068712) and γ2 subunit (protein sequence is GenBank accession number: NP_944494) were expressed in HEK-293 cell lines at the same time, which formed the complete functional GABA$_A$ receptors. (2) Cells were stably transfected HEK-293 cells expressing α5β3γ2 receptor, which were labeled by green fluorescent protein (GFP). Cells were grown in 10 cm dishes. The cells were passaged after reaching 80-90% confluence. During passaging, the culture medium was removed and discarded, 3 mL DMEM medium (Gibco™) was added to the dishes, the dishes were shaken slightly, and DMEM was removed and discarded. 3 mL Trypsin (Trypsin-EDTA 0.05%, Gibco™) was added and cells were digested at 37° C. for 3 minutes. Then 3 mL complete growth medium (DMEM+10% horse serum (Gibco™)) was added and the cells at the bottom of the culture dishes were dispersed. The cell suspension were transferred to a 15 mL centrifugal tube (Corning®) and then centrifuged at 200 g for 3 minutes. The supernatant was discarded, 4 mL complete growth medium was added, and the cells were resuspended by gently blowing. The cell suspension was diluted by 1:5 or 1:10 for subculturing. The cell suspension was diluted by 1:12 for electrophysiology experiment, which was added to the 24 well plate (Corning®) which has a glass slide pre-treated with poly-D-lysine. The cells were adhered to the slide before the experiment was conducted. The cells were maintained in culture for no more than 24 hours before use. (3) Compound concentration: for screening, all compounds were diluted to a final concentration of 100 nM. GABA was diluted at the concentration of 0.05-0.1 μM. The compounds were at the concentration of 1 nM, 10 nM, 50 nM, 100 nM and 1000 nM in dose-inverse agonism efficacy (%) experiment. The whole cell patch clamp technique was used in electrophysiology experiments. The extracellular solution (ECS) contained: 150 mM NaCl, 5 mM KCl, 2.5 mM CaCl$_2$, 1 mM MgCl$_2$, 10 mM HEPES and 10 mM glucose (pH 7.4); Patch electrodes were filled with an intracellular solution containing: 140 mM KCl, 5 mM EGTA, 10 mM HEPES (adjusted to pH 7.4 with KOH and to 320-330 mOsm with water). The currents were recorded by an EPC-10 amplifier and the PatchMaster software (HEKA). Patch electrodes with a resistance of 5-6 MΩ were pulled from borosilicate glass (Sutter). The diluted compounds were perfused by OCTAFLOWII system. GFP positive and independently growing cells were selected for recording. During recording, the membrane voltage was clamped at −60 mV. During experiment, the cells were firstly perfused with ECS for 20 seconds. When the baseline reached to a stable state, cells were then perfused with GABA solution. Then the current induced by GABA can be detected. After about 20-40 seconds, the current was stable. ECS was switched to compounds solution and the effects of the compounds were detected. At last, the perfusion solution was switched to ECS. The experiment was finished when the post-baseline returned to the pre-baseline before compounds perfusion. Only the data whose pre-baseline and post-baseline are at almost the same level were used for analysis. GABA was diluted at the concentration of 0.05-0.1 μM in ECS. Then, compounds were diluted at the desired concentration in GABA ECS. (4) Currents were analyzed with the PatchMaster (HEKA) software. The GABA currents before (Ipre) and after (Ipost) compounds perfusion were recorded respectively. The efficacies of compounds were calculated by the following equation: inverse agonism efficacy=(Ipost-Ipre)*100/Ipre. N indicates experiment numbers. (5) The screening result of the compounds:

| Compound | inverse agonism efficacy(%) | N | Inverse agonism efficacy of the compound/α5IA Inverse agonism efficacy |
|---|---|---|---|
| α5IA | −22.55 | 5 | |
| 01 | −57.99389 | 1 | 2.57179 |
| 02 | −52.15548 | 1 | 2.31288 |
| 03 | −41.3058 | 1 | 1.83174 |
| 06 | −36 | 1 | 1.59645 |
| 07 | −24.8 | 2 | 1.09978 |
| 08 | −34 | 4 | 1.50776 |
| 31 | −47.75859 | 1 | 2.1179 |
| 32 | −39.21993 | 1 | 1.73924 |
| 33 | −33.0 | 2 | 1.46341 |
| 37 | −32.00046 | 1 | 1.41909 |
| 38 | −40. | 2 | 1.77384 |
| 39 | −49.01532 | 1 | 2.17363 |
| 40 | −29.0 | 2 | 1.28603 |
| 41 | −42.10972 | 1 | 1.86739 |
| 43 | −27.93319 | 1 | 1.23872 |
| 45 | −30.19802 | 1 | 1.33916 |
| 47 | −51.5 | 2 | 2.28381 |
| 48 | −43.17402 | 1 | 1.91459 |
| 51 | −30.457 | 1 | 1.35064 |
| 54 | −34.0 | 2 | 1.50776 |
| 55 | −33.295 | 1 | 1.4765 |
| 57 | −38.27404 | 1 | 1.6973 |
| 58 | −30 | 1 | 1.33038 |
| 59 | −39.01163 | 1 | 1.73001 |
| 60 | −32.62113 | 1 | 1.44661 |
| 61 | −46.16142 | 1 | 2.04707 |

1) α5IA, 06 and 07 dose-inverse agonism efficacy data:

| Con. (nM) | log M | Inverse agonism-Efficacy | | | | | | | |
|---|---|---|---|---|---|---|---|---|---|
| | | α 5IA (N = 2) | | 07 (N = 3~4) | | | 06 (N = 2~3) | | |
| 1 | −9 | −4.2 | −3.0 | −10.3 | −5.8 | −8.4 | −11.8 | −10.0 | −12.5 |
| 10 | −8 | −9.4 | −12.3 | −25.5 | −32.6 | −34.4 | −26.3 | −15.4 | −16.0 | −17.0 |

| Con. (nM) | log M | α 5IA (N = 2) | | 07 (N = 3~4) | | | | 06 (N = 2~3) | | |
|---|---|---|---|---|---|---|---|---|---|---|
| 50 | −7.3 | −22.1 | −16 | −40.0 | −24.2 | −30.3 | −42.5 | −17.1 | −24.0 | −23.1 |
| 100 | −7 | −19.0 | −26.1 | −45.8 | −32.6 | −33.3 | −32.3 | −26.0 | −22.5 | −26.0 |
| 1000 | −6 | −20.7 | −22.6 | −39.1 | −42.9 | −40.3 | | −28.0 | −35.7 | −32.3 |

2. Tissue Distribution of the Compounds

The distribution ratio of blood brain tissue was calculated by comparing the concentration of compound in rat plasma and brain tissue. The experimental animals were divided into two groups, the plasma group and the brain group, each with three. Rats were administed compounds in 50% PEG400 p.o. at a dose of 10 mg compound to be tested/kg. One hour later, plasma and brain samples were taken. Concentrations of compounds in brain and plasma were detected using LC-MS/MS-A (Triple Quad 5500) assay and analyzed using Phoenix WinNonlin.

| Compound | Brain/Plasma ratio |
|---|---|
| 07 | <1% |
| 08 | <1% |

3. Supplementary Data for Cell Level Screening

A new electrophysiology method was used to revalidate the efficacies of some compounds. In this assay, we referred to the method reported by I. Lecker et al (I. Lecker, Y Yin, D. S. Wang and B. A. Orser, (2013) Potentiation of GABAA receptor activity by volatile anaesthetics is reduced by α5-GABAA receptor-preferring inverse agonists, British Journal of Anaesthesia 110 (S1): i73-i81). The extracellular solution (ECS) containing 150 mM NaCl, 5 mM KCl, 2.5 mM $CaCl_2$, 1 mM $MgCl_2$, 10 HEPES and 10 mM glucose (adjusted to pH 7.4 with NaOH and to 320 mOsm) was the same as that in the previous method. The intracellular solution was adjusted to 140 mM CsCl, 10 mM HEPES, 11 mM EGTA, 2 mM $MgCl_2$, 1 mM $CaCl_2$, 4 mM MgATP, 2 mM TEA, (adjusted to pH 7.4 with CsOH and to 285-295 mOsm). The GABA concentration was adjusted to 0.1~0.3 CM. Other procedures were the same as the previous method. In every assay, α5IA was used as a reference compound. The inverse agonism efficacy of each compound was also shown as a ratio to that of α5IA.

The data were shown below:

| Compound | Inverse agonism efficacy(%) | N | inverse agonism efficacy of the compound/α5IA inverse agonism efficacy |
|---|---|---|---|
| α5IA | −17.369 | 9 | |
| 01 | −18.66667 | 3 | 1.075 |
| 02 | −21.33333 | 3 | 1.229 |
| 03 | −29.33333 | 3 | 1.689 |
| 04 | −26.5 | 4 | 1.526 |
| 07 | −21.1667 | 3 | 1.219 |
| 11 | −17.71429 | 7 | 1.020 |
| 12 | −19.0625 | 8 | 1.098 |
| 26 | −21.5 | 7 | 1.238 |
| 28 | −19.85714 | 7 | 1.143 |
| 36 | −28.8 | 5 | 1.658 |
| 38 | −52.5 | 4 | 3.023 |
| 39 | −26 | 6 | 1.497 |
| 40 | −25.5 | 4 | 1.468 |
| 42 | −32.5 | 6 | 1.871 |
| 43 | −35 | 5 | 2.015 |
| 44 | −20.8 | 5 | 1.196 |
| 47 | −26.875 | 8 | 1.547 |
| 48 | −20 | 7 | 1.151 |
| 49 | −22.2 | 5 | 1.278 |
| 53 | −22.8 | 5 | 1.313 |
| 55 | −31.6 | 5 | 1.819 |
| 56 | −27.6 | 5 | 1.589 |
| 57 | −25 | 4 | 1.439 |
| 58 | −27 | 3 | 1.554 |
| α5IA | −18.6 | 5 | |
| 08 | −35.375 | 4 | 1.902 |
| 22 | −33 | 5 | 1.774 |
| 24 | −34.5 | 5 | 1.855 |
| 27 | −32.1 | 5 | 1.726 |
| 30 | −52 | 1 | 2.796 |

4. Compound Tissue Distribution

The distribution ratio of blood brain tissue was calculated by comparing the concentration of compound in rat plasma and brain tissue. The experimental animals were divided into two groups, the plasma group and the brain group, each with three. To measure brain to plasma ratio, rats were administed compounds in 50% PEG400 p.o. at a dose of 10 mg compound to be tested/kg. One hour later, plasma and brain samples were taken. Concentrations of compounds in brain and plasma were detected using LC-MS/MS-AJ (Triple Quad 5500) assay and analyzed using Phoenix WinNonlin.

The data were shown below:

| Compound | Brain/Plasma ratio |
|---|---|
| 07 | <1% |
| 08 | <1% |

We also measured the brain to plasma ratio of compound #24. The experimental animals were divided into two groups, the plasma group and the brain group, each with three. To measure the brain to plasma ratio, Rats were administered compounds (1 mg/kg in 5% DMSO+70% PEG400+25% $H_2O$ p.o.). One hour later, plasma and brain samples were taken. Concentrations of compounds in brain and plasma were detected using a LC-MS/MS-AJ (Triple Quad 5500) assay and analyzed using Phoenix WinNonlin.

| Compound | Brain/Plasma ratio |
|---|---|
| 24 | 4.4% |

Taken together, these compounds show better biological efficacies than previous α5-$GABA_A$ receptor inverse agonists. Furthermore, since the compounds do not enter the brain, these compounds will not induce fear and anxiety as the previous α5-GABA$_A$ receptor inverse agonists.

The invention claimed is:

1. A compound of formula II, a cis-trans isomer, an enantiomer, a diastereoisomer, a racemate, a solvate, a hydrate, or a pharmaceutical acceptable salt and ester thereof:

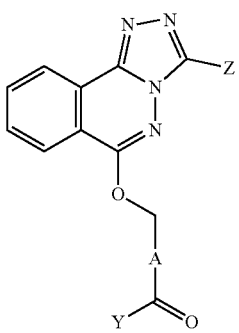

wherein:
Z is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is independently selected from the group consisting of H; C1-6 alkyl; C1-6 alkyl substituted by 1-5 substituents selected from the group consisting of amino, halogen, halogenated C1-6 alkoxy, hydroxyl, C1-6 alkoxy, (C1-6 alkyl, C1-6 alkyl)N-, (C1-6 alkyl, H)N—, nitro and C1-6 alkyl-S(O)$_2$—;

Y2 is independently selected from the group consisting of H; C1-6 alkyl-S(O)$_2$—; amino; NH$_2$—S(O)$_2$—; C1-6 alkoxy; C1-6 alkyl; C1-6 alkyl substituted by 1-5 substituents selected from the group consisting of amino, halogen, halogenated C1-6 alkoxy, hydroxyl, C1-6 alkoxy, carboxyl, cycloalkyl, (C1-6 alkyl, C1-6 alkyl)N-, (C1-6 alkyl, H)N—, nitro, acetylamino, C1-6 alkyl-S(O)$_2$—, C3-7 heterocycloalkyl that contains 1-3 hetero-atoms independently selected from nitrogen, oxygen or sulfur, or C3-7 heterocycloalkyl that contains 1-3 hetero-atoms independently selected from nitrogen, oxygen or sulfur and is substituted by 1-4 substituents selected from the group consisting of acetamido, acetyl, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)$_2$—; C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted by 1-4 substituents selected from the group consisting of acetamido, acetyl, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)$_2$—; cycloalkyl, or cycloalkyl optionally substituted by 1-4 substituents selected from the group consisting of acetamido, acetyl, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)$_2$—; C3-7 heterocycloalkyl that contains 1-3 hetero-atoms independently selected from nitrogen, oxygen or sulfur, or C3-7 heterocycloalkyl that contains 1-3 hetero-atoms independently selected from nitrogen, oxygen or sulfur and is substituted by 1-4 substituents selected from the group consisting of acetamido, acetyl, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)$_2$—;

alternatively, Y1 and Y2 together with the nitrogen atom to which they are attached, form a 4-6 membered heterocycloalkyl which contains the nitrogen atom and 0, 1 or more other atoms selected from O and S; the sulfur atom can be its oxide form;

alternatively, Y1 and Y2 together with the nitrogen atom to which they are attached, form a 4-6 membered heterocycloalkyl which contains 1-3 heteroatoms selected from N, O and S, the sulfur atom can be its oxide form, and the heterocycloalkyl is substituted by 1-4 substituents selected from the group consisting of C1-6 alkyl, C1-6 alkyl-S(O)$_2$—, C1-6 alkoxy, halogenated C1-6 alkyl, NH$_2$C(=O)—, and halogen;

alternatively, Y1 and Y2 together with the nitrogen atom to which they are attached, form C5-10 oxaazabicycloalkyl;

Y3 and Y4 are independently selected from the group consisting of hydrogen, C1-6 alkyl, SO$_2$—C1-6 alkyl, cycloalkyl and C3-C7 heterocyclyl that contains 1-3 hetero-atoms independently selected from nitrogen, oxygen or sulfur, optionally substituted by 1-4 substituents selected from the group consisting of halogen, cyano, hydroxyl, C1-6 alkyl and C1-6 alkoxy, alternatively, Y3 and Y4 together with the nitrogen atom to which they are attached, form a C3-7 heterocyclyl, and the C3-7 heterocyclyl contains 1-3 hetero-atoms independently selected from nitrogen, oxygen or sulfur and is optionally substituted by 1-4 substituents selected from the group consisting of halogen, cyano, hydroxyl, oxo, C1-6 alkyl and C1-6 alkoxy;

all of hydrogen atoms of the above substituents can be replaced by deuterium.

2. A compound according to claim 1, having a structure of formula II:

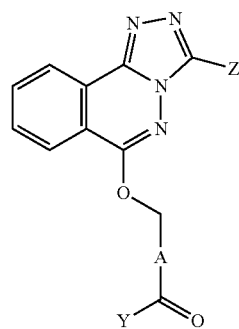

wherein:
Y is —NY1Y2 or —NH—NY3Y4;
Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, and C1-6 alkyl-S(O)$_2$—;

Y2 is independently selected from the group consisting of C1-6 alkyl; C1-6 alkyl substituted by 1-5 substituents selected from the group consisting of amino, hydroxyl, C1-6 alkoxy, carboxyl, halogen, cycloalkyl, (C1-6 alkyl, C1-6 alkyl)N-, (C1-6 alkyl, H)N—, acetylamino, and C1-6 alkyl-S(O)$_2$—, C3-7 heterocycloalkyl that contains 1-3 hetero-atoms independently selected from nitrogen, oxygen or sulfur, or C3-7 heterocycloalkyl that contains 1-3 hetero-atoms independently selected from nitrogen, oxygen or sulfur and is substituted by 1-4 substituents selected from the group consisting of acetamido, acetyl, C1-6 alkoxy and C1-6 alkyl;

H; C1-6 alkyl-S(O)$_2$—; amino; NH$_2$—S(O)$_2$—; C1-6 alkoxy;

C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with C1-6 alkyl;

C3-6 cycloalkyl, C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl) N-(C1-6 alkyl, H)N— and C1-6 alkyl-S(O)$_2$—;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, acetyl, C1-6 alkoxyC1-6 alkyl, C1-6 alkyl and C1-6 alkyl-S(O)$_2$—;

alternatively, Y1 and Y2 together with the nitrogen atom to which they are attached, form a 4-6 membered heterocycloalkyl which contains the nitrogen atom and 0,1 or more heteroatom selected from O and S; the sulfur atom can be its oxide form;

alternatively, Y1 and Y2 together with the nitrogen atom to which they are attached, form a 4-6 membered heterocycloalkyl which contains 1-3 heteroatoms selected from N, O and S, the sulfur atom can be its oxide form, wherein the heterocycloalkyl is substituted by 1-4 substituents selected from the group consisting of C1-6 alkyl, C1-6 alkyl-S(O)$_2$—, C1-6 alkoxy, halogenated C1-6 alkyl, NH$_2$C(=O)—, and halogen;

alternatively, Y1 and Y2 together with the nitrogen atom to which they are attached, form C5-10 oxaazabicycloalkyl;

Y3 and Y4 are independently selected from the group consisting of hydrogen, C1-6 alkyl, and SO$_2$—C1-6 alkyl;

alternatively, Y3 and Y4 together with the nitrogen atom to which they are attached, form a C3-7 heterocyclyl, the C3-7 heterocyclyl contains 1-3 hetero-atoms independently selected from nitrogen, oxygen or sulfur and is selected from the group consisting of piperidinyl, morpholinyl, dioxidothiomorpholinyl and oxidothiomorpholinyl.

3. A compound according to claim 1 wherein

Z is oxadiazolyl, furyl, thienyl or isoxazolyl, the isoxazolyl is optionally substituted by one or more substituents selected from the group consisting of H, C1-6 alkyl, and hydroxyl C1-6 alky;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or C1-6 alkyl;

Y2 is independently selected from the group consisting of C1-6 alkyl; C1-6 alkyl substituted by 1-5 substituents selected from the group consisting of amino, hydroxyl, C1-6 alkoxy, carboxyl, halogen, C1-6 alkyl-S(O)$_2$—; cycloalkyl, C3-7 heterocycloalkyl that contains 1-3 hetero-atoms independently selected from nitrogen, oxygen or sulfur, or C3-7 heterocycloalkyl that contains 1-3 hetero-atoms independently selected from nitrogen, oxygen or sulfur and is substituted by 1-4 substituents selected from the group consisting of acetamido, acetyl, C1-6 alkoxy, and C1-6 alkyl;

H; C1-6 alkyl-S(O)$_2$—; amino; NH$_2$—S(O)$_2$—; C1-6 alkoxy;

C5-6 heteroaryl that contains 1-3 hetero-atoms independently selected from nitrogen, oxygen or sulfur; C5-6 heteroaryl substituted by alkyl, wherein the C5-6 heteroaryl contains 1-3 hetero-atoms independently selected from nitrogen, oxygen or sulfur;

C4-6 cycloalkyl, cyclopropyl, C3-6 cycloalkyl substituted by 1-4 substituents selected from the group consisting of hydroxyl, C1-6 alkyl, C1-6 alkoxy;

C4-6 heterocycloalkyl that contains 1-3 hetero-atoms independently selected from nitrogen, oxygen or sulfur, or C4-6 heterocycloalklyl that contains 1-3 heteroatoms independently selected from nitrogen, oxygen or sulfur and is substituted by 1-4 substituents selected from the group consisting of C1-6 alkyl, acetyl, and C1-6 alkyl-S(O)$_2$—;

alternatively, Y1 and Y2 together with the nitrogen atom to which they are attached, form a 4-6 membered heterocycloalkyl which contains the nitrogen atom and 0,1 or more heteroatom selected from O and S, and the sulfur atom can be its oxide form;

alternatively, Y1 and Y2 together with the nitrogen atom to which they are attached, form a 4-6 membered heterocycloalkyl which contains 1-3 heteroatoms selected from N, O and S, the sulfur atom can be its oxide form, and the heterocycloalkyl is substituted by 1-4 substituents selected from the group consisting of C1-6 alkyl, C1-6 alkyl-S(O)$_2$—, C1-6 alkoxy, halogenated C1-6 alkyl, NH$_2$C(=O)—, and halogen;

alternatively, Y1 and Y2 together with the nitrogen atom to which they are attached, form C5-10 oxaazabicycloalkyl;

Y3 and Y4 are independently selected from the group consisting of hydrogen, methyl, SO$_2$-methyl;

alternatively, Y3 and Y4 together with the nitrogen atom to which they are attached, form a heterocyclyl, and the heterocyclyl is selected from the group consisting of piperidinyl, morpholinyl, dioxidothiomorpholinyl.

4. A compound according to claim 1 wherein

Z is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or C1-6 alkyl;

Y2 is independently selected from the group consisting of C1-6 alkyl; C1-6 alkyl substituted by 1-5 substituents selected from the group consisting of hydroxyl, C1-6 alkoxy, amino, halogen, carboxyl, C3-6 cycloalkyl, C4-6 heterocycloalkyl that contains 1-3 hetero-atoms independently selected from nitrogen, oxygen or sulfur, C1-6 alkyl-S(O)$_2$—;

H; amino; NH$_2$—S(O)$_2$—; C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted by alkyl;

C4-6 cycloalkyl, cyclopropyl, C3-6 cycloalkyl substituted by 1-4 substituents selected from the group consisting of hydroxyl, C1-6 alkyl, and C1-6 alkoxy;

C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents selected from the group consisting of C1-6 alkyl, acetyl, and C1-6 alkyl-S(O)$_2$—;

alternatively, Y1 and Y2 together with the nitrogen atom to which they are attached, form morpholinyl, piperidinyl, piperazinyl, azetidinyl, oxazabicycloheptanyl; the morpholinyl, piperidinyl, piperazinyl, azetidinyl, oxaazabicycloheptanyl are optionally substituted by 1-4 substituents selected from the group consisting of C1-6 alkyl, C1-6 alkyl-S(O)$_2$—, C1-6 alkoxy, halogen, NH$_2$C(=O)—; the sulfur atom of the morpholinyl can be its oxide form;

Y3 and Y4 are independently selected from the group consisting of hydrogen, methyl, SO$_2$-methyl;

alternatively, Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

5. A compound according to claim 1 wherein

Z is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or methyl;

Y2 is independently selected from the group consisting of C1-6 alkyl; C1-6 alkyl substituted by 1-5 substituents selected from the group consisting of hydroxyl, C1-6 alkoxy, acetamido, fluorine, carboxyl, morpholinyl, cyclopropyl, tetrahydrofuryl;

H; C1-6 alkyl-S(O)$_2$—; amino; NH$_2$—S(O)$_2$—; C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted by alkyl;

C3-6 cycloalkyl; C3-6 cycloalkyl substituted by 1-4 substituents selected from the group consisting of hydroxyl, methoxy, and methyl;

C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents selected from the group consisting of methyl, and acetyl;

alternatively, Y1 and Y2 together with the nitrogen atom to which they are attached, form morpholinyl, piperidinyl, piperazinyl, azetidinyl, oxaazabicycloheptanyl; the morpholinyl, piperidinyl, piperazinyl, azetidinyl, and oxaazabicycloheptanyl are optionally substituted by 1-4 substituents selected from the group consisting of methyl, methoxy, fluorine, and NH$_2$C(=O)—; the sulfur atom of the morpholinyl can be its oxide form;

Y3 and Y4 are independently selected from the following groups: hydrogen, and methyl;

alternatively, Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

6. A compound according to claim 1 wherein,

Z is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is H or methyl;

Y2 is selected from the group consisting of methyl, ethyl, methoxyethyl, hydroxypropyl, acetamidoethyl, H, —CH$_2$COOH, hydroxycyclopentyl, cyclopropyl, methylpyrazolyl, morpholinyl, hydroxyethyl, butyl, methylpiperidinyl, morpholinylethyl, tetrahydrofuranyl, methoxycyclopentyl, acetylpyrrolidinyl, tetrahydrofuranylmethyl, difluoroethyl, cyclopropylmethyl, methylsulfonylethyl, trifluoroethyl, isopropyl, tetrahydropyranyl, cyclobutyl, amino, piperidinyl, methyl sulfonyl, dioxidothiomorpholinyl, and hydroxymethylethyl;

alternatively, Y1 and Y2 together with the nitrogen atom to which they are attached, form methylpiperazinyl, carboxamidepiperidinyl, methoxypiperidinyl, difluoropiperidinyl, oxaazabicycloheptanyl, dioxidothiomorpholinyl, morpholinyl, azetidinyl, oxidothiomorpholinyl;

Y3 and Y4 are independently selected from the following groups: hydrogen, and methyl;

alternatively, Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

7. A compound according to claim 1, having formula III:

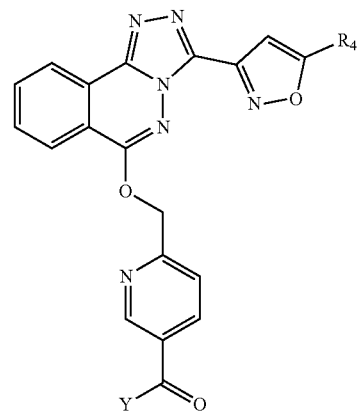

III

Wherein
R4 is C1-4 alkyl, hydroxyl substituted C1-4 alkyl;
Y is —NY1Y2 or —NH—NY3Y4;
Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, and C1-6 alkyl-S(O)$_2$—;
Y2 is independently selected from the group consisting of C1-6 alkyl; C1-6 alkyl substituted by 1-5 substituents selected from the group consisting of amino, hydroxyl, C1-6 alkoxy, carboxyl, halogen, cycloalkyl, (C1-6 alkyl, C1-6 alkyl)N-, (C1-6 alkyl, H)N— and C1-6 alkyl-S(O)$_2$—, C3-7 heterocycloalkyl that contains 1-3 hetero-atoms independently selected from nitrogen, oxygen or sulfur, or C3-7 heterocycloalkyl that contains 1-3 hetero-atoms independently selected from nitrogen, oxygen or sulfur and is substituted by 1-4 substituents selected from the group consisting of acetamido, acetyl, C1-6 alkoxy, C1-6 alkyl;
H; C1-6 alkyl-S(O)$_2$—; amino; NH$_2$—S(O)$_2$—; C1-6 alkoxy;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with C1-6 alkyl;
C3-6 cycloalkyl; C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)$_2$—;
C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, acetyl, C1-6 alkoxyC1-6 alkyl, C1-6 alkyl and C1-6 alkyl-S(O)$_2$—;
alternatively, Y1 and Y2 together with the nitrogen atom to which they are attached, form a 4-6 membered heterocycloalkyl which contains the nitrogen atom and 0,1 or more heteroatom selected from O and S, and the sulfur atom can be its oxide form;
alternatively, Y1 and Y2 together with the nitrogen atom to which they are attached, form a 4-6 membered heterocycloalkyl which contains 1-3 heteroatoms selected from N, O and S, the sulfur atom can be its oxide form, and the heterocycloalkyl is substituted by 1-4 substituents selected from the group consisting of C1-6 alkyl, C1-6 alkyl-S(O)$_2$—, C1-6 alkoxy, halogenated C1-6 alkyl, NH$_2$C(=O)—, and halogen;
alternatively, Y1 and Y2 together with the nitrogen atom to which they are attached, form C5-10 oxaazabicycloalkyl;
Y3 and Y4 are independently selected from the group consisting of hydrogen, C1-6 alkyl, and SO$_2$—C1-6 alkyl;
alternatively, Y3 and Y4 together with the nitrogen atom to which they are attached, form a heterocyclyl, and the heterocyclyl is selected from the group consisting of piperidinyl, morpholinyl, dioxidothiomorpholinyl and oxidothiomorpholinyl.

8. A compound according to claim 1, having formula IV:

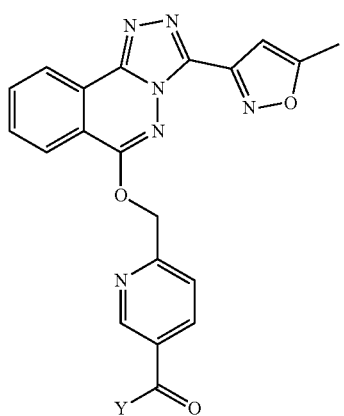

IV

Wherein
Y is —NY1Y2 or —NH—NY3Y4;
Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, and C1-6 alkyl-S(O)$_2$—;
Y2 is independently selected from the group consisting of C1-6 alkyl; C1-6 alkyl substituted by 1-5 substituents selected from the group consisting of amino, hydroxyl, C1-6 alkoxy, carboxyl, halogen, cycloalkyl, (C1-6 alkyl, C1-6 alkyl)N-, (C1-6 alkyl, H)N— and C1-6 alkyl-S(O)$_2$—, C3-7 heterocycloalkyl that contains 1-3 hetero-atoms independently selected from nitrogen, oxygen or sulfur, or C3-7 heterocycloalkyl that contains 1-3 hetero-atoms independently selected from nitrogen, oxygen or sulfur and is substituted by 1-4 substituents selected from the group consisting of acetamido, acetyl, C1-6 alkoxy, and C1-6 alkyl;
H; C1-6 alkyl-S(O)$_2$—; amino; NH$_2$—S(O)$_2$—; C1-6 alkoxy;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with C1-6 alkyl;
C3-6 cycloalkyl; C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)$_2$—;
C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, acetyl, C1-6 alkoxyC1-6 alkyl, C1-6 alkyl and C1-6 alkyl-S(O)$_2$—;
alternatively, Y1 and Y2 together with the nitrogen atom to which they are attached, form a 4-6 membered heterocycloalkyl which contains the nitrogen atom and 0,1 or more heteroatom selected from O and S, and the sulfur atom can be its oxide form;
alternatively, Y1 and Y2 together with the nitrogen atom to which they are attached, form a 4-6 membered heterocycloalkyl which contains 1-3 heteroatoms selected from N, O and S, the sulfur atom can be its oxide form, and the heterocycloalkyl is substituted by 1-4 substituents selected from the group consisting of C1-6 alkyl, C1-6 alkyl-S(O)$_2$—, C1-6 alkoxy, halogenated C1-6 alkyl, NH$_2$C(=O)—, and halogen;

alternatively, Y1 and Y2 together with the nitrogen atom to which they are attached, form C5-10 oxaazabicycloalkyl;

Y3 and Y4 are independently selected from the group consisting of hydrogen, C1-6 alkyl, and SO$_2$—C1-6 alkyl;

alternatively, Y3 and Y4 together with the nitrogen atom to which they are attached, form a heterocyclyl, and the heterocyclyl is selected from the group consisting of piperidinyl, morpholinyl, dioxidothiomorpholinyl and oxidothiomorpholinyl.

9. A compound according to claim 1, having formula IV:

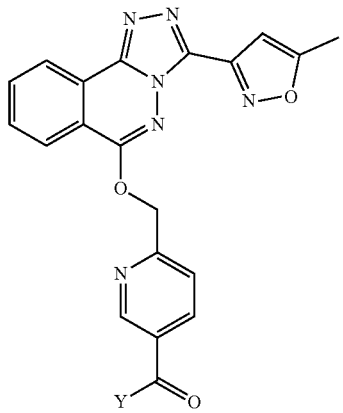

IV

Wherein
Y is —NY1Y2 or —NH—NY3Y4;
Y1 is independently selected from the group consisting of H, C1-6 alkyl, or C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, and C1-6 alkyl-S(O)$_2$—;
Y2 is independently selected from the group consisting of C1-6 alkyl; C1-6 alkyl substituted by 1-5 substituents selected from the group consisting of amino, hydroxyl, C1-6 alkoxy, halogen, carboxyl, C3-6 cycloalkyl, C4-6 heterocycloalkyl that contains 1-3 hetero-atoms independently selected from nitrogen, oxygen or sulfur; H; C1-6 alkyl-S(O)$_2$—; amino; NH$_2$—S(O)$_2$—; C1-6 alkoxy;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with C1-6 alkyl;
C4-6 cycloalkyl; cyclopropyl; C3-6 cycloalkyl substituted by 1-4 substituents selected from the group consisting of hydroxyl, C1-6 alkyl, and C1-6 alkoxy;
C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents selected from the group consisting of C1-6 alkyl, acetyl, and C1-6 alkyl-S(O)$_2$—;

alternatively, Y1 and Y2 together with the nitrogen atom to which they are attached, form morpholinyl, piperidinyl, piperazinyl, azetidinyl, oxaazabicycloheptanyl; the morpholinyl, piperidinyl, piperazinyl, azetidinyl, and oxaazabicycloheptanyl are optionally substituted by 1-4 substituents selected from the group consisting of C1-6 alkyl, C1-6 alkyl-S(O)$_2$—, C1-6 alkoxyl, halogen, and NH$_2$C(=O)—; the sulfur atom of the morpholinyl can be its oxide form;

Y3 and Y4 are independently selected from the following groups: hydrogen, methyl and SO$_2$-methyl;

Y3 and Y4 together with the nitrogen atom to which they are attached, form a heterocyclyl, and the heterocyclyl is selected from the group consisting of morpholinyl, piperidinyl and dioxido-thiomorpholinyl.

10. A compound according to claim 1, having formula IV:

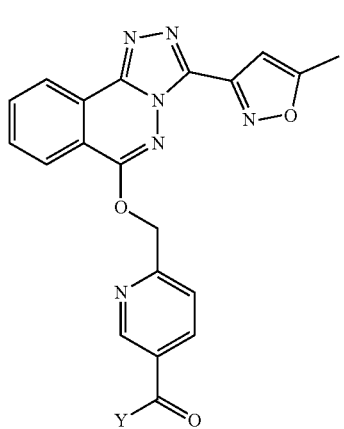

IV

Wherein
Y is —NY1Y2 or —NH—NY3Y4;
Y1 is independently selected from the group consisting of H or C1-6 alkyl;
Y2 is independently selected from the group consisting of C1-6 alkyl; C1-6 alkyl substituted by 1-5 substituents selected from the group consisting of hydroxyl, C1-6 alkoxy, acetamido, fluorine, carboxyl, C3-6 cycloalkyl, C4-6 heterocycloalkyl that contains 1-3 hetero-atoms independently selected from nitrogen, oxygen or sulfur; H; C1-6 alkyl-S(O)$_2$—; amino; NH$_2$—S(O)$_2$—; C1-6 alkoxy;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with methyl;
C4-6 cycloalkyl; cyclopropyl; C3-6 cycloalkyl substituted by 1-4 substituents selected from the group consisting of hydroxyl, C1-6 alkyl, and C1-6 alkoxy;
C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents selected from the group consisting of C1-6 alkyl, acetyl, and C1-6 alkyl-S(O)$_2$—;
Y1 and Y2 together with the nitrogen atom to which they are attached, form morpholinyl, piperidinyl, piperazinyl, azetidinyl, oxaazabicycloheptanyl; the morpholinyl, piperidinyl, piperazinyl, azetidinyl, and oxaazabicycloheptanyl are optionally substituted by 1-4 substituents selected from the group consisting of C1-6 alkyl, C1-6 alkyl-SO$_2$, C1-6 alkoxyl, halogen, and NH$_2$C(=O)—; the sulfur atom of the morpholinyl can be its oxide form;

Y3 and Y4 are independently selected from the following groups: hydrogen, methyl and SO$_2$-methyl;

Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

11. A compound according to claim 1, having formula IV:

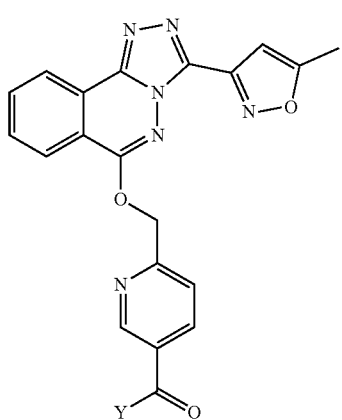

IV

Wherein
Y is —NY1Y2 or —NH—NY3Y4;
Y1 is H or methyl;
Y2 is independently selected from the group consisting of C1-6 alkyl; C1-6 alkyl substituted by 1-5 substituents selected from the group consisting of hydroxyl, C1-6 alkoxy, acetamido, fluorine, carboxyl, morpholinyl, cyclopropyl, and tetrahydro-furanyl;
H; C1-6 alkyl-S(O)$_2$—; amino; NH$_2$—S(O)$_2$—; C1-6 alkoxy;
C3-6 cycloalkyl; C3-6 cycloalkyl substituted by 1-4 substituents selected from the group consisting of hydroxyl, methoxy and methyl;
C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with methyl;
C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents selected from the group consisting of methyl, acetyl and C1-6 alkyl-S(O)$_2$—;
Y1 and Y2 together with the nitrogen atom to which they are attached, form morpholinyl, piperidinyl, piperazinyl, azetidinyl, oxaazabicycloheptanyl; the morpholinyl, piperidinyl, piperazinyl, azetidinyl, and oxaazabicycloheptanyl are optionally substituted by 1-4 substituents selected from the group consisting of C1-6 alkyl, C1-6 alkyl-SO$_2$, C1-6 alkoxyl, halogen, and NH$_2$C(=O)—; the sulfur atom of the morpholinyl can be its oxide form;
Y3 and Y4 are independently selected from the following groups: hydrogen and methyl;
Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

12. A compound according to claim 1, having formula IV:

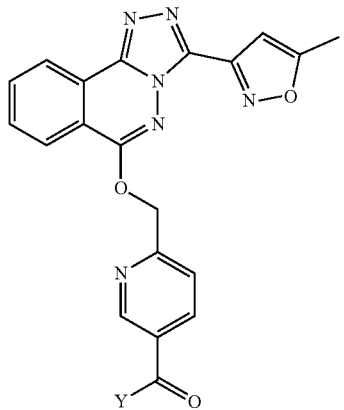

IV

Wherein
Y is —NY1Y2 or —NH—NY3Y4;
Y1 is H or methyl;
Y2 is selected from the group consisting of methyl, ethyl, 2-methoxyethyl, hydroxypropyl, acetamidoethyl, H, —CH$_2$COOH, hydroxycyclopentyl, cyclopropyl, methylpyrazolyl, morpholinyl, hydroxyethyl, butyl, methylpiperidinyl, morpholinylethyl, tetrahydrofuranyl, methoxycyclopentyl, acetylpyrrolidinyl, tetrahydrofuranylmethyl, difluoroethyl, cyclopropylmethyl, methylsulfonylethyl, trifluoroethyl, isopropyl, tetrahydropyranyl, cyclobutyl, amino, piperidinyl, methyl sulfonyl, dioxidothiomorpholinyl, hydroxymethylethyl;
alternatively, Y1 and Y2 together with the nitrogen atom to which they are attached, form methylpiperazinyl, carboxamidepiperidinyl, methoxypiperidinyl, difluoropiperidinyl, oxaazabicycloheptanyl, dioxidothiomorpholinyl, morpholinyl, azetidinyl, or oxidothiomorpholinyl;
Y3 and Y4 are independently selected from the group consisting of hydrogen and methyl;
Y3 and Y4 together with the nitrogen atom to which they are attached, form a heterocyclyl, and the heterocyclyl is selected from the group consisting of morpholin-4-yl, piperidin-1-yl and 1,1-dioxido-thiomorpholin-4-yl.

13. A compound according to claim 1, having formula IV:

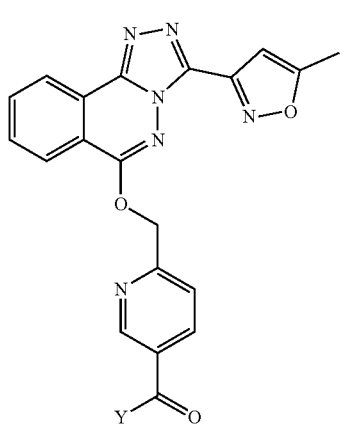

IV

Wherein
Y is —NY1Y2;
Y1 is H;

Y2 is selected from the group consisting of methyl, ethyl, methoxyethyl, hydroxypropyl, acetamidoethyl, H, —CH$_2$COOH, hydroxycyclopentyl, cyclopropyl, methylpyrazolyl, morpholinyl, hydroxyethyl, butyl, methylpiperidinyl, morpholinylethyl, tetrahydrofuranyl, methoxycyclopentyl, acetylpyrrolidinyl, tetrahydrofuranylmethyl, difluoroethyl, cyclopropylmethyl, methyl sulfonyl ethyl and trifluoroethyl;

alternatively, Y1 and Y2 together with the nitrogen atom to which they are attached, form methylpiperazinyl, carboxamidepiperidinyl, methoxypiperidinyl, difluoropiperidinyl, or oxaazabicycloheptanyl.

14. A compound according to claim 1, having formula II,

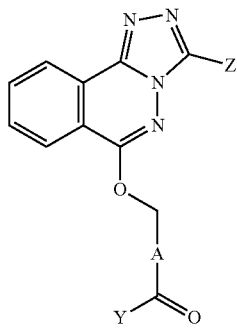

wherein
Z is methylisoxazolyl;
A is cyanophenylene or pyridinylene;
Y is —NY1Y2;
Y1 is H;
Y2 is selected from the group consisting of C1-6 alkyl; C1-6 alkyl substituted by 1-3 substituents selected from C3-6 cycloalkyl or C1-6 alkoxy; and C1-6 alkoxy.

15. A compound according to claim 1 of formula II, a cis-trans isomer, an enantiomer, a diastereoisomer, a racemate, a solvate, a hydrate, or a pharmaceutical acceptable salt and ester thereof:

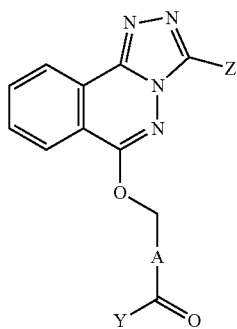

wherein:
Z is oxadiazolyl, furyl, thienyl or isoxazolyl, the isoxazolyl is optionally substituted by one or more substituents selected from the group consisting of H, C1-6 alkyl and hydroxyl C1-6 alkyl;
A is phenylene, pyridinylene, or isoxazolylene; A is optionally substituted by 1, 2 or 3 substituents selected from the group consisting of halogen, cyano, and C1-6 alkyl;

Y is —NY1Y2 or —NH—NY3Y4;

Y1 is independently selected from the group consisting of H; C1-6 alkyl; C1-6 alkyl substituted by 1-5 substituents selected from the group consisting of amino, halogen, halogenated C1-6 alkoxy, hydroxyl, C1-6 alkoxy, (C1-6 alkyl, C1-6 alkyl)N-, (C1-6 alkyl, H)N—, nitro and C1-6 alkyl-S(O)$_2$—;

Y2 is independently selected from the group consisting of H; C1-6 alkyl; C1-6 alkyl substituted by 1-5 substituents selected from the group consisting of amino, halogen, halogenated C1-6 alkoxy, hydroxyl, C1-6 alkoxy, cycloalkyl, (C1-6 alkyl, C1-6 alkyl)N-, (C1-6 alkyl, H)N—, nitro and C1-6 alkyl-S(O)$_2$—; C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted by 1-4 substituents selected from the group consisting of acetamido, acetyl, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)$_2$—; cycloalkyl, or cycloalkyl substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)$_2$—; C3-7 heterocycloalkyl that contains 1-3 hetero-atoms independently selected from nitrogen, oxygen or sulfur, or C3-7 heterocycloalkyl that contains 1-3 hetero-atoms independently selected from nitrogen, oxygen or sulfur and is substituted by 1-4 substituents selected from the group consisting of acetamido, acetyl, acetylamino, acyl amino, amino, carboxyl, cyano, halogen, halogenated C1-6 alkoxy, halogenated C1-6 alkyl, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N—, nitro and C1-6 alkyl-S(O)$_2$—;

alternatively, Y1 and Y2 together with the nitrogen atom to which they are attached, form a 4-6 membered heterocycloalkyl which contains the nitrogen atom and 0, 1 or more other atoms selected from O and S; the sulfur atom can be its oxide form;

Y3 and Y4 are independently selected from the group consisting of hydrogen, C1-6 alkyl, SO$_2$—C1-6 alkyl, cycloalkyl and C3-7 heterocyclyl that contains 1-3 hetero-atoms independently selected from nitrogen, oxygen or sulfur, optionally substituted by 1-4 substituents selected from the group consisting of halogen, cyano, hydroxyl, C1-6 alkyl and C1-6 alkoxy, alternatively, Y3 and Y4 together with the nitrogen atom to which they are attached, form a C3-7 heterocyclyl, and the C3-7 heterocyclyl contains 1-3 hetero-atoms independently selected from nitrogen, oxygen or sulfur and is optionally substituted by 1-4 substituents selected from the group consisting of halogen, cyano, hydroxyl, oxo, C1-6 alkyl and C1-6 alkoxy.

16. A compound according to claim 15, having formula II:

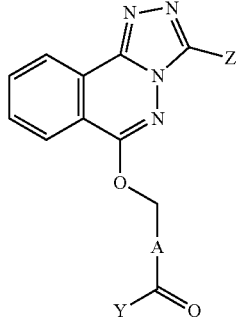

Wherein:
Y is —NY1Y2 or —NH—NY3Y4;
Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, and C1-6 alkyl-S(O)$_2$—;
Y2 is independently selected from the group consisting of C1-6 alkyl; C1-6 alkyl substituted by 1-5 substituents selected from the group consisting of amino, hydroxyl, C1-6 alkoxy, cycloalkyl, (C1-6 alkyl, C1-6 alkyl)N-, (C1-6 alkyl, H)N— and C1-6 alkyl-S(O)$_2$—;
C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;
C3-6 cycloalkyl, C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)$_2$—;
C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, C1-6 alkoxyC1-6 alkyl, C1-6 alkyl and C1-6 alkyl-S(O)$_2$—;
alternatively, Y1 and Y2 together with the nitrogen atom to which they are attached, form a 4-6 membered heterocycloalkyl which contains the nitrogen atom and 0,1 or more heteroatom selected from O and S; the sulfur atom can be its oxide form;
Y3 and Y4 are independently selected from the group consisting of hydrogen, C1-6 alkyl, and SO$_2$—C1-6 alkyl;
alternatively, Y3 and Y4 together with the nitrogen atom to which they are attached, form a heterocyclyl, wherein the heterocyclyl is selected from the group consisting of piperazinyl, morpholinyl, dioxidothiomorpholinyl and oxidothiomorpholinyl.
17. A compound according to claim 15 wherein
Z is oxadiazolyl, furyl, thienyl or isoxazolyl, the isoxazolyl is optionally substituted by one or more substituents selected from the group consisting of H, C1-6 alkyl, and hydroxyl C1-6 alkyl;

A is phenylene, pyridinylene, or isoxazolylene; A is optionally substituted by 1, 2 or 3 substituents selected from the group consisting of halogen, cyano, and C1-6 alkyl;
Y is —NY1Y2 or —NH—NY3Y4;
Y1 is H or C1-6 alkyl;
Y2 is independently selected from the group consisting of C1-6 alkyl; C1-6 alkyl substituted by 1-5 substituents selected from the group consisting of amino, hydroxyl, and C1-6 alkoxy;
C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with alkyl;
C4-6 cycloalkyl, C3-6 cycloalkyl substituted by 1-4 substituents selected from the group consisting of hydroxyl;
C4-6 heterocycloalkyl that contains 1-3 hetero-atoms independently selected from nitrogen, oxygen or sulfur, or C4-6 heterocycloalkyl that contains 1-3 hetero-atoms independently selected from nitrogen, oxygen or sulfur and is substituted by 1-4 substituents;
alternatively, Y1 and Y2 together with the nitrogen atom to which they are attached, form morpholinyl, piperidinyl, oxidothiomorpholinyl and di oxidothiomorpholinyl;
Y3 and Y4 are independently selected from the group consisting of hydrogen, methyl and SO2-methyl,
alternatively, Y3 and Y4 together with the nitrogen atom to which they are attached, form a heterocyclyl selected from the group consisting of piperidinyl, morpholinyl and dioxidothiomorpholinyl.
18. A compound according to claim 15 wherein
Z is oxadiazolyl, furyl, thienyl or isoxazolyl, the isoxazolyl is optionally substituted by one or more substituents selected from the group consisting of H, C1-6 alkyl, and hydroxyl C1-6 alkyl;
A is phenylene, pyridinylene, or isoxazolylene; A is optionally substituted by 1, 2 or 3 substituents selected from the group consisting of halogen, cyano, and C1-6 alkyl;
Y is —NY1Y2 or —NH—NY3Y4;
Y1 is H or C1-6 alkyl;
Y2 is independently selected from the group consisting of C1-6 alkyl; C1-6 alkyl substituted by 1-5 substituents selected from the group consisting of hydroxyl, and C1-6 alkoxy;
C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted by alkyl;
C4-6 cycloalkyl, C3-6 cycloalkyl substituted by 1-4 substituents selected from the group consisting of hydroxyl;
C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents;
alternatively, Y1 and Y2 together with the nitrogen atom to which they are attached, form morpholinyl and piperidinyl;
Y3 and Y4 are independently selected from the group consisting of hydrogen, methyl and SO$_2$-methyl, or Y3 and Y4 together with the nitrogen atom to which they are attached, form a heterocyclyl selected from the group consisting of morpholin-4-yl, piperidin-1-yl and 1,1-dioxido-thiomorpholin-4-yl.

19. A compound according to claim 15 wherein
Z is oxadiazolyl, furyl, thienyl or isoxazolyl, the isoxazolyl is optionally substituted by one or more substituents selected from the group consisting of H, C1-6 alkyl, and hydroxyl C1-6 alkyl;
A is phenylene, pyridinylene, or isoxazolylene; A is optionally substituted by 1, 2 or 3 substituents selected from the group consisting of halogen, cyano, and C1-6 alkyl;
Y is —NY1Y2 or —NH—NY3Y4;
Y1 is H or methyl;
Y2 is independently selected from the group consisting of C1-6 alkyl; C1-6 alkyl substituted by 1-5 substituents selected from the group consisting of hydroxyl, and C1-6 alkoxy;
Y3 and Y4 are independently selected from the group consisting of hydrogen and methyl, or Y3 and Y4 together with the nitrogen atom to which they are attached, form a heterocyclyl selected from the group consisting of morpholin-4-yl, piperidin-1-yl and 1,1-dioxido-thiomorpholin-4-yl.

20. A compound according to claim 15 wherein,
Z is oxadiazolyl, furyl, thienyl or isoxazolyl, the isoxazolyl is optionally substituted by one or more substituents selected from the group consisting of H, C1-6 alkyl, and hydroxyl C1-6 alkyl;
A is phenylene, pyridinylene, or isoxazolylene; A is optionally substituted by 1, 2 or 3 substituents selected from the group consisting of halogen, cyano, and C1-6 alkyl;
Y is —NY1Y2 or —NH—NY3Y4;
Y1 is H or methyl;
Y2 is selected from the group consisting of methyl, ethyl, methoxyethyl and hydroxypropyl;
Y3 and Y4 are independently selected from the group consisting of hydrogen and methyl, or Y3 and Y4 together with the nitrogen atom to which they are attached, form a heterocyclyl selected from the group consisting of morpholin-4-yl, piperidin-1-yl and 1,1-dioxido-thiomorpholin-4-yl.

21. A compound according to claim 15 having formula III:

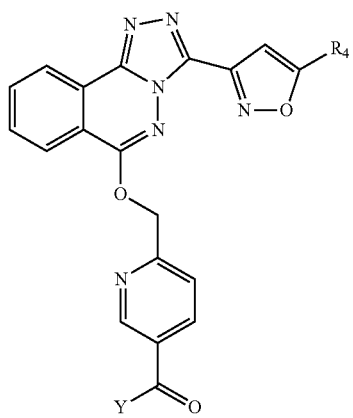

III

Wherein
R4 is C1-4 alkyl, hydroxyl substituted C1-4 alkyl;
Y is —NY1Y2 or —NH—NY3Y4;

Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N— and C1-6 alkyl-S(O)$_2$—;
Y2 is independently selected from the group consisting of C1-6 alkyl; C1-6 alkyl substituted by 1-5 substituents selected from the group consisting of amino, hydroxyl, C1-6 alkoxy, cycloalkyl, (C1-6 alkyl, C1-6 alkyl)N-, (C1-6 alkyl, H)N— and C1-6 alkyl-S(O)$_2$—;
C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;
C3-6 cycloalkyl, C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)$_2$—;
C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, C1-6 alkoxyC1-6 alkyl, C1-6 alkyl and C1-6 alkyl-S(O)$_2$—;
alternatively, Y1 and Y2 together with the nitrogen atom to which they are attached, form a 4-6 membered heterocycloalkyl which contains the nitrogen atom and 0,1 or more heteroatom selected from O and S, and the sulfur atom can be its oxide form;
Y3 and Y4 are independently selected from the group consisting of hydrogen, C1-6 alkyl, and SO$_2$—C1-6 alkyl, alternatively, Y3 and Y4 together with the nitrogen atom to which they are attached, form a heterocyclyl selected from the group consisting of piperidinyl, morpholinyl, dioxidothiomorpholinyl and oxidothiomorpholinyl.

22. A compound according to claim 15, having formula IV:

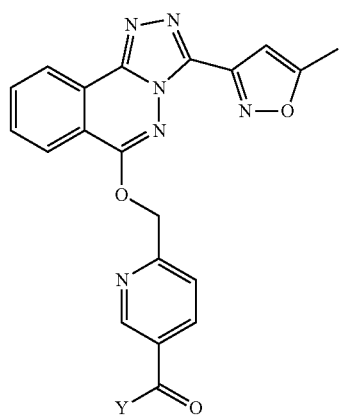

IV

Wherein
Y is —NY1Y2 or —NH—NY3Y4;
Y1 is independently selected from the group consisting of H; C1-6 alkyl; C1-6 alkyl substituted by 1-5 substituents selected from the group consisting of amino, hydroxyl, C1-6 alkoxy, (C1-6 alkyl, C1-6 alkyl)N-, (C1-6 alkyl, H)N— and C1-6 alkyl-S(O)$_2$—;

Y2 is independently selected from the group consisting of C1-6 alkyl; C1-6 alkyl substituted by 1-5 substituents selected from the group consisting of amino, hydroxyl, C1-6 alkoxy, cycloalkyl, (C1-6 alkyl, C1-6 alkyl)N-, (C1-6 alkyl, H)N— and C1-6 alkyl-S(O)$_2$—;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;

C3-6 cycloalkyl, C3-6 cycloalkyl substituted by 1-4 substituents selected from the group consisting of amino, hydroxyl, hydroxylC1-6 alkyl, C1-6 alkoxy, C1-6 alkoxyC1-6 alkyl, C1-6 alkyl, (C1-6 alkyl, C1-6 alkyl)N-, (C1-6 alkyl, H)N— and C1-6 alkyl-S(O)$_2$—;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents selected from the group consisting of amino, hydroxyl, hydroxylC1-6 alkyl, C1-6 alkoxy, C1-6 alkoxyC1-6 alkyl, C1-6 alkyl and C1-6 alkyl-S(O)$_2$—;

alternatively, Y1 and Y2 together with the nitrogen atom to which they are attached, form a 4-6 membered heterocycloalkyl which contains the nitrogen atom and 0,1 or more heteroatom selected from O and S, and the sulfur atom can be its oxide form;

Y3 and Y4 are independently selected from the group consisting of hydrogen, C1-6 alkyl, and SO$_2$—C1-6 alkyl, alternatively, Y3 and Y4 together with the nitrogen atom to which they are attached, form a heterocyclyl, and the heterocyclyl is selected from the group consisting of piperidinyl, morpholinyl, dioxidothiomorpholinyl and oxidothiomorpholinyl.

23. A compound according to claim 15 having formula IV:

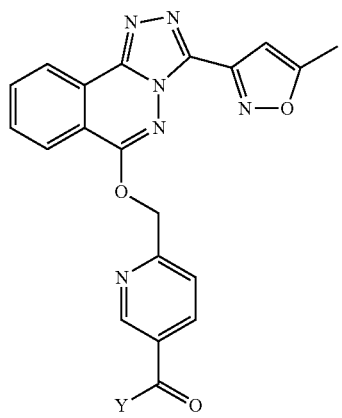

Wherein
Y is —NY1Y2 or —NH—NY3Y4;
Y1 is independently selected from the group consisting of H, C1-6 alkyl, or C1-6 alkyl substituted by 1-5 substituents selected from the group consisting of amino, hydroxyl, C1-6 alkoxy, (C1-6 alkyl, C1-6 alkyl)N-, (C1-6 alkyl, H)N—, and C1-6 alkyl-S(O)$_2$—;
Y2 is independently selected from the group consisting of C1-6 alkyl; C1-6 alkyl substituted by 1-5 substituents selected from the group consisting of amino, hydroxyl, and C1-6 alkoxy;

C5-6 heteroaryl that contains 1-3 hetero-atoms independently selected from nitrogen, oxygen or sulfur; C5-6 heteroaryl that contains 1-3 hetero-atoms independently selected from nitrogen, oxygen or sulfur and is substituted with C1-6 alkyl;

C4-6 cycloalkyl; C3-6 cycloalkyl substituted by 1-4 substituents selected from the group consisting of hydroxyl;

C4-6 heterocycloalkyl that contains 1-3 hetero-atoms independently selected from nitrogen, oxygen or sulfur; C4-6 heterocycloalkyl that contains 1-3 hetero-atoms independently selected from nitrogen, oxygen or sulfur and is substituted by 1-4 substituents;

alternatively, Y1 and Y2 together with the nitrogen atom to which they are attached, form morpholinyl, piperidinyl, oxido-thiomorpholinyl and dioxido-thiomorpholinyl;

Y3 and Y4 are independently selected from the following groups: hydrogen, methyl and SO$_2$-methyl, or Y3 and Y4 together with the nitrogen atom to which they are attached, form a heterocyclyl selected from the group consisting of morpholinyl, piperidinyl and dioxidothiomorpholinyl.

24. A compound according to claim 15 having formula IV:

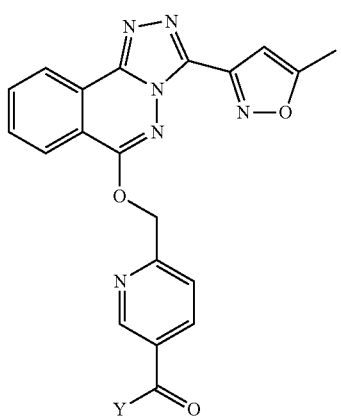

wherein
Y is —NY1Y2 or —NH—NY3Y4;
Y1 is independently selected from the group consisting of H and C1-6 alkyl;
Y2 is independently selected from the group consisting of C1-6 alkyl; C1-6 alkyl substituted by 1-5 substituents selected from the group consisting of hydroxyl, and C1-6 alkoxy;

C5-6 heteroaryl that contains 1-3 hetero-atoms independently selected from nitrogen, oxygen or sulfur, C5-6 heteroaryl that contains 1-3 hetero-atoms independently selected from nitrogen, oxygen or sulfur and is substituted with C1-6 alkyl;

C4-6 cycloalkyl, C3-6 cycloalkyl substituted by 1-4 substituents selected from the group consisting of hydroxyl;

C4-6 heterocycloalkyl that contains 1-3 hetero-atoms independently selected from nitrogen, oxygen or sulfur, C4-6 heterocycloalkyl that contains 1-3 hetero-atoms independently selected from nitrogen, oxygen or sulfur and is substituted by 1-4 substituents;

alternatively, Y1 and Y2 together with the nitrogen atom to which they are attached, form morpholinyl and piperidinyl;

Y3 and Y4 are independently selected from the following groups: hydrogen, methyl and SO$_2$-methyl, or Y3 and Y4 together with the nitrogen atom to which they are attached, form a heterocyclyl selected from the group consisting of morpholin-4-yl, piperidin-1-yl and 1,1-dioxido-thiomorpholin-4-yl.

25. A compound according to claim 15 having formula IV:

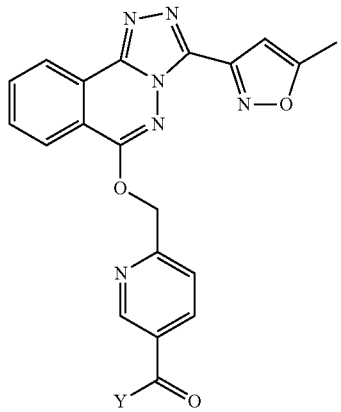

IV

Wherein
Y is —NY1Y2 or —NH—NY3Y4;
Y1 is H or methyl;
Y2 is independently selected from the group consisting of C1-6 alkyl; C1-6 alkyl substituted by 1-5 substituents selected from the group consisting of hydroxyl, and C1-6 alkoxy;
Y3 and Y4 are independently selected from the following groups: hydrogen and methyl, or Y3 and Y4 together with the nitrogen atom to which they are attached, form a heterocyclyl selected from the group consisting of morpholin-4-yl, piperidin-1-yl and 1,1-dioxido-thiomorpholin-4-yl.

26. A compound according to claim 15 having formula IV:

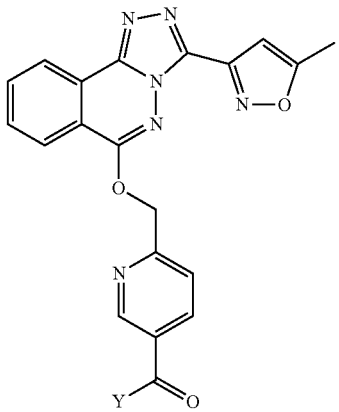

IV

Wherein
Y is —NY1Y2 or —NH—NY3Y4;
Y1 is H or methyl;
Y2 is independently selected from the group consisting of methyl, ethyl, 2-methoxyethyl, and hydroxylpropyl;
Y3 and Y4 are independently selected from the following groups: hydrogen, and methyl, or Y3 and Y4 together with the nitrogen atom to which they are attached, form a heterocyclyl selected from the group consisting of morpholin-4-yl, piperidin-1-yl and 1,1-dioxido-thiomorpholin-4-yl.

27. A compound according to claim 1 which is independently selected from the group consisting of

| number | Chemical structures | Chemical name |
|---|---|---|
| 01 | 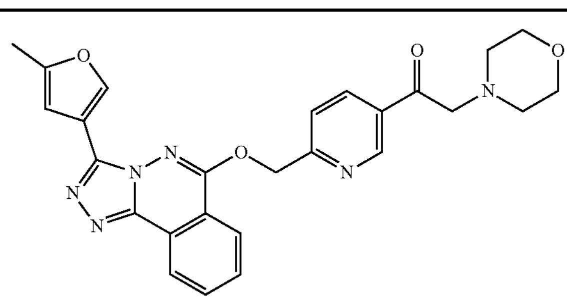 | 6-(((3-(5-methylisoxazol-3-yl)-[1,2,4]triazolo[3,4-a]phthalazin-6-yl)oxy)methyl)-N-morpholinonicotinamide |
| 02 | 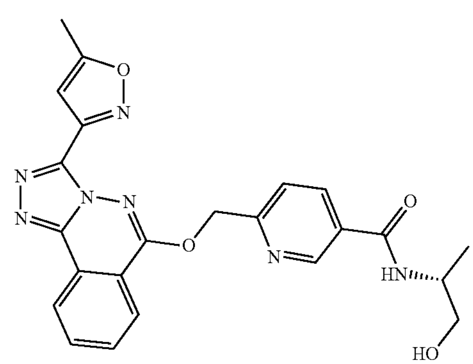 [SMILES: Cc1cc(-c2nnc3c4ccccc4c(OCc4ccc(C(=O)N[C@H](C)CO)cn4)nn23)no1] | (R)-N-(1-hydroxypropan-2-yl)-6-(((3-(5-methylisoxazol-3-yl)-[1,2,4]triazolo[3,4-a]phthalazin-6-yl)oxy)methyl)nicotinamide |

-continued

| number | Chemical structures | Chemical name |
|---|---|---|
| 03 | 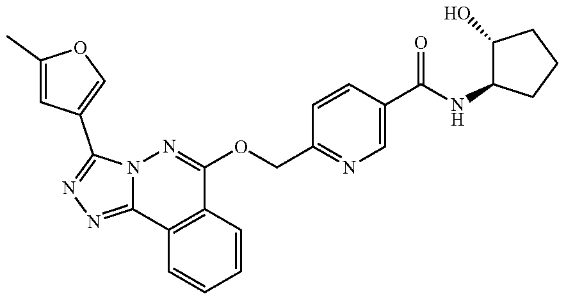 [SMILES: Cc1cc(-c2nnc3c4ccccc4c(OCc4ccc(C(=O)N[C@@H]5CCC[C@H]5O)cn4)nn23)co1] | N-((1S,2S)-2-hydroxycyclopentyl)-6-(((3-(5-methylisoxazol-3-yl)-[1,2,4]triazolo[3,4-a]phthalazin-6-yl)oxy)methyl)nicotinamide |
| 04 | 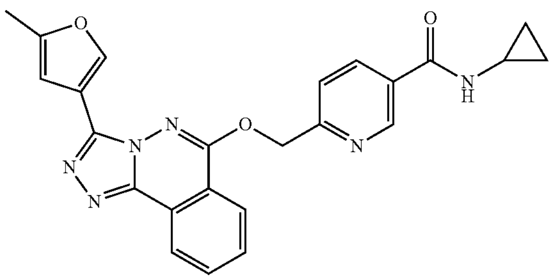 [SMILES: Cc1cc(-c2nnc3c4ccccc4c(OCc4ccc(C(=O)NC5CC5)cn4)nn23)co1] | N-cyclopropyl-6-(((3-(5-methylisoxazol-3-yl)-[1,2,4]triazolo[3,4-a]phthalazin-6-yl)oxy)methyl)nicotinamide |
| 05 | 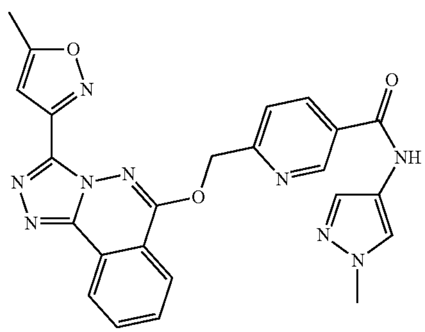 [SMILES: Cc1cc(-c2nnc3c4ccccc4c(OCc4ccc(C(=O)Nc5cnn(C)c5)cn4)nn23)no1] | N-(1-methyl-1H-pyrazol-4-yl)-6-(((3-(5-methylisoxazol-3-yl)-[1,2,4]triazolo[3,4-a]phthalazin-6-yl)oxy)methyl)nicotinamide |
| 06 | 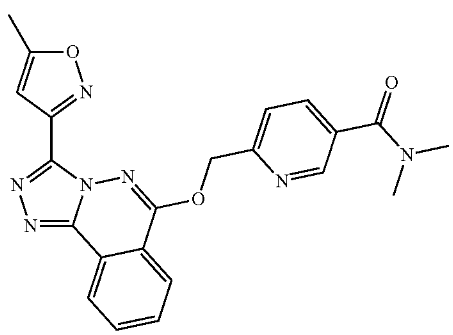 | N,N-dimethyl-6-(((3-(5-methylisoxazol-3-yl)-[1,2,4]triazolo[3,4-a]phthalazin-6-yl)oxy)methyl)nicotinamide |
| 07 | 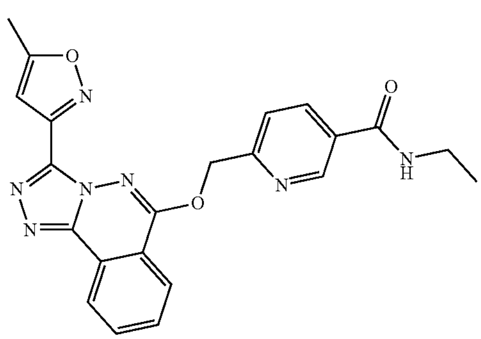 [SMILES: CCNC(=O)c1ccc(COc2nn3c(-c4cc(C)on4)nnc3c3ccccc23)nc1] | N-ethyl-6-(((3-(5-methylisoxazol-3-yl)-[1,2,4]triazolo[3,4-a]phthalazin-6-yl)oxy)methyl)nicotinamide |

-continued

| number | Chemical structures | Chemical name |
|---|---|---|
| 08 | 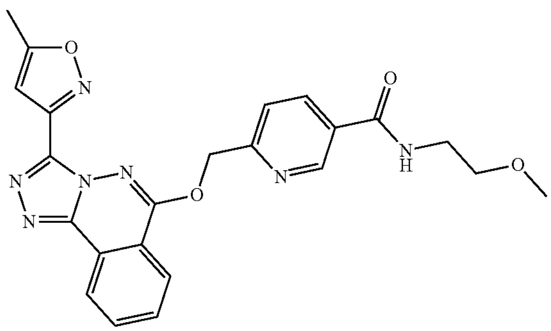 | N-(2-methoxyethyl)-6-(((3-(5-methylisoxazol-3-yl)-[1,2,4]triazolo[3,4-a]phthalazin-6-yl)oxy)methyl)nicotinamide |
| 09 | 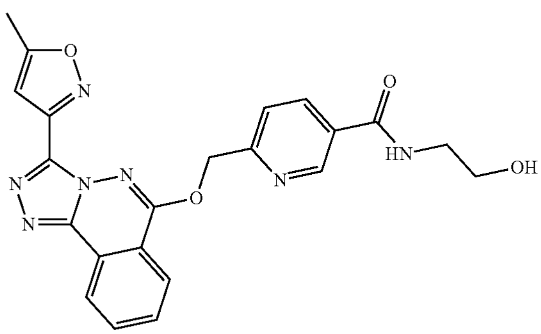 [SMILES: Cc1cc(-c2nnc3c4ccccc4c(OCc4ccc(C(=O)NCCO)cn4)nn23)no1] | N-(2-hydroxyethyl)-6-(((3-(5-methylisoxazol-3-yl)-[1,2,4]triazolo[3,4-a]phthalazin-6-yl)oxy)methyl)nicotinamide |
| 10 | 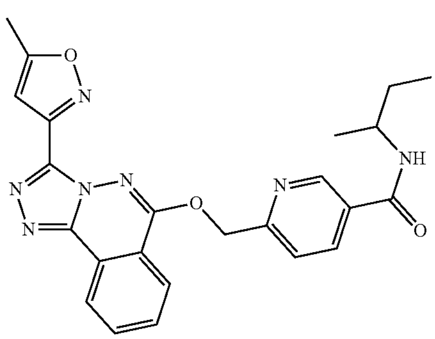 [SMILES: CCC(C)NC(=O)c1ccc(COc2nn3c(-c4cc(C)on4)nnc3c3ccccc23)nc1] | N-(2-butyl)-6-(((3-(5-methylisoxazol-3-yl)-[1,2,4]triazolo[3,4-a]phthalazin-6-yl)oxy)methyl)nicotinamide |
| 11 | 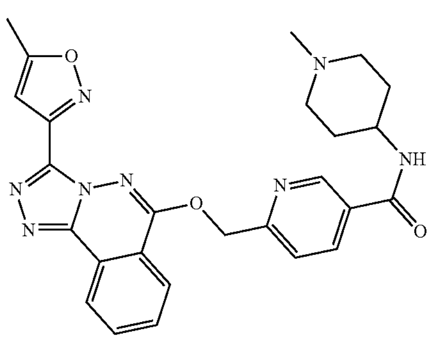 [SMILES: Cc1cc(-c2nnc3c4ccccc4c(OCc4ccc(C(=O)NC5CCN(C)CC5)cn4)nn23)no1] | 6-(((3-(5-methylisoxazol-3-yl)-[1,2,4]triazolo[3,4-a]phthalazin-6-yl)oxy)methyl)-N-(1-methylpiperidin-4-yl)nicotinamide |

| number | Chemical structures | Chemical name |
|---|---|---|
| 12 | 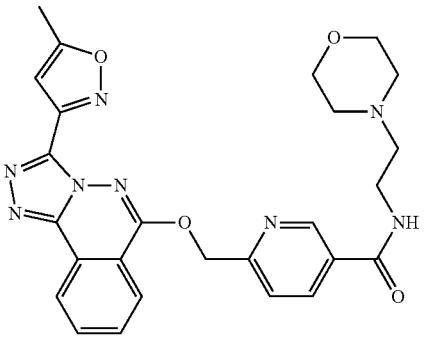 [SMILES: Cc1cc(-c2nnc3c4ccccc4c(OCc4ccc(C(=O)NCCN5CCOCC5)cn4)nn23)no1] | 6-(((3-(5-methylisoxazol-3-yl)-[1,2,4]triazolo[3,4-a]phthalazin-6-yl)oxy)methyl)-N-(2-morpholinoethyl)nicotinamide |
| 13 | 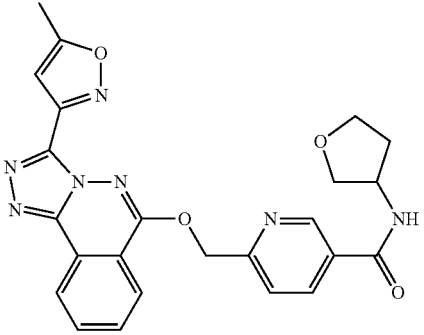 [SMILES: Cc1cc(-c2nnc3c4ccccc4c(OCc4ccc(C(=O)NC5CCOC5)cn4)nn23)no1] | 6-(((3-(5-methylisoxazol-3-yl)-[1,2,4]triazolo[3,4-a]phthalazin-6-yl)oxy)methyl)-N-(tetrahydrofuran-3-yl)nicotinamide |
| 14 | 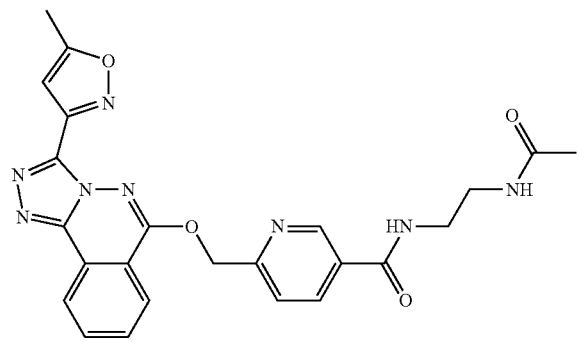 [SMILES: CC(=O)NCCNC(=O)c1ccc(COc2nn3c(-c4cc(C)on4)nnc3c3ccccc23)nc1] | N-(2-acetamidoethyl)-6-(((3-(5-methylisoxazol-3-yl)-[1,2,4]triazolo[3,4-a]phthalazin-6-yl)oxy)methyl)nicotinamide |
| 15 | 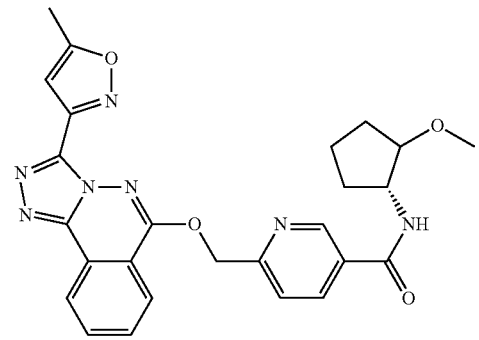 [SMILES: COC1CCC[C@H]1NC(=O)c1ccc(COc2nn3c(-c4cc(C)on4)nnc3c3ccccc23)nc1] | N-((1S)-2-methoxycyclopentyl)-6-(((3-(5-methylisoxazol-3-yl)-[1,2,4]triazolo[3,4-a]phthalazin-6-yl)oxy)methyl)nicotinamide |

| number | Chemical structures | Chemical name |
|---|---|---|
| 16 | 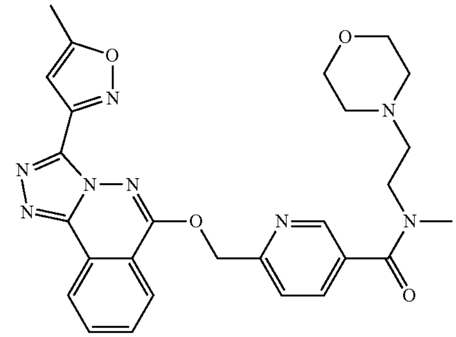 [SMILES: Cc1cc(-c2nnc3c4ccccc4c(OCc4ccc(C(=O)N(C)CCN5CCOCC5)cn4)nn23)no1] | N-methyl-6-(((3-(5-methylisoxazol-3-yl)-[1,2,4]triazolo[3,4-a]phthalazin-6-yl)oxy)methyl)-N-(2-morpholinoethyl)nicotinamide |
| 17 | 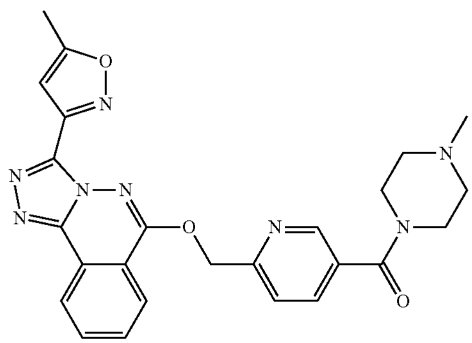 [SMILES: Cc1cc(-c2nnc3c4ccccc4c(OCc4ccc(C(=O)N5CCN(C)CC5)cn4)nn23)no1] | (6-(((3-(5-methylisoxazol-3-yl)-[1,2,4]triazolo[3,4-a]phthalazin-6-yl)oxy)methyl)pyridin-3-yl)(4-methylpiperazin-1-yl)methanone |
| 18 | 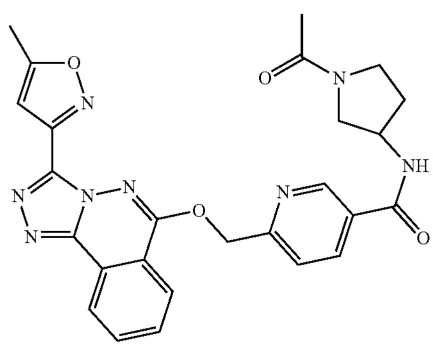 [SMILES: CC(=O)N1CCC(NC(=O)c2ccc(COc3nn4c(-c5cc(C)on5)nnc4c4ccccc34)nc2)C1] | N-(1-acetylpyrrolidin-3-yl)-6-(((3-(5-methylisoxazol-3-yl)-[1,2,4]triazolo[3,4-a]phthalazin-6-yl)oxy)methyl)nicotinamide |
| 19 | 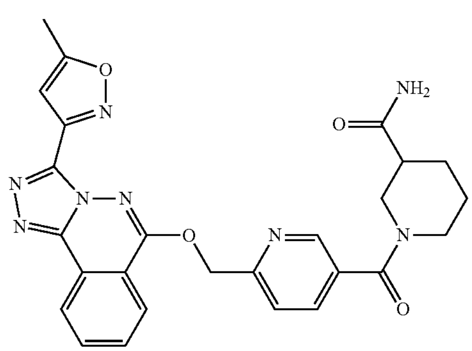 [SMILES: Cc1cc(-c2nnc3c4ccccc4c(OCc4ccc(C(=O)N5CCCC(C(N)=O)C5)cn4)nn23)no1] | 1-(6-(((3-(5-methylisoxazol-3-yl)-[1,2,4]triazolo[3,4-a]phthalazin-6-yl)oxy)methyl)nicotinoyl)piperidine-3-carboxamide |

| number | Chemical structures | Chemical name |
| --- | --- | --- |
| 20 | 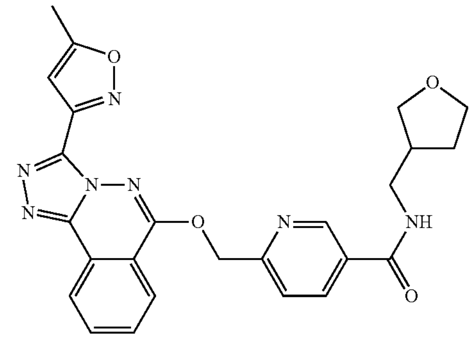 [SMILES: Cc1cc(-c2nnc3c4ccccc4c(OCc4ccc(C(=O)NCC5CCOC5)cn4)nn23)no1] | 6-(((3-(5-methylisoxazol-3-yl)-[1,2,4]triazolo[3,4-a]phthalazin-6-yl)oxy)methyl)-N-((tetrahydrofuran-3-yl)methyl)nicotinamide |
| 21 | 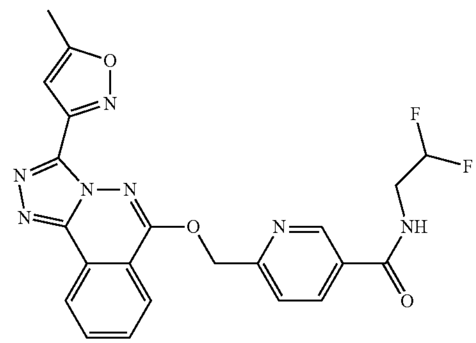 [SMILES: Cc1cc(-c2nnc3c4ccccc4c(OCc4ccc(C(=O)NCC(F)F)cn4)nn23)no1] | N-(2,2-difluoroethyl)-6-(((3-(5-methylisoxazol-3-yl)-[1,2,4]triazolo[3,4-a]phthalazin-6-yl)oxy)methyl)nicotinamide |
| 22 | 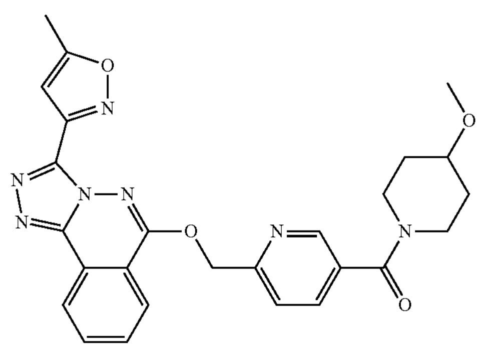 [SMILES: COC1CCN(C(=O)c2ccc(COc3nn4c(-c5cc(C)on5)nnc4c4ccccc34)nc2)CC1] | (4-methoxypiperidin-1-yl)(6-(((3-(5-methylisoxazol-3-yl)-[1,2,4]triazolo[3,4-a]phthalazin-6-yl)oxy)methyl)pyridin-3-yl)methanone |
| 23 | 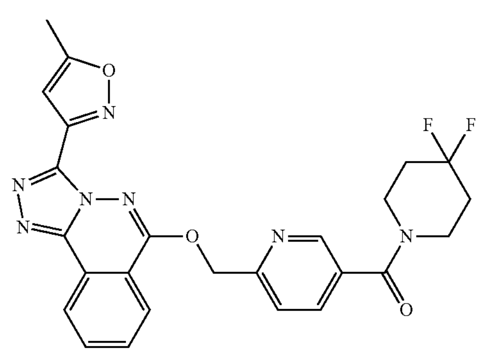 [SMILES: Cc1cc(-c2nnc3c4ccccc4c(OCc4ccc(C(=O)N5CCC(F)(F)CC5)cn4)nn23)no1] | (4,4-difluoropiperidin-1-yl)(6-(((3-(5-methylisoxazol-3-yl)-[1,2,4]triazolo[3,4-a]phthalazin-6-yl)oxy)methyl)pyridin-3-yl)methanone |

-continued

| number | Chemical structures | Chemical name |
| --- | --- | --- |
| 24 | 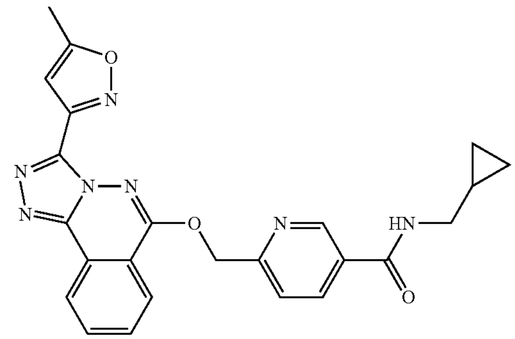 [SMILES: Cc1cc(-c2nnc3c4ccccc4c(OCc4ccc(C(=O)NCC5CC5)cn4)nn23)no1] | N-(cyclopropylmethyl)-6-(((3-(5-methylisoxazol-3-yl)-[1,2,4]triazolo[3,4-a]phthalazin-6-yl)oxy)methyl)nicotinamide |
| 25 | 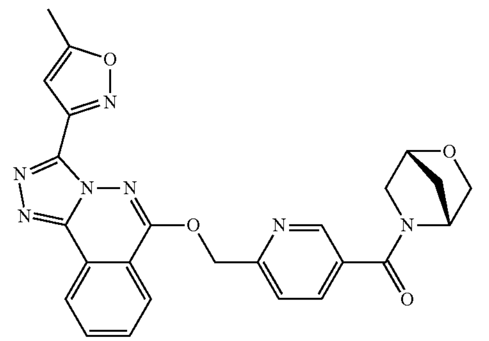 [SMILES: Cc1cc(-c2nnc3c4ccccc4c(OCc4ccc(C(=O)N5C[C@H]6C[C@@H]5CO6)cn4)nn23)no1] | (1R,4R)-2-oxa-5-azabicyclo[2.2.1]heptan-5-yl(6-(((3-(5-methylisoxazol-3-yl)-[1,2,4]triazolo[3,4-a]phthalazin-6-yl)oxy)methyl)pyridin-3-yl)methanone |
| 26 | 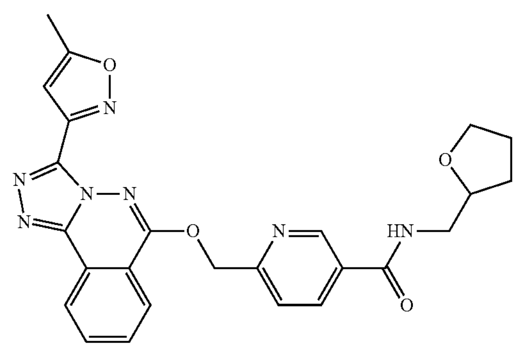 [SMILES: Cc1cc(-c2nnc3c4ccccc4c(OCc4ccc(C(=O)NCC5CCCO5)cn4)nn23)no1] | 6-(((3-(5-methylisoxazol-3-yl)-[1,2,4]triazolo[3,4-a]phthalazin-6-yl)oxy)methyl)-N-((tetrahydrofuran-2-yl)methyl)nicotinamide |
| 27 | 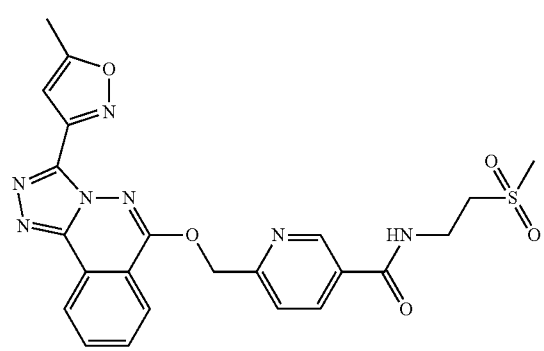 [SMILES: Cc1cc(-c2nnc3c4ccccc4c(OCc4ccc(C(=O)NCCS(C)(=O)=O)cn4)nn23)no1] | 6-(((3-(5-methylisoxazol-3-yl)-[1,2,4]triazolo[3,4-a]phthalazin-6-yl)oxy)methyl)-N-(2-(methylsulfonyl)ethyl)nicotinamide |

-continued

| number | Chemical structures | Chemical name |
| --- | --- | --- |
| 28 | 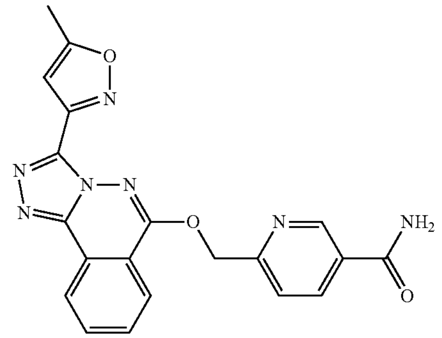 [SMILES: Cc1cc(-c2nnc3c4ccccc4c(OCc4ccc(C(N)=O)cn4)nn23)no1] | 6-(((3-(5-methylisoxazol-3-yl)-[1,2,4]triazolo[3,4-a]phthalazin-6-yl)oxy)methyl)nicotinamide |
| 29 | 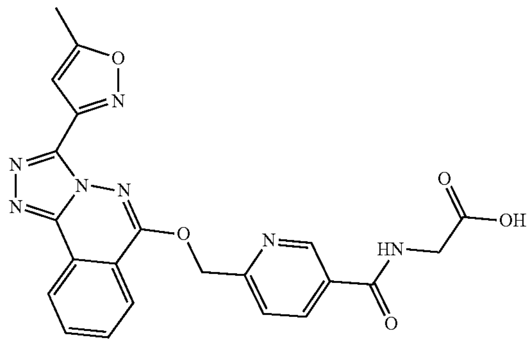 [SMILES: Cc1cc(-c2nnc3c4ccccc4c(OCc4ccc(C(=O)NCC(=O)O)cn4)nn23)no1] | 2-(6-(((3-(5-methylisoxazol-3-yl)-[1,2,4]triazolo[3,4-a]phthalazin-6-yl)oxy)methyl)nicotinamido)acetic acid |
| 30 | 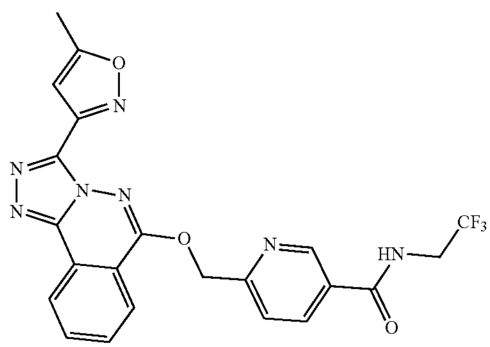 [SMILES: Cc1cc(-c2nnc3c4ccccc4c(OCc4ccc(C(=O)NCC(F)(F)F)cn4)nn23)no1] | 6-(((3-(5-methylisoxazol-3-yl)-[1,2,4]triazolo[3,4-a]phthalazin-6-yl)oxy)methyl)-N-(2,2,2-trifluoroethyl)nicotinamide |
| 31 | 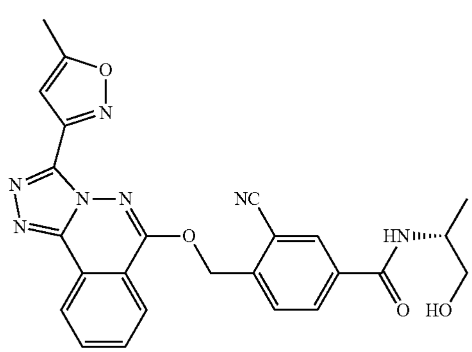 [SMILES: Cc1cc(-c2nnc3c4ccccc4c(OCc4ccc(C(=O)N[C@H](C)CO)cc4C#N)nn23)no1] | (R)-3-cyano-N-(1-hydroxypropan-2-yl)-4-(((3-(5-methyl-1,2,4-oxadiazol-3-yl)-[1,2,4]triazolo[3,4-a]phthalazin-6-yl)oxy)methyl)benzamide |

| number | Chemical structures | Chemical name |
|---|---|---|
| 32 | 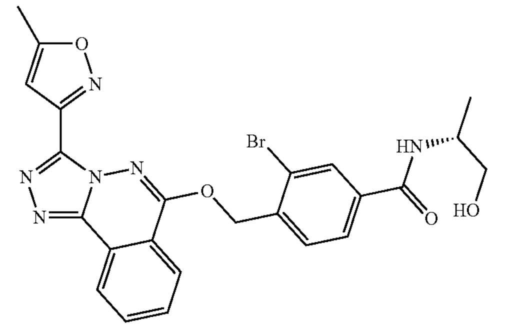 [SMILES: Cc1cc(-c2nnc3c4ccccc4c(OCc4ccc(C(=O)N[C@H](C)CO)cc4Br)nn23)no1] | (R)-3-bromo-N-(1-hydroxypropan-2-yl)-4-(((3-(5-methylisoxazol-3-yl)-[1,2,4]triazolo[3,4-a]phthalazin-6-yl)oxy)methyl)benzamide |
| 33 | 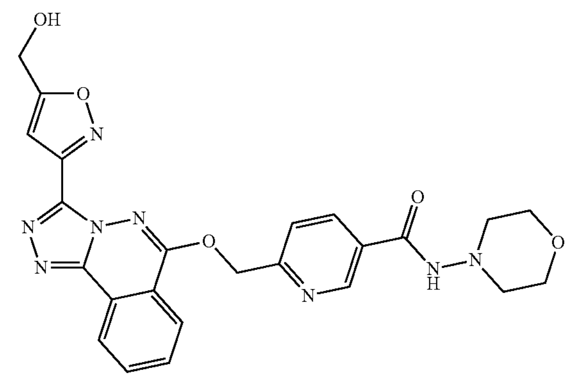 [SMILES: O=C(NN1CCOCC1)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N-morpholinonicotinamide |
| 34 | 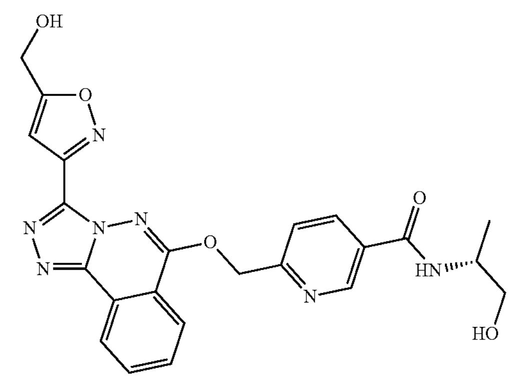 [SMILES: C[C@H](CO)NC(=O)c1ccc(COc2nn3c(-c4cc(CO)on4)nnc3c3ccccc23)nc1] | (R)-6-(((3-(5-(hydroxymethyl)isoxazol-3-yl)-[1,2,4]triazolo[3,4-a]phthalazin-6-yl)oxy)methyl)-N-(1-hydroxypropan-2-yl)nicotinamide |
| 35 | 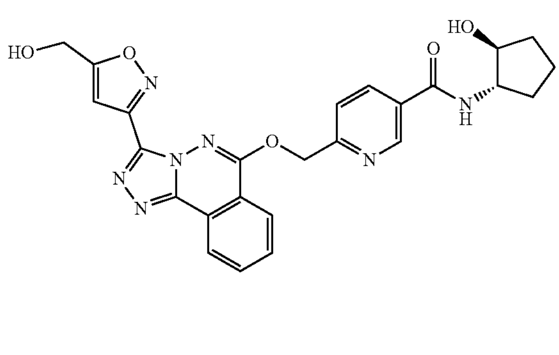 [SMILES: O=C(N[C@H]1CCC[C@@H]1O)c1ccc(COc2nn3c(-c4cc(CO)on4)nnc3c3ccccc23)nc1] | N-((1S,2S)-2-hydroxycyclopentyl)-6-(((3-(5-(hydroxymethyl)isoxazol-3-yl)-[1,2,4]triazolo[3,4-a]phthalazin-6-yl)oxy)methyl)nicotinamide |

-continued

| number | Chemical structures | Chemical name |
|---|---|---|
| 36 | 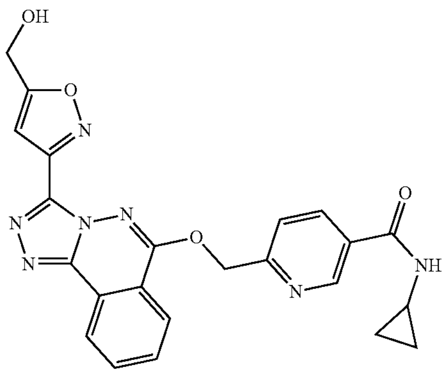 [SMILES: O=C(NC1CC1)c1ccc(COc2nn3c(-c4cc(CO)on4)nnc3c3ccccc23)nc1] | N-cyclopropyl-6-(((3-(5-(hydroxymethyl)isoxazol-3-yl)-[1,2,4]triazolo[3,4-a]phthalazin-6-yl)oxy)methyl)nicotinamide |
| 37 | 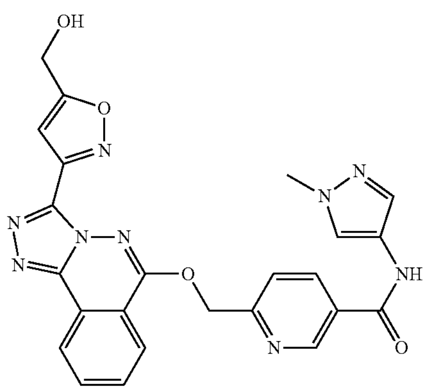 [SMILES: Cn1cc(NC(=O)c2ccc(COc3nn4c(-c5cc(CO)on5)nnc4c4ccccc34)nc2)cn1] | 6-(((3-(5-(hydroxymethyl)isoxazol-3-yl)-[1,2,4]triazolo[3,4-a]phthalazin-6-yl)oxy)methyl)-N-(1-methyl-1H-pyrazol-4-yl)nicotinamide |
| 38 | 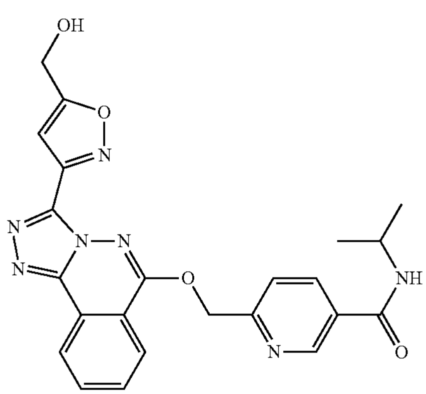 [SMILES: CC(C)NC(=O)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N-isopropylnicotinamide |
| 39 | 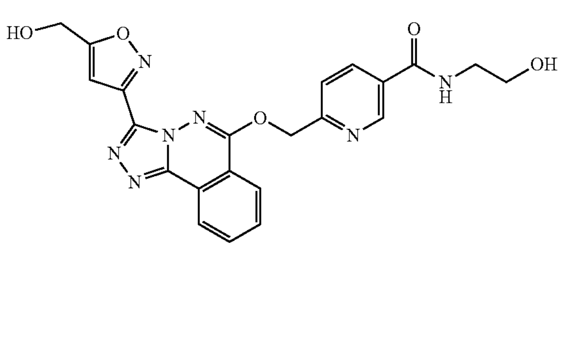 [SMILES: O=C(NCCO)c1ccc(COc2nn3c(-c4cc(CO)on4)nnc3c3ccccc23)nc1] | N-(2-hydroxyethyl)-6-(((3-(5-(hydroxymethyl)isoxazol-3-yl)-[1,2,4]triazolo[3,4-a]phthalazin-6-yl)oxy)methyl)nicotinamide |

-continued

| number | Chemical structures | Chemical name |
| --- | --- | --- |
| 40 | 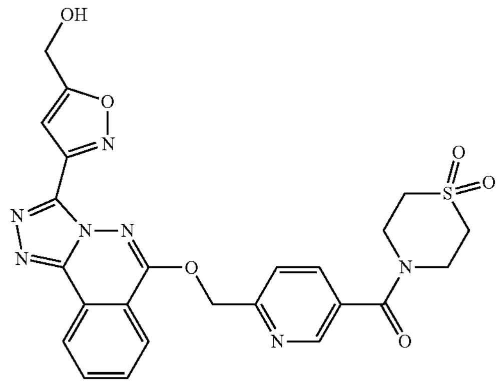 [SMILES: O=C(c1ccc(COc2nn3c(-c4cc(CO)on4)nnc3c3ccccc23)nc1)N1CCS(=O)(=O)CC1] | (1,1-dioxidothiomorpholino)(6-(((3-(5-(hydroxymethyl)isoxazol-3-yl)-[1,2,4]triazolo[3,4-a]phthalazin-6-yl)oxy)methyl)pyridin-3-yl)methanone |
| 41 | 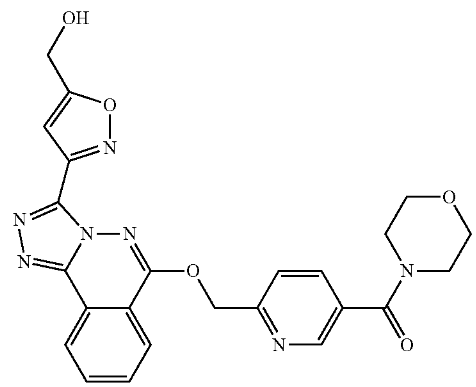 [SMILES: O=C(c1ccc(COc2nn3c(-c4cc(CO)on4)nnc3c3ccccc23)nc1)N1CCOCC1] | (6-(((3-(5-(hydroxymethyl)isoxazol-3-yl)-[1,2,4]triazolo[3,4-a]phthalazin-6-yl)oxy)methyl)pyridin-3-yl)(morpholino)methanone |
| 42 | 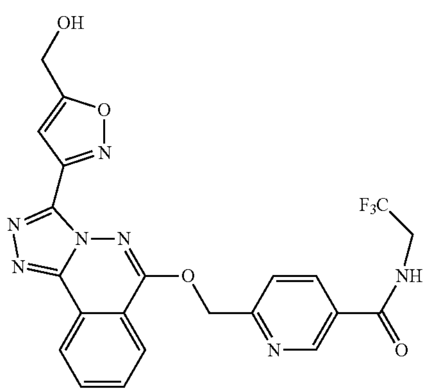 [SMILES: O=C(NCC(F)(F)F)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N-(2,2,2-trifluoroethyl)nicotinamide |
| 43 | 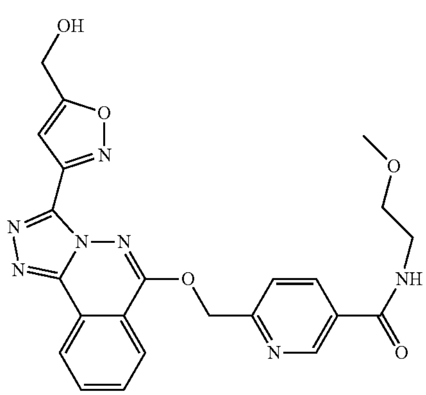 [SMILES: COCCNC(=O)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N-(2-methoxyethyl)nicotinamide |

| number | Chemical structures | Chemical name |
| --- | --- | --- |
| 44 | 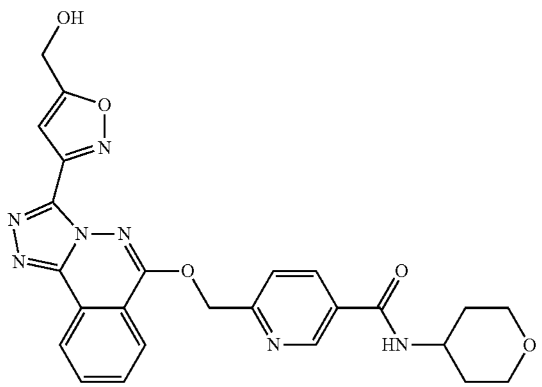 [SMILES: O=C(NC1CCOCC1)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N-(tetrahydro-2H-pyran-4-yl)nicotinamide |
| 45 | 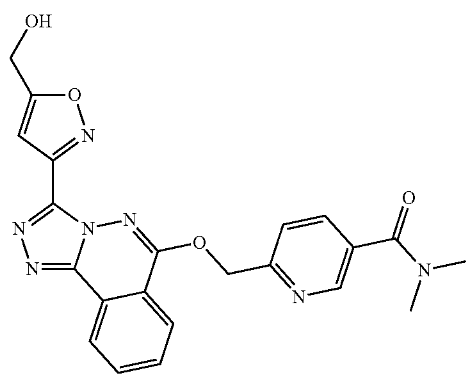 [SMILES: CN(C)C(=O)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N,N-dimethylnicotinamide |
| 46 | 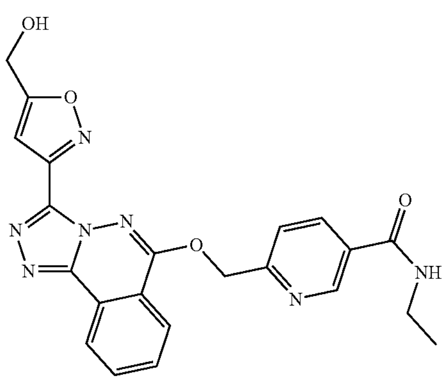 [SMILES: CCNC(=O)c1ccc(COc2nn3c(-c4cc(CO)on4)nnc3c3ccccc23)nc1] | N-ethyl-6-(((3-(5-(hydroxymethyl)isoxazol-3-yl)-[1,2,4]triazolo[3,4-a]phthalazin-6-yl)oxy)methyl)nicotinamide |
| 47 | 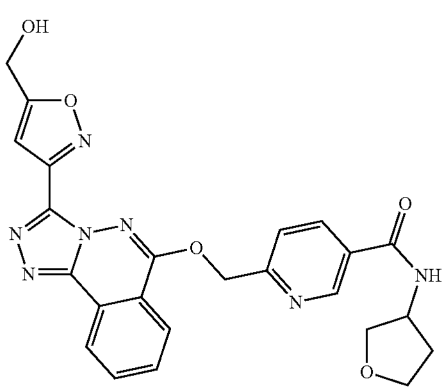 [SMILES: O=C(NC1CCOC1)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N-(tetrahydrofuran-3-yl)nicotinamide |

-continued

| number | Chemical structures | Chemical name |
|---|---|---|
| 48 | 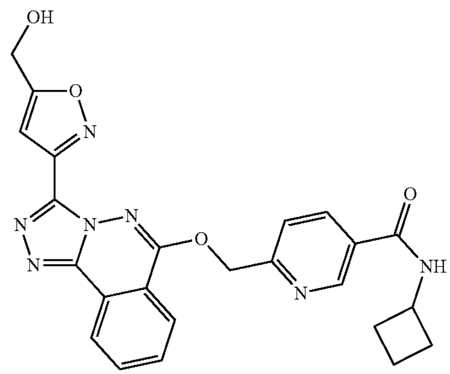 [SMILES: O=C(NC1CCC1)c1ccc(COc2nn3c(-c4cc(CO)on4)nnc3c3ccccc23)nc1] | N-cyclobutyl-6-(((3-(5-(hydroxymethyl)isoxazol-3-yl)-[1,2,4]triazolo[3,4-a]phthalazin-6-yl)oxy)methyl)nicotinamide |
| 49 | 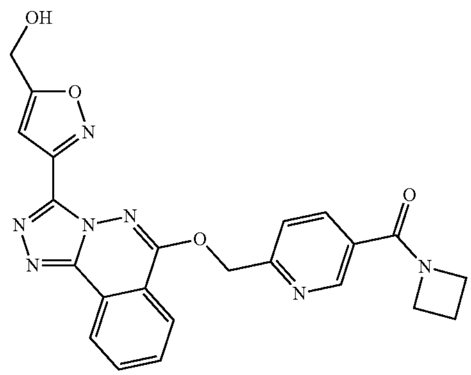 [SMILES: O=C(c1ccc(COc2nn3c(-c4cc(CO)on4)nnc3c3ccccc23)nc1)N1CCC1] | azetidin-1-yl(6-(((3-(5-(hydroxymethyl)isoxazol-3-yl)-[1,2,4]triazolo[3,4-a]phthalazin-6-yl)oxy)methyl)pyridin-3-yl)methanone |
| 50 | 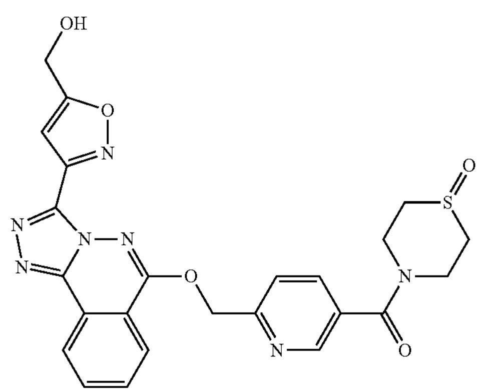 [SMILES: O=C(c1ccc(COc2nn3c(-c4cc(CO)on4)nnc3c3ccccc23)nc1)N1CCS(=O)CC1] | (6-(((3-(5-(hydroxymethyl)isoxazol-3-yl)-[1,2,4]triazolo[3,4-a]phthalazin-6-yl)oxy)methyl)pyridin-3-yl)(1-oxidothiomorpholino)methanone |
| 51 | 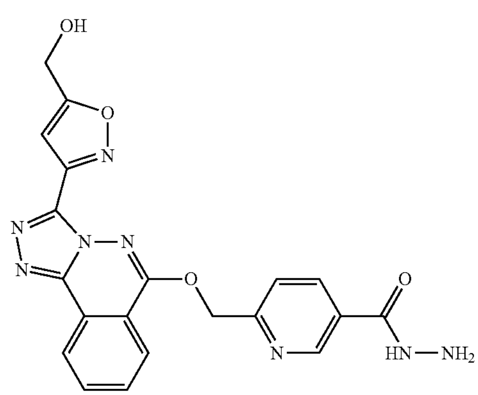 [SMILES: NNC(=O)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)nicotinohydrazide |

-continued

| number | Chemical structures | Chemical name |
|---|---|---|
| 52 | 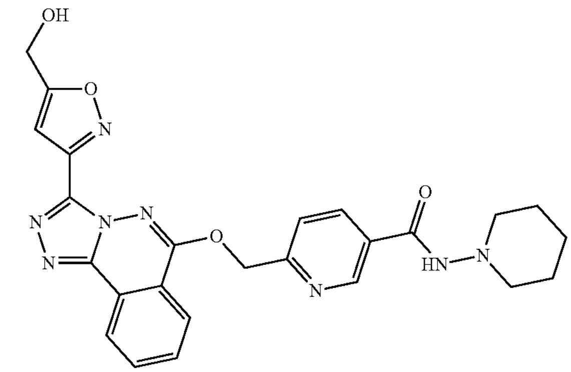 [SMILES: O=C(NN1CCCCC1)c1ccc(COc2nn3c(-c4cc(CO)on4)nnc3c3ccccc23)nc1] | 6-(((3-(5-(hydroxymethyl)isoxazol-3-yl)-[1,2,4]triazolo[3,4-a]phthalazin-6-yl)oxy)methyl)-N-(piperidin-1-yl)nicotinamide |
| 53 | 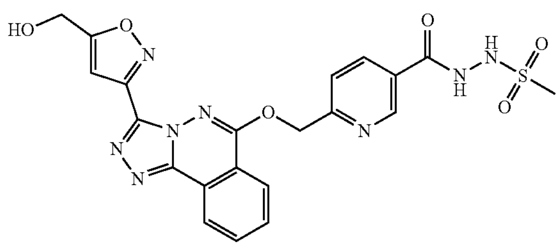 [SMILES: CS(=O)(=O)NNC(=O)c1ccc(COc2nn3c(-c4cc(CO)on4)nnc3c3ccccc23)nc1] | N'-(6-(((3-(5-(hydroxymethyl)isoxazol-3-yl)-[1,2,4]triazolo[3,4-a]phthalazin-6-yl)oxy)methyl)nicotinoyl)methanesulfonohydrazide |
| 54 | 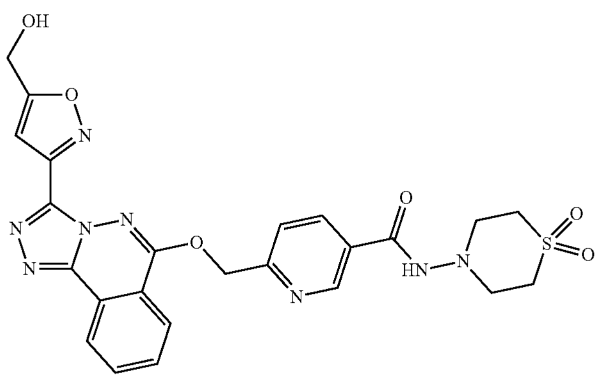 [SMILES: O=C(NN1CCS(=O)(=O)CC1)c1ccc(COc2nn3c(-c4cc(CO)on4)nnc3c3ccccc23)nc1] | N-(1,1-dioxidothiomorpholino)-6-(((3-(5-(hydroxymethyl)isoxazol-3-yl)-[1,2,4]triazolo[3,4-a]phthalazin-6-yl)oxy)methyl)nicotinamide |
| 55 | 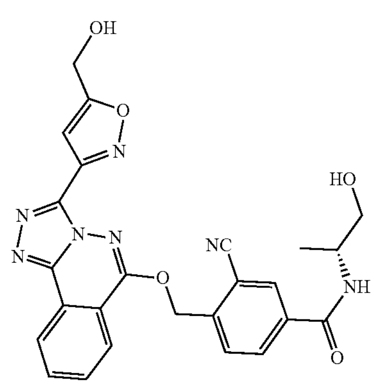 | (R)-3-cyano-4-(((3-(5-(hydroxymethyl)isoxazol-3-yl)-[1,2,4]triazolo[3,4-a]phthalazin-6-yl)oxy)methyl)-N-(1-hydroxypropan-2-yl)benzamide |

-continued

| number | Chemical structures | Chemical name |
|---|---|---|
| 56 | 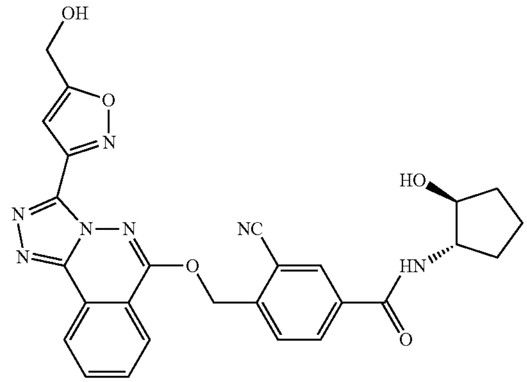 [SMILES: N#Cc1cc(C(=O)N[C@H]2CCC[C@@H]2O)ccc1COc1nn2c(-c3cc(CO)on3)nnc2c2ccccc12] | 3-cyano-N-((1S,2S)-2-hydroxycyclopentyl)-4-(((3-(5-(hydroxymethyl)isoxazol-3-yl)-[1,2,4]triazolo[3,4-a]phthalazin-6-yl)oxy)methyl)benzamide |
| 57 | 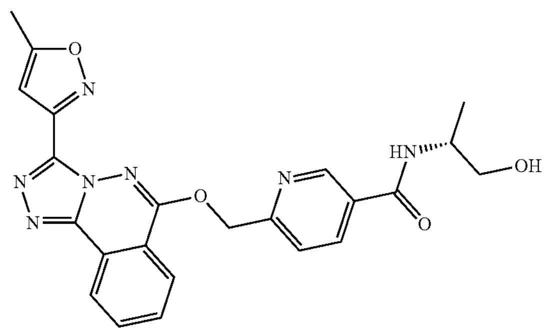 [SMILES: Cc1cc(-c2nnc3c4ccccc4c(OCc4ccc(C(=O)N[C@H](C)CO)cn4)nn23)no1] | (R)-N-(1-hydroxypropan-2-yl)-6-(((3-(5-methyl-1,2,4-oxadiazol-3-yl)-[1,2,4]triazolo[3,4-a]phthalazin-6-yl)oxy)methyl)nicotinamide |
| 58 | 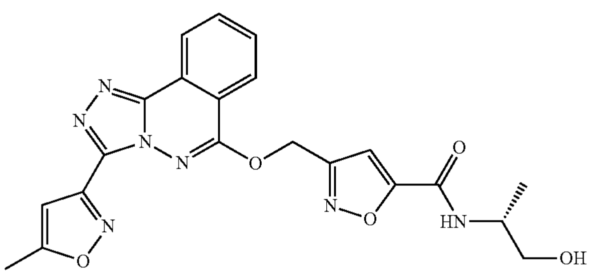 [SMILES: Cc1cc(-c2nnc3c4ccccc4c(OCc4cc(C(=O)N[C@H](C)CO)on4)nn23)no1] | (R)-N-(1-hydroxypropan-2-yl)-3-(((3-(5-methylisoxazol-3-yl)-[1,2,4]triazolo[3,4-a]phthalazin-6-yl)oxy)methyl)isoxazole-5-carboxamide |
| 59 | 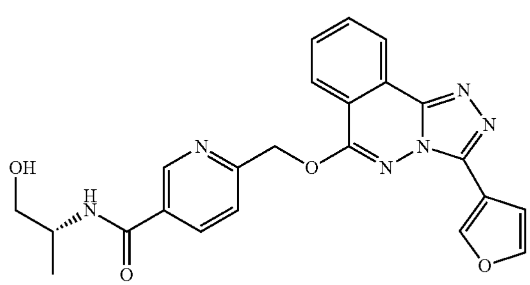 [SMILES: C[C@H](CO)NC(=O)c1ccc(COc2nn3c(-c4ccoc4)nnc3c3ccccc23)nc1] | (R)-6-(((3-(furan-3-yl)-[1,2,4]triazolo[3,4-a]phthalazin-6-yl)oxy)methyl)-N-(1-hydroxypropan-2-yl)nicotinamide |
| 60 | 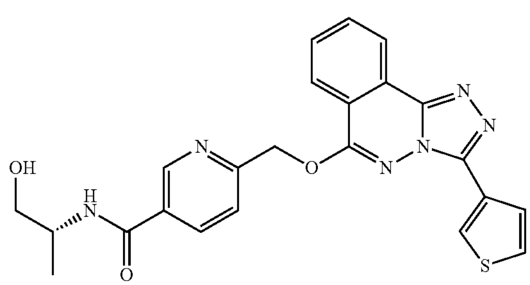 | (R)-N-(1-hydroxypropan-2-yl)-6-(((3-(thiophen-3-yl)-[1,2,4]triazolo[3,4-a]phthalazin-6-yl)oxy)methyl)nicotinamide |

-continued

| number | Chemical structures | Chemical name |
|---|---|---|
| 61 | 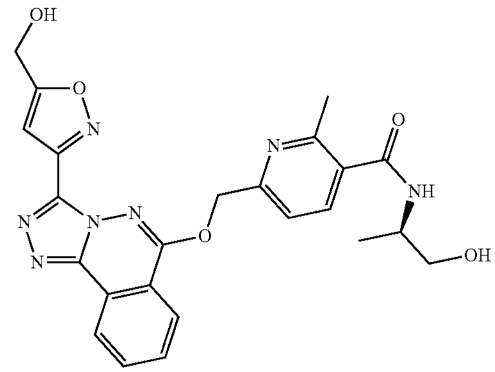 [SMILES: Cc1nc(COc2nn3c(-c4cc(CO)on4)nnc3c3ccccc23)ccc1C(=O)N[C@H](C)CO] | (R)-6-(((3-(5-(hydroxymethyl)isoxazol-3-yl)-[1,2,4]triazolo[3,4-a]phthalazin-6-yl)oxy)methyl)-N-(1-hydroxypropan-2-yl)-2-methylnicotinamide |
| 62 | 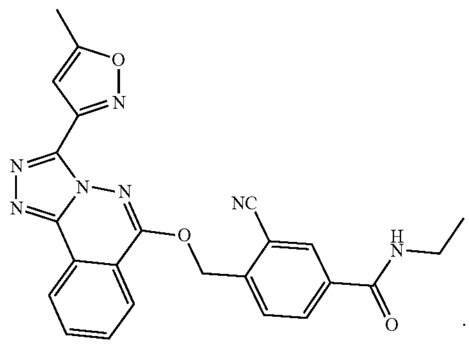 [SMILES: CCNC(=O)c1ccc(COc2nn3c(-c4cc(C)on4)nnc3c3ccccc23)c(C#N)c1] | 3-cyano-N-ethyl-4-(((3-(5-methylisoxazol-3-yl)-[1,2,4]triazolo[3,4-a]phthalazin-6-yl)oxy)methyl)benzamide |

28. A compound according to claim 1 which is independently selected from the group consisting of

| number | Chemical structures | Chemical name |
|---|---|---|
| 07 | 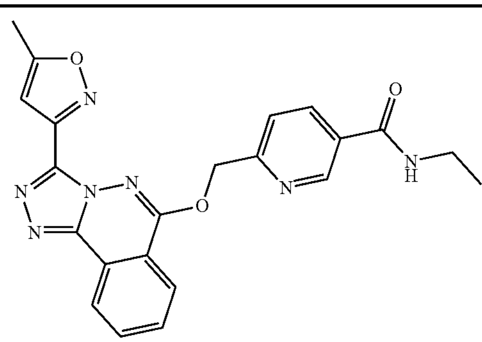 | N-ethyl-6-(((3-(5-methylisoxazol-3-yl)-[1,2,4]triazolo[3,4-a]phthalazin-6-yl)oxy)methyl)nicotinamide |
| 08 | 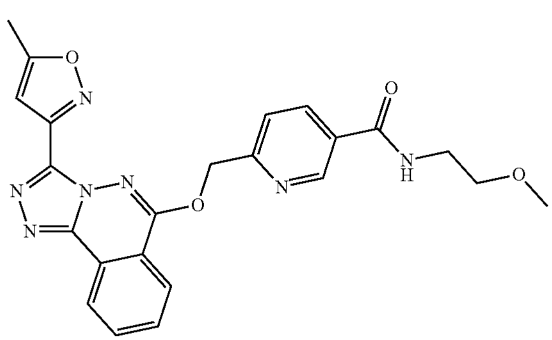 | N-(2-methoxyethyl)-6-(((3-(5-methylisoxazol-3-yl)-[1,2,4]triazolo[3,4-a]phthalazin-6-yl)oxy)methyl)nicotinamide |

| number | Chemical structures | Chemical name |
|---|---|---|
| 24 | 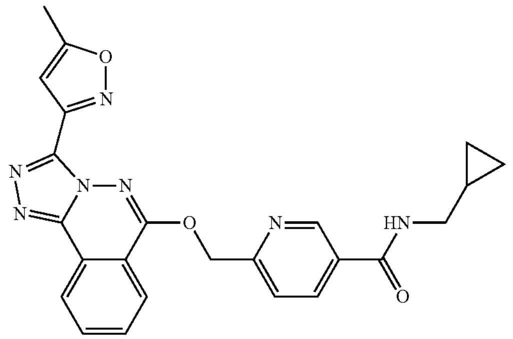 | N-(cyclopropylmethyl)-6-(((3-(5-methylisoxazol-3-yl)-[1,2,4]triazolo[3,4-a]phthalazin-6-yl)oxy)methyl)nicotinamide. |

29. A composition comprising a compound as defined in claim 1 or a pharmaceutically acceptable salt thereof.

30. A compound according to claim 1 wherein
Z is oxadiazolyl substituted by C1-6 alkyl or hydroxyl C1-6 alkyl;
A is phenylene, pyridinylene, or isoxazolylene; A is optionally substituted by 1, 2 or 3 substituents selected from the group consisting of halogen, cyano, and C1-6 alkyl;
Y is —NY1Y2 or —NH—NY3Y4;
Y1 is H or methyl;
Y2 is C1-6 alkyl or hydroxyl substituted C1-6 alkyl.

31. A compound according to claim 1 wherein
Z is oxadiazolyl substituted by C1-6 alkyl;
A is phenylene, pyridinylene, or isoxazolylene; A is optionally substituted by 1, 2 or 3 substituents selected from the group consisting of halogen, cyano, and C1-6 alkyl;
Y is —NY1Y2;
Y1 is H or methyl;
Y2 is C1-6 alkyl or hydroxyl substituted C1-6 alkyl.

* * * * *